(12) United States Patent
Dahlman et al.

(10) Patent No.: US 12,390,528 B2
(45) Date of Patent: *Aug. 19, 2025

(54) CONJUGATED LIPOMERS AND USES THEREOF

(71) Applicant: Massachusetts Institute of Technology, Cambridge, MA (US)

(72) Inventors: James E. Dahlman, Cambridge, MA (US); Avraham D. Schroeder, Newton, MA (US); Daniel Griffith Anderson, Framingham, MA (US); Robert S. Langer, Newton, MA (US); Christopher G. Levins, Flemington, NJ (US)

(73) Assignee: Massachusetts Institute of Technology, Cambridge, MA (US)

( * ) Notice: Subject to any disclaimer, the term of this patent is extended or adjusted under 35 U.S.C. 154(b) by 642 days.

This patent is subject to a terminal disclaimer.

(21) Appl. No.: 17/122,068

(22) Filed: Dec. 15, 2020

(65) Prior Publication Data

US 2021/0260195 A1     Aug. 26, 2021

Related U.S. Application Data

(63) Continuation of application No. 16/181,109, filed on Nov. 5, 2018, now Pat. No. 10,933,139, which is a continuation of application No. 14/995,842, filed on Jan. 14, 2016, now Pat. No. 10,117,934, which is a continuation of application No. 13/428,695, filed on Mar. 23, 2012, now Pat. No. 9,238,716.

(60) Provisional application No. 61/468,455, filed on Mar. 28, 2011.

(51) Int. Cl.

| | |
|---|---|
| A61K 47/54 | (2017.01) |
| A61K 9/00 | (2006.01) |
| A61K 9/1272 | (2025.01) |
| A61K 47/22 | (2006.01) |
| A61K 47/34 | (2017.01) |
| A61K 47/59 | (2017.01) |
| A61K 47/69 | (2017.01) |
| C07D 257/02 | (2006.01) |
| C07D 273/00 | (2006.01) |
| C07D 273/08 | (2006.01) |
| C07D 295/084 | (2006.01) |
| C08G 73/10 | (2006.01) |
| C12N 15/113 | (2010.01) |

(52) U.S. Cl.
CPC ............ *A61K 47/22* (2013.01); *A61K 9/0019* (2013.01); *A61K 9/1272* (2013.01); *A61K 47/34* (2013.01); *A61K 47/543* (2017.08); *A61K 47/59* (2017.08); *A61K 47/6907* (2017.08); *A61K 47/6911* (2017.08); *A61K 47/6921* (2017.08); *C07D 257/02* (2013.01); *C07D 273/00* (2013.01); *C07D 273/08* (2013.01); *C07D 295/084* (2013.01); *C08G 73/10* (2013.01); *C12N 15/1137* (2013.01); *C12N 15/1138* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 2,580,922 | A | 1/1952 | Jacoby |
| 2,647,121 | A | 7/1953 | Jacoby |
| 2,717,909 | A | 9/1955 | Kosmin |
| 2,759,021 | A | 8/1956 | Gaar et al. |
| 2,819,718 | A | 1/1958 | Goldman |
| 2,844,629 | A | 7/1958 | William et al. |
| 3,096,560 | A | 7/1963 | Liebig |
| 3,102,107 | A | 8/1963 | Lou |
| 3,170,953 | A | 2/1965 | Lashua |

(Continued)

FOREIGN PATENT DOCUMENTS

| | | |
|---|---|---|
| CA | 2518132 A1 | 3/2006 |
| CA | 2769408 A1 | 2/2011 |

(Continued)

OTHER PUBLICATIONS

Keana. Journal of Organic Chemistry, 1987, 52, 2571-2576 (Year: 1987).*

(Continued)

*Primary Examiner* — Noble E Jarrell
(74) *Attorney, Agent, or Firm* — Wolf, Greenfield & Sacks, P.C.

(57) ABSTRACT

The present invention provides inventive conjugated polyethyleneimine (PEI) polymers and conjugated aza-macrocycles (collectively referred to herein as "conjugated lipomers" or "lipomers") containing one or more groups of the formula (iii):

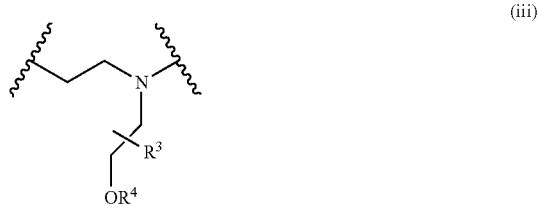

wherein $R^3$ and $R^4$ are as defined herein. Also provided are compositions comprising the inventive conjugated lipomers, and methods of preparation and use.

20 Claims, 35 Drawing Sheets

Specification includes a Sequence Listing.

(56) References Cited

U.S. PATENT DOCUMENTS

| | | |
|---|---|---|
| 3,268,576 A | 8/1966 | Wilkinson et al. |
| 3,278,478 A | 10/1966 | Masterson et al. |
| 3,350,325 A | 10/1967 | Ashby et al. |
| 3,354,209 A | 11/1967 | Brack |
| 3,535,289 A | 10/1970 | Yoshihara et al. |
| 3,542,581 A | 11/1970 | France et al. |
| 3,614,954 A | 10/1971 | Mirowski et al. |
| 3,614,955 A | 10/1971 | Mirowski |
| 3,656,185 A | 4/1972 | Carpentier |
| 3,682,980 A | 8/1972 | Braid et al. |
| 3,805,301 A | 4/1974 | Liebig |
| 3,850,853 A | 11/1974 | Marumo |
| 3,931,430 A | 1/1976 | Tada et al. |
| 3,945,052 A | 3/1976 | Liebig |
| 3,956,502 A | 5/1976 | Slovinsky et al. |
| 3,964,861 A | 6/1976 | Lofquist et al. |
| 3,995,623 A | 12/1976 | Blake et al. |
| 4,013,507 A | 3/1977 | Rembaum |
| 4,022,833 A | 5/1977 | Diana et al. |
| 4,072,146 A | 2/1978 | Howes |
| 4,096,860 A | 6/1978 | McLaughlin |
| 4,099,528 A | 7/1978 | Sorenson et al. |
| 4,106,129 A | 8/1978 | Carpentier et al. |
| 4,134,402 A | 1/1979 | Mahurkar |
| 4,140,126 A | 2/1979 | Choudhury |
| 4,180,068 A | 12/1979 | Jacobsen et al. |
| 4,182,833 A | 1/1980 | Hicks |
| 4,227,533 A | 10/1980 | Godfrey |
| 4,258,061 A | 3/1981 | Cronin et al. |
| 4,284,459 A | 8/1981 | Patel et al. |
| 4,308,085 A | 12/1981 | Horhold et al. |
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,375,817 A | 3/1983 | Engle et al. |
| 4,385,631 A | 5/1983 | Uthmann |
| 4,401,472 A | 8/1983 | Gerber |
| 4,406,656 A | 9/1983 | Hattler et al. |
| 4,475,972 A | 10/1984 | Wong |
| 4,507,466 A | 3/1985 | Tomalia et al. |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,863,621 A | 9/1989 | Wirth et al. |
| 4,873,370 A | 10/1989 | Chiu |
| 4,878,908 A | 11/1989 | Martin et al. |
| 4,892,540 A | 1/1990 | Vallana |
| 4,897,355 A | 1/1990 | Eppstein et al. |
| 4,937,269 A | 6/1990 | Smith et al. |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,141,749 A | 8/1992 | Herting et al. |
| 5,151,105 A | 9/1992 | Kwan-Gett |
| 5,171,678 A | 12/1992 | Behr et al. |
| 5,176,661 A | 1/1993 | Evard et al. |
| 5,197,977 A | 3/1993 | Hoffman, Jr. et al. |
| 5,200,395 A | 4/1993 | Eto et al. |
| 5,201,998 A | 4/1993 | Topfl et al. |
| 5,261,419 A | 11/1993 | Osypka |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,330,888 A | 7/1994 | Morigaki et al. |
| 5,334,761 A | 8/1994 | Gebeyehu et al. |
| 5,352,461 A | 10/1994 | Feldstein et al. |
| 5,386,028 A | 1/1995 | Tilstam et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,594,150 A | 1/1997 | David et al. |
| 5,607,385 A | 3/1997 | Francischelli et al. |
| 5,609,624 A | 3/1997 | Kalis |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,679,852 A | 10/1997 | Platzek et al. |
| 5,693,088 A | 12/1997 | Lazarus |
| 5,697,953 A | 12/1997 | Kroll et al. |
| 5,700,437 A | 12/1997 | Fujii et al. |
| 5,705,188 A | 1/1998 | Junichi et al. |
| 5,736,573 A | 4/1998 | Galat |
| 5,772,694 A | 6/1998 | Bokros et al. |
| 5,776,165 A | 7/1998 | Ripart |
| 5,776,747 A | 7/1998 | Schinstine et al. |
| 5,817,873 A | 10/1998 | Meyer et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,958,894 A | 9/1999 | Heath et al. |
| 5,976,569 A | 11/1999 | Milstein |
| 6,013,429 A | 1/2000 | Franke et al. |
| 6,034,056 A | 3/2000 | Dutta |
| 6,055,454 A | 4/2000 | Heemels |
| 6,067,471 A | 5/2000 | Warren |
| 6,071,497 A | 6/2000 | Steiner et al. |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,152,955 A | 11/2000 | KenKnight et al. |
| 6,169,923 B1 | 1/2001 | Kroll |
| 6,171,612 B1 | 1/2001 | Byk et al. |
| 6,176,877 B1 | 1/2001 | Buchanan et al. |
| 6,204,297 B1 | 3/2001 | Tracy et al. |
| 6,271,209 B1 | 8/2001 | Smith et al. |
| 6,299,604 B1 | 10/2001 | Ragheb et al. |
| 6,331,318 B1 | 12/2001 | Milstein |
| 6,335,199 B1 | 1/2002 | Bischoff et al. |
| 6,344,436 B1 | 2/2002 | Smith et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,372,903 B1 | 4/2002 | Mehdi et al. |
| 6,398,808 B1 | 6/2002 | Palasis |
| 6,444,226 B1 | 9/2002 | Steiner et al. |
| 6,696,424 B1 | 2/2004 | Wheeler |
| 6,737,485 B1 | 5/2004 | St. Clair et al. |
| 6,756,055 B2 | 6/2004 | McDonald et al. |
| 6,821,530 B2 | 11/2004 | Koob et al. |
| 6,887,665 B2 | 5/2005 | Trulson et al. |
| 6,998,115 B2 | 2/2006 | Langer et al. |
| 7,022,214 B2 | 4/2006 | Olech |
| 7,063,936 B2 | 6/2006 | Kakino et al. |
| 7,084,303 B2 | 8/2006 | Watanabe et al. |
| 7,101,995 B2 | 9/2006 | Lewis et al. |
| 7,427,394 B2 | 9/2008 | Anderson et al. |

(56) References Cited

U.S. PATENT DOCUMENTS

| | | |
|---|---|---|
| 7,507,859 B2 | 3/2009 | Grinstaff et al. |
| 7,556,684 B2 | 7/2009 | Bury et al. |
| 7,972,435 B2 | 7/2011 | Bury et al. |
| 7,977,452 B2 | 7/2011 | Tomalia et al. |
| 8,071,082 B2 | 12/2011 | Zugates et al. |
| RE43,612 E | 8/2012 | Anderson et al. |
| 8,268,631 B2 | 9/2012 | Kunz et al. |
| 8,287,849 B2 | 10/2012 | Langer et al. |
| 8,361,555 B2 | 1/2013 | Paquet, Jr. |
| 8,450,298 B2 | 5/2013 | Mahon et al. |
| 8,557,231 B2 | 10/2013 | Langer et al. |
| 8,562,966 B2 | 10/2013 | Zugates et al. |
| 8,808,681 B2 | 8/2014 | Anderson et al. |
| 8,969,353 B2 | 3/2015 | Mahon et al. |
| 9,006,487 B2 | 4/2015 | Anderson et al. |
| 9,101,666 B2 | 8/2015 | Langer et al. |
| 9,193,827 B2 | 11/2015 | Ma et al. |
| 9,227,197 B2 | 1/2016 | Kim |
| 9,238,716 B2 | 1/2016 | Dahlman et al. |
| 9,315,472 B2 | 4/2016 | Dong et al. |
| 9,439,968 B2 | 9/2016 | Anderson et al. |
| 9,512,073 B2 | 12/2016 | Dong et al. |
| 9,556,110 B2 | 1/2017 | Mahon et al. |
| 9,629,804 B2 | 4/2017 | Heartlein et al. |
| 9,700,627 B2 | 7/2017 | Langer et al. |
| 9,840,479 B2 | 12/2017 | Fenton et al. |
| 9,895,443 B2 | 2/2018 | Alabi et al. |
| 10,086,013 B2 | 10/2018 | Dong et al. |
| 10,117,934 B2 | 11/2018 | Dahlman et al. |
| 10,189,802 B2 | 1/2019 | Mahon et al. |
| 10,201,618 B2 | 2/2019 | Anderson et al. |
| 10,682,374 B2 | 6/2020 | Dong et al. |
| 10,695,444 B2 | 6/2020 | Anderson et al. |
| 10,844,028 B2 | 11/2020 | Mahon et al. |
| 10,933,139 B2 | 3/2021 | Dahlman et al. |
| 11,414,393 B2 | 8/2022 | Mahon et al. |
| 11,458,158 B2 | 10/2022 | Dong et al. |
| 11,679,165 B2 | 6/2023 | Anderson et al. |
| 2002/0022721 A1 | 2/2002 | Trulson et al. |
| 2002/0094528 A1 | 7/2002 | Salafsky |
| 2002/0131951 A1 | 9/2002 | Langer et al. |
| 2002/0192721 A1 | 12/2002 | Rizzuto et al. |
| 2002/0193622 A1 | 12/2002 | Watanabe et al. |
| 2003/0215395 A1 | 11/2003 | Yu et al. |
| 2004/0071654 A1 | 4/2004 | Anderson et al. |
| 2004/0181077 A1 | 9/2004 | Raymond et al. |
| 2004/0235982 A1 | 11/2004 | Rabasco et al. |
| 2005/0059005 A1 | 3/2005 | Tuschl et al. |
| 2005/0069590 A1 | 3/2005 | Buehler et al. |
| 2005/0123596 A1 | 6/2005 | Kohane et al. |
| 2005/0143332 A1 | 6/2005 | Monahan et al. |
| 2005/0148562 A1 | 7/2005 | Pairet et al. |
| 2005/0148786 A1 | 7/2005 | Ikeda et al. |
| 2005/0244961 A1 | 11/2005 | Short et al. |
| 2006/0223939 A1 | 10/2006 | Lange et al. |
| 2006/0228404 A1 | 10/2006 | Anderson et al. |
| 2007/0059373 A1 | 3/2007 | Oberg |
| 2007/0185128 A1 | 8/2007 | Conde-Frieboes et al. |
| 2007/0196503 A1 | 8/2007 | Wilson et al. |
| 2007/0275923 A1 | 11/2007 | Chen et al. |
| 2008/0145338 A1 | 6/2008 | Anderson et al. |
| 2008/0242626 A1 | 10/2008 | Zugates et al. |
| 2009/0023673 A1 | 1/2009 | Manoharan et al. |
| 2009/0221684 A1 | 9/2009 | Grinstaff et al. |
| 2010/0036084 A1 | 2/2010 | Langer et al. |
| 2010/0178699 A1 | 7/2010 | Gao et al. |
| 2010/0240072 A1 | 9/2010 | Wester et al. |
| 2010/0331234 A1 | 12/2010 | Mahon et al. |
| 2011/0009641 A1 | 1/2011 | Anderson et al. |
| 2011/0158935 A1 | 6/2011 | Kraft |
| 2011/0245344 A1 | 10/2011 | Wakita et al. |
| 2011/0257431 A1 | 10/2011 | Baumann et al. |
| 2011/0293703 A1 | 12/2011 | Mahon et al. |
| 2012/0009222 A1 | 1/2012 | Nguyen et al. |
| 2012/0065358 A1 | 3/2012 | Langer et al. |
| 2012/0128760 A1 | 5/2012 | Manoharan et al. |
| 2012/0196923 A1 | 8/2012 | Rege et al. |
| 2012/0251560 A1 | 10/2012 | Dahlman et al. |
| 2013/0158021 A1 | 6/2013 | Dong et al. |
| 2013/0302401 A1 | 11/2013 | Ma et al. |
| 2014/0094399 A1 | 4/2014 | Langer et al. |
| 2014/0161830 A1 | 6/2014 | Anderson et al. |
| 2014/0329884 A1 | 11/2014 | Dong et al. |
| 2015/0110857 A1 | 4/2015 | DeRosa et al. |
| 2015/0140070 A1 | 5/2015 | Heartlein et al. |
| 2015/0203439 A1 | 7/2015 | Mahon et al. |
| 2016/0002178 A1 | 1/2016 | Fenton et al. |
| 2016/0009657 A1 | 1/2016 | Anderson et al. |
| 2016/0022821 A1 | 1/2016 | Langer et al. |
| 2016/0114042 A1 | 4/2016 | Anderson et al. |
| 2016/0137785 A1 | 5/2016 | Ma et al. |
| 2016/0158363 A1 | 6/2016 | Alabi et al. |
| 2016/0206740 A1 | 7/2016 | Dahlman et al. |
| 2016/0367686 A1 | 12/2016 | Anderson et al. |
| 2017/0152213 A1 | 6/2017 | Anderson et al. |
| 2017/0165290 A1 | 6/2017 | Dong et al. |
| 2017/0204075 A1 | 7/2017 | Mahon et al. |
| 2018/0036333 A9 | 2/2018 | Dong et al. |
| 2019/0076462 A1 | 3/2019 | Dong et al. |
| 2019/0167795 A1 | 6/2019 | Dahlman et al. |
| 2019/0177289 A1 | 6/2019 | Mahon et al. |
| 2019/0240349 A1 | 8/2019 | Anderson et al. |
| 2020/0330501 A1 | 10/2020 | Dong et al. |
| 2020/0353099 A1 | 11/2020 | Anderson et al. |
| 2021/0101875 A1 | 4/2021 | Mahon et al. |
| 2023/0124955 A1 | 4/2023 | Dong et al. |
| 2023/0338577 A1 | 10/2023 | Anderson et al. |
| 2024/0316216 A1 | 9/2024 | Langer et al. |

FOREIGN PATENT DOCUMENTS

| | | |
|---|---|---|
| CL | 201301810 | 1/2014 |
| CL | 201400988 | 11/2014 |
| CL | 201400395 | 12/2014 |
| CN | 1433478 A | 7/2003 |
| CN | 101506196 A | 8/2009 |
| CN | 100569877 C | 12/2009 |
| CN | 101863544 B | 9/2011 |
| CN | 104136419 A | 11/2014 |
| CN | 107848988 B | 10/2021 |
| DE | 1155118 B | 10/1963 |
| DE | 2430998 A1 | 1/1975 |
| DE | 2520814 A1 | 11/1976 |
| DE | 2530243 A1 | 1/1977 |
| DE | 2903979 A1 | 8/1980 |
| DE | 19541788 A1 | 5/1997 |
| EP | 0030389 A1 | 6/1981 |
| EP | 168930 A1 | 1/1986 |
| EP | 211305 A2 | 2/1987 |
| EP | 0545305 A1 | 6/1993 |
| EP | 0673637 A1 | 9/1995 |
| EP | 0959092 A1 | 11/1999 |
| EP | 1277829 A2 | 1/2003 |
| EP | 1 912 679 A2 | 4/2008 |
| EP | 2045251 A1 | 4/2009 |
| EP | 2 476 756 A1 | 7/2012 |
| EP | 2532649 A1 | 12/2012 |
| EP | 1854789 B1 | 10/2013 |
| FR | 1378382 A | 11/1964 |
| FR | 2235112 A1 | 1/1975 |
| GB | 866408 A | 4/1961 |
| GB | 1072118 A | 6/1967 |
| GB | 1377449 A | 12/1974 |
| GB | 1602085 A | 11/1981 |
| JP | S48-22365 A | 3/1973 |
| JP | S49-127908 A | 12/1974 |
| JP | S50-24216 A | 3/1975 |
| JP | S51-20639 A | 2/1976 |
| JP | S51-23537 A | 2/1976 |
| JP | S51-125144 A | 11/1976 |
| JP | S52-10847 A | 1/1977 |
| JP | S52-78924 A | 7/1977 |
| JP | S52-82910 A | 7/1977 |
| JP | S57-74371 A | 5/1982 |

(56) References Cited

FOREIGN PATENT DOCUMENTS

| | | |
|---|---|---|
| JP | S58-8770 A | 1/1983 |
| JP | S58-96062 A | 6/1983 |
| JP | S63-39378 A | 2/1988 |
| JP | S63-125144 A | 5/1988 |
| JP | S63-154788 A | 6/1988 |
| JP | S63-258833 A | 10/1988 |
| JP | S63-284267 A | 11/1988 |
| JP | 1099679 B | 4/1989 |
| JP | H02-212471 A | 8/1990 |
| JP | H03-145461 A | 6/1991 |
| JP | H04-108173 A | 4/1992 |
| JP | H04-225954 A | 8/1992 |
| JP | H04-364112 A | 12/1992 |
| JP | H06-200073 A | 7/1994 |
| JP | H06-211978 A | 8/1994 |
| JP | H07-53535 A | 2/1995 |
| JP | H09-95691 A | 4/1997 |
| JP | H09-505593 A | 6/1997 |
| JP | H10-101607 A | 4/1998 |
| JP | H10-197978 A | 7/1998 |
| JP | H11-5786 A | 1/1999 |
| JP | H11-80142 A | 3/1999 |
| JP | H11-241095 A | 9/1999 |
| JP | 2000-501383 A | 2/2000 |
| JP | 2000-505788 A | 5/2000 |
| JP | 2001-131449 A | 5/2001 |
| JP | 2001-523215 A | 11/2001 |
| JP | 2002-167368 A | 6/2002 |
| JP | 2003-519199 A | 6/2003 |
| JP | 2005-010476 A | 1/2005 |
| JP | 2005-519976 A | 7/2005 |
| JP | 2005-227441 A | 8/2005 |
| JP | 2005-532323 A | 10/2005 |
| JP | 2006-091276 A | 4/2006 |
| JP | 2007-254625 A | 10/2007 |
| JP | 4020247 B2 | 12/2007 |
| JP | 2008-074903 A | 4/2008 |
| JP | 2008-202015 A | 9/2008 |
| JP | 2008-247749 A | 10/2008 |
| JP | 2008-303210 A | 12/2008 |
| JP | 2011-501742 A | 1/2011 |
| JP | 2011-516413 A | 5/2011 |
| JP | 2012-197433 A | 10/2012 |
| JP | 2014-172827 A | 9/2014 |
| JP | 2014-534220 A | 12/2014 |
| JP | 5777846 B2 | 9/2015 |
| JP | 6087504 B2 | 3/2017 |
| WO | WO 90/03399 A1 | 4/1990 |
| WO | WO 93/18229 A1 | 9/1993 |
| WO | WO 1993/18754 A1 | 9/1993 |
| WO | WO 95/10272 A1 | 4/1995 |
| WO | WO 1995/11004 A1 | 4/1995 |
| WO | WO 1995/14651 A1 | 6/1995 |
| WO | WO 1995/18863 A1 | 7/1995 |
| WO | WO 1996/25508 A1 | 8/1996 |
| WO | WO 1996/26179 A1 | 8/1996 |
| WO | WO 1996/36314 A2 | 11/1996 |
| WO | WO 1997/23457 A1 | 7/1997 |
| WO | WO 1998/16202 A1 | 4/1998 |
| WO | WO 98/050078 A1 | 11/1998 |
| WO | 99/15580 A1 | 4/1999 |
| WO | WO 99/015129 A2 | 4/1999 |
| WO | WO 2000/03044 A1 | 1/2000 |
| WO | WO 00/22030 A1 | 4/2000 |
| WO | WO 2000/32045 A1 | 6/2000 |
| WO | WO 2000/55141 A1 | 9/2000 |
| WO | WO 2001/010845 A1 | 2/2001 |
| WO | WO 2001/15726 A2 | 3/2001 |
| WO | WO 2001/49324 A2 | 7/2001 |
| WO | WO 2002/22709 A1 | 3/2002 |
| WO | WO 2002/031025 A2 | 4/2002 |
| WO | WO 2002/097068 A2 | 12/2002 |
| WO | WO 2003/024401 A2 | 3/2003 |
| WO | WO 2003/040288 A2 | 5/2003 |
| WO | WO 2003/070735 A2 | 8/2003 |
| WO | WO 2004/024858 A1 | 3/2004 |
| WO | WO 2004/043588 A2 | 5/2004 |
| WO | WO 2004/048345 A2 | 6/2004 |
| WO | WO 2004/106411 A2 | 12/2004 |
| WO | WO 2005/028619 A2 | 3/2005 |
| WO | WO 2005/055979 A2 | 6/2005 |
| WO | WO 2005/080669 A1 | 9/2005 |
| WO | WO 2005/121348 A1 | 12/2005 |
| WO | WO 2006/015775 A2 | 2/2006 |
| WO | WO 2006/065266 A2 | 6/2006 |
| WO | WO 2006/082088 A1 | 8/2006 |
| WO | WO 2006/105043 A2 | 10/2006 |
| WO | WO 2006/138380 A2 | 12/2006 |
| WO | WO 2007/035019 A1 | 3/2007 |
| WO | WO 2007/096662 A2 | 8/2007 |
| WO | WO 2007/143659 A2 | 12/2007 |
| WO | WO 2008/011561 A2 | 1/2008 |
| WO | WO 2008/030006 A1 | 3/2008 |
| WO | WO 2008/036168 A2 | 3/2008 |
| WO | WO 2008/113364 A2 | 9/2008 |
| WO | WO 2008/119741 A2 | 10/2008 |
| WO | WO 2009/046220 A2 | 4/2009 |
| WO | WO 2009/086547 A1 | 7/2009 |
| WO | WO 2010/042877 A1 | 4/2010 |
| WO | WO 2010/045512 A2 | 4/2010 |
| WO | WO-2010053572 A2 * | 5/2010 ......... A61K 31/7088 |
| WO | WO 2010/078373 A1 | 7/2010 |
| WO | WO 2010/099387 A1 | 9/2010 |
| WO | WO 2010/114789 A1 | 10/2010 |
| WO | WO 2010/129709 A1 | 11/2010 |
| WO | WO 2011/012746 A2 | 2/2011 |
| WO | WO 2011/068810 A1 | 6/2011 |
| WO | WO 2011/072345 A1 | 6/2011 |
| WO | WO 2012/027675 A2 | 3/2012 |
| WO | WO 2012/133737 A1 | 10/2012 |
| WO | WO 2012/135025 A2 | 10/2012 |
| WO | WO 2012/170889 A1 | 12/2012 |
| WO | WO 2012/170930 A1 | 12/2012 |
| WO | WO 2013/063468 A1 | 5/2013 |
| WO | WO 2014/028487 A1 | 2/2014 |
| WO | WO 2014/152774 A1 | 9/2014 |
| WO | WO 2014/179562 A1 | 11/2014 |
| WO | WO 2014/210356 A1 | 12/2014 |
| WO | WO 2015/061467 A1 | 4/2015 |

OTHER PUBLICATIONS

Extended European Search Report for European Application No. 22158860.1, mailed Sep. 15, 2022.
Invitation to Pay Additional Fees for PCT/US2012/062222 mailed Dec. 14, 2012.
International Search Report and Written Opinion for PCT/US2012/062222 mailed Mar. 27, 2013.
International Preliminary Report on Patentability for PCT/US2012/062222, mailed May 8, 2014.
Extended European Search Report for European Application No. 06784878.8 mailed Jun. 29, 2009.
Extended European Search Report for European Application No. 11186795.8, mailed Jun. 19, 2012.
International Search Report and Written Opinion for PCT/US2006/023171 mailed May 29, 2008.
International Preliminary Report on Patentability for PCT/US2006/023171 mailed Jul. 3, 2008.
Extended European Search Report, mailed Jan. 28, 2008, for EP 07013193.3.
Invitation to Pay Additional Fees for PCT/US2004/016521 mailed Sep. 29, 2004.
International Search Report and Written Opinion for PCT/US2004/016521 mailed Dec. 8, 2004.
International Preliminary Report on Patentability for PCT/US2004/016521 mailed Dec. 15, 2005.
International Search Report for PCT/US2001/031270 mailed May 22, 2002.
Written Opinion for PCT/US2001/031270 mailed Jan. 2, 2003.
International Preliminary Examination Report for PCT/US2001/031270 mailed Aug. 19, 2003.

(56) References Cited

OTHER PUBLICATIONS

Extended European Search Report, mailed Oct. 5, 2009, for EP 07813156.2.
International Search Report and Written Opinion for PCT/US2007/073976 mailed Sep. 29, 2008.
International Preliminary Report on Patentability for PCT/US2007/073976 mailed Feb. 5, 2009.
Extended European Search Report for EP 07798132.2 mailed Jul. 18, 2011.
International Search Report and Written Opinion for PCT/US2007/070430 mailed Dec. 13, 2007.
International Preliminary Report on Patentability for PCT/US2007/070430 mailed Dec. 24, 2008.
Extended European Search Report for European Application No. 09825132.5 dated Jul. 16, 2013.
Extended European Search Report for European Application No. 17179391.2, mailed Dec. 18, 2017...
International Search Report and Written Opinion for PCT/US2009/006018 mailed May 25, 2010.
International Preliminary Report on Patentability for PCT/US2009/006018 mailed May 19, 2011.
International Search Report and Written Opinion for PCT/US2009/005810 mailed Jun. 16, 2010.
International Preliminary Report on Patentability for PCT/US2009/005810 mailed May 12, 2011.
Partial Supplementary European Search Report for European Application No. 11820727.3, mailed Nov. 26, 2014.
Extended European Search Report for European Application No. 11820727.3, mailed Apr. 22, 2015.
International Search Report and Written Opinion for PCT/US2011/049360 mailed Mar. 20, 2012.
International Preliminary Report on Patentability for PCT/US2011/049360 mailed Mar. 7, 2013.
Invitation to Pay Additional Fees for PCT/US2013/054726, mailed Oct. 31, 2013.
International Search Report and Written Opinion for PCT/US2013/054726, mailed Jan. 7, 2014.
International Preliminary Report on Patentability for PCT/US2013/054726, mailed Feb. 26, 2015.
International Search Report and Written Opinion for PCT/US2014/036355, mailed Aug. 5, 2014.
International Preliminary Report on Patentability for PCT/US2014/036355, mailed Nov. 12, 2015.
International Search Report and Written Opinion for PCT/US2014/044408, mailed Oct. 24, 2014.
International Preliminary Report on Patentability for PCT/US2014/044408, mailed Jan. 7, 2016.
Invitation to Pay Additional Fees for PCT/US2015/038827, mailed Sep. 24, 2015.
International Search Report and Written Opinion for PCT/US2015/038827, mailed Dec. 8, 2015.
International Preliminary Report on Patentability for PCT/US2015/038827, mailed Jan. 12, 2017.
Invitation to Pay Additional Fees for PCT/US2016/038141 mailed Sep. 20, 2016.
International Search Report and Written Opinion for PCT/US2016/038141 mailed Nov. 22, 2016.
International Preliminary Report on Patentability for PCT/US2016/038141, mailed Dec. 28, 2017.
Adami et al., An amino acid-based amphoteric liposomal delivery system for systemic administration of siRNA. Mol Ther. Jun. 2011;19(6):1141-51.
Agarwal et al. Synthesis and antimicrobial activity of fatty 2-morpholinones prepared from epoxy fatty acid methyl esters. J Am Oil Chem Soc 66, 825-827 (1989). https://doi.org/10.1007/BF02653677.
Akhtar et al., Toxicogenomics of non-viral drug delivery systems for RNAi: potential impact on siRNA-mediated gene silencing activity and specificity. Adv Drug Deliv Rev. Mar. 30, 2007;59(2-3):164-82.
Akinc et al., A combinatorial library of lipid-like materials for delivery of RNAi therapeutics. Nat Biotech. 2008;26(5):561-69.
Akinc et al., Development of lipidoid-siRNA formulations for systemic delivery to the liver. Mol Ther. May 2009;17(5):872-9. doi: 10.1038/mt.2009.36. Epub Mar. 3, 2009.
Akinc et al., Exploring polyethylenimine-mediated DNA transfection and the proton sponge hypothesis. J Gene Med. May 2005;7(5):657-63.
Akinc et al., Parallel synthesis and biophysical characterization of a degradable polymer library for gene delivery. J Am Chem Soc. May 7, 2003;125(18):5316-23.
Akinc et al., Targeted delivery of RNAi therapeutics with endogenous and exogenous ligand-based mechanisms. Mol Ther. Jul. 2010;18(7):1357-64. doi: 10.1038/mt.2010.85. Epub May 11, 2010.
Akira et al., Functions of toll-like receptors: lessons from KO mice. C R Biol. Jun. 2004;327(6):581-9.
Ali et al., Derivation of type II alveolar epithelial cells from murine embryonic stem cells. Tissue Eng. Aug. 2002;8(4):541-50.
Allison, The mode of action of immunological adjuvants. Dev Biol Stand. 1998;92:3-11. Review.
Alshamsan et al., The induction of tumor apoptosis in B16 melanoma following STAT3 siRNA delivery with a lipid-substituted polyethylenimine. Biomaterials. Feb. 2010;31(6):1420-8. Epub Nov. 13, 2009.
Anderson et al., Nanoliter-scale synthesis of arrayed biomaterials and application to human embryonic stem cells. Nat Biotechnol. Jul. 2004;22(7):863-6. Epub Jun. 13, 2004.
Anderson et al., Structure/property studies of polymeric gene delivery using a library of poly(beta-amino esters). Mol Ther. Mar. 2005;11(3):426-34.
Anderson, Biological Responses to Materials. Annu Rev Mater Res. 2001;31:81-110.
Anderson, Chapter 4. Mechanisms of Inflammation and Infection With Implanted Devices. Cardiovasc Pathol. 1993;2:33S-41S.
Anderson, Human gene therapy. Nature. Apr. 30, 1998;392(6679 Suppl):25-30. Review.
Asokan et al., Cytosolic delivery of macromolecules. 3. Synthesis and characterization of acid-sensitive bis-detergents. Bioconjug Chem. Nov.-Dec. 2004;15(6):1166-73.
Astle et al., A VEGFR2 Antagonist and Other Peptoids Evade Immune Recognition. Int J Pept Res Ther. 2008;14(3):223-227.
Bajaj et al., Synthesis and gene transfection efficacies of PEI-cholesterol-based lipopolymers. Bioconjug Chem. Aug. 2008;19(8):1640-51. Epub Jul. 11, 2008.
Ballermann et al., Shear stress and the endothelium. Kidney Int Suppl. Sep. 1998;67:S100-8.
Bartel, MicroRNAs: Genomics, Biogenesis, Mechanism, and Function. Cell. 2004; 116:281-97.
Behr et al., Efficient gene transfer into mammalian primary endocrine cells with lipopolyamine-coated DNA. Proc Natl Acad Sci U S A. Sep. 1989;86(18):6982-6.
Behr, Synthetic gene-transfer vectors. Acc Chem Res. 1993;26:274-278.
Berge et al., Pharmaceutical salts. J Pharm Sci. Jan. 1977;66(1):1-19.
Bossle et al., Synthesis and biological activity of new 2-substituted analogs of fluphenazine. J Med Chem. Mar. 1, 1976;19(3):370-3.
Boudou et al., Multiple functionalities of polyelectrolyte multilayer films: new biomedical applications. Adv Mater. Jan. 26, 2010;22(4):441-67.
Bourque et al., Hydroformylation Reactions Using Recyclable Rhodium-Complexed Dendrimers on Silica. J Am Chem Soc. 2000;122(5):956-957.
Boussif et al., A versatile vector for gene and oligonucleotide transfer into cells in culture and in vivo: polyethylenimine. Proc Natl Acad Sci U S A. Aug. 1, 1995;92(16):7297-301.
Bowman et al., 273 N-substituted amino-acids. Part II. The reductive alkylation of amino-acids. Journal of the Chemical Society. Jan. 1, 1950: 1348.
Bratlie et al., Rapid biocompatibility analysis of materials via in vivo fluorescence imaging of mouse models. PLoS One. Apr. 6, 2010;5(4):e10032.

(56) References Cited

OTHER PUBLICATIONS

Braun et al., Structure/function relationships of polyamidoamine/DNA dendrimers as gene delivery vehicles. J Pharm Sci. Feb. 2005;94(2):423-36.

Breunig et al., Breaking up the correlation between efficacy and toxicity for nonviral gene delivery. Proc Natl Acad Sci U S A. Sep. 4, 2007;104(36):14454-9. Epub Aug. 28, 2007.

Breunig et al., Mechanistic investigation of poly(ethylene imine)-based siRNA delivery: disulfide bonds boost intracellular release of the cargo. J Control Release. Aug. 25, 2008;130(1):57-63. Epub May 24, 2008.

Brey et al., Controlling poly(beta-amino ester) network properties through macromer branching. Acta Biomater. Mar. 2008;4(2):207-17. Epub Oct. 22, 2007.

Brey et al., Influence of macromer molecular weight and chemistry on poly(beta-amino ester) network properties and initial cell interactions. J Biomed Mater Res A. Jun. 1, 2008;85(3):731-41.

Brito et al. Enhanced interfacial properties of novel amino acid-derived surfactants: Effects of headgroup chemistry and of alkyl chain length and unsaturation. Colloids Surf ; B Biointerfaces. Aug. 1, 2011;86(1):65-70. doi: 10.1016/j.colsurfb.2011.03.017. Epub Mar. 23, 2011.

Brodbeck et al., Biomaterial surface chemistry dictates adherent monocyte/macrophage cytokine expression in vitro. Cytokine. Jun. 21, 2002;18(6):311-9.

Burnett et al., Current progress of siRNA/shRNA therapeutics in clinical trials. Biotechnol J. Sep. 2011;6(9):1130-46. doi: 10.1002/biot.201100054. Epub Jul. 11, 2011.

Byk et al., Synthesis, activity, and structure—activity relationship studies of novel cationic lipids for DNA transfer. J Med Chem. 1998;41(2):224-235.

Campbell et al., Application of cytokeratin 7 and 20 immunohistochemistry to diagnostic pathology. Current Diagnostic Pathology. 2001;7:113-22.

Carter et al., Mechanobiology of skeletal regeneration. Clin Orthop Relat Res. Oct. 1998;(355 Suppl):S41-55.

Castanotto et al.,. The promises and pitfalls of RNA-interference-based therapeutics. Nature. Jan. 22, 2009;457(7228):426-33. doi: 10.1038/nature07758.

Chakraborty, Potentiality of Small Interfering RNAs (siRNA) as Recent Therapeutic Targets for Gene-Silencing. Curr Drug Targets. 2007;8:469-82.

Chan et al., Triplex DNA: fundamentals, advances, and potential applications for gene therapy. J Mol Med. Apr. 1997;75(4):267-82. Review.

Chang, Therapeutic applications of polymeric artificial cells. Nat Rev Drug Discov. Mar. 2005;4(3):221-35.

Chen et al., Polymeric growth factor delivery strategies for tissue engineering. Pharm Res. Aug. 2003;20(8):1103-12.

Chen et al., Rapid discovery of potent siRNA-containing lipid nanoparticles enabled by controlled microfluidic formulation. J Am Chem Soc. Apr. 25, 2012;134(16):6948-51. doi: 10.1021/ja301621z. Epub Apr. 10, 2012.

Chen et al., Tumor-targeted delivery of siRNA by non-viral vector: safe and effective cancer therapy. Expert Opin Drug Deliv. Dec. 2008;5(12):1301-11. doi: 10.1517/17425240802568505.

Chiang et al., Synthesis, characterization and properties of novel self-extinguishing organic-inorganic nanocomposites containing nitrogen, silicon and phosphorus via sol-gel method. Composite Science and Technology. 2008;68(14):2849-57.

Chiavarelli et al., Esteri de acidi carbossilici della N,N'-DI-(2-Idrossietil)-piperazina. Nota I. Annali di Chimica. Jan. 1, 1973;63:607-611.

Chu et al., Cytokeratin 7 and cytokeratin 20 expression in epithelial neoplasms: a survey of 435 cases. Mod Pathol. Sep. 2000;13(9):962-72.

Conley et al., Derivation, propagation and differentiation of human embryonic stem cells. Int J Biochem Cell Biol. Apr. 2004;36(4):555-67.

Conte et al., Regioselective ring opening of [(perfluoroalkyl)methyl] oxiranes with N-nucleophiles. J Fluorine Chem. 2005;126(9-10):1274-80.

Cotten et al., Receptor-mediated transport of DNA into eukaryotic cells. Methods Enzymol. 1993;217:618-44.

Creusat et al., Proton sponge trick for pH-sensitive disassembly of polyethylenimine-based siRNA delivery systems. Bioconjug Chem. May 19, 2010;21(5):994-1002.

Cristofaro et al., Role of Toll-like receptors in infection and immunity: clinical implications. Drugs. 2006;66(1):15-29.

Crooke, Evaluating the mechanism of action of antiproliferative antisense drugs. Antisense Nucleic Acid Drug Dev. Apr. 2000;10(2):123-6.

Crooke, Molecular mechanisms of action of antisense drugs. Biochim Biophys Acta. Dec. 10, 1999;1489(1):31-44. Review.

Crystal, Transfer of genes to humans: early lessons and obstacles to success. Science. Oct. 20, 1995;270(5235):404-10. Review.

Damen et al., Delivery of DNA and siRNA by novel gemini-like amphiphilic peptides. J Control Release. Jul. 1, 2010;145(1):33-9. doi: 10.1016/j.jconrel.2010.03.028. Epub Apr. 8, 2010.

Davis et al., Evidence of RNAi in humans from systemically administered siRNA via targeted nanoparticles. Nature. Apr. 15, 2010;464(7291):1067-70. Epub Mar. 21, 2010.

Davis, The first targeted delivery of siRNA in humans via a self-assembling, cyclodextrin polymer-based nanoparticle: from concept to clinic. Mol Pharm. May-Jun. 2009;6(3):659-68. doi: 10.1021/mp900015y.

Decher, Fuzzy Nanoassemblies: Toward Layered Polymeric Multicomposites. Science. 1997;277;1232-37.

Dern et al., Toxicity studies of pyrimethamine (daraprim). Am J Trop Med Hyg. Mar. 1955;4(2):217-20.

Deshmukh et al., Liposome and polylysine mediated gene therapy. New J Chem. 1997;21:113-124.

Diebold et al., Innate antiviral responses by means of TLR7-mediated recognition of single-stranded RNA. Science. Mar. 5, 2004;303(5663):1529-31. Epub Feb. 19, 2004.

Discher et al., Polymer vesicles. Science. Aug. 9, 2002;297(5583):967-73. Review.

Discher et al., Polymersomes: tough vesicles made from diblock copolymers. Science. May 14, 1999;284(5417):1143-6.

Dong et al., Lipopeptide nanoparticles for potent and selective siRNA delivery in rodents and nonhuman primates. Proc Natl Acad Sci U S A. Mar. 18, 2014;111(11):3955-60. doi: 10.1073/pnas.1322937111. Epub Feb. 10, 2014.

Dushnik-Levinson et al., Embryogenesis in vitro: study of differentiation of embryonic stem cells. Biol Neonate. 1995;67(2):77-83.

Eberle et al., Modifications in small interfering RNA that separate immunostimulation from RNA interference. J Immunol. Mar. 1, 2008;180(5):3229-37.

Elbashir et al., Duplexes of 21-nucleotide RNAs mediate RNA interference in cultured mammalian cells. Nature. May 24, 2001;411(6836):494-8.

Elbashir et al., RNA interference is mediated by 21- and 22-nucleotide RNAs. Genes Dev. 2001;15:188-200.

Ewaschuk et al., Metabolic acidosis: separation methods and biological relevance of organic acids and lactic acid enantiomers. Journal of Chromatography. Dec. 5, 2002;781(1-2):39-56.

Ewert et al., Cationic lipid-DNA complexes for gene therapy: understanding the relationship between complex structure and gene delivery pathways at the molecular level. Curr Med Chem. Jan. 2004;11(2):133-49.

Felgner et al., Lipofection: a highly efficient, lipid-mediated DNA-transfection procedure. Proc Natl Acad Sci U S A. Nov. 1987;84(21):7413-7.

Fenske et al., Liposomal nanomedicines. Expert Opin Drug Deliv. Jan. 2008;5(1):25-44.

Fenton et al., Bioinspired Alkenyl Amino Alcohol Ionizable Lipid Materials for Highly Potent In Vivo mRNA Delivery. Adv Mater. Apr. 20, 2016;28(15):2939-43. doi: 10.1002/adma.201505822. Epub Feb. 18, 2016. With supporting information.

Ferruti et al., Linear amino polymers: Synthesis, protonation and complex formation. Advances in Polymer Science. 1984;58:55-92.

(56) References Cited

OTHER PUBLICATIONS

Fire et al., Potent and specific genetic interference by double-stranded RNA in Caenorhabditis elegans. Nature. Feb. 19, 1998;391(6669):806-11.
Fisher et al., Photoinitiated Polymerization of Biomaterials. Annu Rev Mater Res. 2001;31:171-81.
Forsbach et al., Identification of RNA sequence motifs stimulating sequence-specific TLR8-dependent immune responses. J Immunol. Mar. 15, 2008;180(6):3729-38.
Fourneau et al., Two new series of local anesthetics derived from piperazine. Bulletin de la Societe Chimique de France. 1930;47:1003-16. French.
Frank-Kamenetsky et al., Therapeutic RNAi targeting PCSK9 acutely lowers plasma cholesterol in rodents and LDL cholesterol in non-human primates. Proc Natl Acad Sci U S A. Aug. 19, 2008;105(33):11915-20. doi: 10.1073/pnas.0805434105. Epub Aug. 11, 2008.
Friedmann, Human gene therapy—an immature genie, but certainly out of the bottle. Nat Med. Feb. 1996;2(2):144-7.
Furgeson et al., Modified linear polyethylenimine-cholesterol conjugates for DNA complexation. Bioconjug Chem. Jul.-Aug. 2003;14(4):840-7.
Furgeson et al., Novel water insoluble lipoparticulates for gene delivery. Pharm Res. Apr. 2002;19(4):382-90.
Gademann et al., The fourth helical secondary structure of beta-peptides: the (P)-28-helix of a beta-hexapeptide consisting of (2R,3S)-3-amino-2-hydroxy acid residues. Angew Chem Int Ed Engl. Apr. 4, 2003;42(13):1534-7.
Gardner, Stem cells and regenerative medicine: principles, prospects and problems. C R Biol. Jun.-Jul. 2007;330(6-7):465-73. Epub Feb. 15, 2007.
Geisbert et al., Postexposure protection of non-human primates against a lethal Ebola virus challenge with RNA interference: a proof-of-concept study. Lancet. May 29, 2010;375(9729):1896-905. doi:10.1016/S0140-6736(10)60357-1.
Geissmann et al., Development of monocytes, macrophages, and dendritic cells. Science. Feb. 5, 2010;327(5966):656-61. doi: 10.1126/science.1178331.
Geng et al., Hydrolytic degradation of poly(ethylene oxide)-block-polycaprolactone worm micelles. J Am Chem Soc. Sep. 21, 2005;127(37):12780-1.
Ghosh et al., Toll-like receptor (TLR) 2-9 agonists-induced cytokines and chemokines: I. Comparison with T cell receptor-induced responses. Cell Immunol. Sep. 2006;243(1):48-57. Epub Jan. 23, 2007.
Giuliani et al., Beyond natural antimicrobial peptides: multimeric peptides and other peptidomimetic approaches. Cell Mol Life Sci. Jul. 2011;68(13):2255-66. doi: 10.1007/s00018-011-0717-3. Epub May 20, 2011.
Godbey et al., Size matters: molecular weight affects the efficiency of poly(ethylenimine) as a gene delivery vehicle. J Biomed Mater Res. Jun. 5, 1999;45(3):268-75.
Gonzalez et al., New class of polymers for the delivery of macromolecular therapeutics. Bioconjug Chem. Nov.-Dec. 1999;10(6):1068-74.
Grayson et al., Biophysical and structural characterization of polyethylenimine-mediated siRNA delivery in vitro. Pharm Res. Aug. 2006;23(8):1868-76.
Griffiths et al., The Structure of Metallomicelles. Chem. Eur. J., 10: 2022-8. doi:10.1002/chem.200305670.
Grivennikov et al., Immunity, inflammation, and cancer. Cell. Mar. 19, 2010;140(6):883-99. doi: 10.1016/j.cell.2010.01.025.
Gross et al., Bioluminescence imaging of myeloperoxidase activity in vivo. Nat Med. Apr. 2009;15(4):455-61. Epub Mar. 22, 2009.
Grunlan et al., Synthesis of 1,9-bis[glycidyloxypropyl]penta(1'H, 1'H, 2'H, 2'H-perfluoroalkylmethylsiloxane)s and copolymerization with piperazine. Polymer. 2004;45:2517- 23.
Grzelinski et al., RNA interference-mediated gene silencing of pleiotrophin through polyethylenimine-complexed small interfering RNAs in vivo exerts antitumoral effects in glioblastoma xenografts. Hum Gene Ther. Jul. 2006;17(7):751-66.

Guan et al., Embryonic stem cell-derived neurogenesis. Retinoic acid induction and lineage selection of neuronal cells. Cell Tissue Res. Aug. 2001;305(2):171-6.
Guan et al., Surface photo-grafting of polyurethane with 2-hydroxyethyl acrylate for promotion of human endothelial cell adhesion and growth. J Biomater Sci Polym Ed. 2000;11(5):523-36.
Gunatillake et al., Recent developments in biodegradable synthetic polymers. Biotechnol Annu Rev. 2006;12:301-47.
Gupta et al., A review of in vitro-in vivo investigations on dendrimers: the novel nanoscopic drug carriers. Nanomedicine. Jun. 2006;2(2):66-73.
Haensler et al., Polyamidoamine cascade polymers mediate efficient transfection of cells in culture. Bioconjug Chem. Sep.-Oct. 1993;4(5):372-9.
Hammond et al., An RNA-directed nuclease mediates post-transcriptional gene silencing in Drosophila cells. Nature. 2000;404:293-96.
Harder et al., Molecular Conformation in Oligo(ethylene glycol)-Terminated Self-Assembled Monolayers on Gold and Silver Surfaces Determines Their Ability to Resist Protein Adsorpotion. J Phys Chem B. 1998;102:426-36.
Hasan et al., Identification of cytokeratin 1 as a binding protein and presentation receptor for kininogens on endothelial cells. Proc Natl Acad Sci U S A. Mar. 31, 1998;95(7):3615-20.
Heil et al., Species-specific recognition of single-stranded RNA via toll-like receptor 7 and 8. Science. Mar. 5, 2004;303(5663):1526-9. Epub Feb. 19, 2004.
Hemmi et al., Small anti-viral compounds activate immune cells via the TLR7 MyD88-dependent signaling pathway. Nat Immunol. Feb. 2002;3(2):196-200. Epub Jan. 22, 2002.
Heyes et al., Cationic lipid saturation influences intracellular delivery of encapsulated nucleic acids. J Control Release. Oct. 3, 2005;107(2):276-87.
Hill et al., Enantioselective Epoxidation of Allylic Alcohols: (2S,3S)-3-Propyloxiranemethanol. Org Syn. 1990;7:461.
Hill et al., In vitro cytotoxicity of poly(amidoamine)s: relevance to DNA delivery. Biochim Biophys Acta. Apr. 19, 1999;1427(2):161-74.
Hoekenga, The treatment of malaria with hydroxychloroquine. Am J Trop Med Hyg. Mar. 1955;4(2):221-3.
Hofland et al., Formation of stable cationic lipid/DNA complexes for gene transfer. Proc Natl Acad Sci USA. Jul. 9, 1996;93(14):7305-9.
Holmlin et al., Zwitterionic SAMs that Resist Nonspecific Adsorption of Protein from Aqueous Buffer. Langmuir. 2001;17:2841-50.
Hope et al., Cationic Lipids, Phosphatidylethanolamine and the Intracellular Delivery of Polymeric, Nucleic Acid-Based Drugs. Molecular Membrane Technology. 1998;15:1-14.
Hornung et al., Quantitative expression of toll-like receptor 1-10 mRNA in cellular subsets of human peripheral blood mononuclear cells and sensitivity to CpG oligodeoxynucleotides. J Immunol. May 1, 2002;168(9):4531-7.
Hornung et al., Sequence-specific potent induction of IFN-alpha by short interfering RNA in plasmacytoid dendritic cells through TLR7. Nat Med. Mar. 2005;11(3):263-70. Epub Feb. 20, 2005.
Howard, Delivery of RNA interference therapeutics using polycation-based nanoparticles. Adv Drug Deliv Rev. Jul. 25, 2009;61(9):710-20. Epub Apr. 5, 2009.
Hsu et al., Diethanolamine (DEA) degradation under gas-treating conditions. Industrial and Engineering Chemistry Product Research and Development. 1985;24(4):630-35.
Huang et al., Claudin-3 gene silencing with siRNA suppresses ovarian tumor growth and metastasis. Proc Natl Acad Sci U S A. Mar. 3, 2009;106(9):3426-30. doi: 10.1073/pnas.0813348106. Epub Feb. 10, 2009.
Hunt et al., Effect of biomaterial surface charge on the inflammatory response: evaluation of cellular infiltration and TNF alpha production. J Biomed Mater Res. May 1996;31(1):139-44.
Ikeda et al., Role of micafungin in the antifungal armamentarium. Curr Med Chem. 2007;14(11):1263-75.
Incani et al., Lipid and hydrophobic modification of cationic carriers on route to superior gene vectors. Soft Matter. 2010;6:2124-38.

(56) References Cited

OTHER PUBLICATIONS

Ingber et al., Mechanochemical switching between growth and differentiation during fibroblast growth factor-stimulated angiogenesis in vitro: role of extracellular matrix. J Cell Biol. Jul. 1989;109(1):317-30.
Irwin et al., Modulus-dependent macrophage adhesion and behavior. J Biomater Sci Polym Ed. 2008;19(10):1363-82.
Ito, Surface micropatterning to regulate cell functions. Biomaterials. Dec. 1999;20(23-24):2333-42.
Itskovitz-Eldor et al., Differentiation of human embryonic stem cells into embryoid bodies compromising the three embryonic germ layers. Mol Med. Feb. 2000;6(2):88-95.
Iwasaki et al., Toll-like receptor control of the adaptive immune responses. Nat Immunol. Oct. 2004;5(10):987-95.
Jarrossay et al., Specialization and complementarity in microbial molecule recognition by human myeloid and plasmacytoid dendritic cells. Eur J Immunol. Nov. 2001;31(11):3388-93.
Jayaraman et al., Maximizing the potency of siRNA lipid nanoparticles for hepatic gene silencing in vivo. Angew Chem Int Ed Engl. Aug. 20, 2012;51(34):8529-33. doi: 10.1002/anie.201203263. Epub Jul. 10, 2012.
Jia et al., Demonstration of two novel methods for predicting functional siRNA efficiency. BMC Bioinformatics. 2006;7:271.
Jiang et al., Electrochemically controlled release of lipid/DNA complexes: a new tool for synthetic gene delivery system. Electrochem Commun. 2004;6:576-82.
Jiang et al., Hyaluronic acid-polyethyleneimine conjugate for target specific intracellular delivery of siRNA. Biopolymers. Jul. 2008;89(7):635-42.
Jiang et al., Ultralow-fouling, functionalizable, and hydrolyzable zwitterionic materials and their derivatives for biological applications. Adv Mater. Mar. 5, 2010;22(9):920-32.
Johansson et al., Evidence for involvement of activin A and bone morphogenetic protein 4 in mammalian mesoderm and hematopoietic development. Mol Cell Biol. Jan. 1995;15(1):141-51.
John et al. Effective RNAi-mediated gene silencing without interruption of the endogenous microRNA pathway. Nature. Oct. 11, 2007;449(7163):745-7. Epub Sep. 26, 2007.
Jolck et al., Solid-phase synthesis of PEGylated lipopeptides using click chemistry. Bioconjug Chem. May 19, 2010;21(5):807-10.
Jon et al., Degradable poly(amino alcohol esters) as potential DNA vectors with low cytotoxicity. Biomacromolecules. Nov.-Dec. 2003;4(6):1759-62.
Judge et al., Design of noninflammatory synthetic siRNA mediating potent gene silencing in vivo. Mol Ther. Mar. 2006;13(3):494-505. Epub Dec. 15, 2005.
Juliano et al., Biological barriers to therapy with antisense and siRNA oligonucleotides. Mol Pharm. May-Jun. 2009;6(3):686-95. doi: 10.1021/mp900093r.
Junior et al., Preparation and antitubercular activity of lipophilic diamines and amino alcohols. Mem Inst Oswaldo Cruz. Aug. 2009;104(5):703-5.
Kabanov et al., DNA complexes with polycations for the delivery of genetic material into cells. Bioconjug Chem. Jan.-Feb. 1995;6(1):7-20.
Kamath et al., Surface chemistry influences implant-mediated host tissue responses. J Biomed Mater Res A. Sep. 2008;86(3):617-26.
Kanetani et al., Synthesis, and physicochemical and antimicrobial properties of 3-(3-alkyl-1-piperazinyl)-1-propanesulfonic acids and some related compounds. Nippon Kagaku Kaishi. 1983(12):1783-91.
Katsuki et al., Chapter 1. Asymmetric Epoxidation of Allylic Alcohols: The Katsuki-Sharpless Epoxidation Reaction. Org React 1996;48:1-299.
Katsuki et al., The First Practical Method for Asymmetric Epoxidation. J Am Chem Soc. 1980:102;5974-76.
Kaufman et al., Hematopoietic colony-forming cells derived from human embryonic stem cells. Proc Natl Acad Sci U S A. Sep. 11, 2001;98(19):10716-21. Epub Sep. 4, 2001.
Kaur et al., A delineation of diketopiperazine self-assembly processes: understanding the molecular events involved in Nepsilon-(fumaroyl)diketopiperazine of L-Lys (FDKP) interactions. Mol Pharm. Mar.-Apr. 2008;5(2):294-315.
Kim et al., Comparative evaluation of target-specific GFP gene silencing efficiencies for antisense ODN, synthetic siRNA, and siRNA plasmid complexed with PEI-PEG-FOL conjugate. Bioconjug Chem. Jan.-Feb. 2006;17(1):241-4.
Kim et al., Efficient siRNA delivery using water soluble lipopolymer for anti-angiogenic gene therapy. J Control Release. Apr. 23, 2007;118(3):357-63. Epub Jan. 9, 2007.
Kim et al., Local and systemic delivery of VEGF siRNA using polyelectrolyte complex micelles for effective treatment of cancer. J Control Release. Jul. 14, 2008;129(2):107-16. Epub Mar. 14, 2008.
Kim et al., Synthesis of biodegradable cross-linked poly(beta-amino ester) for gene delivery and its modification, inducing enhanced transfection efficiency and stepwise degradation. Bioconjug Chem. Sep.-Oct. 2005;16(5):1140-8.
Kleinman et al., Sequence- and target-independent angiogenesis suppression by siRNA via TLR3. Nature. Apr. 3, 2008;452(7187):591-7. Epub Mar. 26, 2008.
Klibanov et al., Amphipathic polyethyleneglycols effectively prolong the circulation time of liposomes. FEBS Lett. Jul. 30, 1990;268(1):235-7.
Koning et al., The synthesis of novel oxygen-containing ligands derived from amine precursors. Tetrahedron Letters, Feb. 1997;38(7):1261-4.
Krieg et al., CpG motifs in bacterial DNA trigger direct B-cell activation. Nature. Apr. 6, 1995;374(6522):546-9.
Krieg et al., Toll-like receptors 7, 8, and 9: linking innate immunity to autoimmunity. Immunol Rev. Dec. 2007;220:251-69.
Krieg, The toll of too much TLR7. Immunity. Nov. 2007;27(5):695-7.
Kukowska-Latallo et al., Efficient transfer of genetic material into mammalian cells using Starburst polyamidoamine dendrimers. Proc Natl Acad Sci USA. May 14, 1996;93(10):4897-902.
Kusumoto et al., Gene transfer effects on various cationic amphiphiles in CHO cells. Cytotechnology. Jun. 2006;51(2):57-66. doi: 10.1007/s10616-006-9014-7. Epub Sep. 7, 2006.
Kwon et al., Application of an HIV gp41-derived peptide for enhanced intracellular trafficking of synthetic gene and siRNA delivery vehicles. Bioconjug Chem. Apr. 2008;19(4):920-7. Epub Apr. 1, 2008.
Lan et al., Stabilized immune modulatory RNA compounds as agonists of Toll-like receptors 7 and 8. Proc Natl Acad Sci U S A. Aug. 21, 2007;104(34):13750-5. Epub Aug. 14, 2007.
Langer, Perspectives and challenges in tissue engineering and regenerative medicine. Adv Mater. Sep. 4, 2009;21(32-33):3235-6.
Lee et al., Enantiomeric Separatino of amino acids using N-alkyl-L-proline coated stationary phase. Bull Korean Chem Soc. 1992;13(3):285-289.
Lee et al., Rapid pharmacokinetic and biodistribution studies using cholorotoxin-conjugated iron oxide nanoparticles: a novel non-radioactive method. PLoS One. Mar. 4, 2010;5(3):e9536. doi: 10.1371/journal.pone.0009536.
Lee et al., Stability and cellular uptake of polymerized siRNA (poly-siRNA)/polyethylenimine (PEI) complexes for efficient gene silencing. J Control Release. Feb. 15, 2010;141(3):339-46. Epub Oct. 14, 2009.
Leuschner et al., Therapeutic siRNA silencing in inflammatory monocytes in mice. Nat Biotechnol. Oct. 9, 2011;29(11):1005-10. doi: 10.1038/nbt.1989.
Levenberg et al., Differentiation of human embryonic stem cells on three-dimensional polymer scaffolds. Proc Natl Acad Sci U S A. Oct. 28, 2003;100(22):12741-6. Epub Oct. 15, 2003.
Li et al., [Analysis of HLA matching probability in Guangzhou Cord Blood Bank]. Zhongguo Shi Yan Xue Ye Xue Za Zhi. Aug. 2003;11(4):424-8. Abstract Only.
Li et al., Defining the optimal parameters for hairpin-based knockdown constructs. RNA. 2007;13:1765-74.

(56) References Cited

OTHER PUBLICATIONS

Li et al., Plasticity of the urothelial phenotype: effects of gastrointestinal mesenchyme/stroma and implications for urinary tract reconstruction. Differentiation. Oct. 2000;66(2-3):126-35.
Li et al., Reverse Atom Transfer Radical Polymerization in Miniemulsion. Macromolecules. 2003;36(16):6028-6035.
Lim, et al., A self-destroying polycationic polymer: biodegradable poly(4-hydroxy-1-proline ester. J. Am. Chem. Soc. 1999;121:5633-5639.
Love et al., Lipid-like materials for low-dose, in vivo gene silencing. Proc Natl Acad Sci U S A. Feb. 2, 2010;107(5):1864-9. Epub Jan. 11, 2010.
Lukyanov et al., Micelles from lipid derivatives of water-soluble polymers as delivery systems for poorly soluble drugs. Adv Drug Deliv Rev. May 7, 2004;56(9):1273-89.
Luo et al., Synthetic DNA delivery systems. Nat Biotechnol. Jan. 2000;18(1):33-7. Review.
Lv et al., Toxicity of cationic lipids and cationic polymers in gene delivery. J Control Release. Aug. 10, 2006;114(1):100-9.
Lyle et al., Cytokeratin 15 (K15) as an Epithelial Stem Cell Marker: Implications for Aging and Carcinogenesis. J Invest Derma. 1999;112(4):623. Abstract #606.
Lynn et al., Accelerated discovery of synthetic transfection vectors: parallel synthesis and screening of a degradable polymer library. J Am Chem Soc. Aug. 22, 2001;123(33):8155-6.
Lynn et al., Degradable Poly(β-amino esters): Synthesis, Characterization, and Self-Assembly with Plasmid DNA. J. Am. Chem. Soc. 2000;122 (44): 10761-8.
Lynn et al., pH-Responsive Polymer Microspheres: Rapid Release of Encapsulated Material within the Range of Intracellular pH. Angew Chem Int Ed Engl. May 4, 2001;40(9):1707-10.
Ma et al., Cationic lipids enhance siRNA-mediated interferon response in mice. Biochem Biophys Res Commun. May 13, 2005;330(3):755-9.
Ma et al., Development of Cationic Polymer Coatings to Regulate Foreign Body Responses. Adv Mater. 2011;23:H189-94.
Margus et al., Cell-penetrating peptides as versatile vehicles for oligonucleotide delivery. Mol Ther. Mar. 2012;20(3):525-33. doi: 10.1038/mt.2011.284. Epub Jan. 10, 2012.
Marques et al., Activation of the mammalian immune system by siRNAs. Nat Biotechnol. Nov. 2005;23(11):1399-405.
Marshak-Rothstein, Toll-like receptors in systemic autoimmune disease. Nat Rev Immunol. Nov. 2006;6(11):823-35.
Martell et al., The Preparation and the Properties of Some N,N'-Disubstituted-ethylenediaminedipropionic Acids. J Am Chem Soc. 1950;72:5357-61.
Mathias et al., Synthesis of New Hydroxylated Monomers Based on Methacrylate, Dimethacrylate, and Tetramethacrylate Michael Adducts and Photopolymerization Kinetics of Bulk Cross-Linkers. Macromolecules. 2004;37(9):3231-38.
Mathiowitz et al., Novel microcapsules for delivery systems. Reactive Polymers. 1987;6:275-283.
Mathiowitz et al., Polyanhydride microspheres as drug carriers I. Hot-melt microencapsulation. J Control Release. 1987;5:13-22.
Mathiowitz et al., Polyanhydride microspheres as drug carriers II. microencapsulation by solvent removal. J. Appl. Polymer Sci. 1988;35:755-774.
Mattey et al., Demonstration of cytokeratin in endothelial cells of the synovial microvasculature in situ and in vitro. Br J Rheumatol. Aug. 1993;32(8):676-82.
Mendelsohn et al., Rational design of cytophilic and cytophobic polyelectrolyte multilayer thin films. Biomacromolecules. Jan.-Feb. 2003;4(1):96-106.
Miller, Cationic Liposomes for Gene Therapy. Angew. Chem. Int. Ed. 1998;37:1769-1785.
Mintzer et al., Nonviral vectors for gene delivery. Chem Rev. Feb. 2009;109(2):259-302.
Moll et al., The human keratins: biology and pathology. Histochem Cell Biol. Jun. 2008; 129(6):705-33. Epub May 7, 2008.

Moll, [Cytokeratins as markers of differentiation. Expression profiles in epithelia and epithelial tumors] Veroff Pathol. 1993;142:1-197. German.
Morris et al., Lentiviral-mediated delivery of siRNAs for antiviral therapy. Gene Ther. 2006;13:553-58.
Morrissey et al., Potent and persistent in vivo anti-HBV activity of chemically modified siRNAs. Nat Biotechnol. Aug. 2005;23(8):1002-7. Epub Jul. 24, 2005.
Moure et al. Chemical modulation of peptoids: synthesis and conformational studies on partially constrained derivatives. Chemistry. Jul. 4, 2011;17(28):7927-39. doi: 10.1002/chem.201100216. Epub May 24, 2011.
Mulligan, The basic science of gene therapy. Science. May 14, 1993;260(5110):926-32. Review.
Nahrendorf et al., Dual channel optical tomographic imaging of leukocyte recruitment and protease activity in the healing myocardial infarct. Circ Res. Apr. 27, 2007;100(8):1218-25. Epub Mar. 22, 2007.
Naito et al., siVirus: web-based antiviral siRNA design software for highly divergent viral sequences. Nucleic Acids Res. 2006;34:W448-450.
Narang et al., Cationic lipids with increased DNA binding affinity for nonviral gene transfer in dividing and nondividing cells. Bioconjug Chem. Jan.-Feb. 2005;16(1):156-68.
Navarro et al., Phospholipid-polyethylenimine conjugate-based micelle-like nanoparticles for siRNA delivery. Drug Deliv and Trans Res. 2011; 25-33.
Neamnark et al., Aliphatic lipid substitution on 2 kDa polyethylenimine improves plasmid delivery and transgene expression. Mol Pharm. Nov.-Dec. 2009;6(6):1798-815.
Neises et al., Simple Method for the Esterification of Carboxylic Acids. Angew Chem Int Ed. Jul. 1978;17(7):522-24.
Nguyen et al., A novel high-throughput cell-based method for integrated quantification of type I interferons and in vitro screening of immunostimulatory RNA drug delivery. Biotechnol Bioeng. Jul. 1, 2009;103(4):664-75.
Nguyen et al., Drug delivery-mediated control of RNA immunostimulation. Mol Ther. Sep. 2009;17(9):1555-62. Epub Jul. 7, 2009.
Niyomtham et al., Synergistic effect of cationic lipids with different polarheads, central core structures and hydrophobic tails on gene transfection efficiency. Biol Pharm Bull. 2014;37(9):1534-42.
Nolan et al., Quantification of mRNA using real-time RT-PCR. Nat Protoc. 2006;1(3):1559-82.
Novak et al., Biomimetic strategies based on viruses and bacteria for the development of immune evasive biomaterials. Biomaterials. Apr. 2009;30(11):1989-2005. Epub Jan. 29, 2009.
Novina et al., The RNAi revolution. Nature. 2004;430:161-64.
Novobrantseva et al., Systemic RNAi-mediated Gene Silencing in Nonhuman Primate and Rodent Myeloid Cells. Mol Ther Nucleic Acids. Jan. 24, 2012;1:e4. doi: 10.1038/mtna.2011.3.
Odorico et al., Multilineage differentiation from human embryonic stem cell lines. Stem Cells. 2001;19(3):193-204.
Okahata et al., Phase Transition of the Bilayer Membrane of Synthetic Dialkyl Amphiphiles as Studied by Differential Scanning Calorimetry. Berichte Der Bunsen-Gesellschaft Fur Physikalische Chemie. Jan. 1, 1981;85:789-798.
Onuki et al., A review of the biocompatibility of implantable devices: current challenges to overcome foreign body response. J Diabetes Sci Technol. Nov. 2008;2(6):1003-15.
Orive et al., Cell encapsulation: promise and progress. Nat Med. Jan. 2003;9(1):104-7.
Ostuni et al., A Survey of Structure-Property Relationships of Surfaces that Resist the Adsorption of Protein . Langmuir. 2001;17:5605-20.
Pajewski et al., Pore formation in and enlargement of phospholipid liposomes by synthetic models of ceramides and sphingomyelin. Bioorg Med Chem. Jan. 3, 2005;13(1):29-37. doi: 10.1016/j.bmc.2004.10.001.
Pajewski et al., The effect of midpolar regime mimics on anion transport mediated by amphiphilic heptapeptides. New J. Chem., 2007,31, 1960-1972.
Parrish et al., Five- and six-membered ring opening of pyroglutamic diketopiperazine. J Org Chem. Mar. 22, 2002;67(6):1820-6.

(56) References Cited

OTHER PUBLICATIONS

Pashine et al., Targeting the innate immune response with improved vaccine adjuvants. Nat Med. Apr. 2005;11(4 Suppl):S63-8.
Paul et al., Topographical control of human macrophages by a regularly microstructured polyvinylidene fluoride surface. Biomaterials. Oct. 2008;29(30):4056-64. Epub Jul. 29, 2008.
Peer et al., Nanocarriers as an emerging platform for cancer therapy. Nat Nanotechnol. Dec. 2007;2(12):751-60.
Pemha et al., Synthesis of (Z)-(2'R)-1-O-(2'-methoxynonadec-10'-enyl)-sn-glycerol, a new analog of bioactive ether lipids. Tetrahedron. 2012;68(14):2973-2983.
Peppas et al., Hydrogels in Biology and Medicine: From Molecular Principles to Bionanotechnology. Mater. 2006;18:1345-60.
Pera et al., Human embryonic stem cells. J Cell Sci. Jan. 2000;113 ( Pt 1):5-10.
Philipp et al., Hydrophobically modified oligoethylenimines as highly efficient transfection agents for siRNA delivery. Bioconjug Chem. Nov. 2009;20(11):2055-61.
Phillips et al., Enhanced antibody response to liposome-associated protein antigens: preferential stimulation of IgG2a/b production. Vaccine. 1992;10(3):151-8.
PLANAS. Biotechnology and Bioengineering, 1999, 66, 211-218 (Year: 1999).
Pollard et al., Ether amino alcohols. II. J Org Chem. 1952;17:1-3.
Prata et al., Lipophilic peptides for gene delivery. Bioconjug Chem. Feb. 2008;19(2):418-20.
Putnam et al., Poly(4-hydroxy-1-proline ester): Low-Temperature Polycondensation and Plasmid DNA Complexation. Macromolecules 1999;32:3658-62.
Putnam, Polymers for gene delivery across length scales. Nat Mater. Jun. 2006;5(6):439-51.
Ramakrishna et al., Synthesis of RGD peptidomimetic analogues of 2,5-diketopiperazine. Indian Journal of Chemistry Dec. 1999;38B:1331-7.
Rao et al., Spermic Acid Diester Derivatives as Pharmacological Carries for Long-Term Controlled Nitric Oxidase Delivery. Chemical and Pharmaceutical Bulletin, Pharmaceutical Society of Japan, 1998;46(11):1846-1847. DOI https://doi.org/10.1248/cpb.46.1846.
Ratner et al., Biomaterials: where we have been and where we are going. Annu Rev Biomed Eng. 2004;6:41-75.
Refai et al., Effect of titanium surface topography on macrophage activation and secretion of proinflammatory cytokines and chemokines. J Biomed Mater Res A. Aug. 1, 2004;70(2):194-205.
Reichmutch et al., mRNA vaccine delivery using lipid nanoparticles. Ther Deliv. 2016;7(5):319-34. doi: 10.4155/tde-2016-0006.
Reynolds et al., Rational siRNA design for RNA interference. Nat Biotechnol. 2004;22(3):326-30.
Robbins et al., 2'-O-methyl-modified RNAs act as TLR7 antagonists. Mol Ther. Sep. 2007;15(9):1663-9. Epub Jun. 19, 2007.
Robbins et al., siRNA and innate immunity. Oligonucleotides. Jun. 2009;19(2):89-102.
Rogers et al., Synthetic Experiments in the Ferrichrome Series. Biochemistry. Dec. 1964;3:1850-5.
Ryng et al., Synthesis and Structure Elucidation of 5-Aminomethinimino-3-methyl-4-isoxazolecarboxylic Acid Phenylamides and Their Immunological Activity. Archiv der Pharmazie. Jan. 1, 1997;330(11):319-26.
Saab-Ismail et al., Synthesis and in vivo evaluation of new contrast agents for cardiac MRI. J Med Chem. Jul. 29, 1999;42(15):2852-61.
Sahay et al., Endocytosis of nanomedicines. J Control Release. Aug. 3, 2010;145(3):182-95. Epub Mar. 10, 2010.
Sakiyama-Elbert et al., Functional Biomaterials: Design of Novel Biomaterials. Ann Rev Mater Res. 2001;31:183-201.
Saltzman, Chapter 19. Cell Interactions with Polymers. In: Principles of Tissue Engineering, 2d ed., 2000:221-35.
Sanford, The biolistic process. Trends Biotechnol. 1988;6:299-302.
Sato et al., Resolution of liver cirrhosis using vitamin A-coupled liposomes to deliver siRNA against a collagen-specific chaperone. Nat Biotechnol. Apr. 2008;26(4):431-42. doi: 10.1038/nbt1396. Epub Mar. 30, 2008.
Sawaf et al., [Cytokeratins, markers of epithelial cell differentiation: expression in normal epithelia.] Pathol Biol (Paris). 1992;40:655-65. French.
Schaus et al., Highly Selective Hydrolytic Kinetic Resolution of Terminal Epoxides Catalyzed by Chiral (salen)CoIII Complexes. Practical Synthesis of Enantioenriched Terminal Epoxides and 1,2-Biols. J Am Chem Soc. 2002;124(7):1307-15.
Scheel et al., Therapeutic anti-tumor immunity triggered by injections of immunostimulating single-stranded RNA. Eur J Immunol. Oct. 2006;36(10):2807-16.
Schena et al., Quantitative monitoring of gene expression patterns with a complementary DNA microarray. Science. Oct. 20, 1995;270(5235):467-70.
Schuldiner et al., Effects of eight growth factors on the differentiation of cells derived from human embryonic stem cells. Proc Natl Acad Sci USA. Oct. 10, 2000;97(21):11307-12.
Schutte et al., Cytokine profiling using monocytes/macrophages cultured on common biomaterials with a range of surface chemistries. J Biomed Mater Res A. Jan. 2009;88(1):128-39.
Schweizer et al., Synthetic Studies towards the Total Synthesis of Providencin. Synthesis. 2007;24:3807-14.
Schön et al., TLR7 and TLR8 as targets in cancer therapy. Oncogene. Jan. 7, 2008;27(2):190-9.
Semple et al., Rational design of cationic lipids for siRNA delivery. Nat Biotechnol. Feb. 2010;28(2):172-6. doi: 10.1038/nbt.1602. Epub Jan. 17, 2010.
Sen, Surfactin: biosynthesis, genetics and potential applications. Adv Exp Med Biol. 2010;672:316-23.
Shchori, Poly(secondary Amine)s from Diacrylates and Diamines. J Polym Sci Polymer. Jun. 1983;21(6):413-15.
Shemper et al., Synthetic clay nanocomposite-based coatings prepared by UV-Cure photopolymerization. J Appl Polymer Sci. 2004;93:1252-63.
Shen et al., Synthesis of Novel Amphiphilic Poly (ester-amine) Dendrimers and Their Recognition of Hg2+ at the Air/Water Interface. Chin. J. Chem. Oct. 2003;21(8):1011-14.
Siegwart et al., Combinatorial synthesis of chemically diverse core-shell nanoparticles for intracellular delivery. Proc Natl Acad Sci U S A. Aug. 9, 2011;108(32):12996-3001. ; doi: 10.1073/pnas.1106379108. Epub Jul. 22, 2011.
Sioud, Induction of inflammatory cytokines and interferon responses by double-stranded and single-stranded siRNAs is sequence-dependent and requires endosomal localization. J Mol Biol. May 20, 2005;348(5):1079-90. Epub Mar. 22, 2005.
Sioud, Innate sensing of self and non-self RNAs by Toll-like receptors. Trends Mol Med. Apr. 2006;12(4):167-76. Epub Mar. 10, 2006.
Sioud, Single-stranded small interfering RNA are more immunostimulatory than their double-stranded counterparts: a central role for 2'-hydroxyl uridines in immune responses. Eur J Immunol. May 2006;36(5):1222-30.
Spradling et al., Stem cells find their niche. Nature. Nov. 1, 2001;414(6859):98-104.
Staubli et al., Hydrolytically degradable amino acid containing polymers. J Am Chem Soc. 1990;45:4419-24.
Steinman et al., Taking dendritic cells into medicine. Nature. Sep. 27, 2007;449(7161):419-26.
STN database Registry No. 790184-08-06. Entered STN-CAS database on Feb. 13, 2020.
STN International HCAPLUS Database. 2001. Accession No. 2001:247547. Van Ness et al., Compositions and methods for reducing oligonucleotide hybridization and priming specificity.
STN International HCAPLUS Database. 2003. Accession No. 2003:901944. Martin et al., Application of Solution-Phase Synthesis to Preparation of Trisubstituted 1,2,4-Triazoles.
STN-CAS database Registry No. 1016794-08-3. Entered STN-CAS database on Apr. 23, 2008.
STN-CAS database Registry No. 1030297-07-4. Entered STN-CAS database on Jun. 24, 2008.
STN-CAS database Registry No. 1030297-42-7. Entered STN-CAS database on Jun. 24, 2008.
STN-CAS database Registry No. 1030297-62-1. Entered STN-CAS database on Jun. 24, 2008. With chemical structure.

(56) References Cited

OTHER PUBLICATIONS

STN-CAS database Registry No. 1043632-07-0. Entered STN-CAS database on Aug. 26, 2008.
STN-CAS database Registry No. 1044533-56-3. Entered STN-CAS database on Aug. 28, 2008.
STN-CAS database Registry No. 104538-56-9. Entered STN-CAS database on Oct. 4, 1986.
STN-CAS database Registry No. 105317-96-2. Entered STN-CAS database on Nov. 22, 1986.
STN-CAS database Registry No. 1056016-23-9. Entered STN-CAS database on Oct. 1, 2008.
STN-CAS database Registry No. 1067642-37-8. Entered STN-CAS database on Oct. 29, 2008.
STN-CAS database Registry No. 1071084-05-3. Entered STN-CAS database on Nov. 6, 2008.
STN-CAS database Registry No. 116071-63-7. Entered STN-CAS database on Aug. 27, 1988.
STN-CAS database Registry No. 136581-83-4. Entered STN-CAS database on Oct. 4, 1991.
STN-CAS database Registry No. 295781-15-6. Entered STN-CAS database on Oct. 19, 2000.
STN-CAS database Registry No. 302899-57-6. Entered STN-CAS database on Nov. 15, 2000.
STN-CAS database Registry No. 42381-51-1. Entered STN-CAS database on Nov. 16, 1984.
STN-CAS database Registry No. 488783-17-1. Entered STN-CAS database on Feb. 12, 2003.
STN-CAS database Registry No. 490035-26-2. Entered STN-CAS database on Feb. 14, 2003.
STN-CAS database Registry No. 51750-80-2. Entered STN-CAS database on Nov. 16, 1984.
STN-CAS database Registry No. 56619-89-7. Entered STN-CAS database on Nov. 16, 1984.
STN-CAS database Registry No. 60068-43-1. Entered STN-CAS database on Nov. 16, 1984.
STN-CAS database Registry No. 60068-44-2. Entered STN-CAS database on Nov. 16, 1984.
STN-CAS database Registry No. 63888-68-6. Entered STN-CAS database on Nov. 16, 1984.
STN-CAS database Registry No. 63888-69-7. Entered STN-CAS database on Nov. 16, 1984.
STN-CAS database Registry No. 63888-70-0. Entered STN-CAS database on Nov. 16, 1984.
STN-CAS database Registry No. 63888-73-3. Entered STN-CAS database on Nov. 16, 1984.
STN-CAS database Registry No. 698698-42-9. Entered STN-CAS database on Jun. 24, 2004.
STN-CAS database Registry No. 757226-26-9. Entered STN-CAS database on Oct. 6, 2004.
STN-CAS database Registry No. 85438-36-4. Entered STN-CAS database on Nov. 16, 1984.
STN-CAS database Registry No. 90018-95-4. Entered STN-CAS database on Nov. 16, 1984.
STN-CAS database Registry No. 909783-96-6. Entered STN-CAS database on Oct. 6, 2006.
STN-CAS database Registry No. 909784-08-3. Entered STN-CAS database on Oct. 6, 2006.
STN-CAS database Registry No. 909784-14-1. Entered STN-CAS database on Oct. 6, 2006.
STN-CAS database Registry No. 94159-80-5. Entered STN-CAS database on Sep. 8, 1985.
Stocum, Stem cells in regenerative biology and medicine. Wound Repair Regen. Nov.-Dec. 2001;9(6):429-42.
Streuli, Extracellular matrix remodeling and cellular differentiation. Curr Opin Cell Biol. 1999;11:634-40.
Suh et al., Ionization of Poly(ethylenimine) and Poly(allylamine) at Various PHS. Bioorg Chem. 1994;22:318-27.
Swali et al., Solid-Phase Dendrimer Synthesis and the Generation of Super-High-Loading Resin Beads for Combinatorial Chemistry. J Org Chem Am Chem Soc. 1997;62:4902-03.

Szoka et al., Comparative properties and methods of preparation of lipid vesicles (liposomes). Annu Rev Biophys Bioeng. 1980;9:467-508.
Tabara et al., The rde-1 Gene, RNA Interference, and Transposon Silencing in C. elegans. Cell. 1999;99:123-32.
Tan et al., Engineering Nanocarriers for siRNA Delivery. Small. Apr. 4, 2011;7(7):841-56. doi: 10.1002/smll.201001389. Epub Feb. 25, 2011.
Tang et al., In vitro gene delivery by degraded polyamidoamine dendrimers. Bioconjug Chem. Nov.-Dec. 1996;7(6):703-14.
Tarcha et al., Synthesis and characterization of chemically condensed oligoethylenimine containing beta-aminopropionamide linkages for siRNA delivery. Biomaterials. Sep. 2007;28(25):3731-40. Epub May 3, 2007.
Thiel et al., Therapeutic applications of DNA and RNA aptamers. Oligonucleotides. Sep. 2009;19(3):209-22. doi: 10.1089/oli.2009.0199.
Thompson et al., Antiamebic action of 5-chloro-7-diethylaminomethyl-8-quinolinol and of other substituted 8-quinolinols in vitro and in experimental animals. Am J Trop Med Hyg. Mar. 1955;4(2):224-48.
Thomson et al., Embryonic stem cell lines derived from human blastocysts. Science. Nov. 6, 1998;282(5391):1145-7.
Thorgeisson. Acta Dermatovener (Stockholm), 1978, 58, 332-336 (Year: 1978).
Toom et al., Synthesis of amphiphilic amino alcohols. Synthetic Communication. 2008;38(23):4295-4313.
Tranchant et al., Physicochemical optimisation of plasmid delivery by cationic lipids. J Gene Med. Feb. 2004;6 Suppl 1:S24-35.
Tsvetkov et al., [Neoglycoconjugates based on dendrimeric poly(aminoamides)]. Bioorg Khim. Nov.-Dec. 2002;28(6):518-34. Russian. Published in English in Russian Journal of Bioorganic Chemistry, 2002:28(6):470-86.
Unkeless et al., Structure and function of human and murine receptors for IgG. Annu Rev Immunol. 1988;6:251-81.
Urban-Klein et al., RNAi-mediated gene-targeting through systemic application of polyethylenimine (PEI)-complexed siRNA in vivo. Gene Ther. Mar. 2005;12(5):461-6.
Valente et al., External Coordination of Europium(III) Prior to Its Encapsulation within a Cyclen-Based Pendant Donor Macrocycle. Inorg. Chem., 1998;37(12):2846-7. DOI: 10.1021/ic980012.
Van Balen et al., Liposome/water lipophilicity: methods, information content, and pharmaceutical applications. Med Res Rev. May 2004;24(3):299-324.
Van De Wetering et al., Structure-activity relationships of water-soluble cationic methacrylate/methacrylamide polymers for nonviral gene delivery. Bioconjug Chem. Jul.-Aug. 1999;10(4):589-97.
Van Dijkhuizen-Radersma et al., Biocompatibility and degradation of poly(ether-ester) microspheres: in vitro and in vivo evaluation. Biomaterials. Dec. 2002;23(24):4719-29.
Vandenbroucke et al., Prolonged gene silencing in hepatoma cells and primary hepatocytes after small interfering RNA delivery with biodegradable poly(beta-amino esters). J Gene Med. Jul. 2008;10(7):783-94.
Vita et al., Synthesis of N6, N6-bis(2-chloroethyl)-DL-Lysine. J. Med. Chem. Jan. 1, 1964;7:468-471.
Von Harpe et al., Characterization of commercially available and synthesized polyethylenimines for gene delivery. J Control Release. Nov. 3, 2000;69(2):309-22.
Walde et al., Preparation of Vesicles (Liposomes). In: Encyclopedia of Nanoscience and Nanotechnology. Nalwa, ed. American Scientific Publishers: Los Angeles. 2004;9:43-79.
Wang et al., The functions of microRNAs in plants. Front Biosci. 2007;12:3975-82.
Ward, A Review of the Foreign-body Response to Subcutaneously-implanted Devices: The Role of Macrophages and Cytokines in Biofouling and Fibrosis. J Diabetes Sci Technol. 2008;2:768-77.
Webb et al., Pyromellitamide aggregates and their response to anion stimuli. J Am Chem Soc. Jun. 6, 2007;129(22):7155-62. Epub May 11, 2007.
Weinstein et al., RNAi nanomedicines: challenges and opportunities within the immune system. Nanotechnology. Jun. 11, 2010;21(23):232001. doi: 10.1088/0957-4484/21/23/232001. Epub May 13, 2010.

(56) References Cited

OTHER PUBLICATIONS

Werth et al., A low molecular weight fraction of polyethylenimine (PEI) displays increased transfection efficiency of DNA and siRNA in fresh or lyophilized complexes. J Control Release. May 15, 2006;112(2):257-70. Epub Mar. 6, 2006.
Whitbread et al., Diastereomeric ?-1,4,7,10-Tetrakis((R)-2-hydroxy-2-phenylethyl)-1,4,7,10-tetraazacyclododecane and Its Alkali Metal Complex Ions. A Potentiometric Titration, Nuclear Magnetic Resonance, and Molecular Orbital Study J. Am. Chem. Soc. 1998;120:2862?9.
White et al., Poly(hydroxyaminoethers): A New Family of Epoxy-Based Thermoplastics. Adv Mater. 2000;12:1791-1800.
White et al., Step-growth polymerization of 10,11-epoxyundecanoic acid. Synthesis and properties of a new hydroxy-functionalized thermopastic polyester. Adv Mater. 2007;48:3990-98.
Whitehead et al., In vitro-in vivo translation of lipid nanoparticles for hepatocellular siRNA delivery. ACS Nano. Aug. 28, 2012;6(8):6922-9. doi:10.1021/nn301922x. Epub Jul. 6, 2012.
Whitehead et al., Knocking down barriers: advances in siRNA delivery. Nat Rev Drug Discov. Feb. 2009;8(2):129-38.
Williams, On the mechanisms of biocompatibility. Biomaterials. Jul. 2008;29(20):2941-53. Epub Apr. 28, 2008.
Winter et al., Transforming terpene-derived aldehydes into 1,2-epoxides via asymmetric ?-chlorination: subsequent epoxide opening with carbon nucleophiles. Chem Commun (Camb). Nov. 28, 2011;47(44):12200-2. doi: 10.1039/c1cc15173h. Epub Oct. 10, 2011.
Wintermantel et al., Blocked polyurethane prepolymers as component A in reactive adhesives. STN International HCAPLUS Database. 2006. Accession No. 2006:215601.
Wobus, Potential of embryonic stem cells. Mol Aspects Med. Jun. 2001;22(3):149-64.
Wu et al., Cationic lipid polymerization as a novel approach for constructing new DNA delivery agents. Bioconjug Chem. Mar.-Apr. 2001;12(2):251-7.
Yaffee et al., Serial passaging and differentiation of myogenic cells isolated from dystrophic mouse muscle. Nature. 1977;270:725-27.
Yiu et al., Filtering of Ineffective siRNAs and Improved siRNA Design Tool. Bioinformatics. 2005;21(2):144-51.
Yoshioka et al., Epoxy-based Electroactive Polymer Gels. Experimental Mechanics. 2002;42:404-08.
Zamora et al., RNA interference therapy in lung transplant patients infected with respiratory syncytial virus. Am J Respir Crit Care Med. Feb. 15, 2011;183(4):531-8. doi: 10.1164/rccm.201003-0422OC. Epub Sep. 17, 2010.
Zamore et al., RNAi: Double-Stranded RNA Directs the ATP-Dependent Cleavage of mRNA at 21 to 23 Nucleotide Intervals. Cell. 2000;101:25-33.
Zaugg et al., 3-Carboxy-2,5-piperazinedione and Derivatives. J Amer Chem Soc. Jun. 5, 1956;78(11):2626-2631.
Zauner et al., Polylysine-based transfection systems utilizing receptor-mediated delivery. Adv Drug Deliv Rev. Mar. 2, 1998;30(1-3):97-113.
Zhang et al., A comparative study of amphiphilic PAMAM dendrimers at the air-water interface with different hydrophobe attachment groups. Langmuir. Oct. 9, 2007;23(21):10589-97. Epub Sep. 12, 2007.
Zhang et al., Human Toll-like receptor-dependent induction of interferons in protective immunity to viruses. Immunol Rev. Dec. 2007;220:225-36.
Zhang et al., Ionization behavior of amino lipids for siRNA delivery: determination of ionization constants, SAR, and the impact of lipid pKa on cationic lipid-biomembrane interactions. Langmuir. Mar. 1, 2011;27(5):1907-14. doi: 10.1021/la104590k. Epub Jan. 20, 2011.
Zhao et al., A developmental view of microRNA function. Trends Biochem. 2007;32(4):189-97.
Zintchenko et al., Simple modifications of branched PEI lead to highly efficient siRNA carriers with low toxicity. Bioconjug Chem. Jul. 2008;19(7):1448-55. Epub Jun. 14, 2008.
PCT/US2012/030349, Jul. 24, 2012, Invitation to Pay Additional Fees.
PCT/US2012/030349, Oct. 5, 2012, International Search Report and Written Opinion.
PCT/US2012/030349, Oct. 10, 2013, International Preliminary Report on Patentability.
International Search Report and Written Opinion for PCT/US2012/030349, mailed on Nov. 5, 2012.
Invitation to Pay Additional Fees for PCT/US2012/030349, mailed on Jul. 24, 2012.
International Preliminary Report on Patentability for PCT/US2012/030349 mailed on Oct. 10, 2013.
EP 23168103.2, Oct. 27, 2023, Extended European Search Report.
Extended European Search Report for EP 23168103.2, mailed Oct. 27, 2023.
Martens et al., [A Simple Synthesis of New Ring-Fused Pyrroles.] Synthesis. 1989;12:965-67. doi: 10.1055/s-1989-27450. English Abstract Only.
Winter et al., Transforming terpene-derived aldehydes into 1,2-epoxides via asymmetric α-chlorination: subsequent epoxide opening with carbon nucleophiles. Chem Commun (Camb). Nov. 28, 2011;47(44):12200-2. doi: 10.1039/c1cc15173h. Epub Oct. 10, 2011. Supporting Information, 48 pages.
*U.S. Appl. No. 18/698,888, filed Apr. 5, 2024, Langer et al.
Amor et al., Inflammation in neurodegenerative diseases. Immunology. Feb. 2010;129(2):154-69. doi: 10.1111/j.1365-2567.2009.03225.x.
Cruz et al., Aberrant Cdk5 activation by p25 triggers pathological events leading to neurodegeneration and neurofibrillary tangles. Neuron. Oct. 30, 2003;40(3):471-83. doi: 10.1016/s0896-6273(03)00627-5.
Friberg et al., A non-aqueous lyotropic liquid crystal with a starburst dendrimer as a solvent Mol Cryst Liq Cryst. Jan. 1988;164:157-65. doi: 10.1080/00268948808072120.
Gao et al., Synthesis of molecular brushes by "grafting onto" method: combination of ATRP and click reactions. J Am Chem Soc. May 23, 2007;129(20):6633-9. doi: 10.1021/ja0711617. Epub Apr. 28, 2007.
Holtzman et al., Apolipoprotein E and apolipoprotein E receptors: normal biology and roles in Alzheimer disease. Cold Spring Harb Perspect Med. Mar. 2012;2(3):a006312. doi: 10.1101/cshperspect.a006312.
Kramer et al., Dendritic polyamines: simple access to new materials with defined treelike structures for application in nonviral gene delivery. Chembiochem. Aug. 6, 2004;5(8):1081-7. doi: 10.1002/cbic.200300905.
Lalka et al., The hepatic first-pass metabolism of problematic drugs. J Clin Pharmacol. Jul. 1993;33(7):657-69. doi: 10.1002/j.1552-4604.1993.tb04720.x.
Lee et al., An efficient synthesis of ethylenimine dendrimer. Bull Korean Chem Soc. 1998;19(11):1270-3. doi: 10.5012/bkcs.1998.19.11.1270.
Navath et al., Injectable PAMAM dendrimer-PEG hydrogels for the treatment of genital infections: formulation and in vitro and in vivo evaluation. Mol Pharm. Aug. 1, 2011;8(4):1209-23. doi: 10.1021/mp200027z. Epub Jun. 20, 2011. Author Manuscript, 31 pages.
Terrier et al., Noncovalent complexes between DNA and basic polypeptides or polyamines by Maldi-Tof. J Am Soc Mass Spectrom. Nov. 2007;18(11):1977-89. doi: 10.1016/j.jasms.2007.07.028. Epub Aug. 3, 2007.
Yemul et al., Synthesis and characterization of poly(ethyleneimine) dendrimers. Colloid Polym Sci. Jan. 17, 2008;286(6-7):747-52. doi: 10.1007/S00396-007-1830-6.

\* cited by examiner

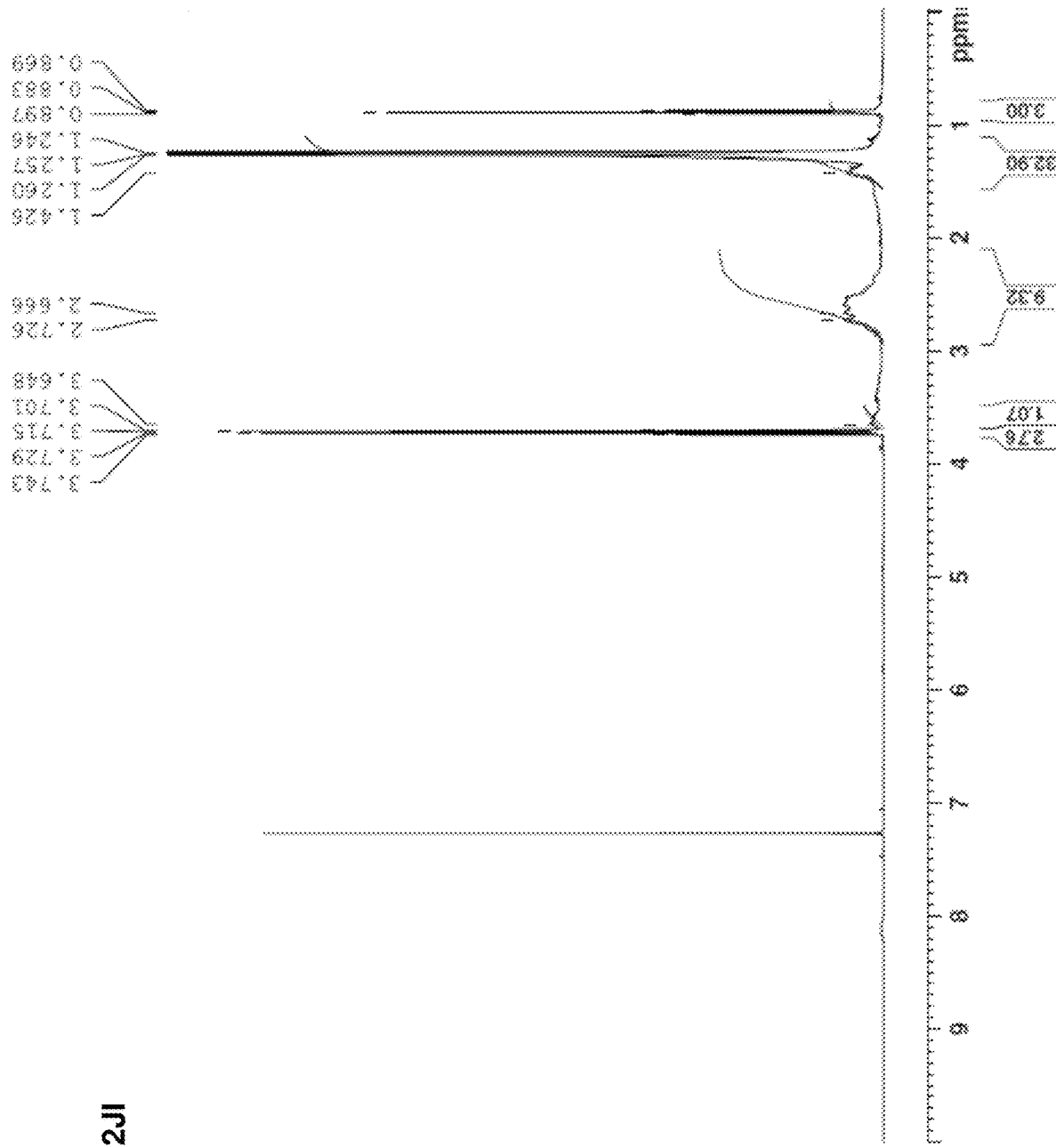
FIGURE 1G: 2JI

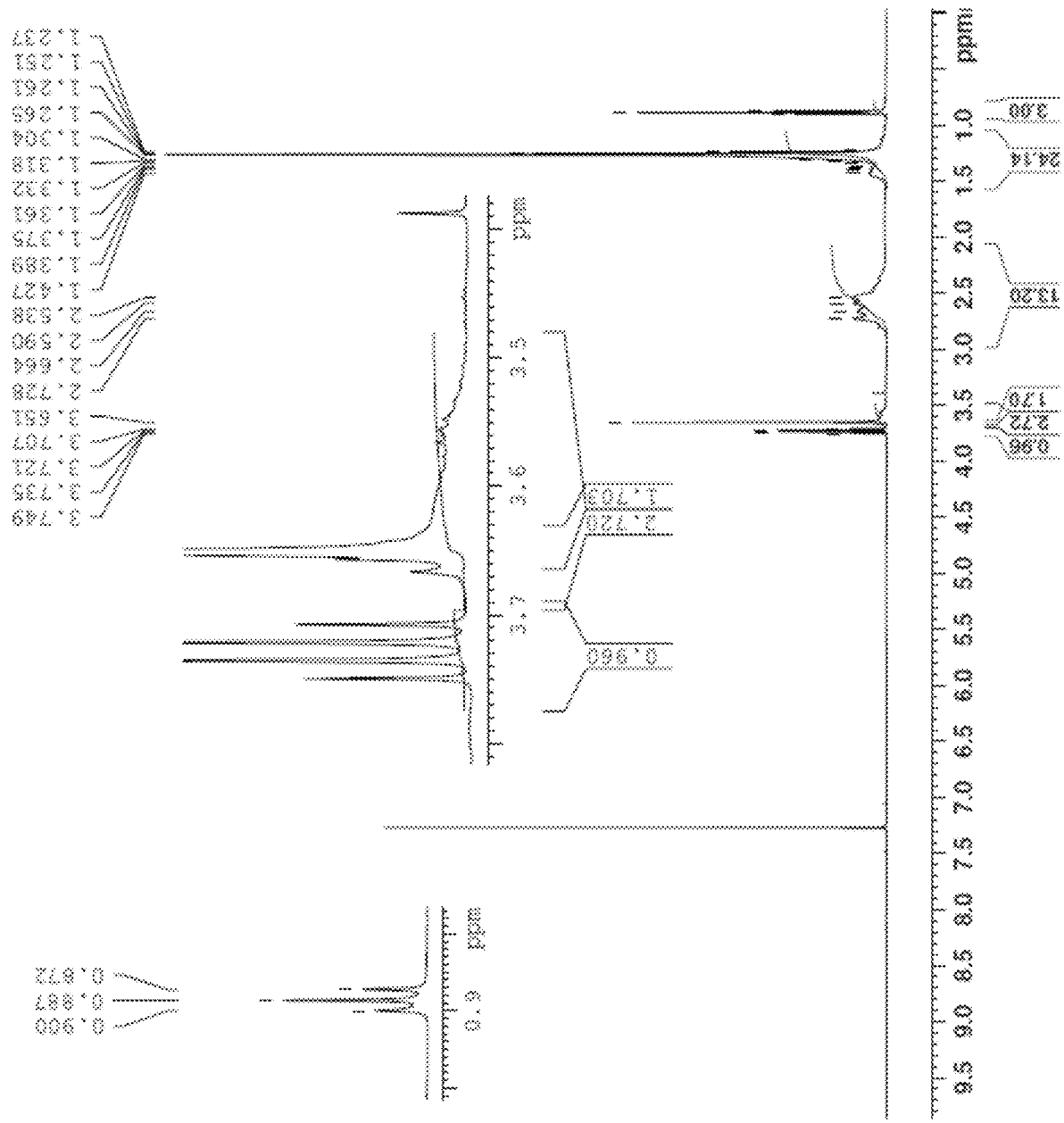
FIGURE 1H: 313

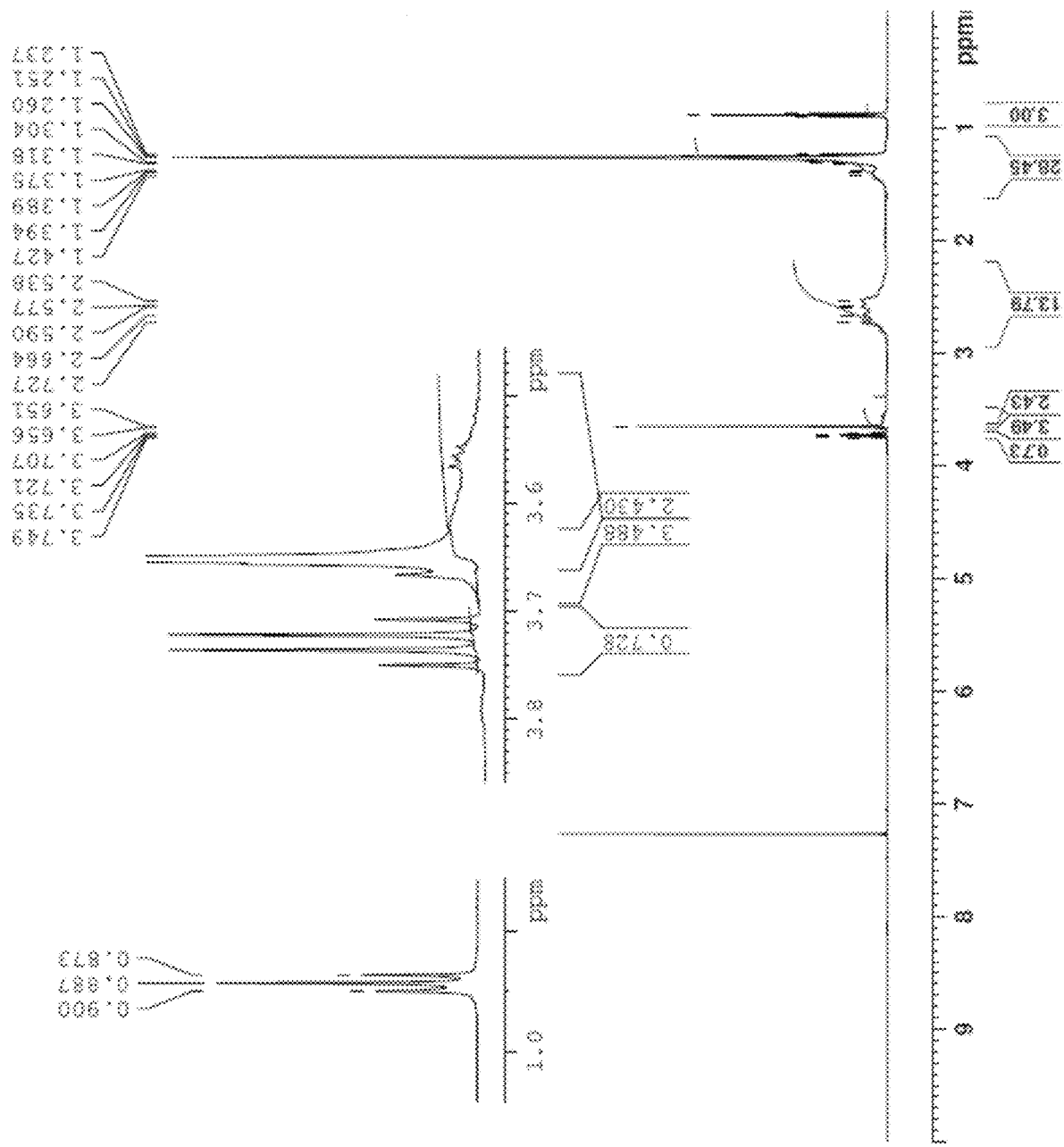
FIGURE 1I: 317

FIGURE 1J: 5H7
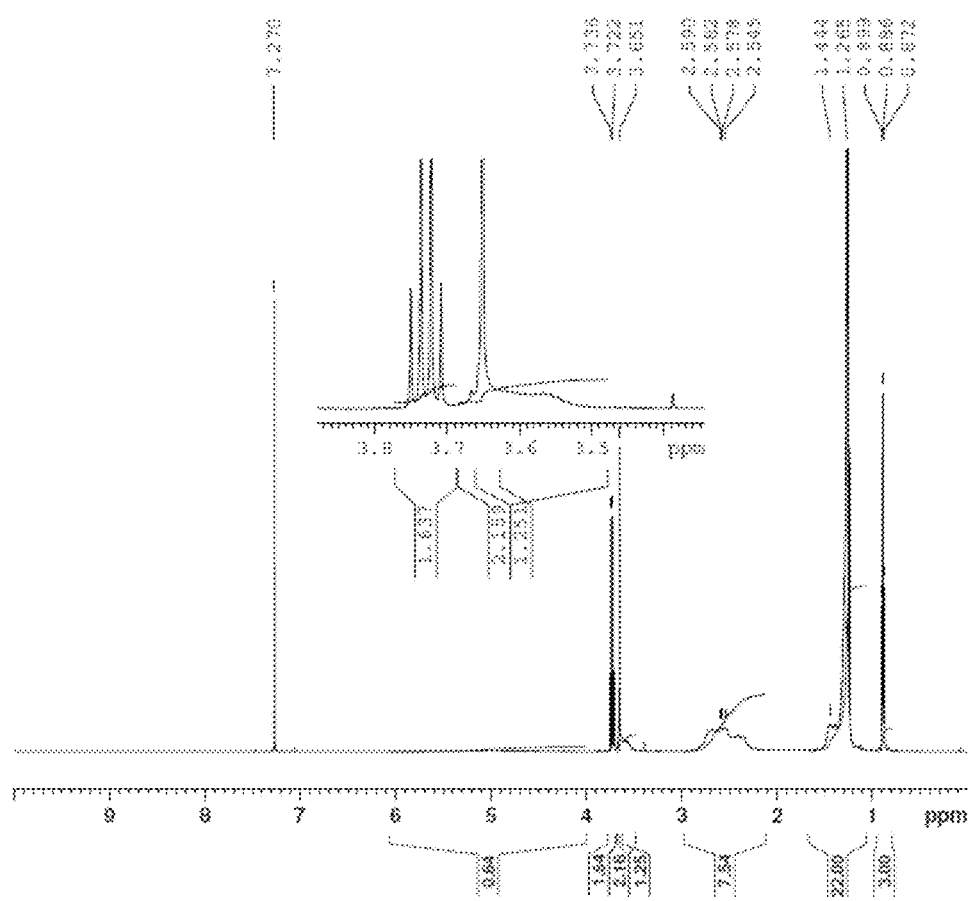

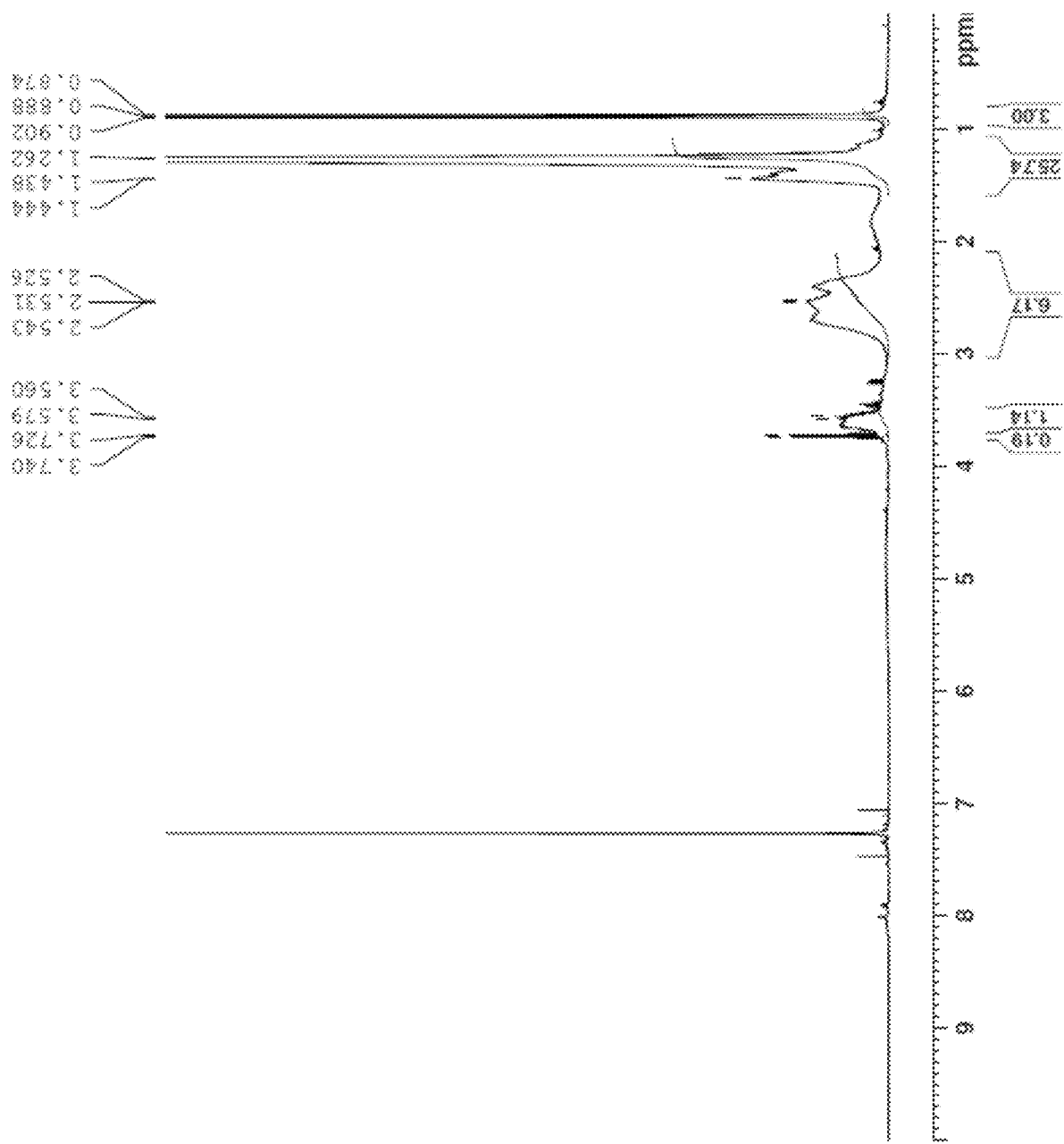
FIGURE 1K: 7C1

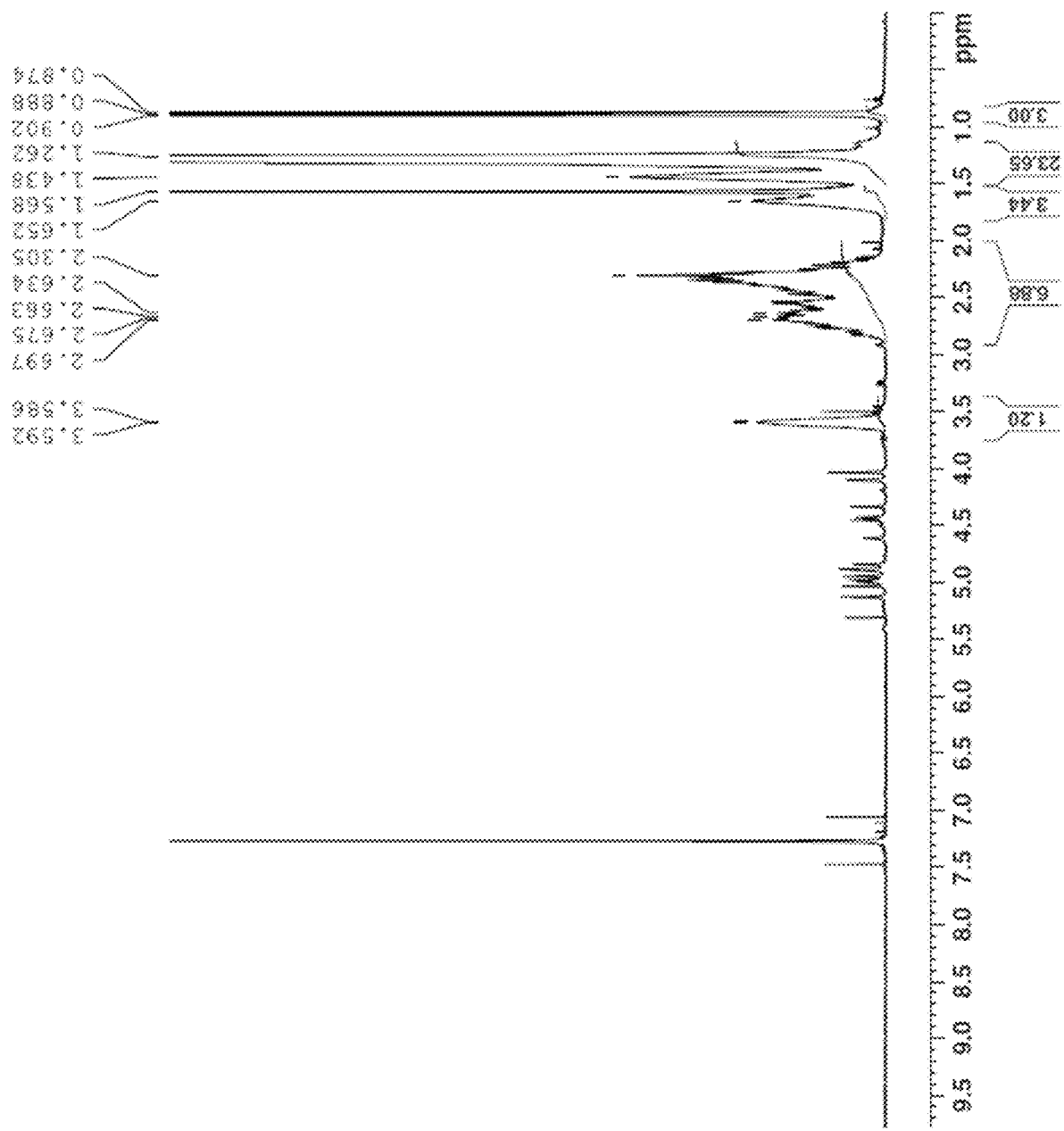
FIGURE 1L: 4C4

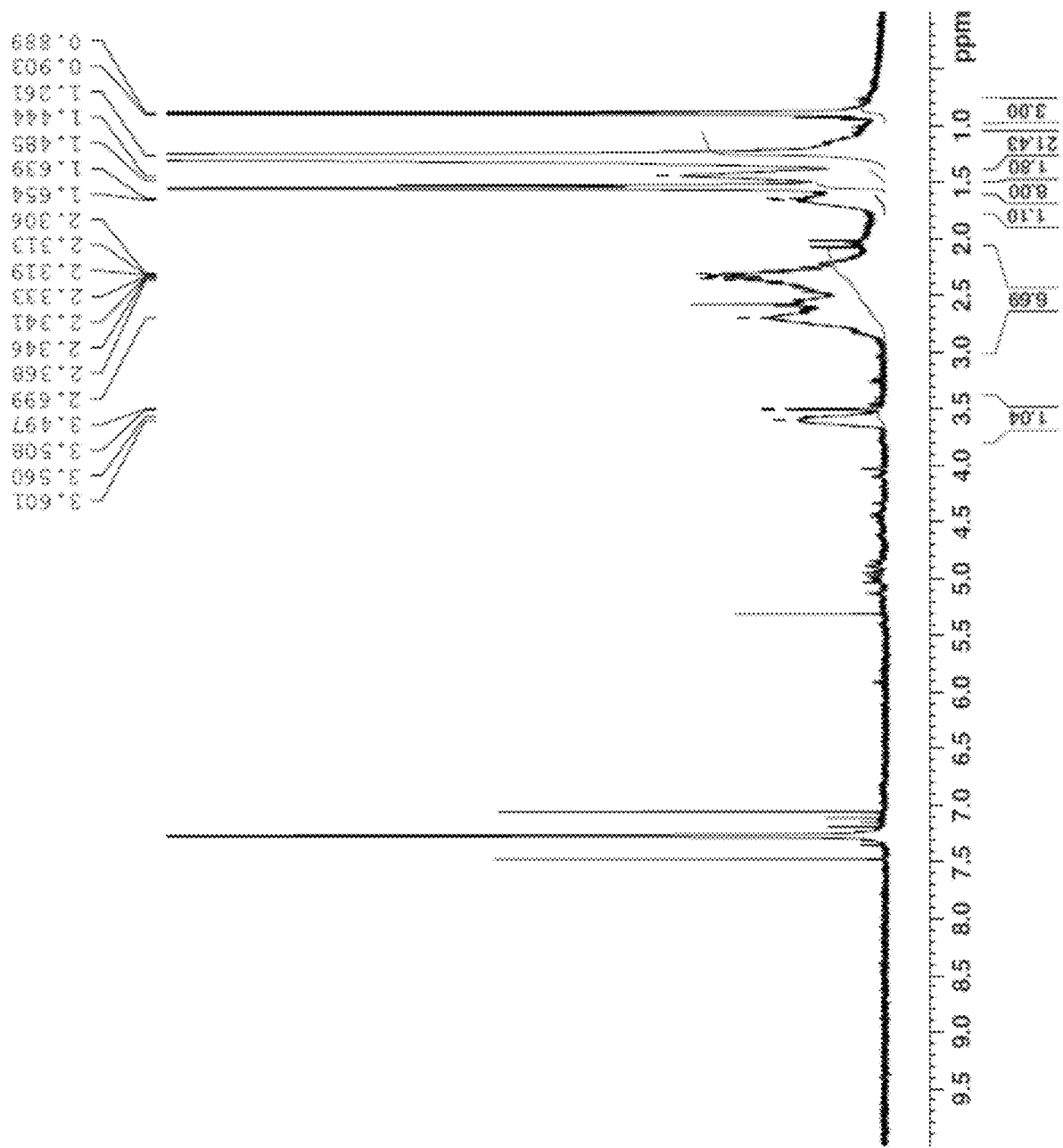
FIGURE 1M: 4C8

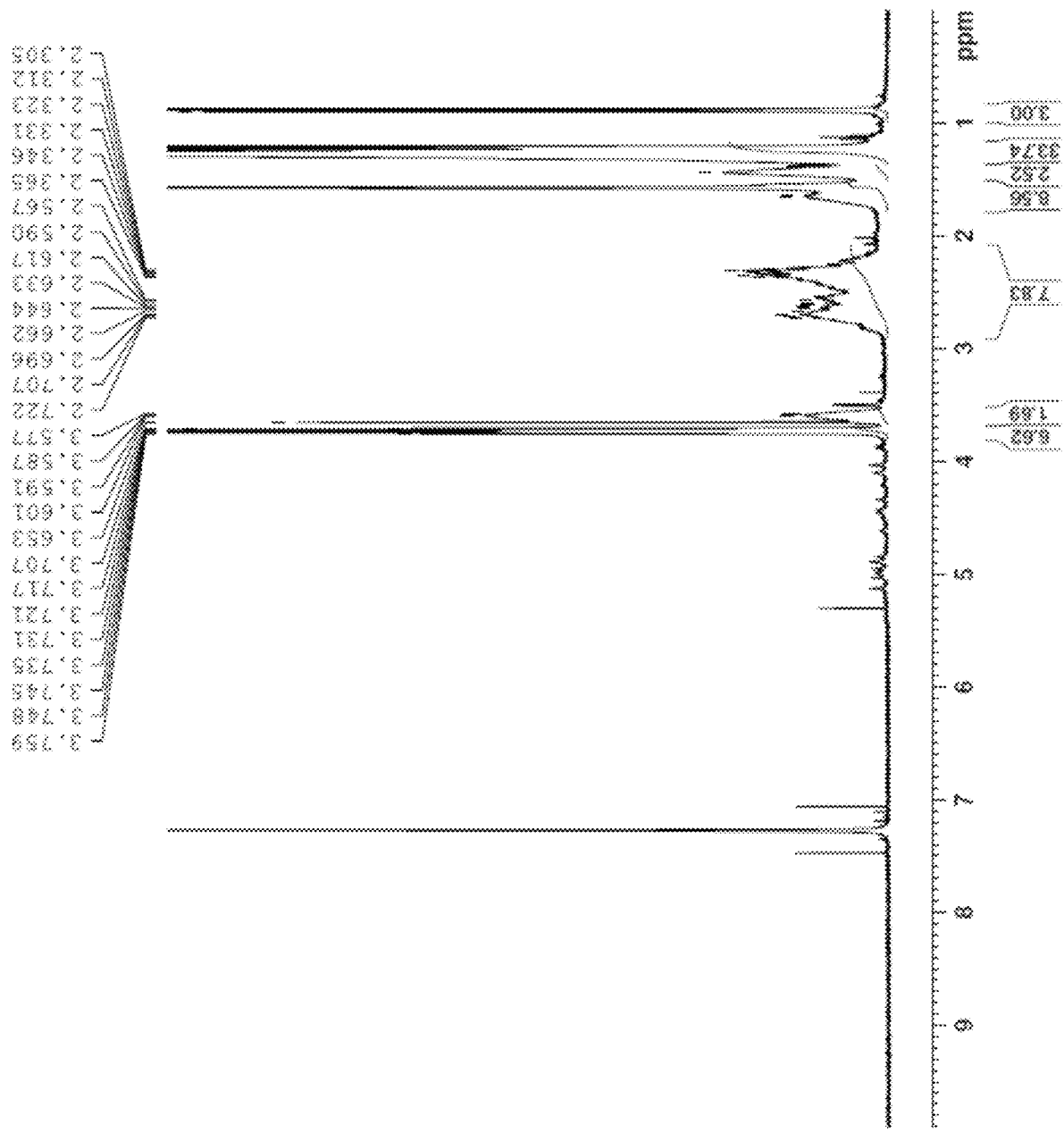
FIGURE 1N: 4D5

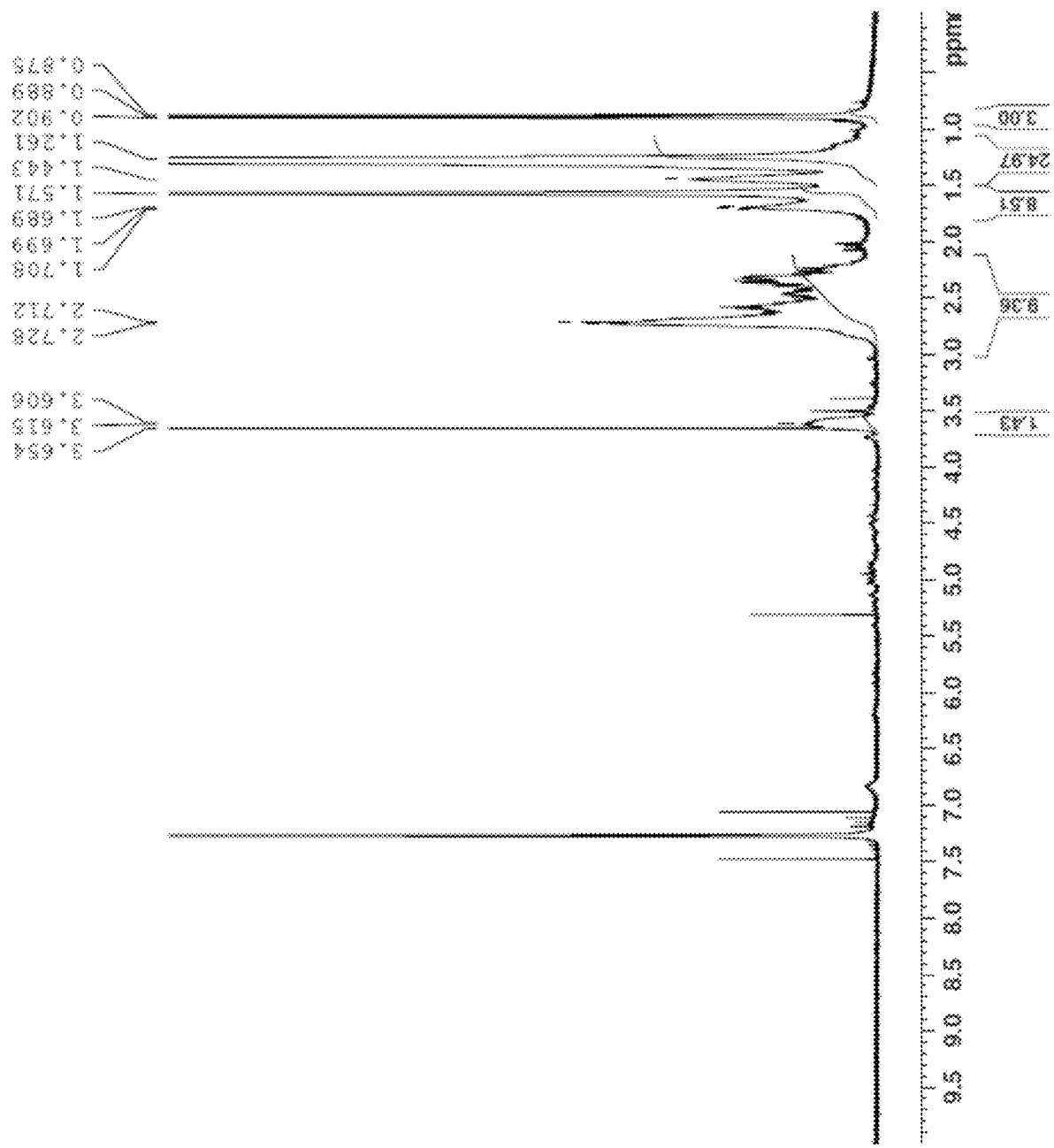
FIGURE 10: 4D9

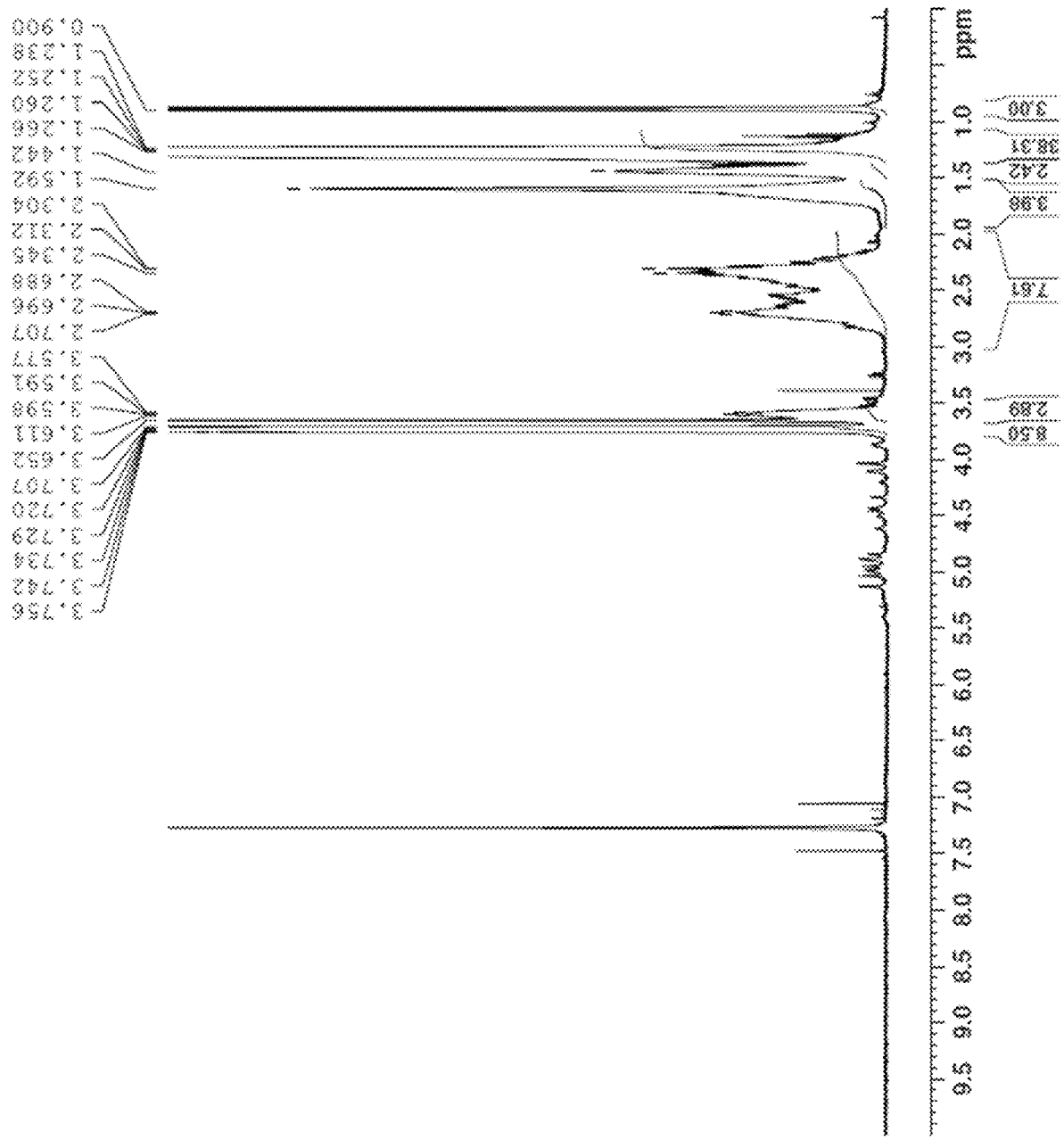
FIGURE 1P: 6B10

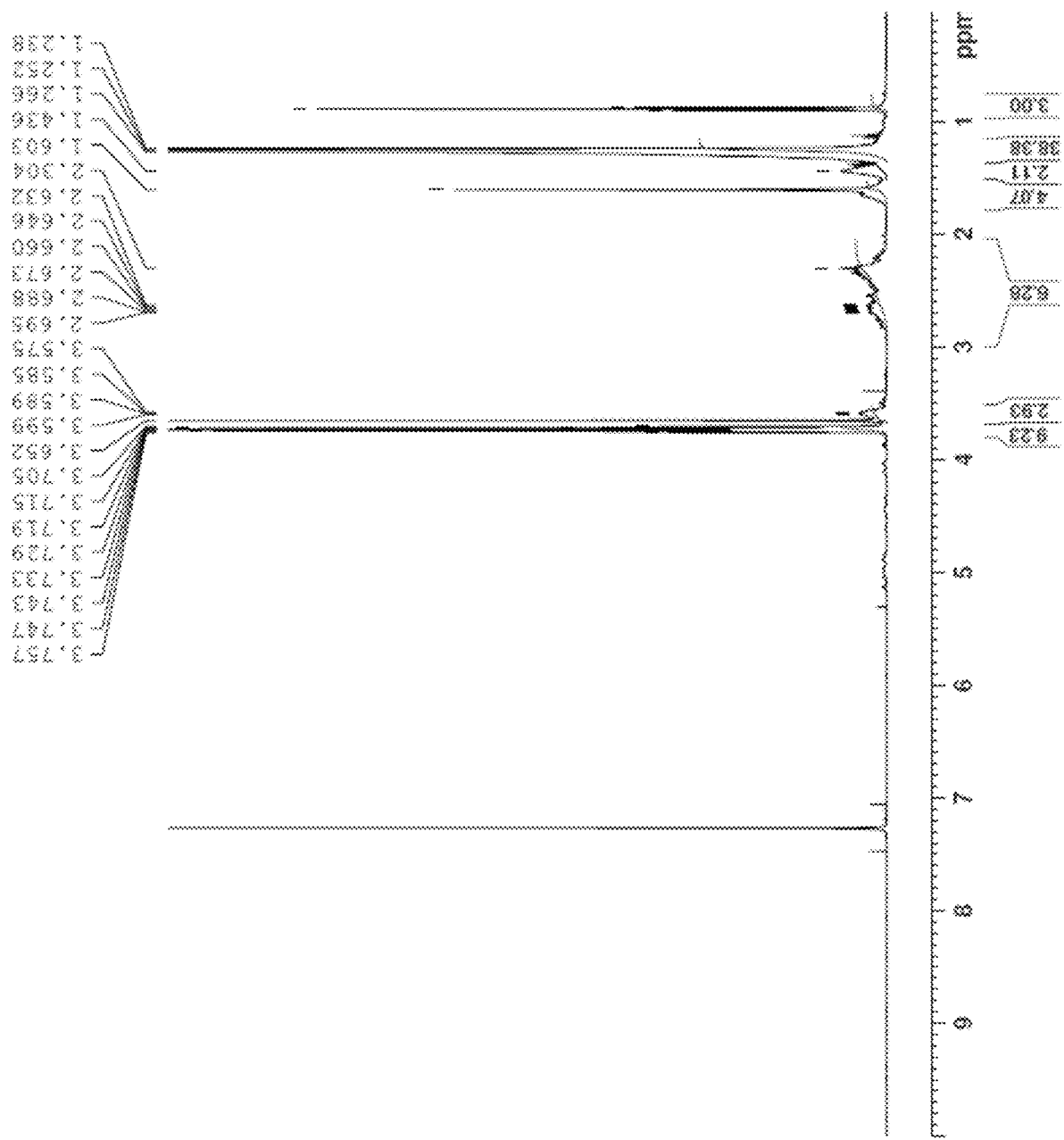
FIGURE 1Q: 6C1

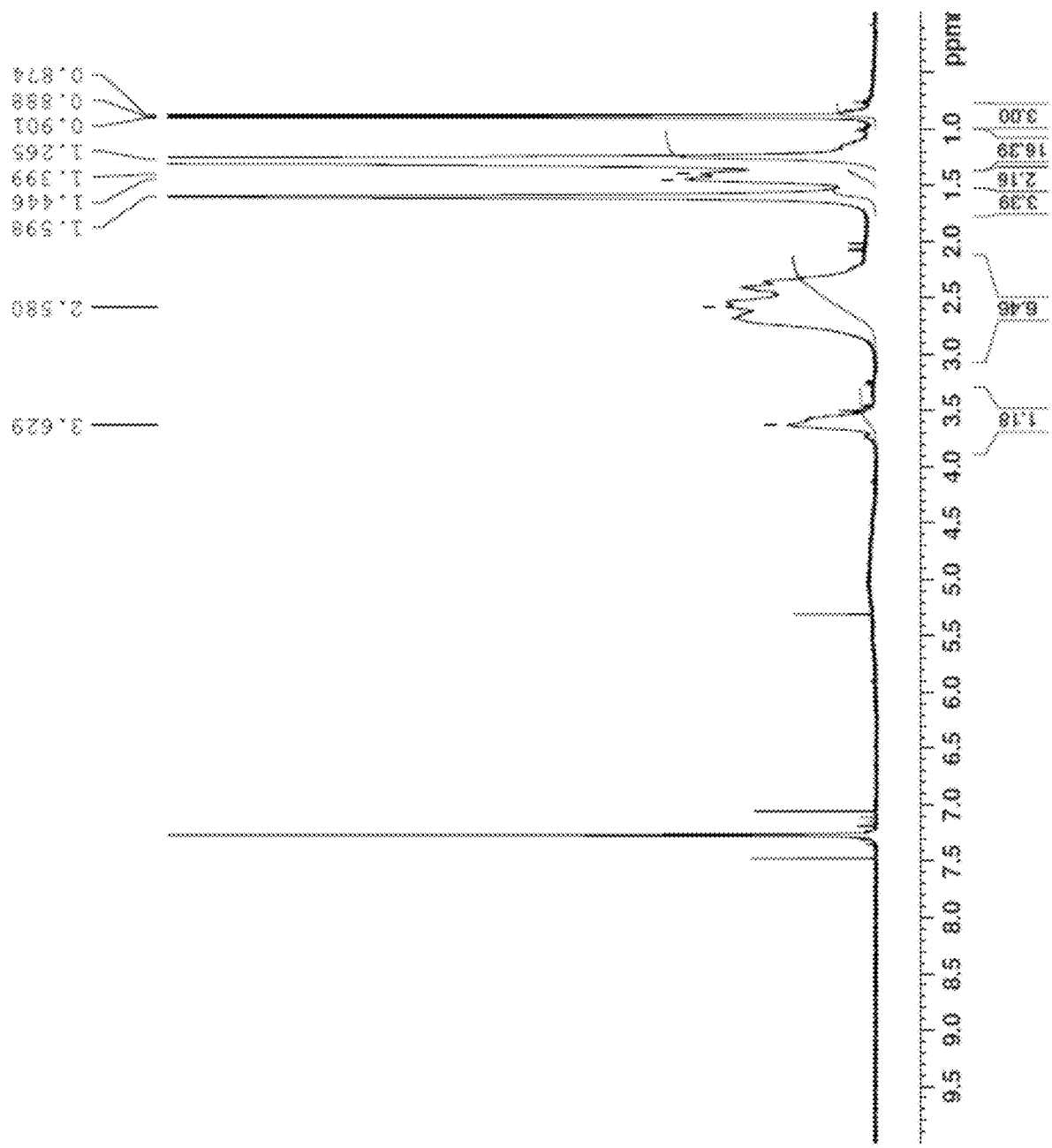
FIGURE 1R: 7H4

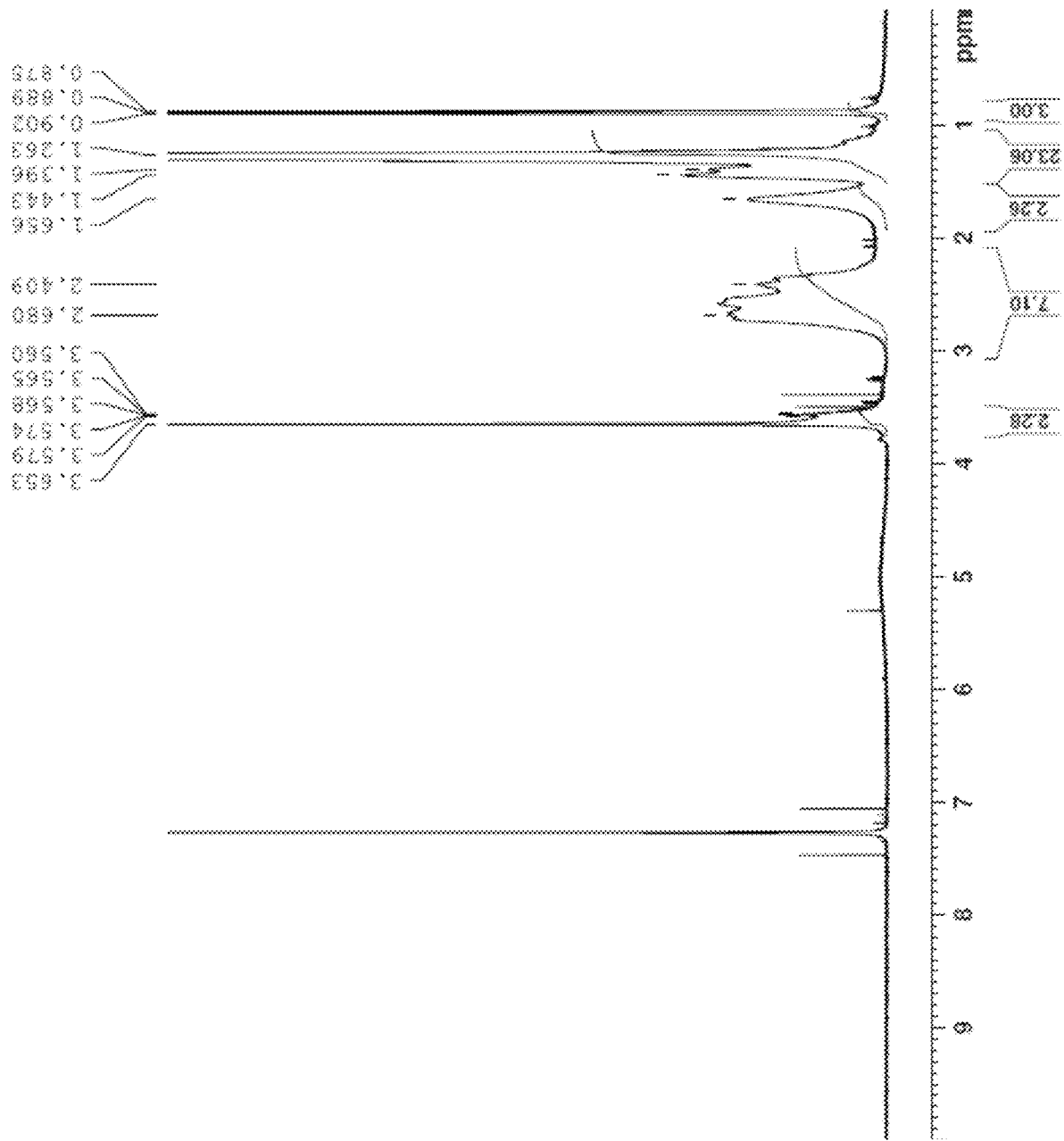
FIGURE 1S: 7H8

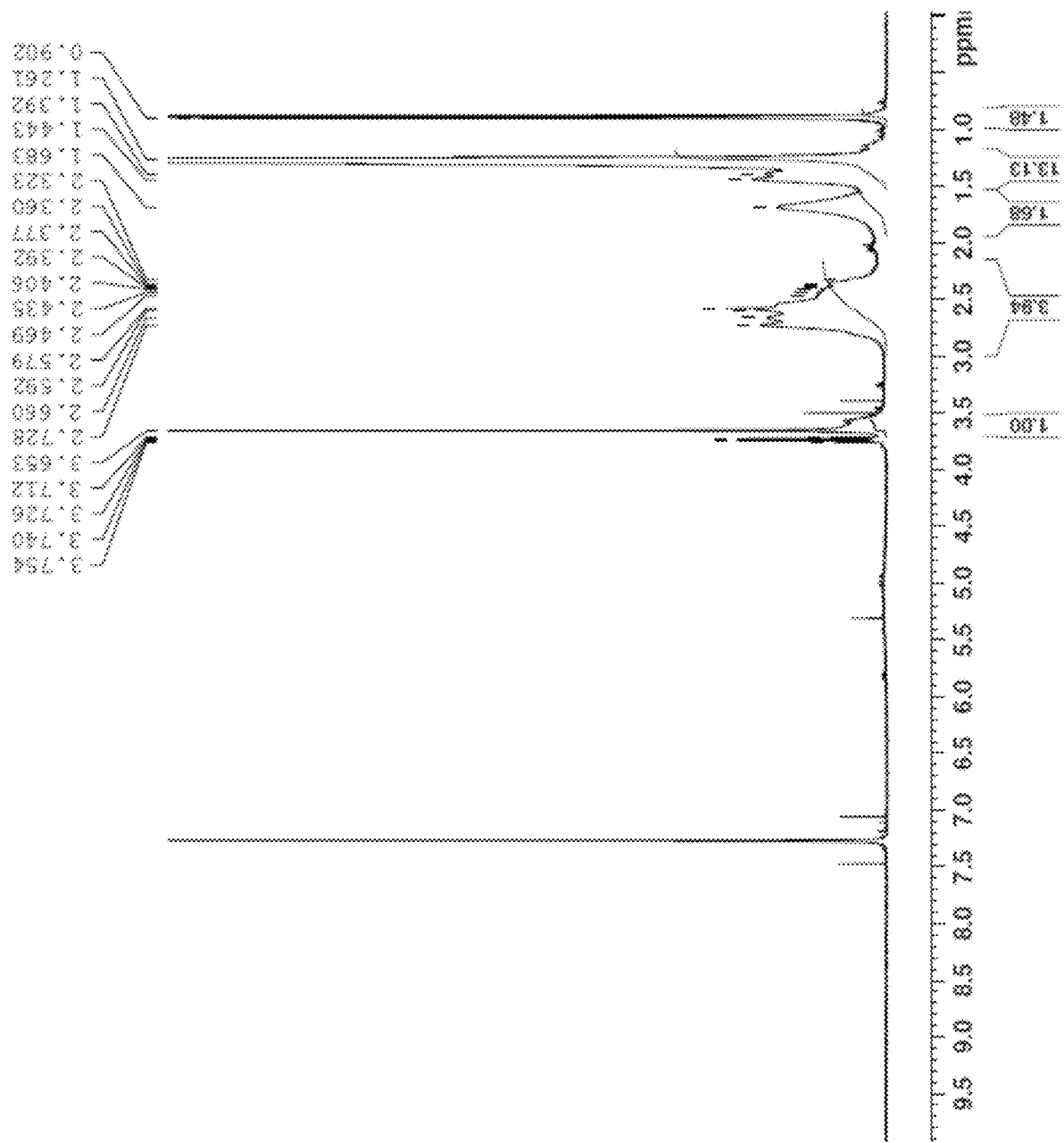
FIGURE 1T: 7H10

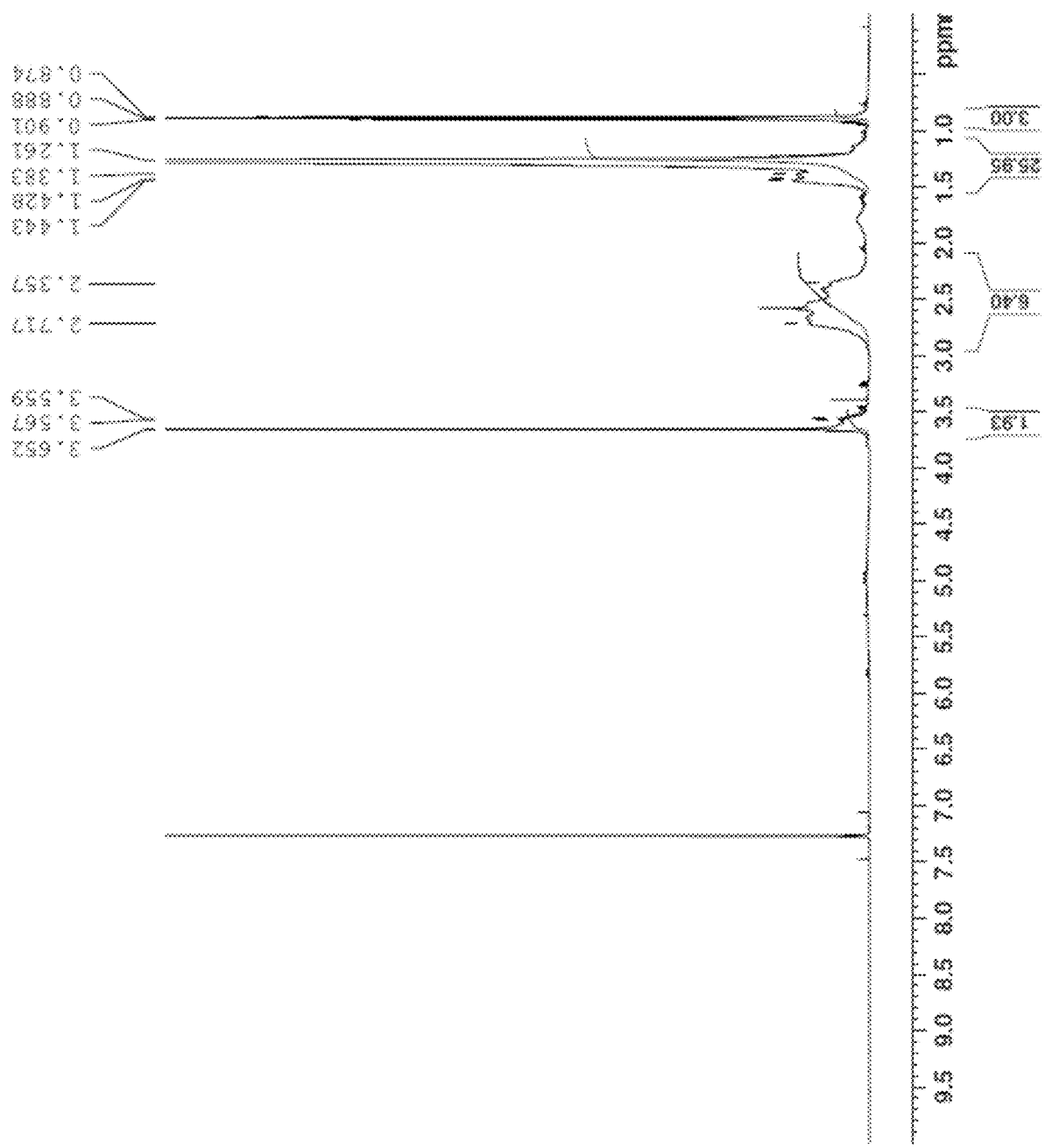
FIGURE 1U: 7I1

CONJUGATED LIPOMERS AND USES THEREOF

RELATED APPLICATIONS

The present application is a continuation of and claims priority under 35 U.S.C. § 120 to U.S. Application, U.S. Ser. No. 16/181,109, filed Nov. 5, 2018, which is a continuation of and claims priority under 35 U.S.C. § 120 to U.S. Application, U.S. Ser. No. 14/995,842, filed Jan. 14, 2016, now U.S. Pat. No. 10,117,934, which is a continuation of and claims priority under 35 U.S.C. § 120 to U.S. Application, U.S. Ser. No. 13/428,695, filed Mar. 23, 2012, now U.S. Pat. No. 9,238,716, which claims priority under 35 U.S.C. § 119 (e) to U.S. provisional patent application, U.S.S.N. 61/468,455, filed Mar. 28, 2011, each of which is incorporated herein by reference.

BACKGROUND OF THE INVENTION

The ability to silence genes via RNA interference (RNAi) was reported by Mello and Fire in 1998 (Fire et al., *Nature* (1998) 391: 806-811). Since then, scientists have rushed to take advantage of the enormous therapeutic potential driven by targeted gene knockdown. This is evidenced by the fact that the first report of small interfering RNA (siRNA) mediated RNAi in human beings was reported only twelve years after the phenomenon was described in *Caenorhabditis elegans* (Davis et al., *Nature* (2010) 464: 1067-1070). Unfortunately, this report represents the only successful therapeutic application to date. It is well understood that development of genetic drugs is slowed by the inability to deliver nucleic acids effectively in vivo. When unprotected, genetic material injected into the bloodstream can be degraded by DNAases and RNAases, or, if not degraded, the genetic material can stimulate an immune response (see, e.g., Whitehead et al., *Nature Reviews Drug Discovery* (2009) 8: 129-138; Robbins et al., *Oligonucleotides* (2009) 19: 89-102). Finally, in-tact siRNA must enter the cytosol, where the antisense strand is incorporated into the RNA-induced silencing complex (RISC) (Whitehead in supra). RISC associates with and degrades complementary mRNA sequences; this prevents translation of the target mRNA into protein, "silencing" the gene.

To overcome these barriers, nucleotides have been complexed with a wide variety of delivery systems, including polymers, lipids, inorganic nanoparticles and viruses (see, e.g., Peer et al. *Nature Nanotechnology*, (2007) 2: 751-760). Although it had been used in commercial products for over thirty years, the cationic polymer polyethyleneimine (PEI) was first reported as an effective gene therapy delivery material in 1995 (Boussif et al., *Proceedings of the National Academy of Sciences of the United States of America* (1995) 92: 7297-7301). The amino groups of PEI are known to be protonated at physiological pH, facilitating electrostatic interactions with the negative phosphate backbone of the nucleotide (see, e.g., Suh et al., *Bioorganic Chemistry* (1994) 22: 318-327). Branched PEI (BPEI) is one of the most highly characterized polymeric vectors for genetic delivery owing to increased interactions between the branched cation and the relatively linear phosphate backbone (Von Harpe et al., *Journal of Controlled Release* (2000) 69: 309-322). In addition to this stability, BPEI is considered an ideal delivery vector because the primary, secondary and tertiary amino groups have different pKas, and can therefore accept a large number of protons in the endosome without acidifying the membrane. Since acidification is required for nuclease activity that would disassemble the nucleotide, the nucleotide is protected from degradation. Furthermore, the influx of protons creates a gradient down which ions and water flow, an effect also known as "the proton sponge". The endosomal membrane is filled like a balloon until it bursts open, releasing genetic material into the cytoplasm. In this way, BPEI is able to effectively ferry nucleic acids from the extracellular space into the cytoplasm (see, e.g., Akinc et al., *Journal of Gene Medicine* (2005) 7: 657-663).

The potential for effective delivery of nucleic acids with PEI has driven significant interest in the polymer (see, e.g., Incani et al., *Soft Matter* (2010) 6: 2124-2138; and Howard, *Advanced Drug Delivery Reviews* (2009) 61: 710-720). However, many authors have reported that efficacy, molecular weight and toxicity increase together (see, e.g., Godbey et al., *Journal Of Biomedical Materials Research* (1999) 45: 268-275). For example, it has been reported that a number average molar mass (Mn) of 25,000 BPEI ($BPEI_{25,000}$) was required for effective DNA delivery, while Mn 1200 and Mn 600 PEI failed to yield expression in any trial (Richards-Grayson et al., *Pharmaceutical research* (2006) 23: 1868-1876). In that same report, $BPEI_{800}$ DNA transfection was compared to Mn 22,000 linear PEI ($LPEI_{22,000}$) and $BPEI_{25,000}$, and the authors found that while transfection was only seen with the $BPEI_{25,000}$ formulation, $BPEI_{25,000}$ was also found to be more cytotoxic. Regardless, many researchers have utilized $BPEI_{25,000}$ to delivery DNA and siRNA (see, e.g., Alshamsan et al., *Biomaterials* (2009) 31: 1420-1428; Kim et al., *Bioconj. Chem.* (2006) 17: 241-244; Kim et al., *J. Controlled Release* (2006) 129: 107-116; Kwon et al., *Bioconj. Chem.* (2008) 19: 920-927; Jiang et al., *Biopolymers* (2008) 89: 635-642; Creusat et al., *Bioconjugate chemistry* (2010) 21: 994-1002; Bajaj et al., *Bioconjugate chemistry* (2008) 19: 1640-1651; Furgeson et al., *Pharmaceutical research* (2002) 19: 382-390; and Furgeson et al., *Bioconjugate Chem* (2003) 14: 840-847). In a recent report, $BPEI_{25,000}$ Was conjugated by N-acylation of the PEI to lipid tails and formulated with siRNA targeting STAT3, a protein required for tumor progression (Alshamsan et al. *Biomaterials* (2010) 31: 1420-1428). In vitro analysis showed that the $BPEI_{25,000}$-$C_{16}$ conjugate reduced target gene expression by 50% at 25 nM in vitro and reduced tumor size by 50% at 0.3 mg/kg after intra-tumoral injections.

Investigators have sought to abrogate the cytotoxic effects of using $BPEI_{25,000}$ in a variety of ways. For example, some investigators have conjugated lower molecular weight PEI segments together via biodegradable bonds in an effort to provide a new polymer which delivers nucleotides effectively like a $BPEI_{25,000}$, but degrades into non-toxic constituents (see, e.g., Tarcha et al., *Biomaterials* (2007) 28: 3731-3740; Breunig et al., *Journal of Controlled Release* (2008) 130: 57-63; and Breunig et al., *Proceedings of the National Academy of Sciences of the United States of America* (2007) 104: 14454-14459). Others have used $BPEI_{2000}$ and $BPEI_{1800}$ to a variety of hydrophobic chemical groups in an effort to bolster the molecular weight of the PEI polymer to provide a new polymer without the cytotoxic effects inherent to $BPEI_{25,000}$. In one such report, lipid moieties were conjugated by N-acylation to $BPEI_{2000}$ (2 kDa PEI) and evaluated for gene delivery (Neamnark, et al. *Molecular Pharmaceutics* (2009) 6: 1798-1815). The authors reported that lipid conjugation improved gene delivery, but doses nearing 100 nM were not effective at transfecting the plasmid. In another report, $BPEI_{1800}$ was conjugated to cholesterol in a molar ratio of cholesterol:$BPEI_{1800}$ of approximately 1, but the authors required 5-15 μM for in vitro knockdown, indicating poor efficacy (see Kim et al., *J. Controlled Release* (2007) 118: 357-363). Still others have investigated poly-siRNA conjugated to $BPEI_{1800}$ for gene silencing (see, e.g., Lee et al., *J. Controlled Release* (2010) 141: 339-346). However, the prevailing sense in the research community is that use of LPEI for the delivery of siRNA is still not as effective as use of BPEI, and that low molecular weight LPEI and BPEI polymers, i.e., having a number average molar mass (Mn) of ≤2000 (i.e., approximately ≤2 kDa), are inefficient materials for siRNA delivery (see, e.g., Boussif et al., *Proceedings of the National Academy of Sciences of the United States of America* (1995) 92: 7297-7301; and Philipp et al., *Bioconjugate Chem.* (2009) 20: 2055-2061).

As described above, PEI mediated polynucleotide delivery has been well-studied, but, to date, no highly effective in vivo PEI-based delivery system has been reported. Thus, there continues to remain a need to develop a PEI-based polynucleotide delivery system which is as efficient a delivery system as a high molecular weight PEI, but with little to no cytotoxicity.

SUMMARY OF THE INVENTION

The present invention provides inventive conjugated polyethyleneimine (PEI) polymers and inventive conjugated aza-macrocycles (collectively referred to herein as "conjugated lipomers" or "lipomers"), which are useful, for example, as polynucleotide delivery systems. The conjugated polyethyleneimine polymers are preferably prepared from low molecular weight linear polyethyleneimine (LPEI) and branched polyethyleneimine (BPEI) polymers, i.e., having a number average molar mass (Mn) of ≤2000 (i.e., approximately ≤2 kDa).

In one aspect, provided is a conjugated lipomer of the Formula (II):

(II)

or salt thereof;
wherein:
each instance of $L^1$ is independently selected from formulae:

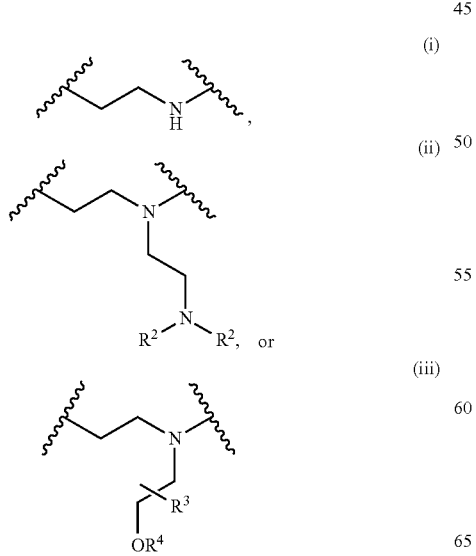

provided that at least one $L^1$ is selected from formulae (iii);

n is an integer of between 3 to 45, inclusive;

each instance of $R^2$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; a substituted or unsubstituted polyethyleneimine; or a group of the formula (iii'):

(iii')

or the two $R^2$ groups are joined to form a substituted or unsubstituted heterocyclyl;

each instance of $R^3$ is independently substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or a hydrophilic polymer;

each instance of $R^4$ is independently hydrogen, acyl; silyl; a hydroxyl protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl;

A is $-N(R^5)_2$, wherein each instance of $R^5$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or a group of the formula (iii'):

(iii')

or two $R^5$ groups are joined to form a substituted or unsubstituted heterocyclyl; and Z is hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl, or a group of the formula (iii'):

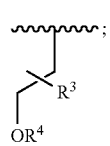

(iii')

or Z and the nitrogen atom to which it is attached form a substituted or unsubstituted heterocyclyl group.

In another aspect, provided is a cyclic conjugated lipomer of the Formula (IV):

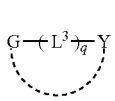

(IV)

or salt thereof; wherein:

each instance of $L^3$ is independently selected from:

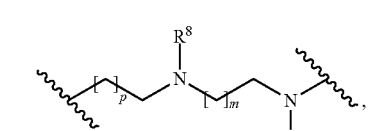

(vi)

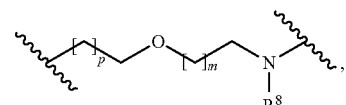

(vii)

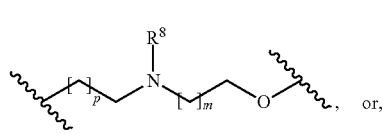

(viii)

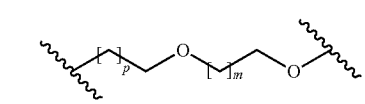

(ix)

provided that the cyclic conjugated lipomer contains at least one group selected from (vi), (vii) or (viii);

each instance of $R^8$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or

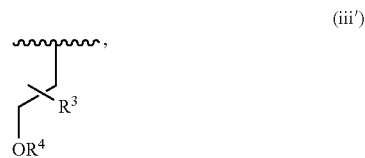

(iii')

provided the conjugated lipomer contains at least one group of the formula (iii');

each instance of $R^3$ is independently substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or a hydrophilic polymer;

each instance of $R^4$ is independently hydrogen, acyl; silyl; a hydroxyl protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl;

each instance of m and p is independently 0, 1 or 2;

q is an integer selected from 2, 3, or 4; and the dashed curved line, together with G and Y, is a covalent bond or a group of the formula:

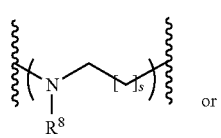

(x)

or

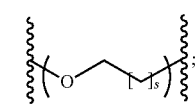

(xi)

wherein s is 0, 1, or 2, and $R^8$ is as defined herein.

In certain embodiments, the cyclic conjugated lipomer comprises at least one instance of the group of the formula (vi). In these embodiments, the conjugated lipomer is of the Formula (V), (VI), or (VII):

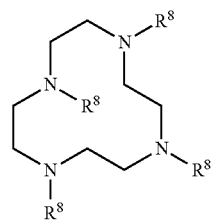

(V)

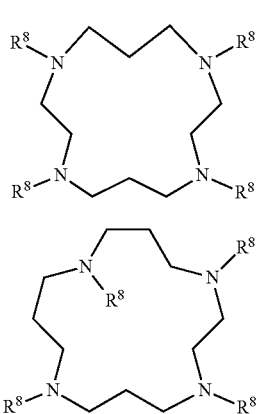

(VI)

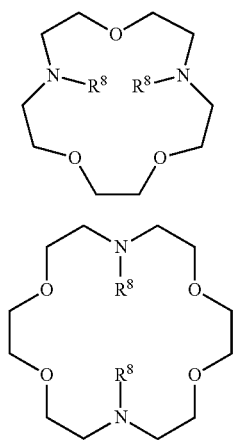

(VII)

or salt thereof.

In certain embodiments, the conjugated lipomer comprises at least one instance of the group of the formula (vii), (viii), or (ix). In these embodiments, the conjugated lipomer is of the Formula (VII) or (IX):

(VII)

(IX)

or salt thereof.

In yet another aspect, provided are compositions comprising the inventive conjugated lipomers. For example, in certain embodiments, provided is a composition comprising one or more conjugated lipomers of the present invention, e.g., a conjugated lipomer of Formula (II) or (IV), and, optionally an excipient. In certain embodiments, the composition is a pharmaceutical composition or a cosmetic composition. In certain embodiments, the composition further comprises an agent. In certain embodiments, the agent is small molecule, organometallic compound, nucleic acid, protein, peptide, polynucleotide, metal, targeting agent, an isotopically labeled chemical compound, drug, vaccine, immunological agent. In certain embodiments, the agent is a polynucleotide, and the polynucleotide is DNA or RNA. In certain embodiments, the RNA is RNAi, dsRNA, siRNA, shRNA, miRNA, or antisense RNA. In certain embodiments, the polynucleotide and the one or more conjugated lipomers are not covalently attached. In certain embodiments, the one or more conjugated lipomers is in the form of a particle. In certain embodiments, the particle is a nanoparticle or microparticle. In certain embodiments, the particle encapsulates an agent, e.g., an agent to be delivered.

In yet another aspect, provided are methods of preparation of the inventive conjugated lipomers. For example, in one embodiment, provided is a method of preparing a conjugated lipomer of the Formula (II), or salt thereof, the method comprising contacting a compound of the Formula (I), or salt thereof, with an epoxide of the formula (xii):

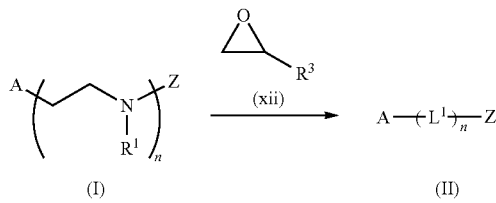

wherein each instance of $R^1$ is independently selected from hydrogen or a group of the formula (ii'):

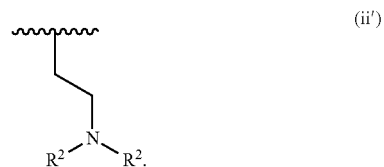

(ii')

In another embodiment, provided is a method of preparing a cyclic conjugated lipomer of the Formula (IV), or salt thereof, the method comprising contacting a compound of the Formula (III), or salt thereof, with an epoxide of the formula (xii):

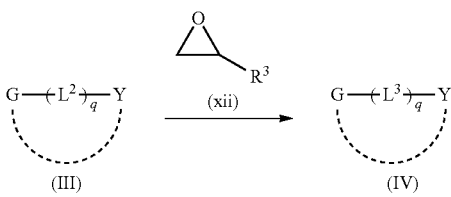

wherein each instance of $L^2$ is independently selected from:

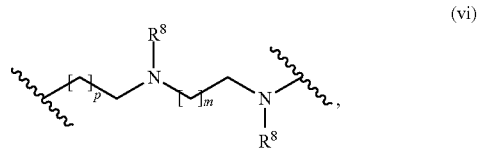

(vi)

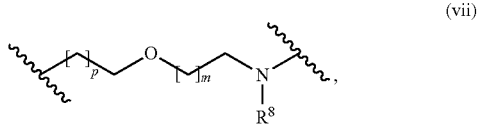

(vii)

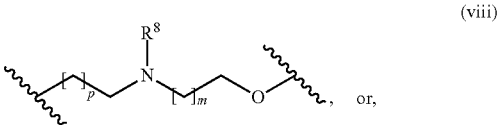

(viii)

or,

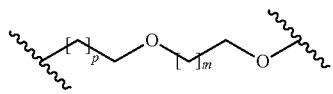
(ix)

provided that the compound of Formula (III) contains at least one group selected from (vi), (vii) or (viii); and further provided that the compound of Formula (III) contains at least one $R^8$ group that is hydrogen.

In yet another aspect, provided are screening methods. For example, in one embodiments, provided is a method of screening a library of conjugated lipomers of the present invention, e.g., conjugated lipomers Formula (II) and/or (IV), the method comprising providing a plurality of conjugated lipomers; and screening the conjugated lipomers for a desired property, e.g., useful in gene therapy. In certain embodiments, the desired property includes a property useful for delivery of an agent (e.g., a small molecule, polynucleotide, protein, peptide) to a cell, tissue, organ, or subject. In certain embodiments, the desired property is an ability to bind a polynucleotide; increase transfection efficiency; support cell growth; support cell attachment; support tissue growth; or to be soluble in an aqueous solution.

In yet another aspect, provided are methods of use of the inventive conjugated lipomers for the treatment of diseases, disorders, or conditions. For example, in certain embodiments, provided is a method of treating cancer comprising administering to a subject in need thereof an effective amount of an inventive conjugated lipomer, or salt thereof, as described herein.

Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 50 carbon atoms ("$C_{1-50}$ alkyl"). In some embodiments, an alkyl group has 1 to 40 carbon atoms ("$C_{1-40}$ alkyl"). In some embodiments, an alkyl group has 1 to 30 carbon atoms ("$C_{1-30}$ alkyl"). In some embodiments, an alkyl group has 1 to 20 carbon atoms ("$C_{1-20}$ alkyl"). In some embodiments, an alkyl group has 1 to 20 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl (Cs), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-50}$ alkyl. In certain embodiments, the alkyl group is a substituted $C_{1-50}$ alkyl.

The term "heteroalkyl," as used herein, refers to an alkyl group, as defined herein, which further comprises 1 or more (e.g., 1 to 25) heteroatoms (e.g., oxygen, sulfur, nitrogen, boron, silicon, phosphorus) included in the parent chain. In certain embodiments, the heteroalkyl group is an unsubstituted $C_{1-50}$ heteroalkyl. In certain embodiments, the heteroalkyl group is a substituted $C_{1-50}$ heteroalkyl.

As used herein, "alkenyl" refers to a radical of a straight-chain or branched hydrocarbon group having from 2 to 50 carbon atoms and one or more carbon-carbon double bonds ("$C_{2-50}$ alkenyl"). In some embodiments, an alkenyl group has 2 to 40 carbon atoms ("$C_{2-40}$ alkenyl"). In some embodiments, an alkenyl group has 2 to 30 carbon atoms ("$C_{2-30}$ alkenyl"). In some embodiments, an alkenyl group has 2 to 20 carbon atoms ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-50}$ alkenyl. In certain embodiments, the alkenyl group is a substituted $C_{2-50}$ alkenyl.

The term "heteroalkenyl," as used herein, refers to an alkenyl group, as defined herein, which further comprises 1 or more (e.g., 1 to 25) heteroatoms (e.g., oxygen, sulfur, nitrogen, boron, silicon, phosphorus) included in the parent chain. In certain embodiments, the heteroalkenyl group is an unsubstituted $C_{2-50}$ heteroalkenyl. In certain embodiments, the heteroalkenyl group is a substituted $C_{2-50}$ heteroalkenyl.

As used herein, "alkynyl" refers to a radical of a straight-chain or branched hydrocarbon group having from 2 to 50 carbon atoms and one or more carbon-carbon triple bonds ("$C_{2-50}$ alkynyl"). In some embodiments, an alkynyl group has 2 to 40 carbon atoms ("$C_{2-40}$ alkynyl"). In some embodiments, an alkynyl group has 2 to 30 carbon atoms ("$C_{2-30}$ alkynyl"). In some embodiments, an alkynyl group has 2 to 20 carbon atoms ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-50}$ alkynyl. In certain embodiments, the alkynyl group is a substituted $C_{2-50}$ alkynyl.

The term "heteroalkynyl," as used herein, refers to an alkynyl group, as defined herein, which further comprises 1 or more (e.g., 1 to 25) heteroatoms (e.g., oxygen, sulfur, nitrogen, boron, silicon, phosphorus) included in the parent chain. In certain embodiments, the heteroalkynyl group is an unsubstituted $C_{2-50}$ heteroalkynyl. In certain embodiments, the heteroalkynyl group is a substituted $C_{2-50}$ heteroalkynyl.

As used herein, "carbocyclyl" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic or tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

Alkyl, alkenyl, alkynyl, heteroalkyl, heteroalkenyl, heteroalkynyl, carbocyclyl, heterocyclyl, aryl, and heteroaryl groups, as defined herein, are optionally substituted. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{2-10}$ alkenyl, C$_{2-10}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$RC, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)$_2$(NR$^{cc}$)$_2$, $C_{1-10}$ alkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3{}^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O) R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$) OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N (R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3{}^+$X$^-$, —NH(C$_{1-6}$ alkyl)$_2{}^+$X$^-$, —NH$_2$(C$_{1-6}$ alkyl)$^+$ X$^-$, —NH$_3{}^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl) C(=O)(C$_{1-6}$ alkyl), —NHCO$_2$ (C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH) O(C$_{1-6}$ alkyl), —OC(=NH)(C$_{1-6}$ alkyl), —OC(=NH) O(C$_{1-6}$ alkyl), —C(=NH)N(C$_{1-6}$ alkyl)$_2$, —C(=NH) NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH (C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S) SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP (=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S;

wherein X$^-$ is a counterion.

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON (R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$) OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein $R^{aa}$, $R^{bb}$, and $R^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC (=O)SR$^{aa}$, —SC(=O)OR$^{aa}$, and —SC(=O)R$^{aa}$, wherein $R^{aa}$ and $R^{cc}$ are as defined herein.

As used herein, the term, "amino" refers to the group —NH$_2$. The term "substituted amino," by extension, refers to a monosubstituted amino, a disubstituted amino, or a trisubstituted amino, as defined herein.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N (R$^{bb}$)$_2$, —NHSO$_2$R$^{aa}$, —NHP(=O)(OR$^{cc}$)$_2$, and —NHP (=O)(NR$^{bb}$)$_2$, wherein $R^{aa}$, $R^{bb}$ and $R^{cc}$ are as defined herein, and wherein $R^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

As used herein, the term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

As used herein, the term "sulfinyl" refers to the group —S(=O)R$^{aa}$, wherein R$^{aa}$ is as defined herein.

As used herein, the term "silyl" refers to the group —Si(R$^{aa}$)$_3$, wherein R$^{aa}$ is as defined herein.

As used herein, the term "acyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR, —P(=O)$_2$R$^{aa}$, —P(=O) (R$^{aa}$)$_2$, —P(=O)$_2$N(R$^{cc}$)$_2$, —P(=O)(NR$^{cc}$)$_2$, C$_{1-10}$ alkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an amino protecting group (also referred to herein as a "nitrogen protecting group"). Amino protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino) acetamide, 3-(p-hydroxyphenyl) propanamide, 3-(0-nitrophenyl) propanamide, 2-methyl-2-(o-nitrophenoxy) propanamide, 2-methyl-2-(0-phenylazophenoxy) propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$a) include, but are not limited to, methyl carbamate, ethyl carbamante, 9-fluorenylmethyl carbamate (Fmoc), 9-(2-sulfo) fluorenylmethyl carbamate, 9-(2,7-dibromo) fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl) methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4 (4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-carbonyl derivative, N'-p-toluenesulfonylaminocarbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4 pyridone, N-methylamine, N-allylamine, N-[2-(trimethylsilyl) ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl) mesityl]methyleneamine, N-(N',N' dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

These and other exemplary substituents are described in more detail in the Detailed Description, the Examples and in the claims. The invention is not intended to be limited in any manner by the above exemplary listing of substituents.

As used herein, a "leaving group" is an art-understood term referring to a molecular fragment that departs with a pair of electrons in heterolytic bond cleavage, wherein the molecular fragment is an anion or neutral molecule. See, for example, Smith, March Advanced Organic Chemistry 6$^{th}$ ed. (501-502). Exemplary leaving groups include, but are not limited to, halo (e.g., chloro, bromo, iodo) and sulfonyl substituted hydroxyl groups (e.g., tosyl, mesyl, besyl).

As used herein, a "polymer" refers to a compound comprised of at least 3 (e.g., at least 10, 20, 30, 40, 50, 60, 70, 80, 90, 100, etc.) repeating covalently bound structural units.

As used herein, an "organic molecule" is a molecule comprising carbon, and encompasses large organic molecules and small organic molecules, as defined herein. The organic molecule may also comprise a metal. In this instance, the organic molecule is also referred to as an "organometallic compound."

As used herein, a "small organic molecule" or "small molecule" refers to an organic molecule with a molecular weight of less than 800 g/mol (e.g., less than 700 g/mol, less than 600 g/mol, less than 500 g/mol, less than 400 g/mol, less than 300 g/mol, less than 200 g/mol, less than 100 g/mol, between 50 to 800 g/mol, inclusive, between 100 to 800 g/mol, inclusive, or between 100 to 500 g/mol, inclusive). In certain embodiments, the small organic molecule is a therapeutically active agent such as a drug (e.g., a small organic molecule approved by the U.S. Food and Drug Administration as provided in the Code of Federal Regulations (CFR)). The small organic molecule may also comprise a metal. In this instance, the small organic molecule is also referred to as an "small organometallic molecule."

As used herein, a "large organic molecule" or "large molecule" refers to an organic compound with a molecular weight of greater than or equal to 800 g/mol (e.g., greater than 800 g/mol, greater than 900 g/mol, greater than 1000 g/mol, greater than 2000 g/mol, between 800 to 2000 g/mol, inclusive, between 1000 to 2000 g/mol, inclusive, or between 800 to 1000 g/mol, inclusive). In certain embodiments, the large organic molecule is a therapeutically active agent such as a drug (e.g., a large organic molecule approved by the U.S. Food and Drug Administration as provided in the Code of Federal Regulations (CFR)). The large organic molecule may also comprise a metal. In this instance, the large organic molecule is also referred to as an "large organometallic compound."

As used herein, an "inorganic molecule" is a molecule which comprises elements other than carbon, and encompasses large inorganic molecules and small inorganic molecules, as defined herein. If an inorganic molecule comprises a transition metal, it is also referred to herein as a "metal."

As used herein, a "small inorganic molecule" refers to an inorganic compound with a molecular weight of less than 800 g/mol (e.g., less than 700 g/mol, less than 600 g/mol, less than 500 g/mol, less than 400 g/mol, less than 300 g/mol, less than 200 g/mol, less than 100 g/mol, between 50 to 800 g/mol, inclusive, between 100 to 800 g/mol, inclusive, or between 100 to 500 g/mol, inclusive). In certain embodiments, the small inorganic molecule is a therapeutically active agent such as a drug (e.g., a small inorganic molecule approved by the U.S. Food and Drug Administration as provided in the Code of Federal Regulations (CFR)).

As used herein, a "large inorganic molecule" refers to an inorganic compound with a molecular weight of greater than or equal to 800 g/mol (e.g., greater than 800 g/mol, greater than 900 g/mol, greater than 1000 g/mol, greater than 2000 g/mol, between 800 to 2000 g/mol, inclusive, between 1000 to 2000 g/mol, inclusive, or between 800 to 1000 g/mol, inclusive). In certain embodiments, the large inorganic molecule is a therapeutically active agent such as a drug (e.g., a large inorganic molecule approved by the U.S. Food and Drug Administration as provided in the Code of Federal Regulations (CFR)).

As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describes pharmaceutically acceptable salts in detail in *J. Pharmaceutical Sciences* (1977) 66: 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quaternization of an amine using an appropriate electrophile, e.g., an alkyl halide, to form a quarternized alkylated amino salt.

As used herein, use of the phrase "at least one instance" refers to one instance, but also encompasses more than one instance, e.g., for example, from 1 instance to 50 instances.

"Molar mass averages": Different average values (e.g., $M_n$, $M_w$, $M_v$ and $M_z$) can be defined depending upon the statistical method that is applied. The weighted mean can be taken with the weight fraction, the mole fraction, or the volume fraction (see, e.g., R. J. Young and P. A. Lovell, Introduction to Polymers, 1991, incorporated herein by reference).

| Dispersity (D) | $M_w/M_n$ |
|---|---|
| Number average molar mass ($M_n$) | $M_n = \dfrac{\sum M_i N_i}{\sum N_i}$ |
| Weight average molar mass ($M_w$) | $M_w = \dfrac{\sum M_i^2 N_i}{\sum M_i N_i}$ |
| Z average molar mass ($M_z$) | $M_z = \dfrac{\sum M_i^3 N_i}{\sum M_i^2 N_i}$ |
| Viscosity average molar mass ($M_v$) | $M_v = \left[\dfrac{\sum M_i^{1+a} N_i}{\sum M_i N_i}\right]^{1/a}$ | wherein "a" is the exponent in the Mark-Houwink equation

"Dispersity": Dispersity (D) is a measure of the distribution of molecular mass in a given polymer sample and is calculated by dividing the weight average molar mass ($M_w$) by the number average molar mass ($M_n$). The dispersity of a given sample can have a value equal to or greater than 1. As the polymer chains approach uniform chain length, the dispersity approaches unity (1). The dispersity of a polymer can be modified, for example, using polymer fractionation (e.g., preparative SEC, Baker-Williams fractionation, continuous spin fractionation), or modifying the work-up procedure (e.g., by partially dissolving a polymer, an insoluble high molar mass fraction may be filtered off resulting in a large reduction in $M_w$ and a small reduction in $M_n$, thus reducing polydispersity).

BRIEF DESCRIPTION OF THE DRAWINGS

FIGS. 1A-1U. FIGS. 1A-1R depict PEI and aza-macrocycle precursors (FIG. 1A); a general synthetic method for the conjugation of various epoxide-terminated groups to the precursors (FIG. 1B); exemplary conjugated $LPEI_{600}$ polymers synthesized according to the present method (FIG. 1C); exemplary conjugated $BPEI_{1800}$ polymers synthesized according to the present method (FIG. 1D); exemplary conjugated aza-macrocycles synthesized according to the present method (FIGS. 1E-1F); and NMR characterization of exemplary conjugated lipomers [FIGS. 1G-1U: $^1$H NMR (500 MHZ) spectra of 2J1 (FIG. 1G), 3I3 (FIG. 1H), 3I7 (FIG. 1I), 5H7 (FIG. 1J), 7C1 (FIG. 1K), 4C4 (FIG. 1L), 4C8 (FIG. 1M), 4D5 (FIG. 1N), 4D9 (FIG. 1O), 6B10 (FIG. 1P), 6C1 (FIG. 1Q), 7H4 (FIG. 1R), 7H8 (FIG. 1S), 7H10 (FIG. 1T), and 7I1 (FIG. 1U)].

FIG. 2A: Target gene expression for 750 lipomers tested at four different mass ratios at a dosage of 45 ng/well (20 nM). More lipomers reduce gene expression at a mass ratio of 10 and 15 than 5 and 2.5, as indicated by a larger curve "shoulder". FIG. 2B: Average target (Firefly) and off-target (Renilla) expression for 200 lipomers tested against HeLa cells at a dose of 45 ng/well. Target gene expression decreases from 78% to 63% as mass ratio increases, while off-target expression remains fairly constant, changing from 88% to 86%.

FIG. 4A: Tie2 expression shows a dose response profile suggesting an $IC_{50}$ concentration between 6.0 and 1.5 nM, indicating a high degree of in vitro potency. FIG. 4B: Control gene GapDH expression remains constant at all doses, indicative of negligible off-target effects.

FIG. 5A depicts the size of lipomers 3I7 and 7H8 during the formulation process. Before siRNA is added, lipomer particle size is stable at pH 5.3. Particle size remains stable after addition of siRNA at low pH. After dialysis to pH 7.4, 3I7 lipomer particle size increases while 7H8 lipomer particle size remains constant. Particle size varied from 20 to 130 nm, sizes which are known to increase nanoparticle efficacy (Peer et al. *Nature nanotechnology* (2007) 2: 751-760). FIG. 5B: 6C1 diameter measured over a period of 18 hours after formulation with cholesterol and conjugation to siRNA. Consistent lipomer particle size indicates that lipomer particles are stable overnight at temperatures ranging from 4° C. to 40° C.

FIG. 9A: When dosed systemically 1.5 mg/kg of siRNA complexed to lipomer 7H6, luciferase tumor expression was reduced by 51%, indicating that lipomers successfully delivered siRNA into tumor cells. Importantly, the gene expression was reduced after tail vein injection instead of intratumoral injection, since intratumoral injections have limited clinical relevance (if a clinician can inject into a tumor, they often can remove it). FIG. 9B: Tumor before and after injection with 7H6 targeting luciferase expression. Tumor gene expression is markedly reduced.

FIG. 12A: 7H8 size remained constant after the addition of siRNA and after extrusion, suggesting that electrostatic interactions are less important for particle stability. In contrast, 3I7 size was variable, particularly after dialysis, indicating that this particle could be useful for applications where pH-triggered physical transformations are needed. Both lipomers formed particles under 200 nm, suggesting they would be ideal for biological applications. FIG. 12B: In both cases, the zeta potential (a rough indicator of surface charge) of 7H8 and 3I7 decreased upon the addition of negatively charged siRNA. It became slightly negative after dialysis, indicating these particles may have reduced toxicity owing to high cationic profiles.

DETAILED DESCRIPTION OF CERTAIN EMBODIMENTS OF THE INVENTION

Figure 1A:
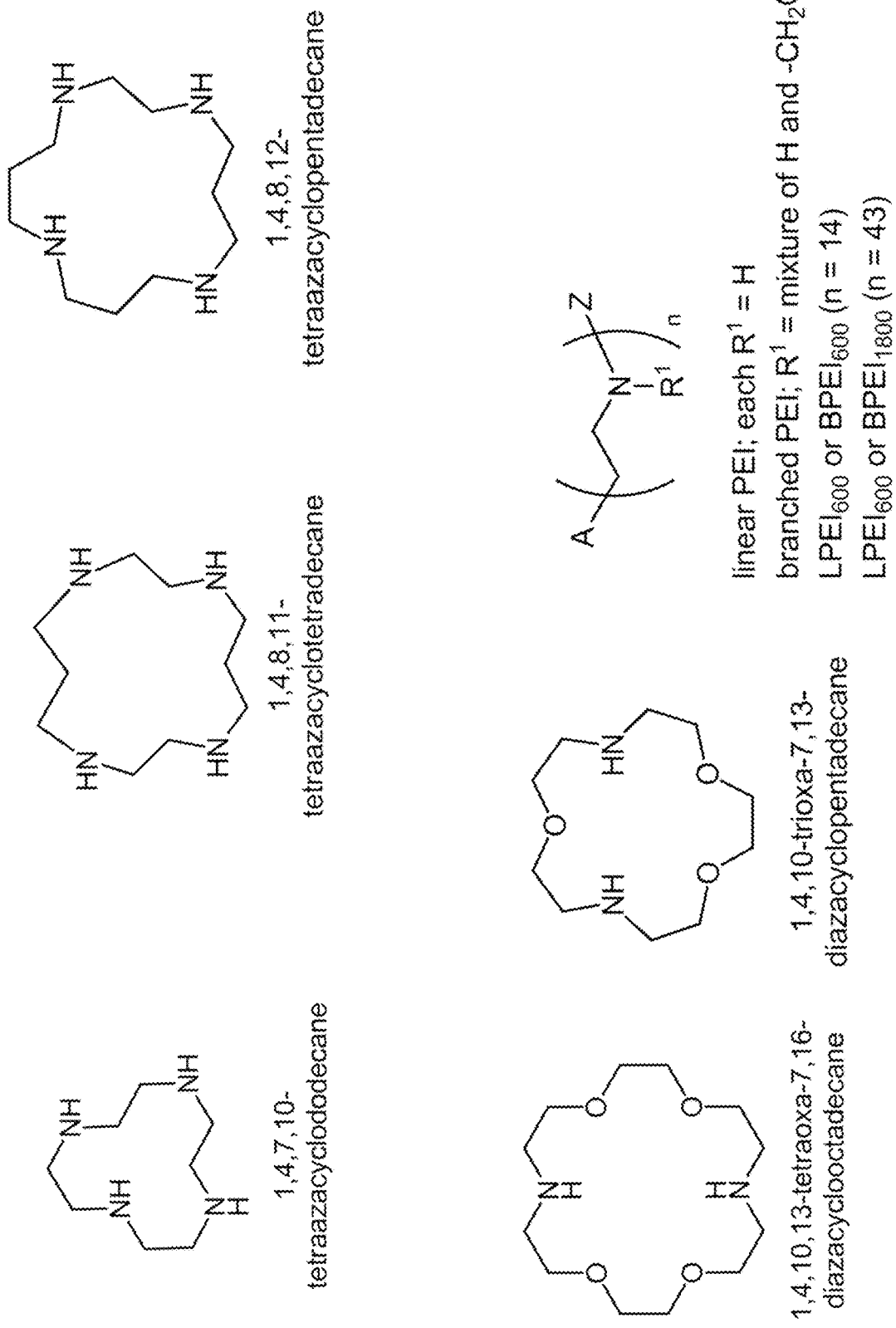

The present invention provides inventive conjugated polyethyleneimine polymers and conjugated aza-macrocycles (collectively referred to herein as "conjugated lipomers" or "lipomers") containing one or more groups of the formula (iii):

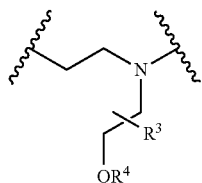

wherein $R^3$ and $R^4$ are as defined herein.

The conjugated polyethyleneimine polymers are preferably prepared from low molecular weight linear polyethyleneimine (LPEI) and branched polyethyleneimine (BPEI) polymers, i.e., having a number average molar mass (Mn) of ≤2000 (i.e., approximately ≤2 kDa).

Also provided are compositions comprising the inventive conjugated lipomers, and methods of preparation and use.

Conjugated Polyethyleneimine Polymers and Preparation Thereof

The present invention provides novel conjugated polyethyleneimine polymers and methods of their preparation.

In one aspect, provided is a conjugated polyethyleneimine polymer of the Formula (II):

or salt thereof; wherein:
each instance of $L^1$ is independently selected from formulae:

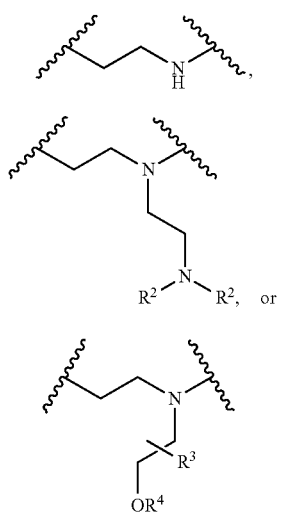

provided that at least one $L^1$ is selected from formulae (iii);
n is an integer of between 3 to 45, inclusive;
each instance of $R^2$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; a substituted or unsubstituted polyethyleneimine; or a group of the formula (iii'):

or the two $R^2$ groups are joined to form a substituted or unsubstituted heterocyclyl;
each instance of $R^3$ is independently substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or a hydrophilic polymer;
each instance of $R^4$ is independently hydrogen, acyl; silyl; a hydroxyl protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or a substituted or unsubstituted heteroaryl;
A is $-N(R^5)_2$, wherein each instance of $R^5$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or a group of the formula (iii'):

or two $R^5$ groups are joined to form a substituted or unsubstituted heterocyclyl; and
Z is hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl, or a group of the formula (iii'):

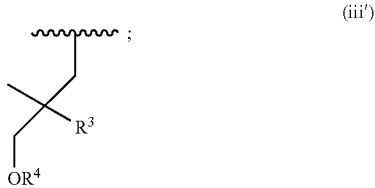

or Z and the nitrogen atom to which it is attached form a substituted or unsubstituted heterocyclyl group.

The inventive conjugated polyethyleneimine polymer of Formula (II), or salt thereof, is prepared by contacting a compound of Formula (I), or salt thereof (the "precursor polyethyleneimine polymer"), with one or more different epoxides of the formula (xii), e.g., provided below in Scheme I:

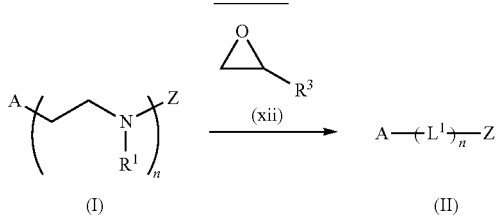

wherein each instance of $R^1$ is independently selected from hydrogen or a group of the formula (ii'):

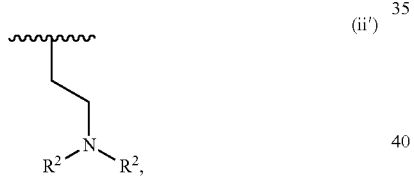

and A, Z, $L^1$, $R^2$, $R^3$, and n is as defined herein; provided that the number average molar mass (Mn) of the precursor polyethyleneimine polymer does not exceed 2000 g/mol (about 2 kDa).

Thus, it is understood that the number average molar mass (Mn) of the compound of Formula (II), as described herein, is approximately ≤2000 (i.e., approximately ≤2 kDa) after subtraction of the molecular weight of each instance of the group (iii') attached thereto:

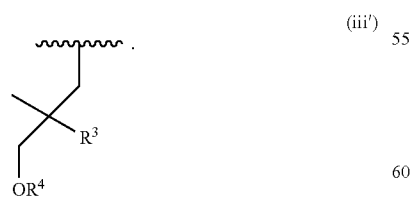

In certain embodiments, the conjugated polyethyleneimine polymer is prepared from low molecular weight precursor polyethyleneimine polymer, i.e., having a number average molar mass (Mn) of ≤2000 (i.e., approximately ≤2 kDa). In certain embodiments, the conjugated polyethyleneimine polymer is prepared from a precursor polyethyleneimine polymer having an number average molar mass (Mn) of less than 1900, less than 1800, less than 1700, less than 1600, less than 1500, less than 1400, less than 1300, less than 1200, less than 1100, less than 1000, less than 900, less than 800, or less than 700 g/mol. In certain embodiments, the precursor polyethyleneimine polymer has an number average molar mass (Mn) of between about 400 to about 2000, of between about 400 to about 1900, of between about 400 to about 1800, of between about 500 to about 1900, of between about 600 to about 1800 g/mol, of between about 600 to about 800, of between about 600 to about 700, of between about 700 to about 1800, of between about 800 to about 1800, of between about 900 to about 1800, or of between about 1000 to about 1800 g/mol, inclusive.

In certain embodiments, the compound of Formula (I) is a branched polyethyleneimine (BPEI) polymer, and at least one $R^1$ is of the formula (ii'); e.g., for example, 1 to 45, 1 to 40, 1 to 30, 1 to 20, 1 to 10, or 1 to 5, $R^1$ groups are of the formula (ii'). In certain embodiments, the compound of Formula (I) is a linear polyethyleneimine (LPEI) polymer, and each $R^1$ group is hydrogen.

In certain embodiments of Formula (I), neither $R^5$, Z, nor $R^2$ is a group of the formula (iii'). For example, in certain embodiments of Formula (I), each instance of $R^2$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or a substituted or unsubstituted polyethyleneimine;

A is $—N(R^5)_2$, wherein each instance of $R^5$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl; or the two $R^5$ groups are joined to form a substituted or unsubstituted heterocyclyl; and Z is hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl; or Z and the nitrogen atom to which it is attached form a substituted or unsubstituted heterocyclyl group.

In certain embodiments of Formula (I), A is $—N(R^5)_2$, wherein at least one $R^5$ is hydrogen. In certain embodiments of Formula (I) A is $—N(R^5)_2$, wherein each $R^5$ is hydrogen. In certain embodiments of Formula (I), Z is hydrogen.

Alternatively, in certain embodiments of Formula (II), either $R^5$, Z, and/or $R^2$ can be a group of the formula (iii) provided that at least one $R^2$, $R^5$ and/or Z is hydrogen in the precursor polyethyleneimine polymer. Thus, in certain embodiments of Formula (II), A is —N(R$^5$)$_2$, wherein each instance of R$^5$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or a group of the formula (iii'); or two R$^5$ groups are joined to form a substituted or unsubstituted heterocyclyl;

and Z is hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl, or a group of the formula (iii'); or Z and the nitrogen atom to which it is attached form a substituted or unsubstituted heterocyclyl group.

In certain embodiments of Formula (II), A is —N(R$^5$)$_2$, wherein each instance of R$^5$ is independently hydrogen; acyl; silyl; sulfonyl; an amino protecting group; substituted or unsubstituted alkyl; substituted or unsubstituted heteroalkyl; or a group of the formula (iii'). In certain embodiments of Formula (II), A is —N(R$^5$)$_2$, wherein each instance of R$^5$ is independently hydrogen; substituted or unsubstituted alkyl; substituted or unsubstituted heteroalkyl; or a group of the formula (iii').

In certain embodiments of Formula (II), Z is hydrogen; acyl; silyl; sulfonyl; an amino protecting group; substituted or unsubstituted alkyl; substituted or unsubstituted heteroalkyl; or a group of the formula (iii'). In certain embodiments of Formula (II), Z is hydrogen; substituted or unsubstituted alkyl; substituted or unsubstituted heteroalkyl; or a group of the formula (iii').

As generally defined above, n is an integer of between 3 to 45, inclusive. In certain embodiments, n is an integer of between 3 to 45, between 5 to 45, between 7 to 45, between 9 to 45, between 10 to 45, between 11 to 45, between 12 to 45, between 13 to 45, between 14 to 45, between 5 to 40, between 5 to 35, between 5 to 30, between 5 to 25, between 5 to 20, between 5 to 15, between 10 to 20, between 10 to 15, or between 40 to 45, inclusive. In certain embodiments, n is 14. In certain embodiments, n is 43.

As generally defined above, each instance of R$^2$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; a substituted or unsubstituted polyethyleneimine; or a group of the formula (iii'); or the two R$^2$ groups are joined to form a substituted or unsubstituted heterocyclyl.

In certain embodiments, each instance of R$^2$ is independently hydrogen; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; a substituted or unsubstituted polyethyleneimine; or a group of the formula (iii'); or the two R$^2$ groups are joined to form a substituted or unsubstituted heterocyclyl.

In certain embodiments, each instance of R$^2$ is independently hydrogen; substituted or unsubstituted alkyl; substituted or unsubstituted heteroalkyl; a substituted or unsubstituted polyethyleneimine; or a group of the formula (iii'); or the two R$^2$ groups are joined to form a substituted or unsubstituted heterocyclyl.

In certain embodiments, each instance of R$^2$ is independently hydrogen; a substituted or unsubstituted polyethyleneimine; or a group of the formula (iii').

In certain embodiments, at least one R$^2$ is a substituted or unsubstituted polyethyleneimine.

As used herein, a substituted or unsubstituted polyethyleneimine refers to a group of the formula (iv):

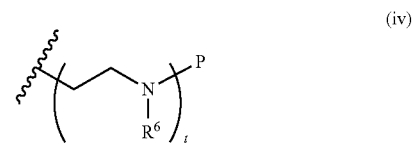

wherein:

t is an integer of between 1 to 50, inclusive;

P is hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or a group of the formula (iii'):

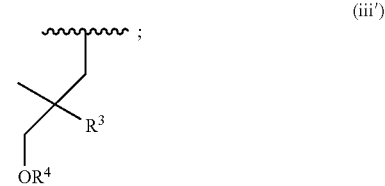

or

P, R$^6$, and the nitrogen atom to which it is attached form a substituted or unsubstituted heterocyclyl group; and each instance of R$^6$ is independently selected from hydrogen or a group of the formula (ii') or (iii'):

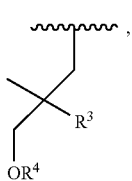

wherein $R^2$, $R^3$, and $R^4$ are as defined herein; provided that the number average molar mass (Mn) of the precursor polyethyleneimine polymer does not exceed 2000 g/mol (about 2 kDa).

In certain embodiments, t is an integer of between 1 to 40, between 1 to 30, between 1 to 20, between 1 to 10, between 1 to 5, or between 1 to 3, inclusive.

In certain embodiments of formula (iv), each instance of $R^2$ is hydrogen or a substituted or unsubstituted polyethyleneimine. For example, each instance of $R^6$ may comprise any number of branched polyethyleneimine groups, e.g., exemplary non-limiting examples include:

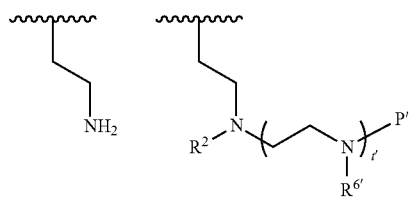

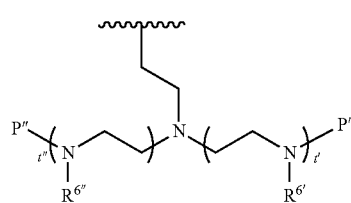

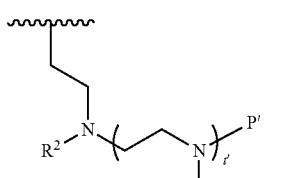

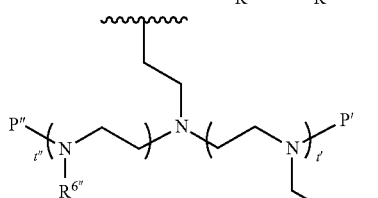

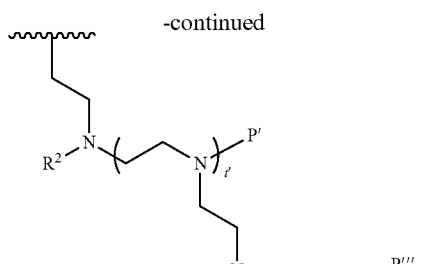

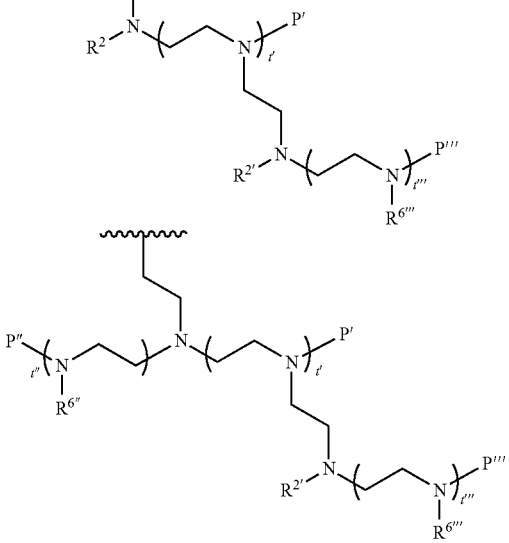

wherein:
each instance of t', t", and t'" is independently an integer of between 1 to 50, inclusive;
each instance of P', P", and P'" is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl, or a group of the formula (iii'):

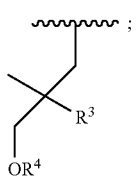

(iii')

or
P', P", and P'", the respective $R^{6\prime}$, $R^{6\prime\prime}$, and $R^{6\prime\prime\prime}$, and the nitrogen atom to which both are attached independently forms a substituted or unsubstituted heterocyclyl group; and
each instance of $R^{6\prime}$, $R^{6\prime\prime}$, and $R^{6\prime\prime\prime}$, is independently hydrogen or a group of the formula

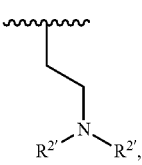

(ii')

-continued

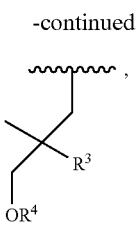
(iii')

wherein $R^{2'}$ is as defined as $R^2$, defined herein; provided that the number average molar mass (Mn) of the precursor polyethyleneimine polymer does not exceed 2000 g/mol (about 2 kDa).

In the instance, wherein at least one $R^2$ is a substituted or unsubstituted polyethyleneimine, the precursor polyethyleneimine polymer of the Formula (I) is a branched polyethyleneimine (BPEI) polymer, as defined herein, wherein P and $R^6$ of the precursor polyethyleneimine polymer of the Formula (I) are not a group of the formula (iii'). In this instance, the conjugated polyethyleneimine polymer further comprises at least one $L^1$ group of the formula (ii); e.g., 1 to 44, 1 to 40, 1 to 30, 1 to 20, 1 to 10, or 1 to 5 groups of the formula (ii). In certain embodiments, the conjugated polyethyleneimine polymer is prepared from a branched polyethyleneimine (BPEI) polymer having an number average molar mass (Mn) of less than 2000 g/mol (approximately 2 kDa). In certain embodiments, the conjugated polyethyleneimine polymer is prepared from a branched polyethyleneimine (BPEI) having an number average molar mass (Mn) of less than 1900, less than 1800, less than 1700, less than 1600, less than 1500, less than 1400, less than 1300, less than 1200, less than 1100, less than 1000, less than 900, less than 800, or less than 700 g/mol. In certain embodiments, the BPEI has an number average molar mass (Mn) of between about 400 to about 2000, of between about 400 to about 1900, of between about 400 to about 1800, of between about 500 to about 1900, of between about 600 to about 1800 g/mol, of between about 600 to about 800, of between about 600 to about 700, of between about 700 to about 1800, of between about 800 to about 1800, of between about 900 to about 1800, or of between about 1000 to about 1800 g/mol, inclusive.

In certain embodiments, the conjugated polyethyleneimine polymer is prepared from a branched polyethyleneimine (BPEI) polymer having an number average molar mass (Mn) of about 600 g/mol ($BPEI_{600}$). In this instance, in certain embodiments, n is 14.

In certain embodiments, the conjugated polyethyleneimine polymer is prepared from a branched polyethyleneimine (BPEI) polymer having an number average molar mass (Mn) of about 1800 g/mol ($BPEI_{1800}$). In this instance, in certain embodiments, n is 43.

In certain embodiments, the precursor polyethyleneimine polymer is a linear polyethyleneimine (LPEI), as defined herein. In this instance, the conjugated polyethyleneimine polymer does not comprise an $L^1$ group of the formula (ii). In certain embodiments, the conjugated polyethyleneimine polymer is prepared from a linear polyethyleneimine (LPEI) having an number average molar mass (Mn) of less than 2000 g/mol (approximately 2 kDa). In certain embodiments, the conjugated polyethyleneimine polymer is prepared from a linear polyethyleneimine (LPEI) having an number average molar mass (Mn) of less than 1900, less than 1800, less than 1700, less than 1600, less than 1500, less than 1400, less than 1300, less than 1200, less than 1100, less than 1000, less than 900, less than 800, or less than 700 g/mol. In certain embodiments, the LPEI has an number average molar mass (Mn) of between about 400 to about 2000, of between about 400 to about 1900, of between about 400 to about 1800, of between about 500 to about 1900, of between about 600 to about 1800 g/mol, of between about 600 to about 800, of between about 600 to about 700, of between about 700 to about 1800, of between about 800 to about 1800, of between about 900 to about 1800, or of between about 1000 to about 1800 g/mol, inclusive.

In certain embodiments, the LPEI polymer having an number average molar mass (Mn) of about 600 g/mol ($LPEI_{600}$). In this instance, in certain embodiments, n is 14.

In certain embodiments, the LPEI polymer having an number average molar mass (Mn) of about 1800 g/mol ($LPEI_{1800}$). In this instance, in certain embodiments, n is 43.

As generally defined above, the conjugated polyethyleneimine polymer comprises at least one instance (e.g., 1 to 44, 1 to 40, 1 to 30, 1 to 20, 1 to 10, or 1 to 5 instances) of a group of the formula (iii):

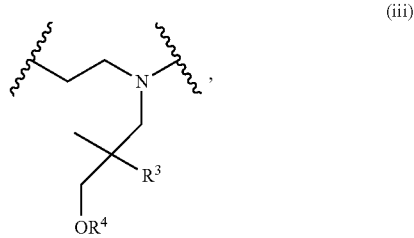
(iii)

wherein each instance of $R^3$ provided in the conjugated polyethyleneimine polymer is independently substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or a hydrophilic polymer; and each instance of $R^4$ is independently hydrogen, acyl; silyl; a hydroxyl protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl.

As generally defined above, each instance of $R^3$ is independently substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or a hydrophilic polymer.

In certain embodiments, each instance of $R^3$ is independently substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; or a hydrophilic polymer.

In certain embodiments, each instance of $R^3$ is independently substituted or unsubstituted alkyl; substituted or unsubstituted heteroalkyl; or a hydrophilic polymer.

In certain embodiments, at least one instance of $R^3$ is substituted or unsubstituted alkyl. In certain embodiments, at least one instance of $R^3$ is substituted or unsubstituted $C_{1-50}$alkyl. In certain embodiments, at least one instance of $R^3$ is substituted or unsubstituted $C_{8-50}$alkyl. In certain embodiments, at least one instance of $R^3$ is substituted or unsubstituted $C_{8-40}$alkyl. In certain embodiments, at least one instance of $R^3$ is substituted or unsubstituted $C_{8-30}$alkyl. In certain embodiments, at least one instance of $R^3$ is substituted or unsubstituted $C_{8-20}$alkyl.

In certain embodiments, at least one instance of $R^3$ is an unsubstituted alkyl. Exemplary unsubstituted alkyl groups include, but are not limited to, $-CH_3$, $-C_2H_5$, $-C_3H_7$, $-C_4H_9$, $-C_5H_{11}$, $-C_6H_{13}$, $-C_7H15$, $-C_8H_{17}$, $-C_9H_{19}$, $-C_{10}H_{21}$, $-C_{11}H_{23}$, $-C_{12}H_{25}$, $-C_{13}H_{27}$, $-C_{14}H_{29}$, $-C_{15}H_{31}$, $-C_{16}H_{33}$, $-C_{17}H35$, $-C_{18}H_{37}$, $-C_{19}H_{39}$, and $-C_{20}H_{41}$.

In certain embodiments, at least one instance of $R^3$ is a substituted alkyl. For example, in certain embodiments, at least one instance of $R^3$ is an alkyl substituted with one or more fluorine substituents. Exemplary substituted alkyl groups include, but are not limited to:

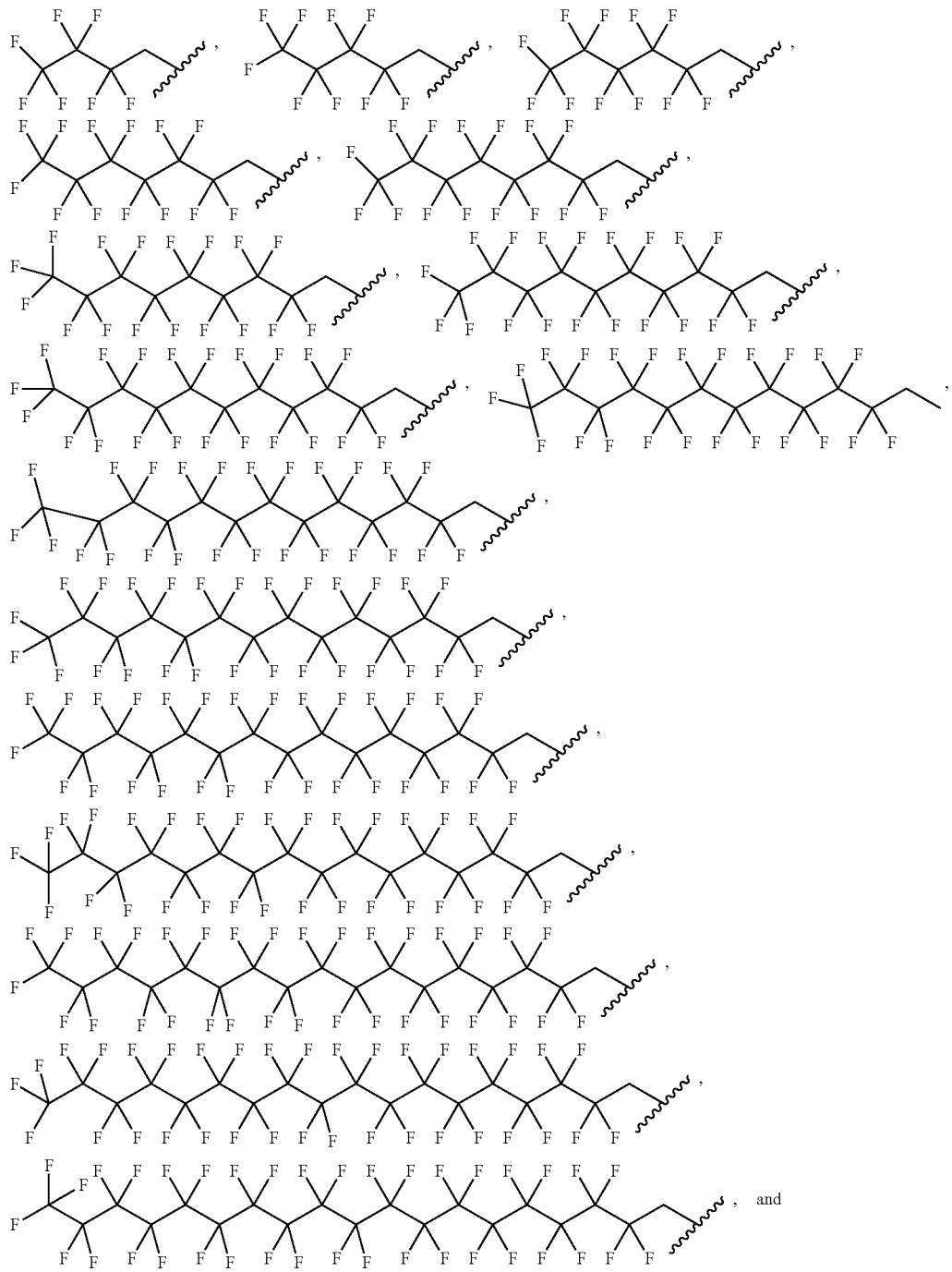

-continued

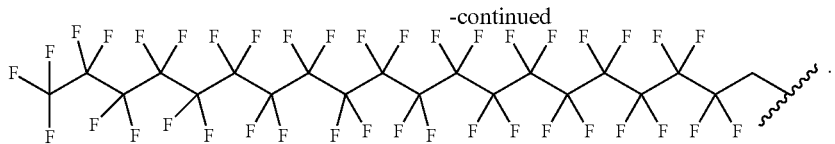

In certain embodiments, at least one instance of $R^3$ is substituted or unsubstituted alkenyl. In certain embodiments, at least one instance of $R^3$ is substituted or unsubstituted $C_{2-50}$alkenyl. In certain embodiments, at least one instance of $R^3$ is substituted or unsubstituted $C_{8-50}$ alkenyl. In certain embodiments, at least one instance of $R^3$ is substituted or unsubstituted $C_{8-40}$ alkenyl. In certain embodiments, at least one instance of $R^3$ is substituted or unsubstituted $C_{8-30}$ alkenyl. In certain embodiments, at least one instance of $R^3$ is substituted or unsubstituted $C_{8-20}$ alkenyl. In certain embodiments, at least one instance of $R^3$ is a substituted $C_{8-20}$ alkenyl. In certain embodiments, at least one instance of $R^3$ is an unsubstituted alkenyl.

Exemplary unsubstituted alkenyl groups include, but are not limited to:

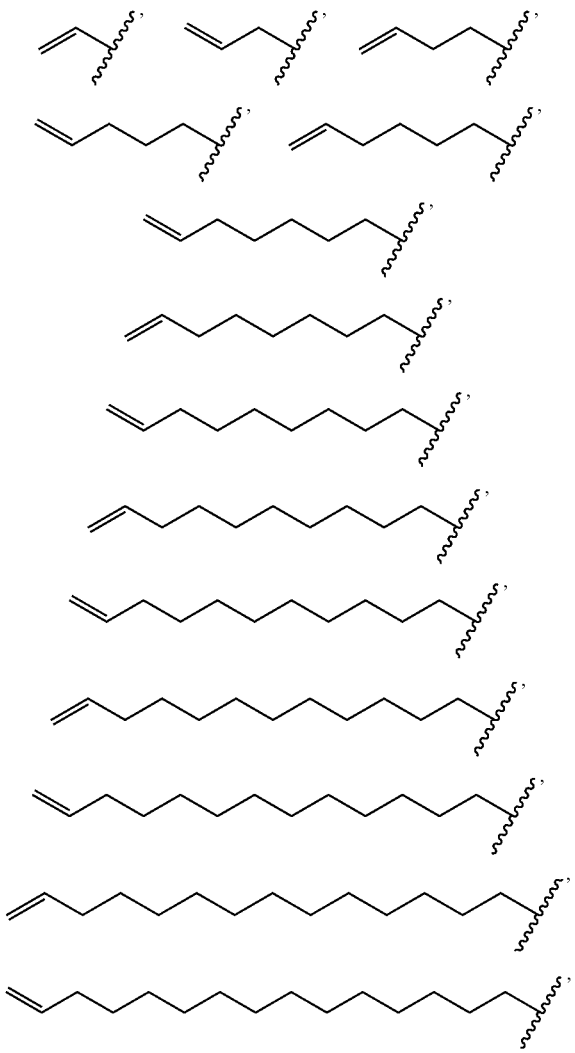

Myristoleic —$(CH_2)$—CH=CH$(CH_2)_3CH_3$,
Palmitoliec —$(CH_2)$—CH=CH$(CH_2)_5CH_3$,
Sapienic —$(CH_2)_4$CH=CH$(CH_2)_8CH_3$,
Oleic —$(CH_2)$—CH=CH$(CH_2)$—$CH_3$,
Linoleic —$(CH_2)$—CH=CHCH$_2$CH=CH$(CH_2)_4CH_3$,
α-Linolenic —$(CH_2)$—CH=CHCH$_2$CH=CHCH$_2$CH=CHCH$_2$CH$_3$,
Arachinodonic —$(CH_2)_3$CH=CHCH$_2$CH=CHCH$_2$CH=CHCH$_2$CH=CH$(CH_2)_4CH_3$,
Eicosapentaenoic —$(CH_2)_3$CH=CHCH$_2$CH=CHCH$_2$CH=CHCH$_2$CH=CHCH$_2$CH=CHCH$_2$CH$_3$,
Erucic —$(CH_2)_{11}$CH=CH$(CH_2)$—$CH_3$, and
Docosahexaenoic —$(CH_2)_2$CH=CHCH$_2$CH=CHCH$_2$CH=CHCH$_2$CH=CHCH$_2$CH=CHCH$_2$CH=CH$CH_2CH_3$.

In embodiments, wherein $R^3$ is defined as a $C_{6-50}$alkyl or $C_{6-50}$alkenyl groups, such groups are meant to encompass lipophilic groups (also referred to as a "lipid tail"). Lipophilic groups comprise a group of molecules that include fats, waxes, oils, fatty acids, and the like. Lipid tails present in these lipid groups can be saturated and unsaturated, depending on whether or not the lipid tail comprises double bonds. The lipid tail can also comprise different lengths, often categorized as medium (i.e., with tails between 7-12 carbons, e.g., $C_{7-12}$ alkyl or $C_{7-12}$ alkenyl), long (i.e., with tails greater than 12 carbons and up to 22 carbons, e.g., $C_{13-22}$ alkyl or $C_{13-22}$ alkenyl), or very long (i.e., with tails greater than 22 carbons, e.g., $C_{23-30}$ alkyl or $C_{23-30}$ alkenyl).

In certain embodiments, at least one instance of $R^3$ is substituted or unsubstituted alkynyl. In certain embodiments, at least one instance of $R^3$ is substituted or unsubstituted $C_{2-50}$alkynyl. In certain embodiments, at least one instance of $R^3$ is substituted or unsubstituted $C_{8-50}$ alkynyl. In certain embodiments, at least one instance of $R^3$ is substituted or unsubstituted $C_{8-40}$ alkynyl. In certain embodiments, at least one instance of $R^3$ is substituted or unsubstituted $C_{8-30}$ alkynyl. In certain embodiments, at least one instance of $R^3$ is substituted or unsubstituted $C_{8-20}$ alkynyl. In certain embodiments, at least one instance of $R^3$ is an unsubstituted alkynyl. In certain embodiments, at least one instance of $R^3$ is a substituted alkynyl.

In certain embodiments, at least one instance of $R^3$ is substituted or unsubstituted heteroalkyl. In certain embodiments, at least one instance of $R^3$ is substituted or unsubstituted $C_{1-50}$ heteroalkyl. In certain embodiments, at least one instance of $R^3$ is substituted or unsubstituted $C_{8-50}$ heteroalkyl. In certain embodiments, at least one instance of $R^3$ is substituted or unsubstituted $C_{8-40}$ heteroalkyl. In certain embodiments, at least one instance of $R^3$ is substituted or unsubstituted $C_{8-30}$ heteroalkyl. In certain embodiments, at least one instance of $R^3$ is substituted or unsubstituted $C_{8-20}$ heteroalkyl. In certain embodiments, at least one instance of $R^3$ is a substituted heteroalkyl. In certain embodiments, at least one instance of $R^3$ is an unsubstituted heteroalkyl.

Exemplary unsubstituted heteroalkyl groups include, but are not limited to:

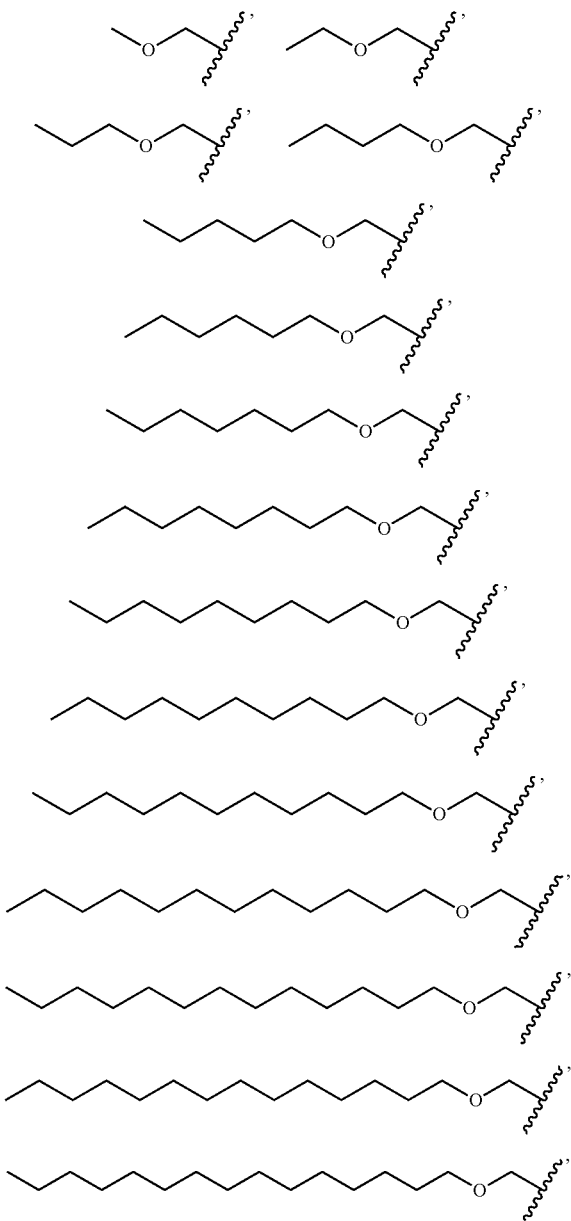
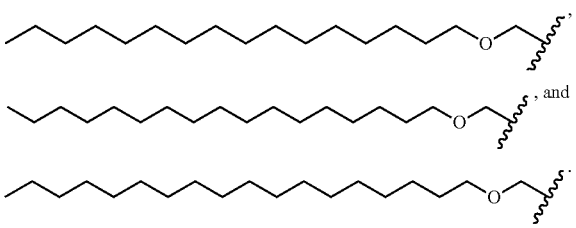

In certain embodiments, at least one instance of $R^3$ is substituted or unsubstituted heteroalkenyl. In certain embodiments, at least one instance of $R^3$ is substituted or unsubstituted $C_{2-50}$ heteroalkenyl. In certain embodiments, at least one instance of $R^3$ is substituted or unsubstituted $C_{8-50}$ heteroalkenyl. In certain embodiments, at least one instance of $R^3$ is substituted or unsubstituted $C_{8-40}$ heteroalkenyl. In certain embodiments, at least one instance of $R^3$ is substituted or unsubstituted $C_{8-30}$ heteroalkenyl. In certain embodiments, at least one instance of $R^3$ is substituted or unsubstituted $C_{8-20}$ heteroalkenyl. In certain embodiments, at least one instance of $R^3$ is a substituted heteroalkenyl. In certain embodiments, at least one instance of $R^3$ is an unsubstituted heteroalkenyl.

In certain embodiments, at least one instance of $R^3$ is substituted or unsubstituted heteroalkynyl. In certain embodiments, at least one instance of $R^3$ is substituted or unsubstituted $C_{2-50}$ heteroalkynyl. In certain embodiments, at least one instance of $R^3$ is substituted or unsubstituted $C_{8-50}$ heteroalkynyl. In certain embodiments, at least one instance of $R^3$ is substituted or unsubstituted $C_{8-40}$ heteroalkynyl. In certain embodiments, at least one instance of $R^3$ is substituted or unsubstituted $C_{8-30}$ heteroalkynyl. In certain embodiments, at least one instance of $R^3$ is substituted or unsubstituted $C_{8-20}$ heteroalkynyl. In certain embodiments, at least one instance of $R^3$ is a substituted heteroalkynyl. In certain embodiments, at least one instance of $R^3$ is an unsubstituted heteroalkynyl.

In certain embodiments, at least one instance of $R^3$ is substituted or unsubstituted carbocyclyl. In certain embodiments, at least one instance of $R^3$ is a substituted carbocyclyl. In certain embodiments, at least one instance of $R^3$ is an unsubstituted carbocyclyl.

In certain embodiments, at least one instance of $R^3$ is substituted or unsubstituted heterocyclyl. In certain embodiments, at least one instance of $R^3$ is a substituted heterocyclyl. In certain embodiments, at least one instance of $R^3$ is an unsubstituted heterocyclyl.

In certain embodiments, at least one instance of $R^3$ is substituted or unsubstituted aryl. In certain embodiments, at least one instance of $R^3$ is an unsubstituted aryl. In certain embodiments, at least one instance of $R^3$ is a substituted aryl.

In certain embodiments, at least one instance of $R^3$ is substituted or unsubstituted heteroaryl. In certain embodiments, at least one instance of $R^3$ is a substituted heteroaryl. In certain embodiments, at least one instance of $R^3$ is an unsubstituted heteroaryl.

In certain embodiments, at least one instance of $R^3$ is hydrophilic polymer. As used herein, a "polymer" refers to a compound comprised of at least 3 (e.g., at least 10, 20, 30, 40, 50, 60, 70, 80, 90, 100, etc.) repeating covalently bound structural units. By extension, a "hydrophilic polymer" is a polymer, as defined herein, further comprising at least one group (e.g., an oxygen, nitrogen, and/or sulfur atom) in the repeating structural unit capable of hydrogen bonding. The hydrophilic polymer is preferably biocompatible (i.e., non-toxic). Exemplary hydrophilic polymers include, but are not limited to, polypeptides (e.g., poly-L-lysine), cellulose polymers (e.g., hydroxyethylcellulose, ethylcellulose, carboxymethylcellulose, methyl cellulose, hydroxypropylmethylcellulose (HPMC)), dextran polymers, polymaleic acid polymers, poly(acrylic acid) polymers, poly(vinylalcohol) polymers, polyvinylpyrrolidone (PVP) polymers, and polyethyleneglycol (PEG) polymers.

In certain embodiments, the hydrophilic polymer is a polyethyleneglycol polymer, e.g., of the formula (v):

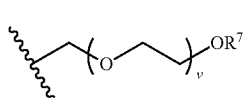

(v)

wherein:
$R^7$ is hydrogen; acyl; silyl; a hydroxyl protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl; and
v is an integer between 3 to 400, inclusive.

In certain embodiments, $R^7$ is hydrogen. In certain embodiments, $R^7$ is acyl. In certain embodiments, $R^7$ is a hydroxyl protecting group. In certain embodiments, $R^7$ is substituted or unsubstituted alkyl. In certain embodiments, $R^7$ is a substituted alkyl. In certain embodiments, $R^7$ is an unsubstituted alkyl. In certain embodiments, $R^7$ is —$CH_3$ (a "polyethyleneglycol monomethylether" polymer). In certain embodiments, $R^7$ is substituted or unsubstituted alkenyl. In certain embodiments, $R^7$ is substituted or unsubstituted alkynyl. In certain embodiments, $R^7$ is substituted or unsubstituted heteroalkyl. In certain embodiments, $R^7$ is substituted or unsubstituted heteroalkenyl. In certain embodiments, $R^7$ is substituted or unsubstituted heteroalkynyl. In certain embodiments, $R^7$ is substituted or unsubstituted carbocyclyl. In certain embodiments, $R^7$ is substituted or unsubstituted heterocyclyl. In certain embodiments, $R^7$ is substituted or unsubstituted aryl. In certain embodiments, $R^7$ is and substituted or unsubstituted heteroaryl.

In certain embodiments, v is an integer between 3 to 300, 3 to 200, 3 to 100, 3 to 90, 3 to 80, 3 to 70, 3 to 60, 3 to 50, 5 to 50, 10 to 50, 15 to 50, 20 to 50, 20 to 40, 20 to 30, 20 to 25, 30 to 50, and 40 to 50, inclusive. $PEG_{1000}$ corresponds, on average, to a v of about 22.7, wherein $R^7$ is —$OCH_3$. $PEG_{2000}$ corresponds, on average, to a v of about 45.4.

In certain embodiments, the number average molar mass (Mn) of the polyethyleneglycol polymer is ≤10,000. In certain embodiments, the number average molar mass (Mn) of the polyethyleneglycol polymer is ≤10,000, ≤9000, ≤8000, ≤7000, ≤6000, ≤5000, ≤4000, ≤3000, or ≤2000. In certain embodiments, the number average molar mass (Mn) of the polyethyleneglycol polymer is between about 100 to about 10,000, inclusive; e.g., between about 100 to about 5000, between about 100 to about 4000, between about 100 to about 3000, between about 100 to about 2500, between about 100 to about 2000, between about 100 to about 1500, between about 100 to about 1000, between about 100 to about 900, between about 100 to about 800, between about 100 to about 700, between about 100 to about 600, between about 100 to about 500, between about 100 to about 400, between about 100 to about 300, between about 100 to about 200, between about 100 to about 1500, between about 2500 to about 10000, between about 2500 to about 9000, between about 2500 to about 8000, between about 2500 to about 7000, between about 2500 to about 6000, between about 2500 to about 5000, between about 2500 to about 4000, or between about 2500 to about 3000, inclusive. In certain embodiments, the number average molar mass (Mn) of the polyethyleneglycol polymer is 1000 ($PEG_{1000}$). In certain embodiments, the number average molar mass (Mn) of the polyethyleneglycol polymer is 2000 ($PEG_{2000}$). A 1:1 mixture of $PEG_{1000}$ and $PEG_{2000}$ is referred to herein as $PEG_{1.5K}$.

In certain embodiments, at least one instance of $R^3$ is a hydrophilic polymer, and at least one instance of $R^3$ is a substituted or unsubstituted alkyl.

As used herein, when the group $R^3$ is depicted as bisecting a carbon-carbon bond, e.g., of the group of the formula (iii), it is understood that $R^3$ may be substituted at either carbon.

Nucleophilic attack of an amino group of the polyethyleneimine polymer at the least sterically hindered carbon of the epoxide provides a group of the formula (iii-a) (route a), while nucleophilic attack at the more sterically hindered carbon of the epoxide provides a group of the formula (iii-b) (route b), wherein $R^4$ is hydrogen; see, e.g., the "conjugation reaction" of Scheme II.

It is understood that compounds of the present invention may comprise a mixture of products attached thereto arising from route (a) and route (b) depending on the preference, or lack thereof, of the mode of addition, and that formulae that depict this bisecting bond may comprise a mixture of compounds. The bisecting group $R^3$ depicted in the formulae seeks to encompasses all contemplated modes of addition.

Scheme II.

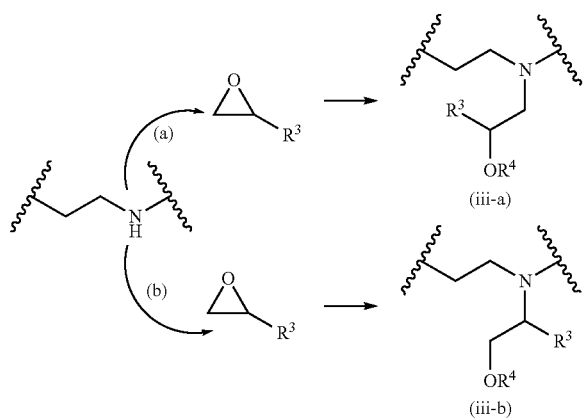

The resulting hydroxyl moiety of the formula (iii-a) or (iii-b), wherein $R^4$ is hydrogen, can optionally be converted to a substituted hydroxyl, wherein $R^4$ is a group other than hydrogen, i.e., is independently selected from acyl; silyl; a hydroxyl protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl; using conventional methods. Alkylation, acylation, and/or protection of a hydroxyl moiety are well-known in the art; see, e.g., *Protecting Groups in Organic Synthesis*, T. W. Greene and P. G. M. Wuts, 3$^{rd}$ edition, John Wiley & Sons, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

For example, in certain non-limiting embodiments, the hydroxyl moiety is reacted with an electrophile of the formula $R^4$—X wherein $R^4$ is a group other than hydrogen, and X is a leaving group, to provide a substituted hydroxyl group in formula (iii).

In certain embodiments, each instance of $R^4$ is independently hydrogen; acyl; silyl; a hydroxyl protecting group; substituted or unsubstituted alkyl; substituted or unsubstituted alkenyl; substituted or unsubstituted alkynyl; substituted or unsubstituted heteroalkyl; or substituted or unsubstituted heteroalkenyl. In certain embodiments, each instance of $R^4$ is independently hydrogen; substituted or unsubstituted alkyl; or substituted or unsubstituted heteroalkyl. In certain embodiments, each instance of $R^4$ is hydrogen.

It is understood from the present disclosure that the group of formula (iii) represents a group of formula (iii-a) or a group of formula (iii-b):

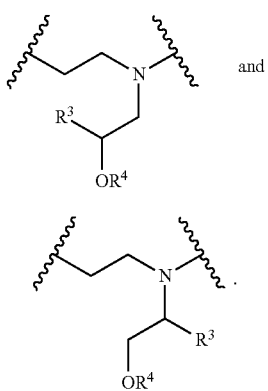

(iii-a) and (iii-b)

In certain embodiments, the conjugation reaction depicted in Scheme II results in a mixture comprising more lipomers conjugated to a group of formula (iii-a) than to a group of formula (iii-b), e.g., the reaction mixture comprises greater than 50%, greater than 60%, greater than 70%, greater than 80%, greater than 90%, greater than 95%, greater than 99%, between about 60% to about 100%, between about 70% to about 100%, between about 80% to about 100%, between about 90% to about 100%, between about 95% to about 100%, or between about 99% to about 100%, of a conjugated lipomer attached to a group of formula (iii-a).

In certain embodiments, the reaction mixture comprises only conjugated lipomers attached to a group formula (iii-a).

In certain embodiments, the epoxide is chiral, i.e., having (R) or (S) stereochemistry. In this instance, in certain embodiments, the conjugation reaction depicted in Scheme II provides a chiral conjugated polyethyleneimine polymer. Chirality in a polymer can be characterized in a variety of ways, e.g., obtaining the optical rotation and/or NMR analysis after chemical modification of the optically active polymer with a chiral derivatizing agent are methods useful in evaluating the chirality of a polymer.

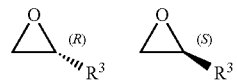

In certain embodiments, wherein the epoxide is chiral, the conjugation reaction depicted in Scheme II results in a mixture comprising more lipomers conjugated to a group of formula (R)-(iii-a) than to a group of formula(S)-(iii-a), e.g., the reaction mixture comprises greater than 50%, greater than 60%, greater than 70%, greater than 80%, greater than 90%, greater than 95%, greater than 99%, between about 60% to about 100%, between about 70% to about 100%, between about 80% to about 100%, between about 90% to about 100%, between about 95% to about 100%, or between about 99% to about 100%, of a conjugated lipomer attached to a group of formula (R)-(iii-a).

In certain embodiments, reaction mixture comprises only conjugated lipomers attached to a group formula (R)-(iii-a).

In certain embodiments, wherein the epoxide is chiral, the conjugation reaction depicted in Scheme II results in a mixture comprising more lipomers conjugated to a group of formula formula(S)-(iii-a) than formula (R)-(iii-a), e.g., the reaction mixture comprises greater than 50%, greater than 60%, greater than 70%, greater than 80%, greater than 90%, greater than 95%, greater than 99%, between about 60% to about 100%, between about 70% to about 100%, between about 80% to about 100%, between about 90% to about 100%, between about 95% to about 100%, or between about 99% to about 100%, of a conjugated lipomer attached to a group of formula(S)-(iii-a).

In certain embodiments, reaction mixture comprises only conjugated lipomers attached to a group formula(S)-(iii-a).

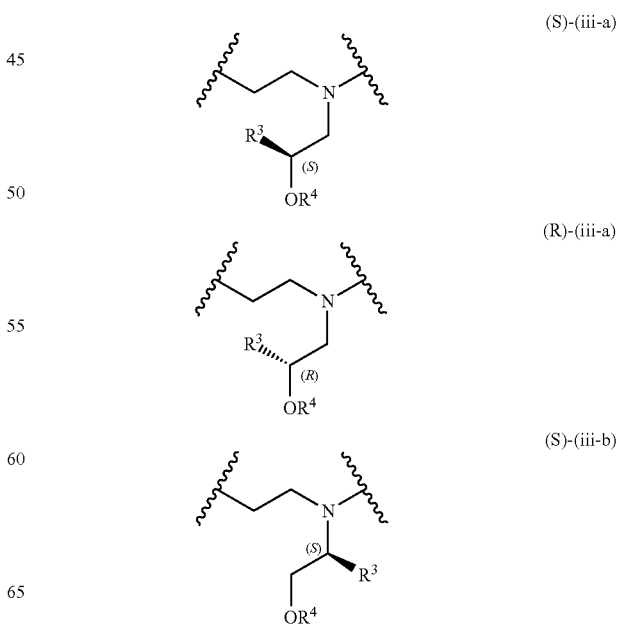

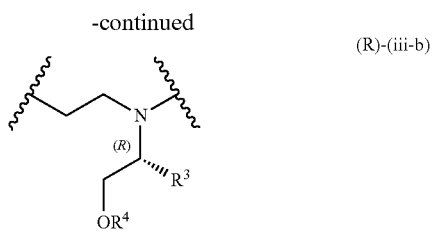

(R)-(iii-b)

In certain embodiments, wherein one epoxide is used in the conjugation reaction, each instance of $R^3$ is the same in the conjugated polyethyleneimine polymer. For example, in certain embodiments, each instance of $R^3$ is the same wherein $R^3$ is a substituted or unsubstituted alkyl. In certain embodiments, each instance of $R^3$ is the same wherein $R^3$ is an unsubstituted alkyl. In certain embodiments, each instance of $R^3$ is the same wherein $R^3$ is selected from the group consisting of —$CH_3$, —$C_2H_5$, —$C_3H_7$, —$C_4H_9$, —$C_5H_{11}$, —$C_6H_{13}$, —$C_7H15$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H35$, —$C_{18}H_{37}$, —$C_{19}H_{39}$, and —$C_{20}H_{41}$. In certain embodiments, each instance of $R^3$ is the same wherein $R^3$ is selected from the group consisting of —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, and —$C_{16}H_{33}$.

Alternatively, in certain embodiments, wherein more than one epoxide is used in the conjugation reaction (e.g., two, three, four, five, six, seven, eight, nine, or ten different epoxides), the conjugated polyethyleneimine polymer comprises two or more (e.g., two, three, four, five, six, seven, eight, nine, or ten) different $R^3$ groups.

For example, in certain embodiments, two different epoxides are used in the conjugation reaction. In this instance, in certain embodiments, the conjugated polyethyleneimine polymer comprises two different $R^3$ groups. For example, in certain embodiments, the conjugated polyethyleneimine polymer comprises a mixture of two different $R^3$ groups, wherein the first $R^3$ group is a substituted or unsubstituted alkyl, and the second $R^3$ group is a hydrophilic polymer (e.g., a polyethyleneglycol polymer). In certain embodiments, the conjugated polyethyleneimine polymer comprises a mixture of two different $R^3$ groups, wherein the first $R^3$ group is an unsubstituted alkyl, and the second $R^3$ group is a polyethyleneglycol polymer. In certain embodiments, the conjugated polyethyleneimine polymer comprises a mixture of two different $R^3$ groups, wherein the first $R^3$ group is selected from the group consisting of —$CH_3$, —$C_2H_5$, —$C_3H_7$, —$C_4H_9$, —$C_5H_{11}$, —$C_6H_{13}$, —$C_7H15$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H35$, —$C_{18}H_{37}$, —$C_{19}H_{39}$, and —$C_{20}H_{41}$, and the second $R^3$ group is $PEG_{1000}$. In certain embodiments, the conjugated polyethyleneimine polymer comprises a mixture of two different $R^3$ groups, wherein the first $R^3$ group is selected from the group consisting of —$CH_3$, —$C_2H_5$, —$C_3H_7$, —$C_4H_9$, —$C_5H_{11}$, —$C_6H_{13}$, —$C_7H15$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H35$, —$C_{18}H_{37}$, —$C_{19}H_{39}$, and —$C_{20}H_{41}$, and the second $R^3$ group is $PEG_{2000}$.

In certain embodiments, three different epoxides are used in the conjugation reaction. In this instance, in certain embodiments, the conjugated polyethyleneimine polymer comprises three different $R^3$ groups. For example, in certain embodiments, the conjugated polyethyleneimine polymer comprises a mixture of three different $R^3$ groups, wherein the first $R^3$ group is a substituted or unsubstituted alkyl, the second $R^3$ group is a first hydrophilic polymer (e.g., a polyethyleneglycol polymer, e.g., $PEG_{1000}$), and the third $R^3$ group is a second hydrophilic polymer (e.g., a different polyethyleneglycol polymer, e.g., $PEG_{2000}$). In certain embodiments, the conjugated polyethyleneimine polymer comprises a mixture of three different $R^3$ groups, wherein the first $R^3$ group is an unsubstituted alkyl, the second $R^3$ group is $PEG_{1000}$, and the third $R^3$ group is $PEG_{2000}$. In certain embodiments, the conjugated polyethyleneimine polymer comprises a mixture of three different $R^3$ groups, wherein the first $R^3$ group is selected from the group consisting of —$CH_3$, —$C_2H_5$, —$C_3H_7$, —$C_4H_9$, —$C_5H_{11}$, —$C_6H_{13}$, —$C_7H15$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H35$, —$C_{18}H_{37}$, —$C_{19}H_{39}$, and —$C_{20}H_{41}$, the second $R^3$ group is $PEG_{1000}$, and the third $R^3$ group is $PEG_{2000}$. In certain embodiments a 1:1 mixture of $PEG_{1000}$ and $PEG_{2000}$ is used. In this instance, the mixture of the second $R^3$ group and the third $R^3$ group are referred to herein as $PEG_{1.5K}$.

In certain embodiments, the conjugated polymer comprises more of formula (iii) than of formula (i). For example, in certain embodiments, the ratio of groups of the formulae (i) to (iii) is between about 0:10 to about 9:10, inclusive. In certain embodiments, the ratio of groups of the formulae (i) to (iii) is between about 0:10 to about 9:10; between about 1:10 to about 8:10; between about 1:10 to about 7:10; between about 1:10 to about 6:10; between about 1:10 to about 5:10; or between about 2:10 to about 4:10, inclusive. In certain embodiments, the ratio of groups of the formulae (i) to (iii) is between about 3:10 to about 4:10, inclusive.

Alternatively, in certain embodiments, the conjugated polymer comprises more of formula (i) than of formula (iii). For example, in certain embodiments, the ratio of groups of the formulae (iii) to (i) is between about 0:10 to about 9:10, inclusive. In certain embodiments, the ratio of groups of the formulae (iiii) to (i) is between about 0:10 to about 9:10; between about 1:10 to about 8:10; between about 1:10 to about 7:10; between about 1:10 to about 6:10; between about 1:10 to about 5:10; or between about 2:10 to about 4:10, inclusive. In certain embodiments, the ratio of groups of the formulae (iii) to (i) is between about 3:10 to about 4:10, inclusive.

In certain embodiments, wherein the conjugated polyethyleneimine polymer comprises two different $R^3$ groups, the ratio of the second $R^3$ group to the first $R^3$ group is between about 0.01:10 to about 10:10, inclusive. In certain embodiments, the ratio of the second $R^3$ group to the first $R^3$ group is between about 0.02:10 to about 10:10; between about 0.03:10 to about 10:10; between about 0.04:10 to about 10:10; between about 0.05:10 to about 10:10; between about 0.06:10 to about 10:10; between about 0.07:10 to about 10:10; between about 0.08:10 to about 10:10; between about 0.08:10 to about 9:10; between about 0.08:10 to about 8:10; between about 0.08:10 to about 7:10; between about 0.08:10 to about 6:10; between about 0.08:10 to about 5:10; between about 0.08:10 to about 4:10; between about 0.08:10 to about 3:10; between about 0.08:10 to about 2:10; or between about 0.08:10 to about 1:10, inclusive. In certain embodiments, the ratio of the second $R^3$ group to the first $R^3$ group is about 0.1:10.

In certain embodiments, wherein the conjugated polyethyleneimine polymer comprises three different $R^3$ groups, the ratio of the sum of the second and third $R^3$ groups to the first $R^3$ group is between about 0.01:10 to about 10:10, inclusive. In certain embodiments, the ratio of the sum of the second and third $R^3$ groups to the first $R^3$ group is 0.02:10 to about 10:10; between about 0.03:10 to about 10:10; between about 0.04:10 to about 10:10; between about 0.05:10 to about 10:10; between about 0.06:10 to about 10:10; between about 0.07:10 to about 10:10; between about 0.08:10 to about 10:10; between about 0.08:10 to about 9:10; between about 0.08:10 to about 8:10; between about 0.08:10 to about 7:10; between about 0.08:10 to about 6:10; between about 0.08:10 to about 5:10; between about 0.08:10 to about 4:10; between about 0.08:10 to about 3:10; between about 0.08:10 to about 2:10; or between about 0.08:10 to about 1:10, inclusive. In certain embodiments, the ratio of the sum of the second and third $R^3$ groups to the first $R^3$ group is about 0.1:10.

Exemplary conjugated polyethyleneimine polymers of the Formula (II) include, but are not limited to, any of the following LPEI conjugated polymers and BPEI conjugated polymers, or salts thereof, provided in Tables 1 and 2, defining the one or more $L_1$ groups present along the polymer backbone.

TABLE 1

LPEI conjugated polymers

TABLE 1-continued

| | (i) | (ii) | (iii) |
|---|---|---|---|
| 8 | — | N, CH₂OH, C₉H₁₉ | N, CH₂OH, R³ |
| 9 | — | N, CH₂OH, C₁₀H₂₁ | — |
| 10 | NH | N, CH₂OH, C₁₀H₂₁ | — |
| 11 | NH | N, CH₂OH, C₁₀H₂₁ | N, CH₂OH, R³ |
| 12 | — | N, CH₂OH, C₁₀H₂₁ | N, CH₂OH, R³ |
| 13 | — | N, CH₂OH, C₁₁H₂₃ | — |
| 14 | NH | N, CH₂OH, C₁₁H₂₃ | — |
| 15 | NH | N, CH₂OH, C₁₁H₂₃ | N, CH₂OH, R³ |
| 16 | — | N, CH₂OH, C₁₁H₂₃ | N, CH₂OH, R³ |

TABLE 1-continued

| | (i) | (ii) | (iii) |
|---|---|---|---|
| 17 | — | N(CH₂CH(OH)C₁₂H₂₅) | — |
| 18 | NH | N(CH₂CH(OH)C₁₂H₂₅) | — |
| 19 | NH | N(CH₂CH(OH)C₁₂H₂₅) | N(CH₂CH(OH)R³) |
| 20 | — | N(CH₂CH(OH)C₁₂H₂₅) | N(CH₂CH(OH)R³) |
| 21 | — | N(CH₂CH(OH)C₁₃H₂₇) | — |
| 22 | NH | N(CH₂CH(OH)C₁₃H₂₇) | — |
| 23 | NH | N(CH₂CH(OH)C₁₃H₂₇) | N(CH₂CH(OH)R³) |
| 24 | — | N(CH₂CH(OH)C₁₃H₂₇) | N(CH₂CH(OH)R³) |
| 25 | — | N(CH₂CH(OH)C₁₄H₂₉) | — |

TABLE 1-continued

LPEI conjugated polymers

| | (i) | (ii) | (iii) |
|---|---|---|---|
| 26 | —NH— structure | —N(CH₂CH(OH)C₁₄H₂₉)— | — |
| 27 | —NH— structure | —N(CH₂CH(OH)C₁₄H₂₉)— | —N(CH₂CH(OH)R³)— |
| 28 | — | —N(CH₂CH(OH)C₁₄H₂₉)— | —N(CH₂CH(OH)R³)— |
| 29 | — | —N(CH₂CH(OH)C₁₅H₃₁)— | — |
| 30 | —NH— structure | —N(CH₂CH(OH)C₁₅H₃₁)— | — |
| 31 | —NH— structure | —N(CH₂CH(OH)C₁₅H₃₁)— | —N(CH₂CH(OH)R³)— |
| 32 | — | —N(CH₂CH(OH)C₁₅H₃₁)— | —N(CH₂CH(OH)R³)— |
| 33 | — | —N(CH₂CH(OH)C₁₆H₃₃)— | — |
| 34 | —NH— structure | —N(CH₂CH(OH)C₁₆H₃₃)— | — |

TABLE 1-continued

LPEI conjugated polymers

| | (i) | (iii) | (iii) |
|---|---|---|---|
| 35 | [structure: -(CH2)n-NH-] | [structure: -(CH2)n-N- with CH(C16H33)CH2OH substituent] | [structure: -(CH2)n-N- with CH(R3)CH2OH substituent] |
| 36 | — | [structure: -(CH2)n-N- with CH(C16H33)CH2OH substituent] | [structure: -(CH2)n-N- with CH(R3)CH2OH substituent] |

TABLE 2

BPEI conjugated polymers

| | (i) | (ii) | (iii) | (iii) |
|---|---|---|---|---|
| 1 | — | [structure: -(CH2)n-N- with CH2CH2NR2 substituent] | [structure: -(CH2)n-N- with CH(C8H17)CH2OH substituent] | — |
| 2 | [structure: -(CH2)n-NH-] | [structure: -(CH2)n-N- with CH2CH2NR2 substituent] | [structure: -(CH2)n-N- with CH(C8H17)CH2OH substituent] | — |
| 3 | [structure: -(CH2)n-NH-] | [structure: -(CH2)n-N- with CH2CH2NR2 substituent] | [structure: -(CH2)n-N- with CH(C8H17)CH2OH substituent] | [structure: -(CH2)n-N- with CH(R3)CH2OH substituent] |
| 4 | — | [structure: -(CH2)n-N- with CH2CH2NR2 substituent] | [structure: -(CH2)n-N- with CH(C8H17)CH2OH substituent] | [structure: -(CH2)n-N- with CH(R3)CH2OH substituent] |
| 5 | — | [structure: -(CH2)n-N- with CH2CH2NR2 substituent] | [structure: -(CH2)n-N- with CH(C9H19)CH2OH substituent] | — |

TABLE 2-continued

BPEI conjugated polymers

| | (i) | (ii) | (iii) | (iii) |
|---|---|---|---|---|
| 6 | -CH$_2$CH$_2$-NH- | -CH$_2$CH$_2$-N(CH$_2$CH$_2$NR$^2$)- | -CH$_2$CH$_2$-N(CH$_2$CH(C$_9$H$_{19}$)OH)- | — |
| 7 | -CH$_2$CH$_2$-NH- | -CH$_2$CH$_2$-N(CH$_2$CH$_2$NR$^2$)- | -CH$_2$CH$_2$-N(CH$_2$CH(C$_9$H$_{19}$)OH)- | -CH$_2$CH$_2$-N(CH$_2$CH(R$^3$)OH)- |
| 8 | — | -CH$_2$CH$_2$-N(CH$_2$CH$_2$NR$^2$)- | -CH$_2$CH$_2$-N(CH$_2$CH(C$_9$H$_{19}$)OH)- | -CH$_2$CH$_2$-N(CH$_2$CH(R$^3$)OH)- |
| 9 | — | -CH$_2$CH$_2$-N(CH$_2$CH$_2$NR$^2$)- | -CH$_2$CH$_2$-N(CH$_2$CH(C$_{10}$H$_{21}$)OH)- | — |
| 10 | -CH$_2$CH$_2$-NH- | -CH$_2$CH$_2$-N(CH$_2$CH$_2$NR$^2$)- | -CH$_2$CH$_2$-N(CH$_2$CH(C$_{10}$H$_{21}$)OH)- | — |
| 11 | -CH$_2$CH$_2$-NH- | -CH$_2$CH$_2$-N(CH$_2$CH$_2$NR$^2$)- | -CH$_2$CH$_2$-N(CH$_2$CH(C$_{10}$H$_{21}$)OH)- | -CH$_2$CH$_2$-N(CH$_2$CH(R$^3$)OH)- |
| 12 | — | -CH$_2$CH$_2$-N(CH$_2$CH$_2$NR$^2$)- | -CH$_2$CH$_2$-N(CH$_2$CH(C$_{10}$H$_{21}$)OH)- | -CH$_2$CH$_2$-N(CH$_2$CH(R$^3$)OH)- |
| 13 | — | -CH$_2$CH$_2$-N(CH$_2$CH$_2$NR$^2$)- | -CH$_2$CH$_2$-N(CH$_2$CH(C$_{11}$H$_{23}$)OH)- | — |

TABLE 2-continued

| | BPEI conjugated polymers | | | |
|---|---|---|---|---|
| | (i) | (ii) | (iii) | (iii) |
| 14 | —NH— structure | —N(CH₂CH₂NR²)— structure | —N(CH₂CH(OH)C₁₁H₂₃)— structure | — |
| 15 | —NH— structure | —N(CH₂CH₂NR²)— structure | —N(CH₂CH(OH)C₁₁H₂₃)— structure | —N(CH₂CH(OH)R³)— structure |
| 16 | — | —N(CH₂CH₂NR²)— structure | —N(CH₂CH(OH)C₁₁H₂₃)— structure | —N(CH₂CH(OH)R³)— structure |
| 17 | — | —N(CH₂CH₂NR²)— structure | —N(CH₂CH(OH)C₁₂H₂₅)— structure | — |
| 18 | —NH— structure | —N(CH₂CH₂NR²)— structure | —N(CH₂CH(OH)C₁₂H₂₅)— structure | — |
| 19 | —NH— structure | —N(CH₂CH₂NR²)— structure | —N(CH₂CH(OH)C₁₂H₂₅)— structure | —N(CH₂CH(OH)R³)— structure |
| 20 | — | —N(CH₂CH₂NR²)— structure | —N(CH₂CH(OH)C₁₂H₂₅)— structure | —N(CH₂CH(OH)R³)— structure |
| 21 | — | —N(CH₂CH₂NR²)— structure | —N(CH₂CH(OH)C₁₃H₂₇)— structure | — |

TABLE 2-continued

BPEI conjugated polymers

| | (i) | (ii) | (iii) | (iii) |
|---|---|---|---|---|
| 22 | [structure: NH] | [structure: N-CH2CH2-NR$^2$] | [structure: N-CH2-CH(C$_{13}$H$_{27}$)-OH] | — |
| 23 | [structure: NH] | [structure: N-CH2CH2-NR$^2$] | [structure: N-CH2-CH(C$_{13}$H$_{27}$)-OH] | [structure: N-CH2-CH(R$^3$)-OH] |
| 24 | — | [structure: N-CH2CH2-NR$^2$] | [structure: N-CH2-CH(C$_{13}$H$_{27}$)-OH] | [structure: N-CH2-CH(R$^3$)-OH] |
| 25 | — | [structure: N-CH2CH2-NR$^2$] | [structure: N-CH2-CH(C$_{14}$H$_{29}$)-OH] | — |
| 26 | [structure: NH] | [structure: N-CH2CH2-NR$^2$] | [structure: N-CH2-CH(C$_{14}$H$_{29}$)-OH] | — |
| 27 | [structure: NH] | [structure: N-CH2CH2-NR$^2$] | [structure: N-CH2-CH(C$_{14}$H$_{29}$)-OH] | [structure: N-CH2-CH(R$^3$)-OH] |
| 28 | — | [structure: N-CH2CH2-NR$^2$] | [structure: N-CH2-CH(C$_{14}$H$_{29}$)-OH] | [structure: N-CH2-CH(R$^3$)-OH] |
| 29 | — | [structure: N-CH2CH2-NR$^2$] | [structure: N-CH2-CH(C$_{15}$H$_{31}$)-OH] | — |

TABLE 2-continued

BPEI conjugated polymers

| | (i) | (ii) | (iii) | (iii) |
|---|---|---|---|---|
| 30 | ~(CH$_2$CH$_2$NH)~ | ~CH$_2$CH$_2$N(CH$_2$CH$_2$NR$^2$)~ | ~CH$_2$CH$_2$N(CH(C$_{15}$H$_{31}$)CH$_2$OH)~ | — |
| 31 | ~(CH$_2$CH$_2$NH)~ | ~CH$_2$CH$_2$N(CH$_2$CH$_2$NR$^2$)~ | ~CH$_2$CH$_2$N(CH(C$_{15}$H$_{31}$)CH$_2$OH)~ | ~CH$_2$CH$_2$N(CH(R$^3$)CH$_2$OH)~ |
| 32 | — | ~CH$_2$CH$_2$N(CH$_2$CH$_2$NR$^2$)~ | ~CH$_2$CH$_2$N(CH(C$_{15}$H$_{31}$)CH$_2$OH)~ | ~CH$_2$CH$_2$N(CH(R$^3$)CH$_2$OH)~ |
| 33 | — | ~CH$_2$CH$_2$N(CH$_2$CH$_2$NR$^2$)~ | ~CH$_2$CH$_2$N(CH(C$_{16}$H$_{33}$)CH$_2$OH)~ | — |
| 34 | ~(CH$_2$CH$_2$NH)~ | ~CH$_2$CH$_2$N(CH$_2$CH$_2$NR$^2$)~ | ~CH$_2$CH$_2$N(CH(C$_{16}$H$_{33}$)CH$_2$OH)~ | — |
| 35 | ~(CH$_2$CH$_2$NH)~ | ~CH$_2$CH$_2$N(CH$_2$CH$_2$NR$^2$)~ | ~CH$_2$CH$_2$N(CH(C$_{16}$H$_{33}$)CH$_2$OH)~ | ~CH$_2$CH$_2$N(CH(R$^3$)CH$_2$OH)~ |
| 36 | — | ~CH$_2$CH$_2$N(CH$_2$CH$_2$NR$^2$)~ | ~CH$_2$CH$_2$N(CH(C$_{16}$H$_{33}$)CH$_2$OH)~ | ~CH$_2$CH$_2$N(CH(R$^3$)CH$_2$OH)~ |

Conjugated Aza-Macrocycles and Preparation Thereof

The present invention further provides conjugated aza-macrocycles; i.e., of the Formula (IV):

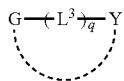

(IV)

or salt thereof, wherein:

each instance of $L^3$ is independently selected from:

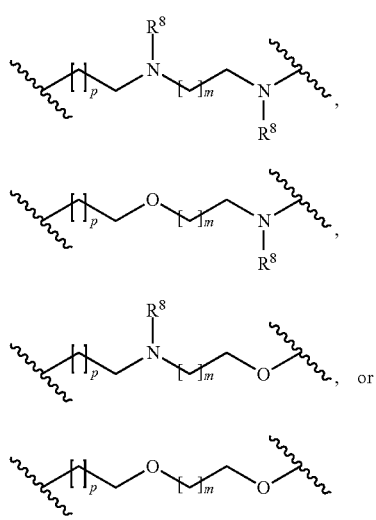

provided that the aza-macrocycle contains at least one group selected from (vi), (vii) or (viii);

each instance of $R^8$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or

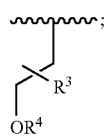

(iii')

provided the aza-macrocycle contains at least one group of the formula (iii');

each instance of $R^3$ is independently substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or a hydrophilic polymer;

each instance of $R^4$ is independently hydrogen, acyl; silyl; a hydroxyl protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl;

each instance of m and p is independently 0, 1 or 2;

q is an integer selected from 2, 3, or 4; and the dashed curved line, together with G and Y, is a covalent bond or a group of the formula:

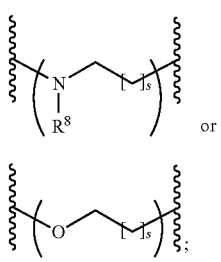

wherein s is 0, 1, or 2.

The conjugated aza-macrocyle, or salt thereof, is prepared similarly to the above described method of preparing a conjugated polyethyleneimine polymer, i.e., by contacting a compound of Formula (III), or salt thereof (an "aza-macrocycle precursor") with one or more different epoxides; e.g. as provided below in Scheme IV.

Scheme IV.

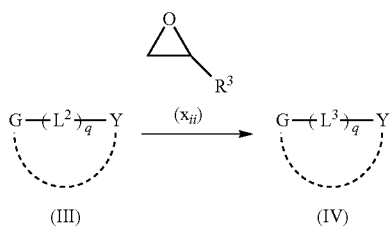

wherein each instance of $L^2$ is independently selected from:

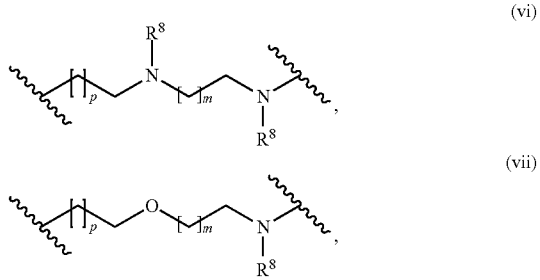

(viii)

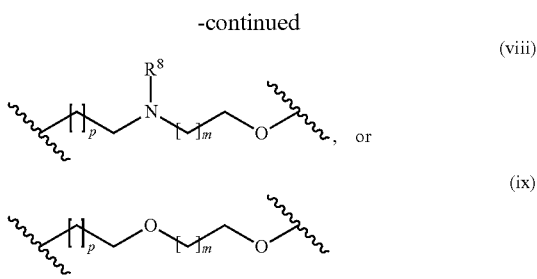

, or (ix)

provided that the aza-macrocycle precursor contains at least one group selected from (vi), (vii) or (viii); and wherein $R^8$, m, p, G, Y, and the dashed curved line, are as defined herein, and further provided that the aza-macrocycle precursor has at least one $R^8$ group which is hydrogen.

Exemplary "aza-macrocycle precursors" are depicted in FIG. 1A. In certain embodiments, the aza-macrocycle precursor is a cyclic structure having from 10 to 30 ring members, inclusive; e.g., from 10 to 20 ring members, inclusive, or from 12 to 18 ring members, inclusive. In certain embodiments, the aza-macrocycle precursor is a 10-membered ring, an 11-membered ring, a 12-membered ring, a 13-membered ring, a 14-membered ring, a 15-membered ring, a 16-membered ring, a 17-membered ring, or an 18-membered ring. By extension, the conjugated aza-macrocycle, prepared therefrom, is also a cyclic structure having from 10 to 30 ring members, inclusive; e.g., from 10 to 20 ring members, inclusive, or from 12 to 18 ring members, inclusive. In certain embodiments, the conjugated aza-macrocycle is a 10-membered ring, an 11-membered ring, a 12-membered ring, a 13-membered ring, a 14-membered ring, a 15-membered ring, a 16-membered ring, a 17-membered ring, or an 18-membered ring.

In certain embodiments of Formula (III), $R^8$ is not a group of the formula (iii'). Thus, in certain embodiments of Formula (III), each instance of $R^8$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl; provided that at least one $R^8$ group is hydrogen. In certain embodiments of Formula (III), each instance of $R^8$ is independently hydrogen; acyl; silyl; sulfonyl; an amino protecting group; substituted or unsubstituted alkyl; or substituted or unsubstituted heteroalkyl. In certain embodiments of Formula (III), each instance of $R^8$ is hydrogen.

Alternatively, the conjugated aza-macrocycle of Formula (IV) requires that at least one $R^8$ group is of the formula (iii'). Thus, in certain embodiments, each instance of $R^8$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; or a group of the formula (iii'), provided the aza-macrocycle contains at least one group of the formula (iii'). In certain embodiments, each instance of $R^8$ is independently selected from hydrogen; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; or a group of the formula (iii'), provided the aza-macrocycle contains at least one group of the formula (iii'). In certain embodiments, each instance of $R^8$ is independently selected from hydrogen or a group of the formula (iii'), provided the aza-macrocycle contains at least one group of the formula (iii').

In certain embodiments, at least one $R^8$ group of the aza-macrocycle is hydrogen. In certain embodiments, one $R^8$ group of the aza-macrocycle is hydrogen. In certain embodiments, two $R^8$ groups of the aza-macrocycle are hydrogen. In certain embodiments, three $R^8$ groups of the aza-macrocycle are hydrogen. In certain embodiments, four $R^8$ groups of the aza-macrocycle are hydrogen.

In certain embodiments, 1 to 9 $R^8$ groups provided in the aza-macrocycle is a group of the formula (iii'); e.g., 1 to 9; 1 to 8; 1 to 7; 1 to 6; 1 to 5; 1 to 4; 1 to 3; 1 to 2 $R^8$ groups, inclusive, are of the formula (iii'). In certain embodiments, 1 $R^8$ group of the aza-macrocycle is of the formula (iii'). In certain embodiments, 2 $R^8$ groups of the aza-macrocycle are groups of the formula (iii'). In certain embodiments, 3 $R^8$ groups of the aza-macrocycle are groups of the formula (iii'). In certain embodiments, 4 $R^8$ groups of the aza-macrocycle are groups of the formula (iii'). In certain embodiments, all of the $R^8$ groups of the aza-macrocycle are groups of the formula (iii').

In certain embodiments, the ratio of —NH— to —NR$^8$-groups provided in the aza-macrocycle, wherein $R^8$ is a group of the formula (iii'), is between about 90:10 to about 0:100.

As generally defined above, each instance of $R^3$ is independently selected from substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or a hydrophilic polymer. In certain embodiments, each instance of $R^3$ is independently selected from substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; or a hydrophilic polymer. In certain embodiments, each instance of $R^3$ is independently selected from substituted or unsubstituted alkyl; substituted or unsubstituted heteroalkyl; or a hydrophilic polymer.

In certain embodiments, at least one instance of $R^3$ is substituted or unsubstituted alkyl. In certain embodiments, at least one instance of $R^3$ is substituted or unsubstituted $C_{1-50}$alkyl. In certain embodiments, at least one instance of $R^3$ is substituted or unsubstituted $C_{8-50}$alkyl. In certain embodiments, at least one instance of $R^3$ is substituted or unsubstituted $C_{8-40}$alkyl. In certain embodiments, at least one instance of $R^3$ is substituted or unsubstituted $C_{8-30}$alkyl. In certain embodiments, at least one instance of $R^3$ is substituted or unsubstituted $C_{8-20}$alkyl.

In certain embodiments, at least one instance of $R^3$ is an unsubstituted alkyl. Exemplary unsubstituted alkyl groups include, but are not limited to, —$CH_3$, —$C_2H_5$, —$C_3H_7$, —$C_4H_9$, —$C_5H_{11}$, —$C_6H_{13}$, —$C_7H15$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H35$, —$C_{18}H_{37}$, —$C_{19}H_{39}$, and —$C_{20}H_{41}$.

In certain embodiments, at least one instance of $R^3$ is a substituted alkyl. For example, in certain embodiments, at least one instance of $R^3$ is an alkyl substituted with one or more fluorine substituents. Exemplary substituted alkyl groups include, but are not limited to:

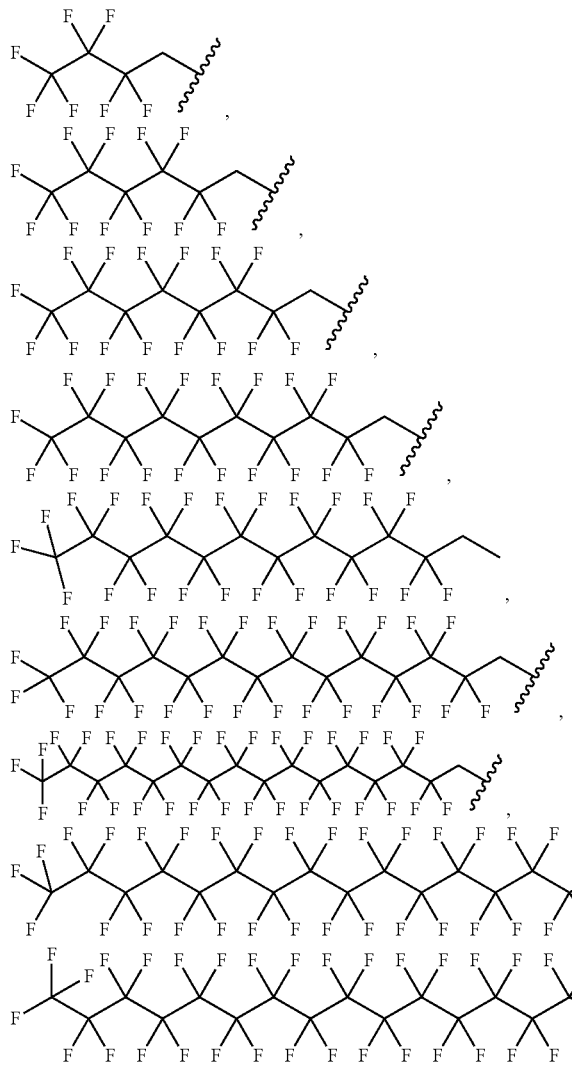

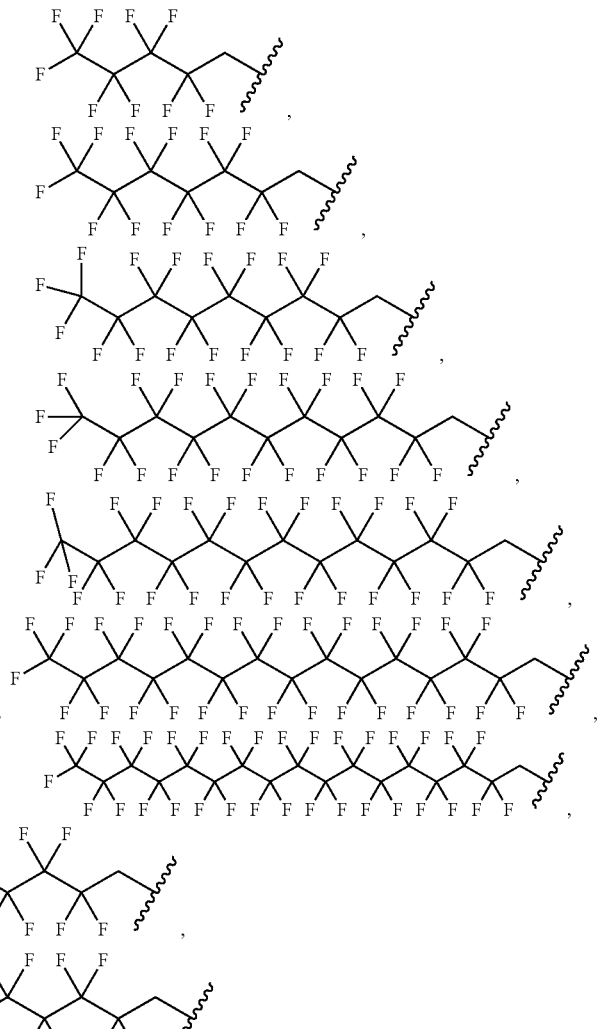

In certain embodiments, at least one instance of $R^3$ is substituted or unsubstituted alkenyl. In certain embodiments, at least one instance of $R^3$ is substituted or unsubstituted $C_{2-50}$alkenyl. In certain embodiments, at least one instance of $R^3$ is substituted or unsubstituted $C_{8-50}$ alkenyl. In certain embodiments, at least one instance of $R^3$ is substituted or unsubstituted $C_{8-40}$ alkenyl. In certain embodiments, at least one instance of $R^3$ is substituted or unsubstituted $C_{8-30}$ alkenyl. In certain embodiments, at least one instance of $R^3$ is substituted or unsubstituted $C_{8-20}$ alkenyl. In certain embodiments, at least one instance of $R^3$ is a substituted $C_{8-20}$ alkenyl. In certain embodiments, at least one instance of $R^3$ is an unsubstituted alkenyl.

Exemplary unsubstituted alkenyl groups include, but are not limited to:

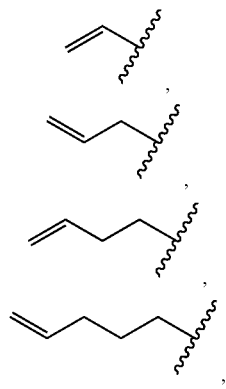

-continued

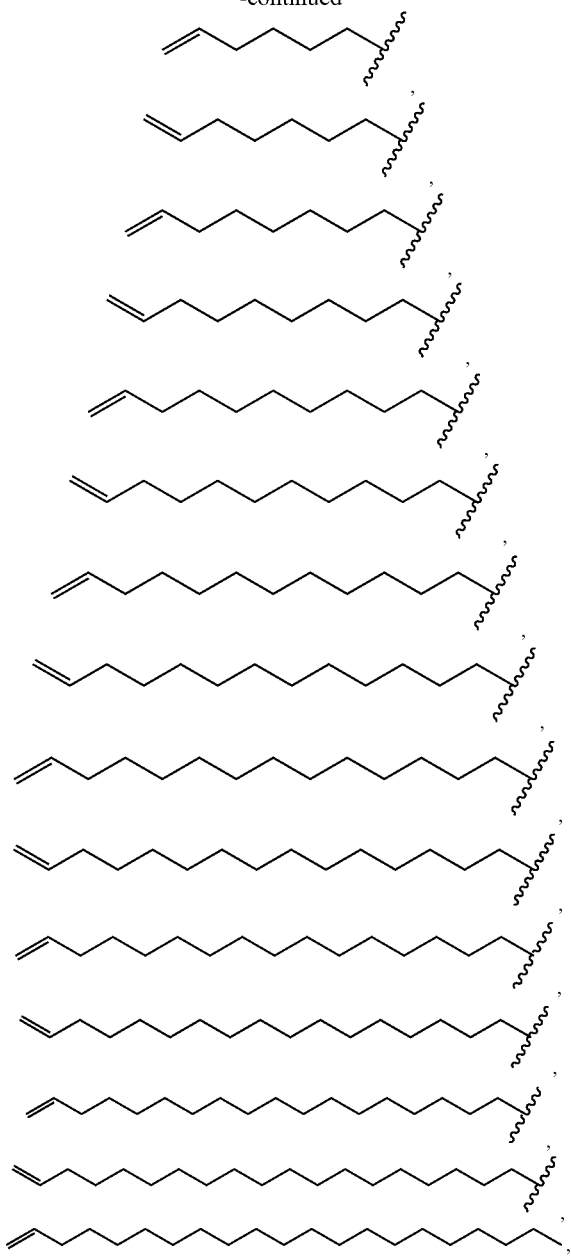

Myristoleic —$(CH_2)$—CH=CH$(CH_2)_3CH_3$,
Palmitoliec —$(CH_2)$—CH=CH$(CH_2)_5CH_3$,
Sapienic —$(CH_2)_4$CH=CH$(CH_2)_8CH_3$,
Oleic —$(CH_2)$—CH=CH$(CH_2)_7CH_3$, Linoleic —$(CH_2)$—CH=CHCH$_2$CH=CH$(CH_2)_4CH_3$,
α-Linolenic —$(CH_2)$—CH=CHCH$_2$CH=CHCH$_2$CH=CHCH$_2$CH$_3$,
Arachinodonic —$(CH_2)_3$CH=CHCH$_2$CH=CHCH$_2$CH=CHCH$_2$CH=CH$(CH_2)_4CH_3$,
Eicosapentaenoic —$(CH_2)_3$CH=CHCH$_2$CH=CHCH$_2$CH=CHCH$_2$CH=CHCH$_2$CH=CHCH$_2$CH$_3$,
Erucic —$(CH_2)_{11}$CH=CH$(CH_2)_7CH_3$, and
Docosahexaenoic —$(CH_2)_2$CH=CHCH$_2$CH=CHCH$_2$CH=CHCH$_2$CH=CHCH$_2$CH=CHCH$_2$CH=CH—CH$_2$CH$_3$.

In embodiments, wherein $R^3$ is defined as a $C_{6-50}$alkyl or $C_{6-50}$alkenyl groups, such groups are meant to encompass lipophilic groups (also referred to as a "lipid tail"). Lipophilic groups comprise a group of molecules that include fats, waxes, oils, fatty acids, and the like. Lipid tails present in these lipid groups can be saturated and unsaturated, depending on whether or not the lipid tail comprises double bonds. The lipid tail can also comprise different lengths, often categorized as medium (i.e., with tails between 7-12 carbons, e.g., $C_{7-12}$ alkyl or $C_{7-12}$ alkenyl), long (i.e., with tails greater than 12 carbons and up to 22 carbons, e.g., $C_{13-22}$ alkyl or $C_{13-22}$ alkenyl), or very long (i.e., with tails greater than 22 carbons, e.g., $C_{23-30}$ alkyl or $C_{23-30}$ alkenyl).

In certain embodiments, at least one instance of $R^3$ is substituted or unsubstituted alkynyl. In certain embodiments, at least one instance of $R^3$ is substituted or unsubstituted $C_{2-50}$alkynyl. In certain embodiments, at least one instance of $R^3$ is substituted or unsubstituted $C_{8-50}$ alkynyl. In certain embodiments, at least one instance of $R^3$ is substituted or unsubstituted $C_{8-40}$ alkynyl. In certain embodiments, at least one instance of $R^3$ is substituted or unsubstituted $C_{8-30}$ alkynyl. In certain embodiments, at least one instance of $R^3$ is substituted or unsubstituted $C_{8-20}$ alkynyl. In certain embodiments, at least one instance of $R^3$ is an unsubstituted alkynyl. In certain embodiments, at least one instance of $R^3$ is a substituted alkynyl.

In certain embodiments, at least one instance of $R^3$ is substituted or unsubstituted heteroalkyl. In certain embodiments, at least one instance of $R^3$ is substituted or unsubstituted $C_{1-50}$ heteroalkyl. In certain embodiments, at least one instance of $R^3$ is substituted or unsubstituted $C_{8-50}$ heteroalkyl. In certain embodiments, at least one instance of $R^3$ is substituted or unsubstituted $C_{8-40}$ heteroalkyl. In certain embodiments, at least one instance of $R^3$ is substituted or unsubstituted $C_{8-30}$ heteroalkyl. In certain embodiments, at least one instance of $R^3$ is substituted or unsubstituted $C_{8-20}$ heteroalkyl. In certain embodiments, at least one instance of $R^3$ is a substituted heteroalkyl. In certain embodiments, at least one instance of $R^3$ is an unsubstituted heteroalkyl.

Exemplary unsubstituted heteroalkyl groups include, but are not limited to:

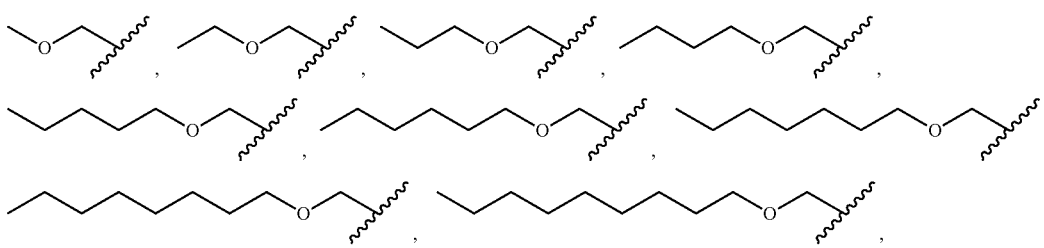

-continued

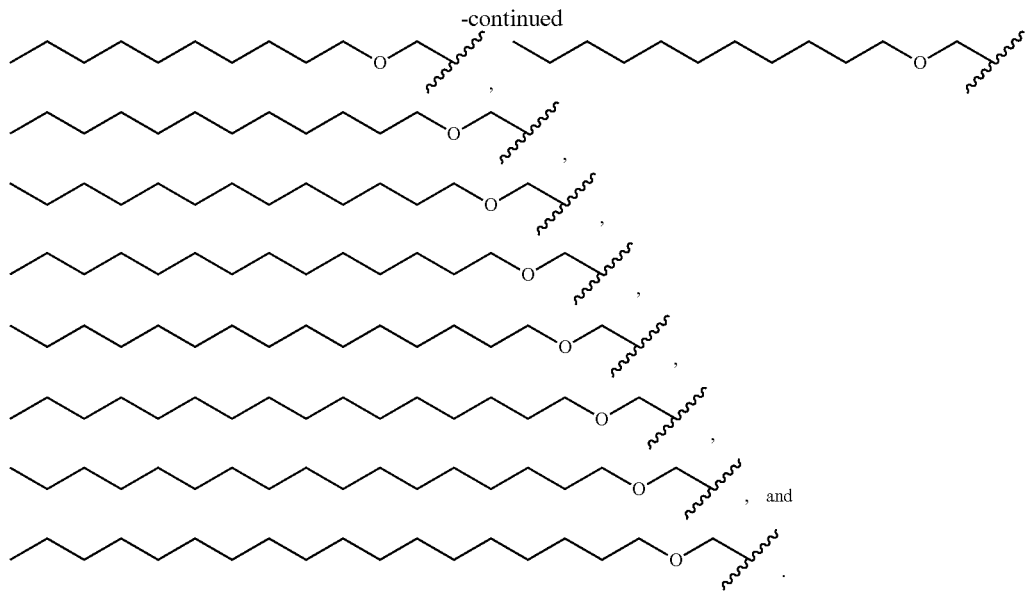

In certain embodiments, at least one instance of $R^3$ is substituted or unsubstituted heteroalkenyl. In certain embodiments, at least one instance of $R^3$ is substituted or unsubstituted $C_{2-50}$ heteroalkenyl. In certain embodiments, at least one instance of $R^3$ is substituted or unsubstituted $C_{8-50}$ heteroalkenyl. In certain embodiments, at least one instance of $R^3$ is substituted or unsubstituted $C_{8-40}$ heteroalkenyl. In certain embodiments, at least one instance of $R^3$ is substituted or unsubstituted $C_{8-30}$ heteroalkenyl. In certain embodiments, at least one instance of $R^3$ is substituted or unsubstituted $C_{8-20}$ heteroalkenyl. In certain embodiments, at least one instance of $R^3$ is a substituted heteroalkenyl. In certain embodiments, at least one instance of $R^3$ is an unsubstituted heteroalkenyl.

In certain embodiments, at least one instance of $R^3$ is substituted or unsubstituted heteroalkynyl. In certain embodiments, at least one instance of $R^3$ is substituted or unsubstituted $C_{2-50}$ heteroalkynyl. In certain embodiments, at least one instance of $R^3$ is substituted or unsubstituted $C_{8-50}$ heteroalkynyl. In certain embodiments, at least one instance of $R^3$ is substituted or unsubstituted $C_{8-40}$ heteroalkynyl. In certain embodiments, at least one instance of $R^3$ is substituted or unsubstituted $C_{8-30}$ heteroalkynyl. In certain embodiments, at least one instance of $R^3$ is substituted or unsubstituted $C_{8-20}$ heteroalkynyl. In certain embodiments, at least one instance of $R^3$ is a substituted heteroalkynyl. In certain embodiments, at least one instance of $R^3$ is an unsubstituted heteroalkynyl.

In certain embodiments, at least one instance of $R^3$ is substituted or unsubstituted carbocyclyl. In certain embodiments, at least one instance of $R^3$ is a substituted carbocyclyl. In certain embodiments, at least one instance of $R^3$ is an unsubstituted carbocyclyl.

In certain embodiments, at least one instance of $R^3$ is substituted or unsubstituted heterocyclyl. In certain embodiments, at least one instance of $R^3$ is a substituted heterocyclyl. In certain embodiments, at least one instance of $R^3$ is an unsubstituted heterocyclyl.

In certain embodiments, at least one instance of $R^3$ is substituted or unsubstituted aryl. In certain embodiments, at least one instance of $R^3$ is an unsubstituted aryl. In certain embodiments, at least one instance of $R^3$ is a substituted aryl.

In certain embodiments, at least one instance of $R^3$ is substituted or unsubstituted heteroaryl. In certain embodiments, at least one instance of $R^3$ is a substituted heteroaryl. In certain embodiments, at least one instance of $R^3$ is an unsubstituted heteroaryl.

In certain embodiments, at least one instance of $R^3$ is hydrophilic polymer. As used herein, a "polymer" refers to a compound comprised of at least 3 (e.g., at least 10, 20, 30, 40, 50, 60, 70, 80, 90, 100, etc.) repeating covalently bound structural units. By extension, a "hydrophilic polymer" is a polymer, as defined herein, further comprising at least one group (e.g., an oxygen, nitrogen, and/or sulfur atom) in the repeating structural unit capable of hydrogen bonding. The hydrophilic polymer is preferably biocompatible (i.e., non-toxic). Exemplary hydrophilic polymers include, but are not limited to, polypeptides (e.g., poly-L-lysine), cellulose polymers (e.g., hydroxyethylcellulose, ethylcellulose, carboxymethylcellulose, methyl cellulose, hydroxypropylmethylcellulose (HPMC)), dextran polymers, polymaleic acid polymers, poly(acrylic acid) polymers, poly(vinylalcohol) polymers, polyvinylpyrrolidone (PVP) polymers, and polyethyleneglycol (PEG) polymers.

In certain embodiments, the hydrophilic polymer is a polyethyleneglycol polymer, e.g., of the formula (v):

(v)

wherein:

$R^7$ is selected from hydrogen; acyl; silyl; a hydroxyl protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl; and v is an integer between 3 to 400, inclusive.

In certain embodiments, $R^7$ is selected from hydrogen. In certain embodiments, $R^7$ is acyl. In certain embodiments, $R^7$ is a hydroxyl protecting group. In certain embodiments, $R^7$ is substituted or unsubstituted alkyl. In certain embodiments, $R^7$ is a substituted alkyl. In certain embodiments, $R^7$ is an unsubstituted alkyl. In certain embodiments, $R^7$ is —$CH_3$ (a "polyethyleneglycol monomethylether" polymer). In certain embodiments, $R^7$ is substituted or unsubstituted alkenyl. In certain embodiments, $R^7$ is substituted or unsubstituted alkynyl. In certain embodiments, $R^7$ is substituted or unsubstituted heteroalkyl. In certain embodiments, $R^7$ is substituted or unsubstituted heteroalkenyl. In certain embodiments, $R^7$ is substituted or unsubstituted heteroalkynyl. In certain embodiments, $R^7$ is substituted or unsubstituted carbocyclyl. In certain embodiments, $R^7$ is substituted or unsubstituted heterocyclyl. In certain embodiments, $R^7$ is substituted or unsubstituted aryl. In certain embodiments, $R^7$ is and substituted or unsubstituted heteroaryl.

In certain embodiments, v is an integer between 3 to 300, 3 to 200, 3 to 100, 3 to 90, 3 to 80, 3 to 70, 3 to 60, 3 to 50, 5 to 50, 10 to 50, 15 to 50, 20 to 50, 20 to 40, 20 to 30, 20 to 25, 30 to 50, and 40 to 50, inclusive. $PEG_{1000}$ corresponds, on average, to a v of about 22.7, wherein $R^7$ is —$OCH_3$. $PEG_{2000}$ corresponds, on average, to a v of about 45.4.

In certain embodiments, the number average molar mass (Mn) of the polyethyleneglycol polymer is ≤10,000. In certain embodiments, the number average molar mass (Mn) of the polyethyleneglycol polymer is ≤10,000, ≤9000, ≤8000, ≤7000, ≤6000, ≤5000, ≤4000, ≤3000, or ≤2000. In certain embodiments, the number average molar mass (Mn) of the polyethyleneglycol polymer is between about 100 to about 10,000, inclusive; e.g., between about 100 to about 5000, between about 100 to about 4000, between about 100 to about 3000, between about 100 to about 2500, between about 100 to about 2000, between about 100 to about 1500, between about 100 to about 1000, between about 100 to about 900, between about 100 to about 800, between about 100 to about 700, between about 100 to about 600, between about 100 to about 500, between about 100 to about 400, between about 100 to about 300, between about 100 to about 200, between about 100 to about 1500, between about 2500 to about 10000, between about 2500 to about 9000, between about 2500 to about 8000, between about 2500 to about 7000, between about 2500 to about 6000, between about 2500 to about 5000, between about 2500 to about 4000, or between about 2500 to about 3000, inclusive. In certain embodiments, the number average molar mass (Mn) of the polyethyleneglycol polymer is 1000 ($PEG_{1000}$). In certain embodiments, the number average molar mass (Mn) of the polyethyleneglycol polymer is 2000 ($PEG_{2000}$). A 1:1 mixture of $PEG_{1000}$ and $PEG_{2000}$ is referred to herein as $PEG_{1.5K}$.

In certain embodiments, at least one instance of $R^3$ is a hydrophilic polymer, and at least one instance of $R^3$ is a substituted or unsubstituted alkyl.

As used herein, when the group $R^3$ is depicted as bisecting a carbon-carbon bond, e.g., of the group of the formula (iii'), it is understood that $R^3$ may be substituted at either carbon. It is understood from the present disclosure that the group of formula (iii') represents a group of formula (iii'-a) or a group of formula (iii'-b). Nucleophilic attack of an amino group of the aza-macrocycle at the least sterically hindered carbon of the epoxide provides a group of the formula (iii'-a) (route a), while nucleophilic attack at the more sterically hindered carbon of the epoxide provides a group of the formula (iii'-b) (route b), wherein $R^4$ is hydrogen; see, e.g., the "conjugation reaction" of Scheme V. It is thus understood that compounds of the present invention may comprise a mixture of products attached thereto arising from route (a) and route (b) depending on the preference, or lack thereof, of the mode of addition, and that formulae that depict this bisecting bond may comprise a mixture of compounds. The bisecting group $R^3$ depicted in the formulae seeks to encompasses all contemplated modes of addition.

Scheme V.

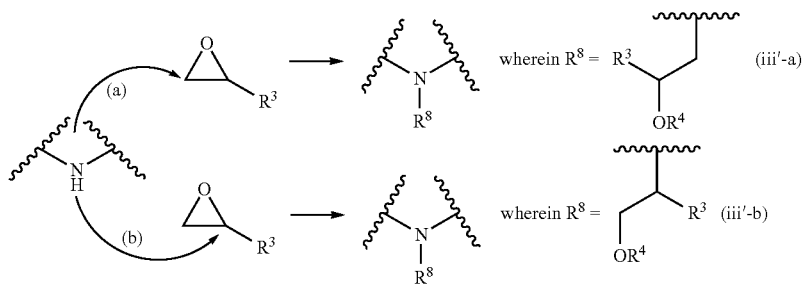

The resulting hydroxyl moiety of the formula (iii'-a) or (iii'-b), wherein $R^4$ is hydrogen, can optionally be converted to a substituted hydroxyl, wherein $R^4$ is a group other than hydrogen, i.e., is independently acyl; silyl; a hydroxyl protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl; using conventional methods. Alkylation, acylation, and/or protection of a hydroxyl moiety are well-known in the art; see, e.g., *Protecting Groups in Organic Synthesis*, T. W. Greene and P. G. M. Wuts, 3rd edition, John Wiley & Sons, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987. For example, in certain non-limiting embodiments, the hydroxyl moiety is reacted with an electrophile of the formula R⁴—X wherein R⁴ is a group other than hydrogen and X is a leaving group to provide a substituted hydroxyl group in formula (iii').

In certain embodiments, each instance of $R^4$ is independently hydrogen; acyl; silyl; a hydroxyl protecting group; substituted or unsubstituted alkyl; substituted or unsubstituted alkenyl; substituted or unsubstituted alkynyl; substituted or unsubstituted heteroalkyl; or substituted or unsubstituted heteroalkenyl. In certain embodiments, each instance of $R^4$ is independently hydrogen; substituted or unsubstituted alkyl; or substituted or unsubstituted heteroalkyl. In certain embodiments, each instance of $R^4$ is hydrogen.

In certain embodiments, the conjugation reaction depicted in Scheme V results in a mixture comprising more lipomers conjugated to a group of formula (iii'-a) than to a group of formula (iii'-b), e.g., the reaction mixture comprises greater than 50%, greater than 60%, greater than 70%, greater than 80%, greater than 90%, greater than 95%, greater than 99%, between about 60% to about 100%, between about 70% to about 100%, between about 80% to about 100%, between about 90% to about 100%, between about 95% to about 100%, or between about 99% to about 100%, of a conjugated lipomer attached to a group of formula (iii'-a).

In certain embodiments, the reaction mixture comprises only conjugated lipomers attached to a group formula (iii'-a).

In certain embodiments, the epoxide is chiral, i.e., having (R) or (S) stereochemistry. In this instance, in certain embodiments, the conjugation reaction depicted in Scheme V provides a chiral conjugated aza-macrocycle.

In certain embodiments, wherein the epoxide is chiral, the conjugation reaction depicted in Scheme V results in a mixture comprising more lipomers conjugated to a group of formula (R)-(iii'-a) than to a group of formula(S)-(iii'-a), e.g., the reaction mixture comprises greater than 50%, greater than 60%, greater than 70%, greater than 80%, greater than 90%, greater than 95%, greater than 99%, between about 60% to about 100%, between about 70% to about 100%, between about 80% to about 100%, between about 90% to about 100%, between about 95% to about 100%, or between about 99% to about 100%, of conjugated lipomer attached to a group of formula (R)-(iii'-a).

In certain embodiments, the reaction mixture comprises only conjugated lipomers attached to a group formula (R)-(iii'-a).

In certain embodiments, wherein the epoxide is chiral, the conjugation reaction depicted in Scheme V results in a mixture comprising more lipomers conjugated to a group of formula(S)-(iii'-a) than to a group of formula (R)-(iii'-a), e.g., the reaction mixture comprises greater than 50%, greater than 60%, greater than 70%, greater than 80%, greater than 90%, greater than 95%, greater than 99%, between about 60% to about 100%, between about 70% to about 100%, between about 80% to about 100%, between about 90% to about 100%, between about 95% to about 100%, or between about 99% to about 100%, of a conjugated lipomer attached to a group of formula(S)-(iii'-a).

In certain embodiments, the reaction mixture comprises only conjugated lipomers attached to a group formula(S)-(iii'-a).

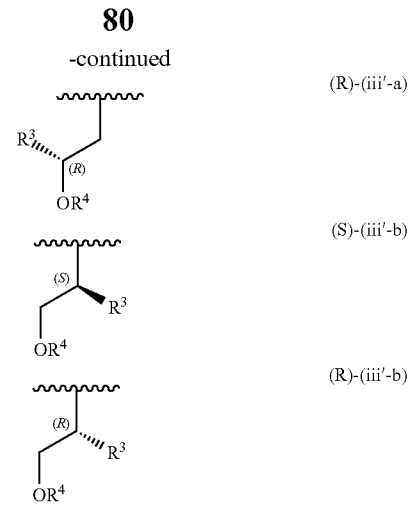

In certain embodiments, wherein one epoxide is used in the conjugation reaction, each instance of $R^3$ is the same in the conjugated aza-macrocycle. For example, in certain embodiments, each instance of $R^3$ is the same wherein $R^3$ is a substituted or unsubstituted alkyl. In certain embodiments, each instance of $R^3$ is the same wherein $R^3$ is an unsubstituted alkyl. In certain embodiments, each instance of $R^3$ is the same wherein $R^3$ is selected from the group consisting of —$CH_3$, —$C_2H_5$, —$C_3H_7$, —$C_4H_9$, —$C_5H_{11}$, —$C_6H_{13}$, —$C_7H15$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H35$, —$C_{18}H_{37}$, —$C_{19}H_{39}$, and —$C_{20}H_{41}$. In certain embodiments, each instance of $R^3$ is the same wherein $R^3$ is selected from the group consisting of —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, and —$C_{16}H_{33}$.

Alternatively, in certain embodiments, wherein more than one epoxide is used in the conjugation reaction (e.g., two, three, four, five, six, seven, eight, nine, or ten different epoxides), the conjugated aza-macrocycle comprises two or more (e.g., two, three, four, five, six, seven, eight, nine, or ten) different $R^3$ groups.

For example, in certain embodiments, two different epoxides are used in the conjugation reaction. In this instance, in certain embodiments, the conjugated aza-macrocycle comprises two different $R^3$ groups. For example, in certain embodiments, the conjugated aza-macrocycle comprises a mixture of two different $R^3$ groups, wherein the first $R^3$ group is a substituted or unsubstituted alkyl, and the second $R^3$ group is a hydrophilic polymer (e.g., a polyethyleneglycol polymer, as defined herein). In certain embodiments, the conjugated aza-macrocycle comprises a mixture of two different $R^3$ groups, wherein the first $R^3$ group is an unsubstituted alkyl, and the second $R^3$ group is a polyethyleneglycol polymer. In certain embodiments, the conjugated aza-macrocycle comprises a mixture of two different $R^3$ groups, wherein the first $R^3$ group is selected from the group consisting of —$CH_3$, —$C_2H_5$, —$C_3H_7$, —$C_4H_9$, —$C_5H_{11}$, —$C_6H_{13}$, —$C_7H15$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H35$, —$C_{18}H_{37}$, —$C_{19}H_{39}$, and —$C_{20}H_{41}$, and the second $R^3$ group is $PEG_{1000}$. In certain embodiments, the conjugated aza-macrocycle comprises a mixture of two different $R^3$ groups, wherein the first $R^3$ group is selected from the group consisting of —$CH_3$, —$C_2H_5$, —$C_3H_7$, —$C_4H_9$, —$C_5H_{11}$, —$C_6H_{13}$, —$C_7H15$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H35$, —$C_{18}H_{37}$, —$C_{19}H_{39}$, and —$C_{20}H_{41}$, and the second $R^3$ group is $PEG_{2000}$.

In certain embodiments, three different epoxides are used in the conjugation reaction. In this instance, in certain embodiments, the conjugated aza-macrocycle comprises three different $R^3$ groups. For example, in certain embodiments, the conjugated aza-macrocycle comprises a mixture of three different $R^3$ groups, wherein the first $R^3$ group is a substituted or unsubstituted alkyl, the second $R^3$ group is a first hydrophilic polymer (e.g., a polyethyleneglycol polymer, as defined herein), and the third $R^3$ group is a second hydrophilic polymer (e.g., a different polyethyleneglycol polymer). In certain embodiments, the conjugated aza-macrocycle comprises a mixture of three different $R^3$ groups, wherein the first $R^3$ group is an unsubstituted alkyl, the second $R^3$ group is $PEG_{1000}$, and the third $R^3$ group is $PEG_{2000}$. In certain embodiments, the conjugated aza-macrocycle comprises a mixture of three different $R^3$ groups, wherein the first $R^3$ group is selected from the group consisting of —$CH_3$, —$C_2H_5$, —$C_3H_7$, —$C_4H_9$, —$C_5H_{11}$, —$C_6H_{13}$, —$C_7H15$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H35$, —$C_{18}H_{37}$, —$C_{19}H_{39}$, and —$C_{20}H_{41}$, the second $R^3$ group is $PEG_{1000}$, and the third $R^3$ group is $PEG_{2000}$.

In certain embodiments, wherein the conjugated aza-macrocycle comprises two different $R^3$ groups, the ratio of the second $R^3$ group to the first $R^3$ group is between about 0.01:10 to about 10:10, inclusive. In certain embodiments, the ratio of the second $R^3$ group to the first $R^3$ group is between about 0.02:10 to about 10:10; between about 0.03:10 to about 10:10; between about 0.04:10 to about 10:10; between about 0.05:10 to about 10:10; between about 0.06:10 to about 10:10; between about 0.07:10 to about 10:10; between about 0.08:10 to about 10:10; between about 0.08:10 to about 9:10; between about 0.08:10 to about 8:10; between about 0.08:10 to about 7:10; between about 0.08:10 to about 6:10; between about 0.08:10 to about 5:10; between about 0.08:10 to about 4:10; between about 0.08:10 to about 3:10; between about 0.08:10 to about 2:10; or between about 0.08:10 to about 1:10, inclusive. In certain embodiments, the ratio of the second $R^3$ group to the first $R^3$ group is about 0.1:10.

In certain embodiments, wherein the conjugated aza-macrocycle comprises three different $R^3$ groups, the ratio of the sum of the second and third $R^3$ groups to the first $R^3$ group is between about 0.01:10 to about 10:10, inclusive. In certain embodiments, the ratio of the sum of the second and third $R^3$ groups to the first $R^3$ group is 0.02:10 to about 10:10; between about 0.03:10 to about 10:10; between about 0.04:10 to about 10:10; between about 0.05:10 to about 10:10; between about 0.06:10 to about 10:10; between about 0.07:10 to about 10:10; between about 0.08:10 to about 10:10; between about 0.08:10 to about 9:10; between about 0.08:10 to about 8:10; between about 0.08:10 to about 7:10; between about 0.08:10 to about 6:10; between about 0.08:10 to about 5:10; between about 0.08:10 to about 4:10; between about 0.08:10 to about 3:10; between about 0.08:10 to about 2:10; or between about 0.08:10 to about 1:10, inclusive. In certain embodiments, the ratio of the sum of the second and third $R^3$ groups to the first $R^3$ group is about 0.1:10.

As generally defined above, each instance of m and p is independently 0, 1 or 2. In certain embodiments, each instance of m is independently 0, 1 or 2. In certain embodiments, each instance of m is 1. In certain embodiments, each instance of m is 2. In certain embodiments, each instance of m is independently 1 or 2. In certain embodiments, each instance of p is independently 0, 1 or 2. In certain embodiments, each instance of p is 1. In certain embodiments, each instance of p is 2. In certain embodiments, each instance of p is independently 1 or 2.

As generally defined above, q is an integer 2, 3, or 4. In certain embodiments, q is 2. In certain embodiments, q is 3. In certain embodiments, q is 2 or 3. In certain embodiments, q is 4.

As generally defined above, the dashed curved line, together with G and Y, is a covalent bond or a group of the formula:

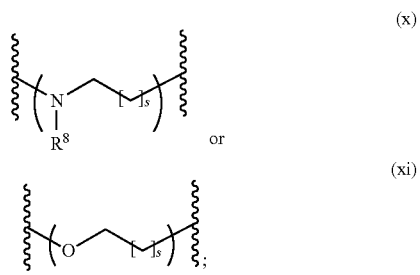

wherein s is 0, 1, or 2.

In certain embodiments, the dashed curved line, together with G and Y, is a covalent bond.

In certain embodiments, the dashed curved line, together with G and Y, a group of the formula:

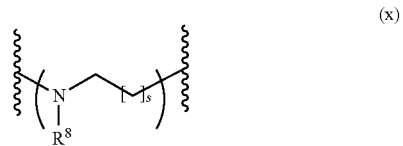

wherein s is 0, 1, or 2. In certain embodiments, s is 1 or 2. In certain embodiments, s is 1.

In certain embodiments, the dashed curved line, together with G and Y, a group of the formula:

wherein s is 0, 1, or 2. In certain embodiments, s is 1 or 2. In certain embodiments, s is 1.

As generally defined above, each instance of $L^3$ is independently:

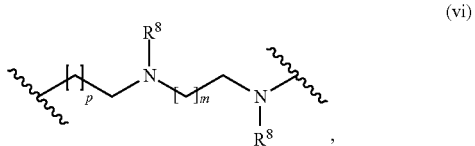

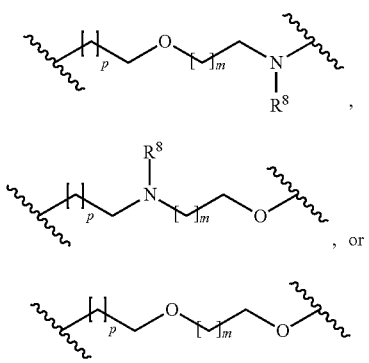

(vii)

(viii)

(ix)

provided that the conjugated aza-macrocycle contains at least one group (vi), (vii) or (viii);

In certain embodiments, the conjugated aza-macrocycle comprises at least one instance of the group of the formula (vi). In certain embodiments, each instance of $L^3$ is a group of the formula (vi). For example, in this instance, the conjugated aza-macrocycle of the Formula (IV) is of the Formula (V), (VI), or (VII):

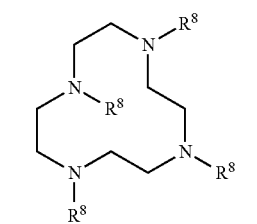

(V)

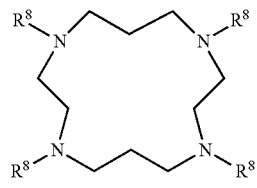

(VI)

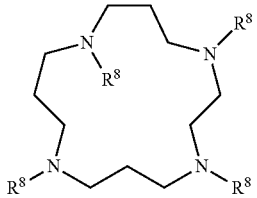

(VII)

or salt thereof, wherein $R^8$ is as defined herein.

In certain embodiments, the conjugated aza-macrocycle comprises at least one instance of the group of the formula (vii), (viii), or (ix). In certain embodiments, the conjugated aza-macrocycle comprises at least one instance of the group of the formula (vii). In certain embodiments, the conjugated aza-macrocycle comprises at least one instance of the group of the formula (viii). In certain embodiments, the conjugated aza-macrocycle comprises at least one instance of the group of the formula (ix). In these instances, in certain embodiments, the conjugated aza-macrocycle of the Formula (IV) is of the Formula (VIII) or (IX):

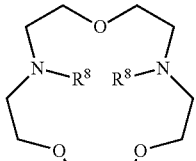

(VIII)

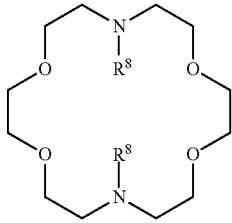

(IX)

or salt thereof, wherein $R^8$ is as defined herein.

Exemplary conjugated aza-macrocycles of the Formula (V) include, but are not limited to:

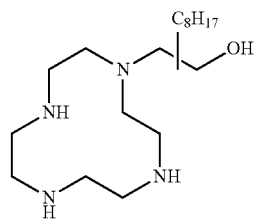

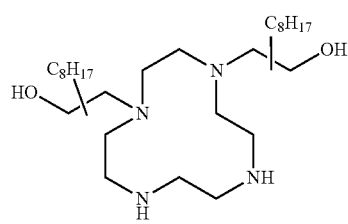

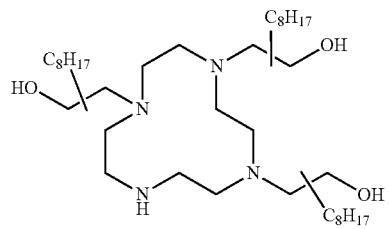

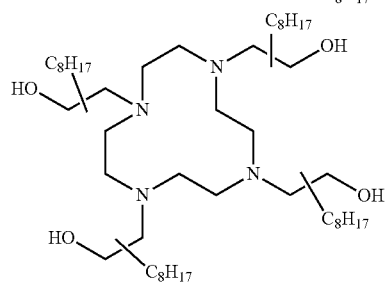

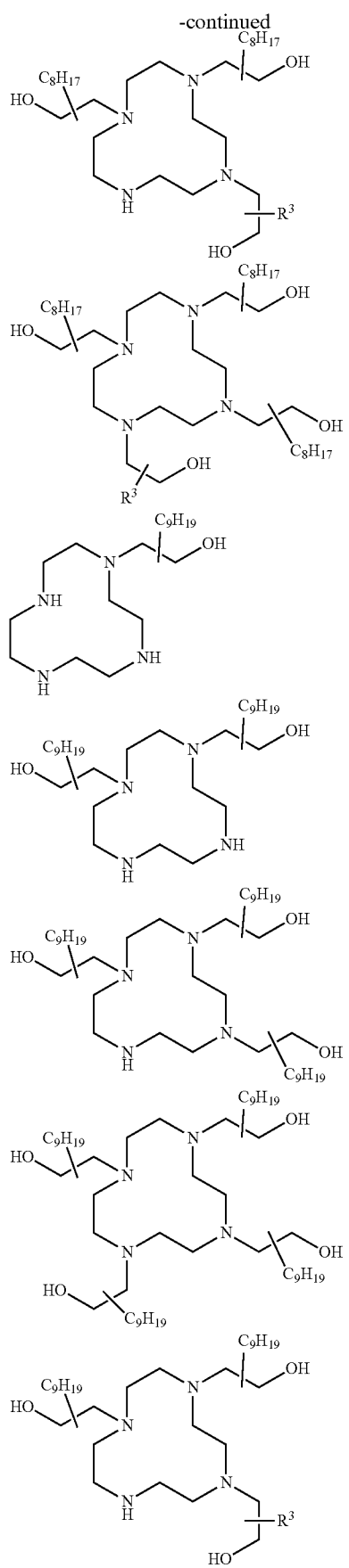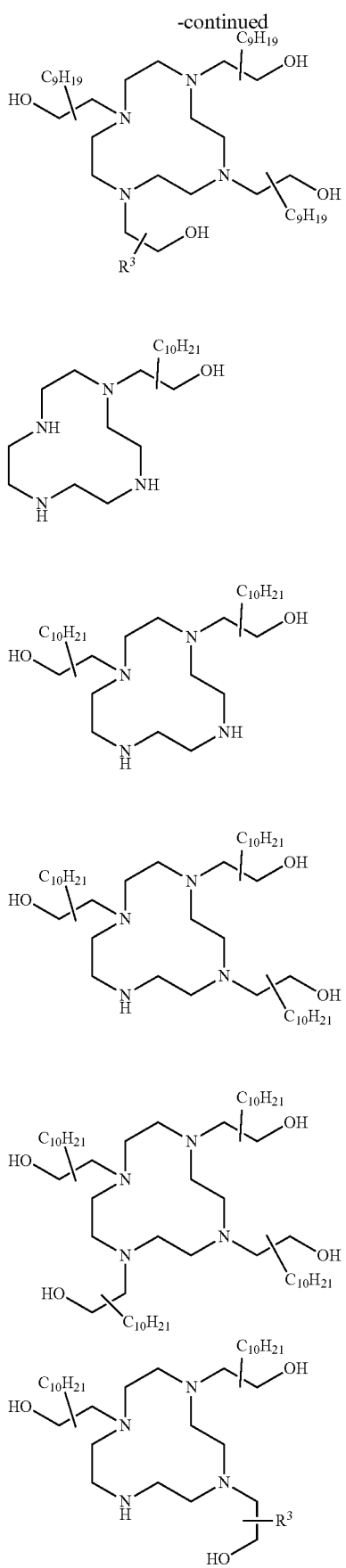

87
-continued
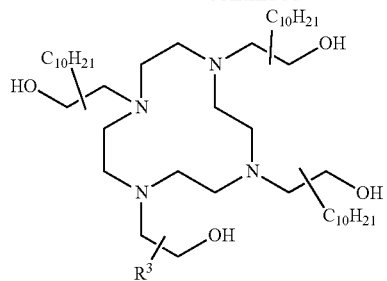
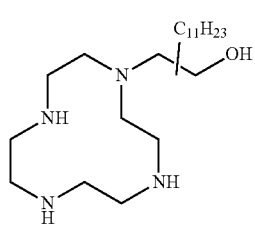
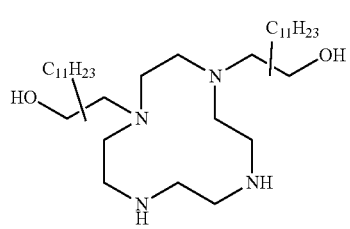
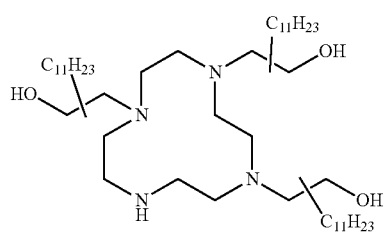
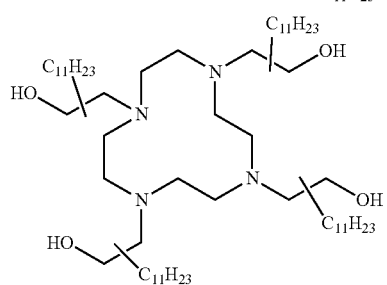
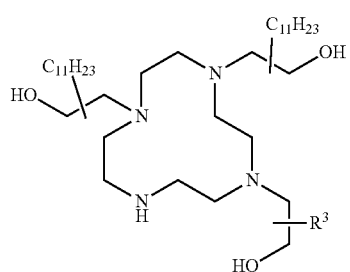
88
-continued
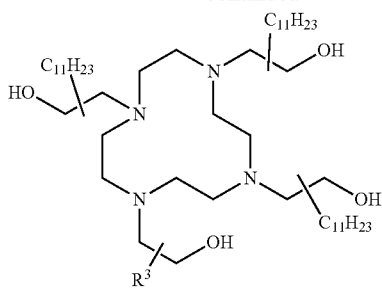
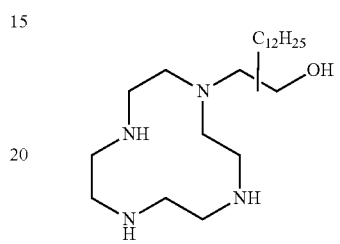
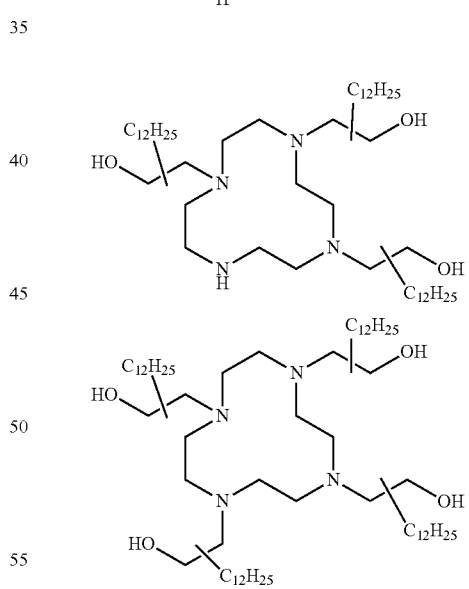
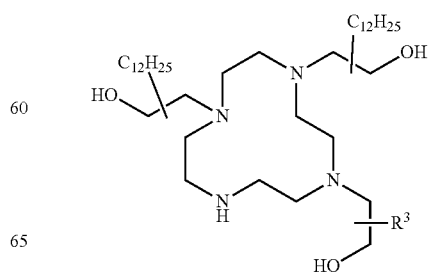

-continued
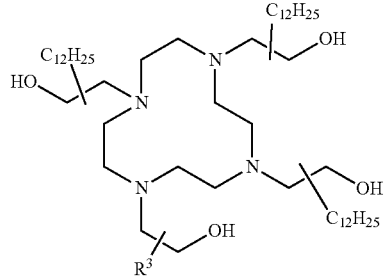
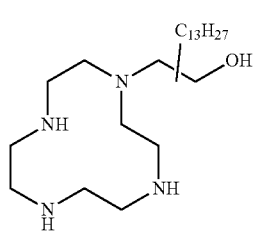
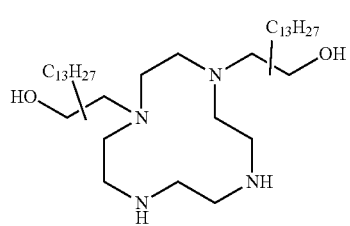
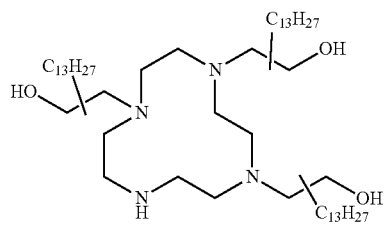
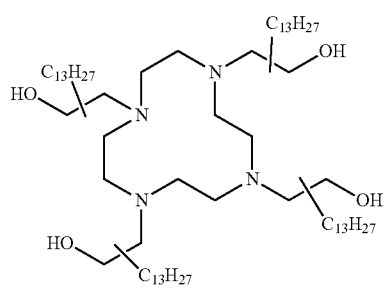
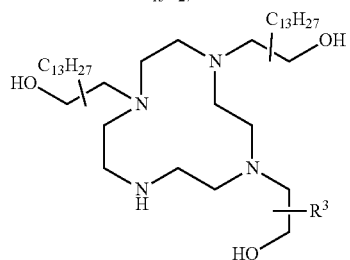
-continued
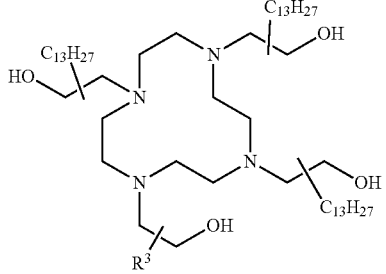
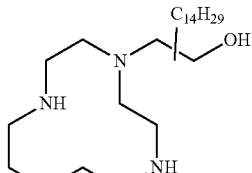
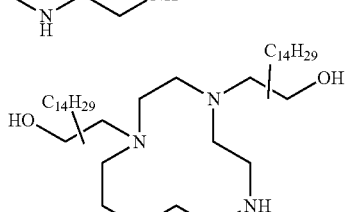
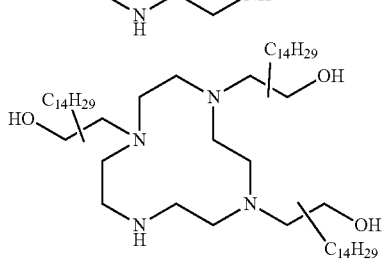
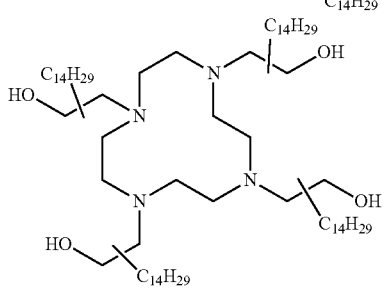
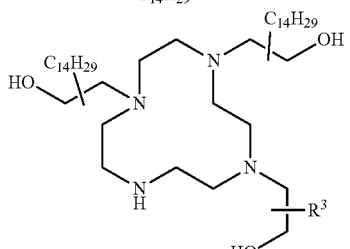
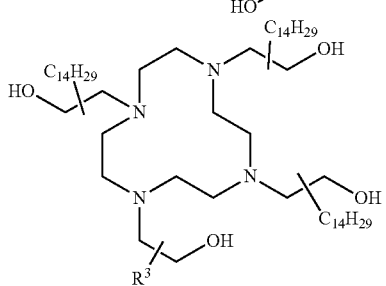

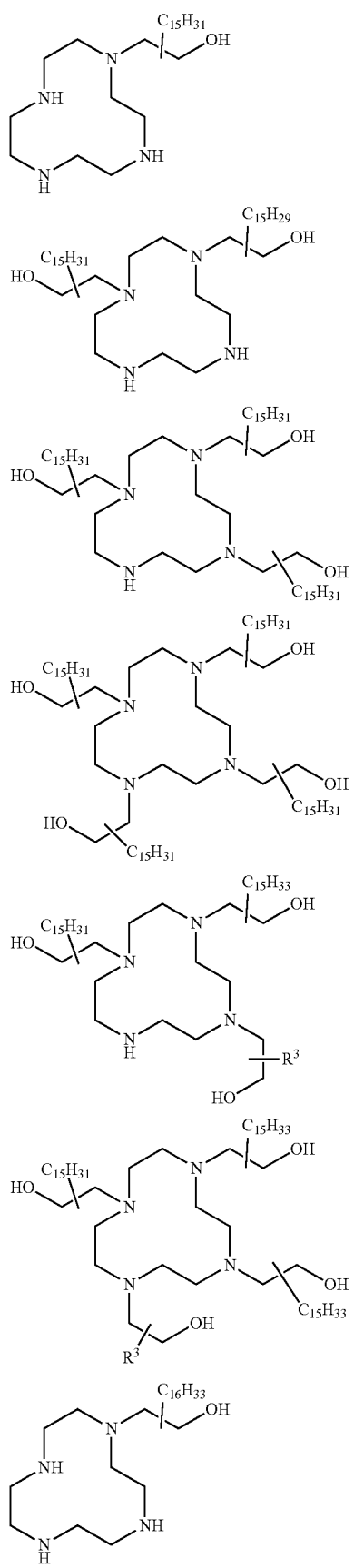
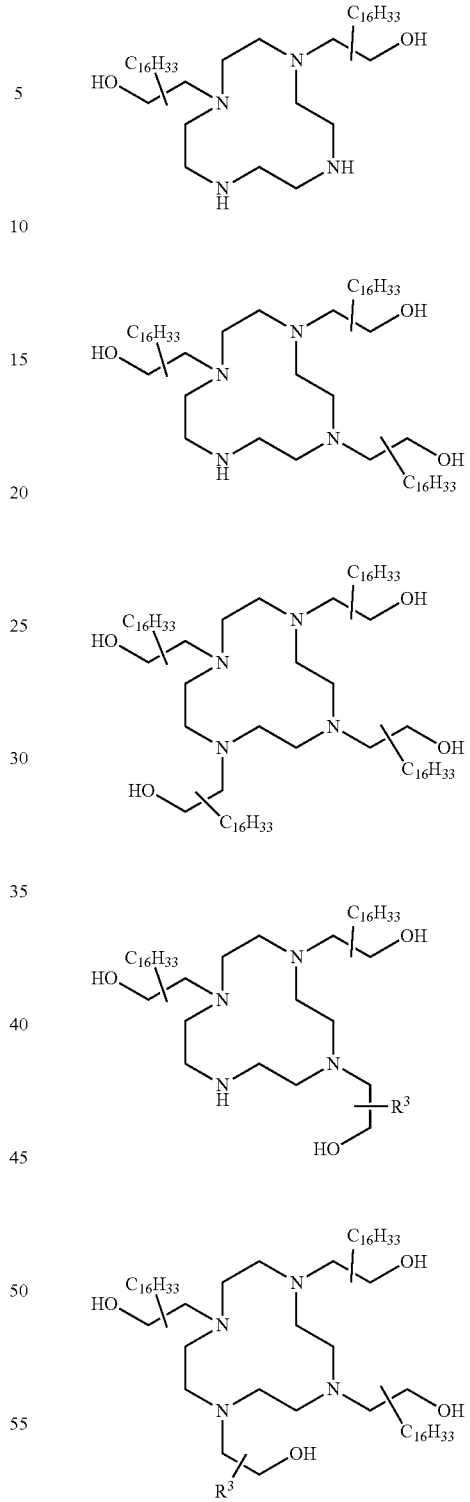
and salts thereof, wherein $R^3$ is defined herein. In certain embodiments, $R^3$ is a polyethyleglycol polymer. In certain embodiments, $R^3$ is $PEG_{1000}$. In certain embodiments, $R^3$ is $PEG_{2000}$. In certain embodiments, $R^3$ is $PEG_{1.5K}$.
Exemplary conjugated aza-macrocycles of the Formula (VI) include, but are not limited to:

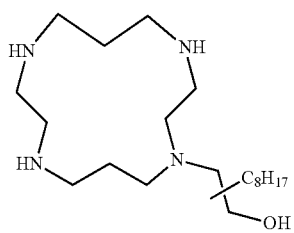
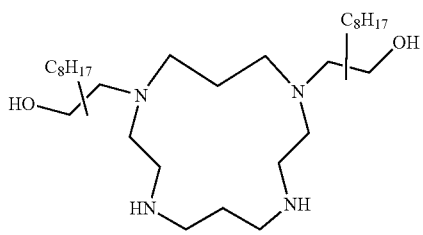
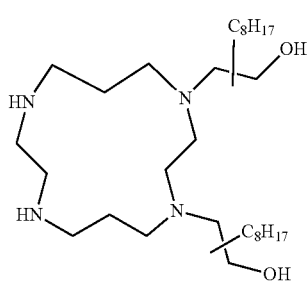
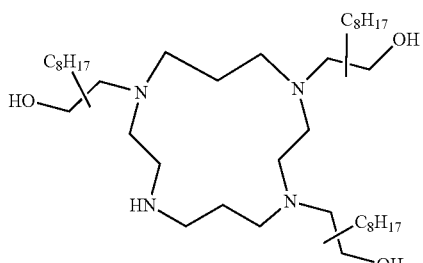
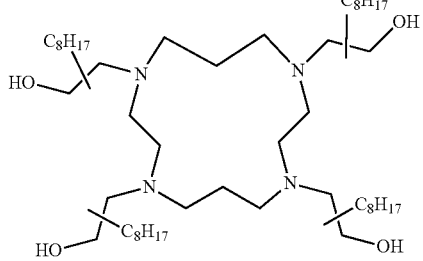
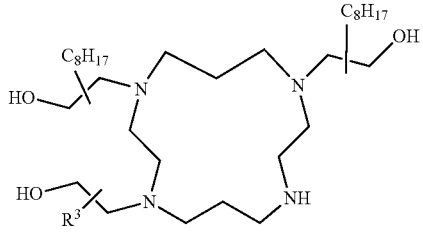
-continued
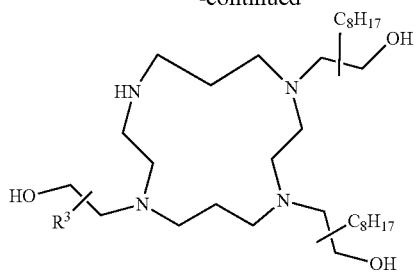
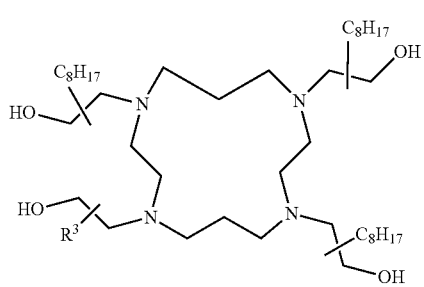
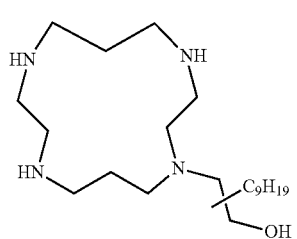
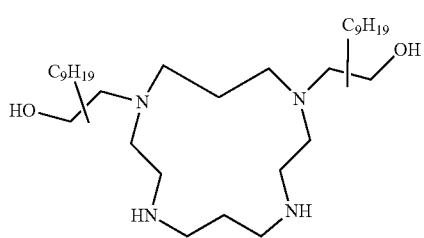
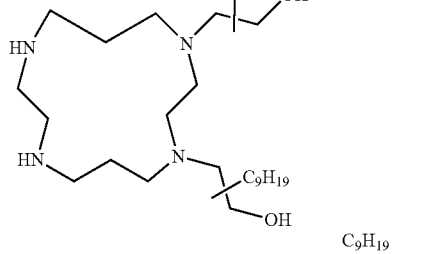
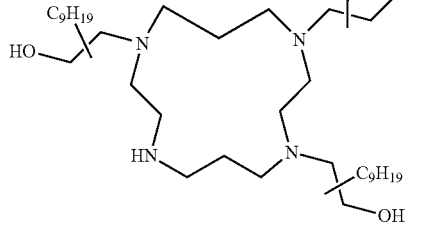

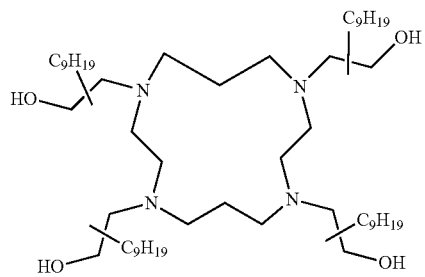
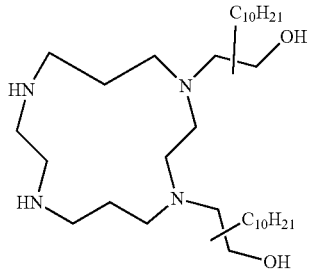
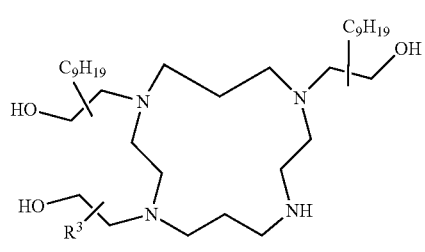
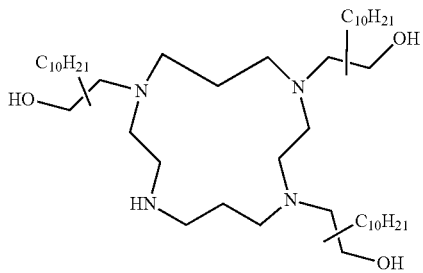
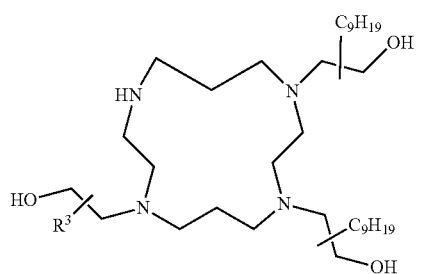
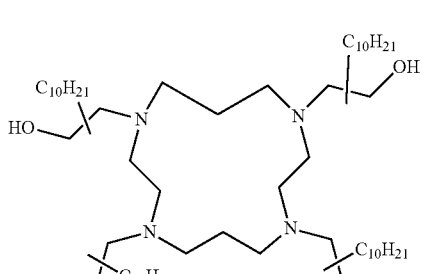
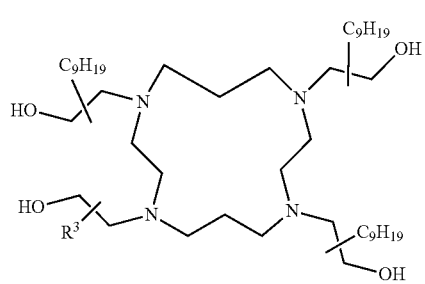
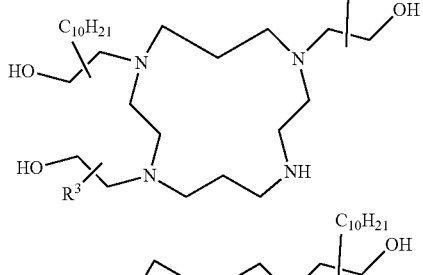
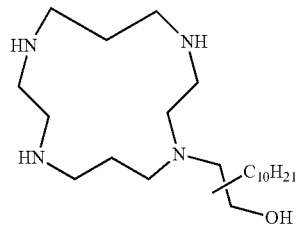
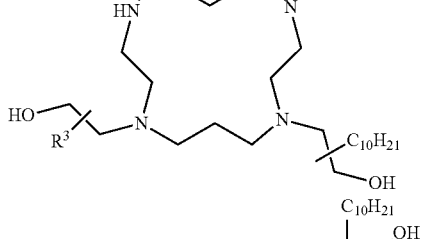
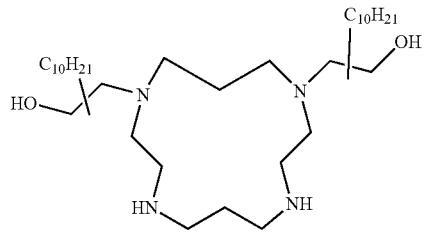
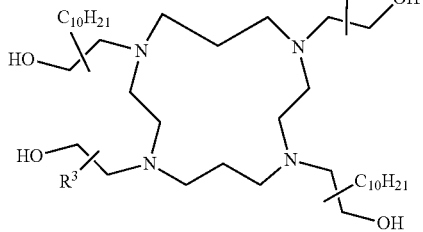

97
-continued
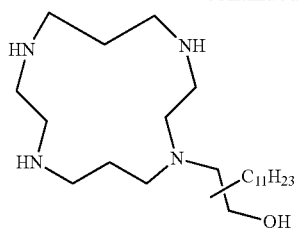
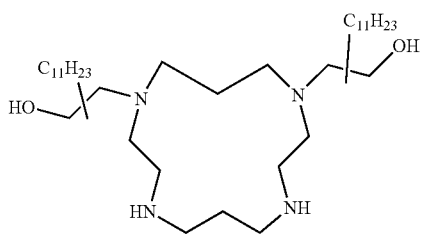
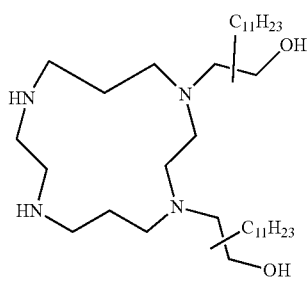
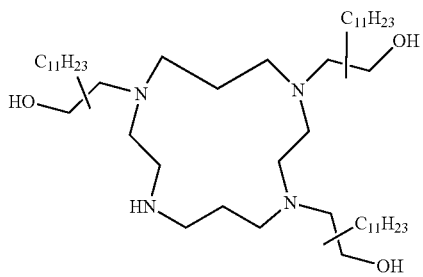
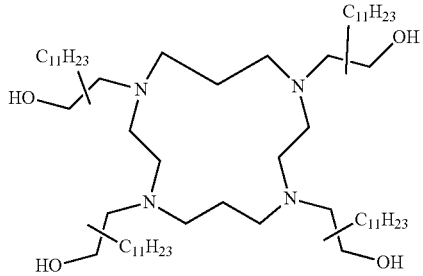
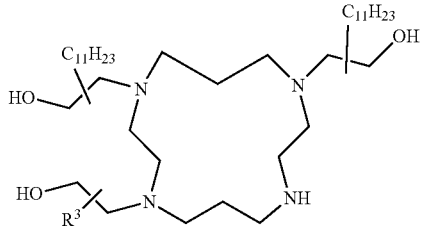
98
-continued
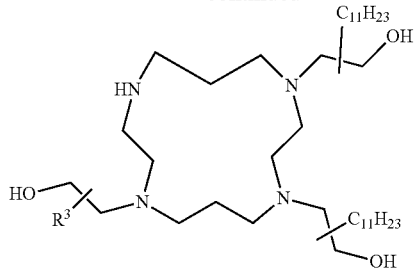
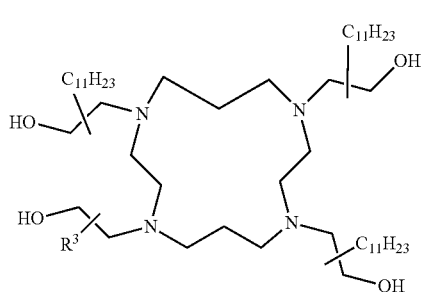
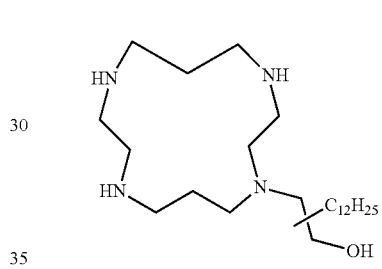
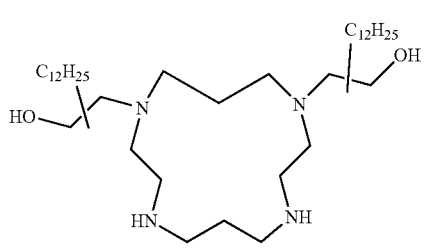
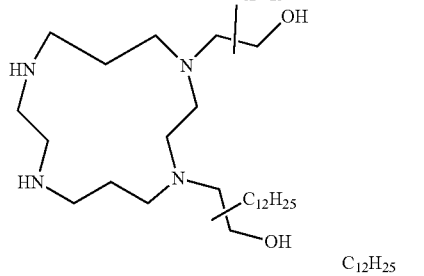
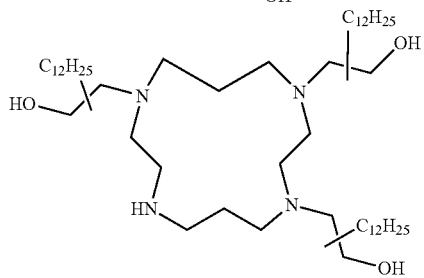

-continued
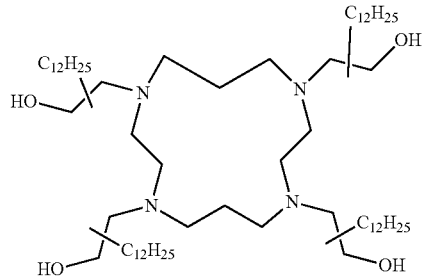
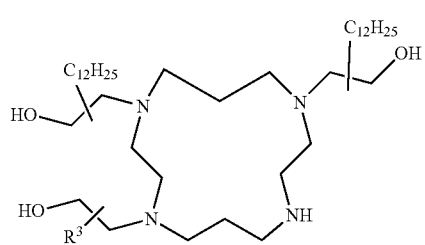
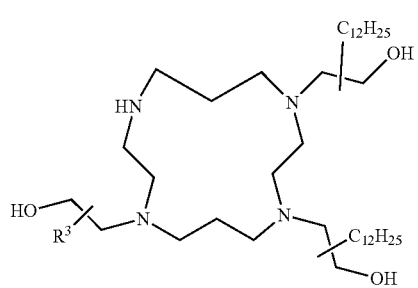
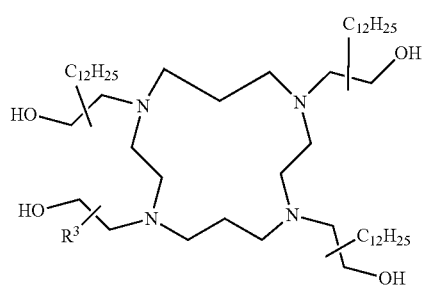
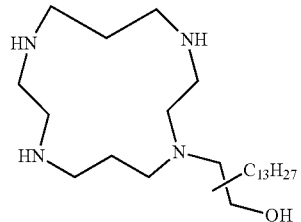
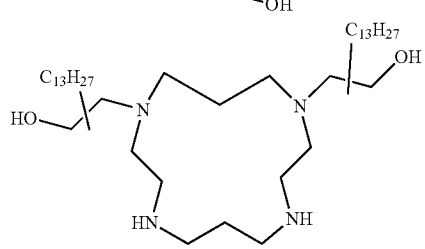
-continued
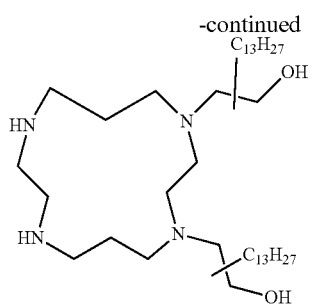
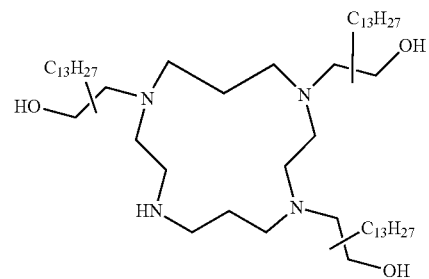
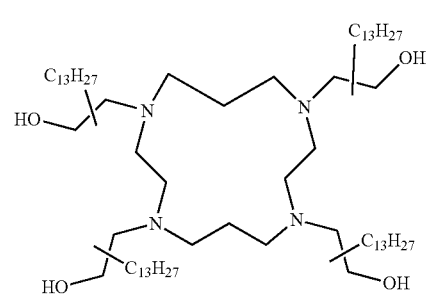
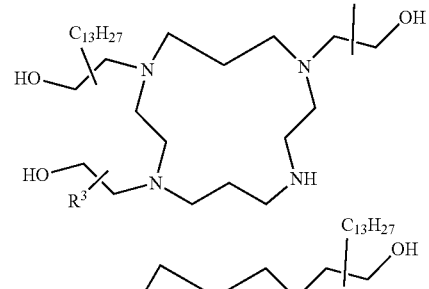
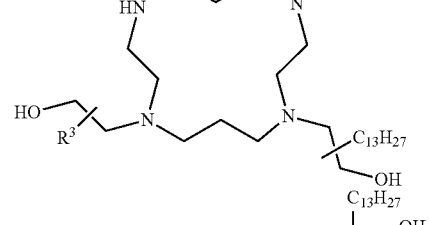
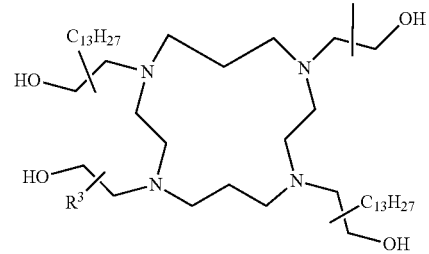

101
-continued
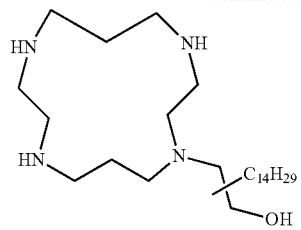
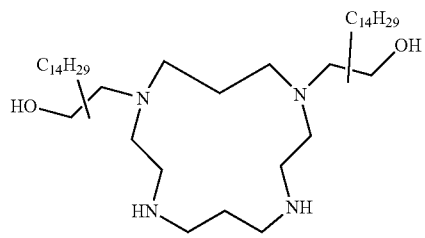
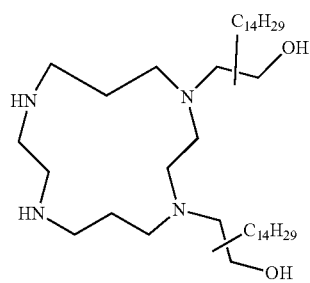
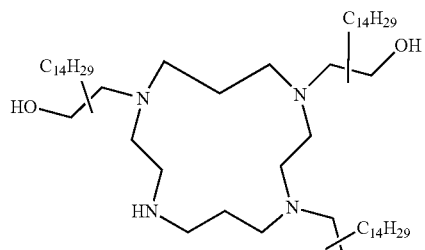
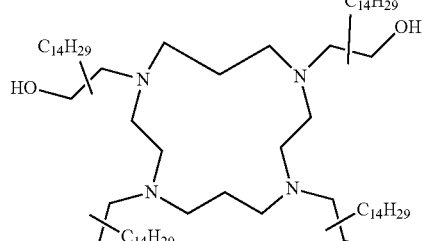
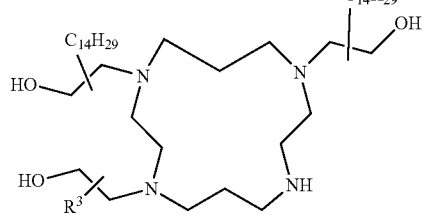
102
-continued
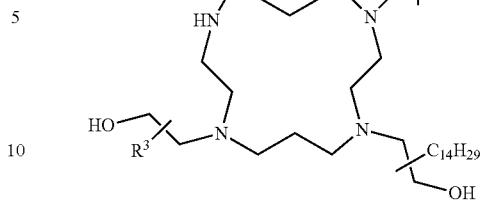
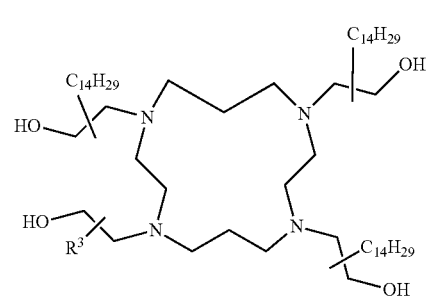
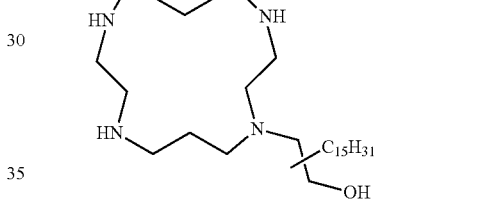
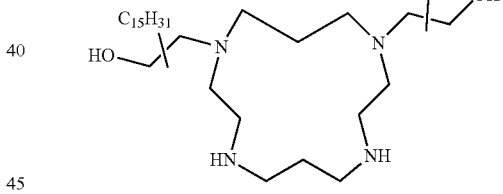
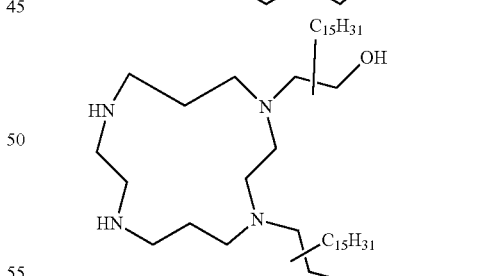
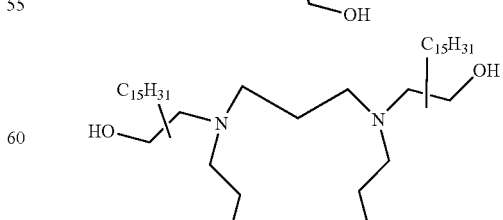
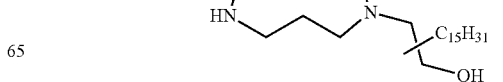

-continued
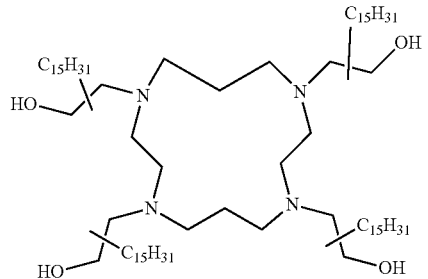
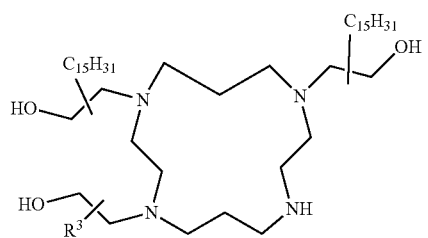
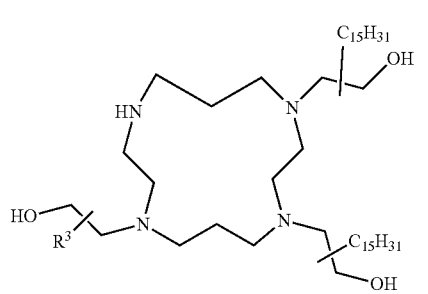
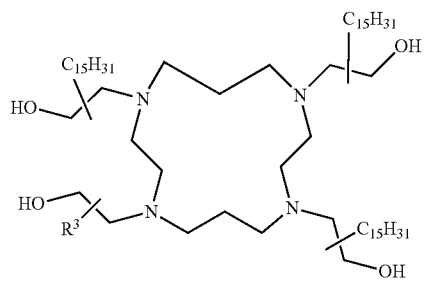
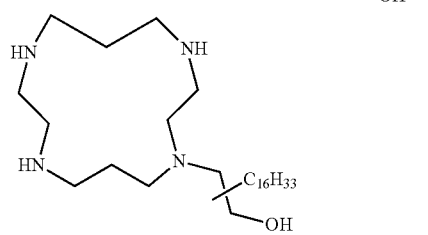
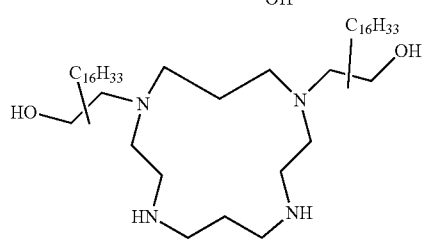
-continued
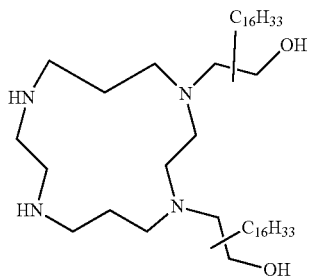
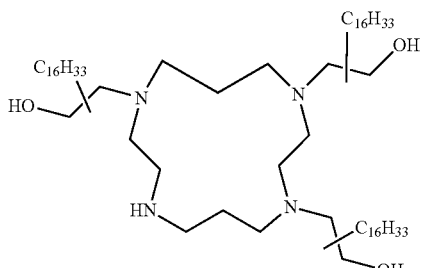
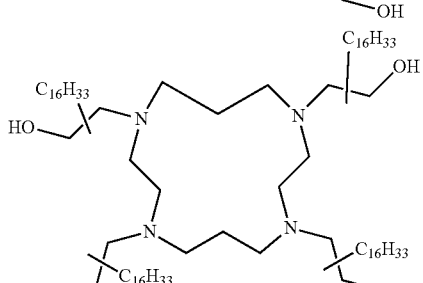
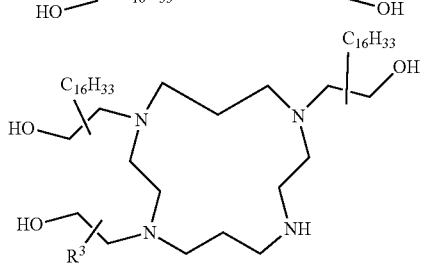
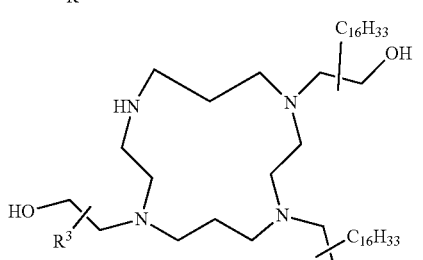
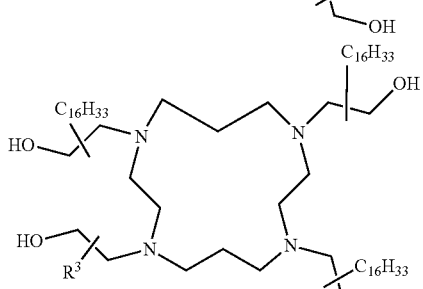
and salts thereof, wherein $R^3$ is defined herein. In certain embodiments, $R^3$ is a polyethyleglycol polymer. In certain embodiments, $R^3$ is $PEG_{1000}$. In certain embodiments, $R^3$ is $PEG_{2000}$. In certain embodiments, $R^3$ is $PEG_{1.5K}$.
Exemplary conjugated aza-macrocycles of the Formula (VII) include, but are not limited to:
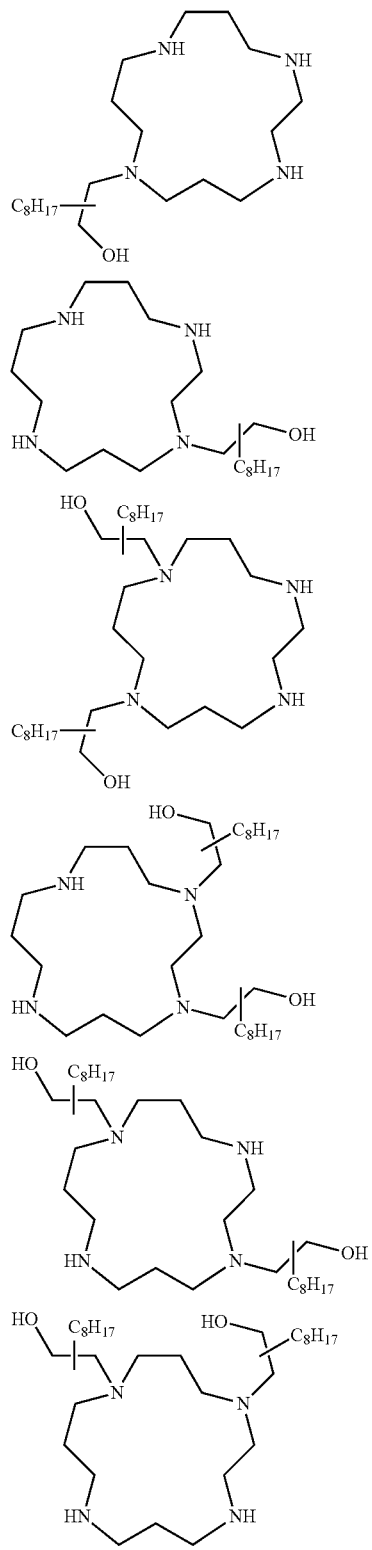
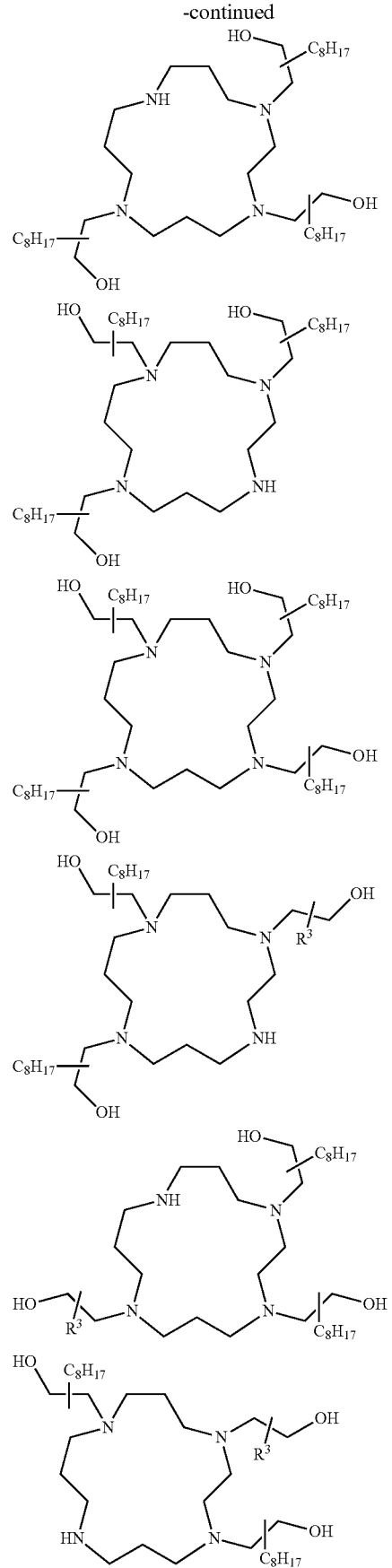

107
-continued
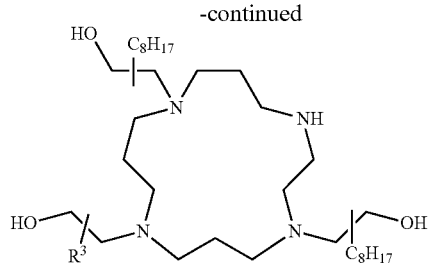
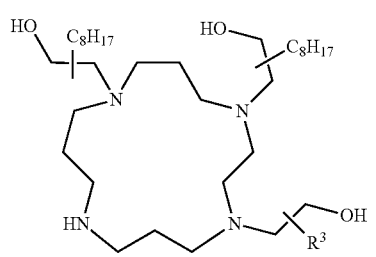
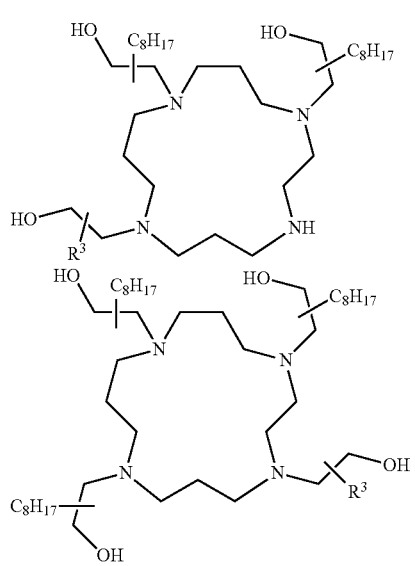
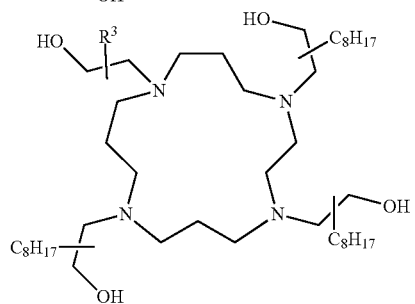
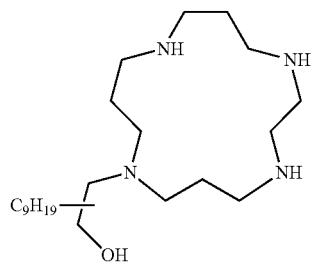
108
-continued
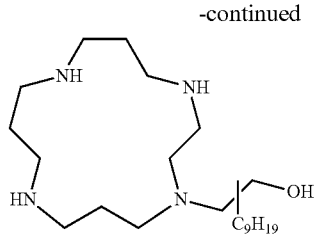
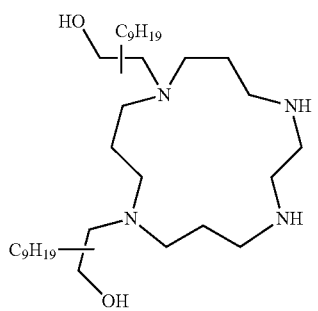
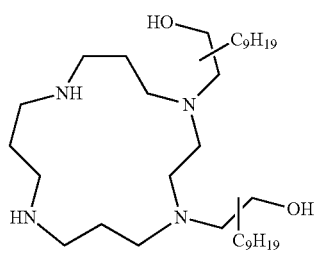
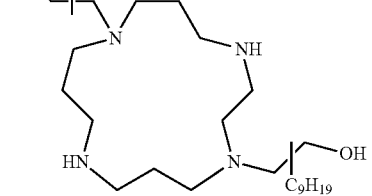
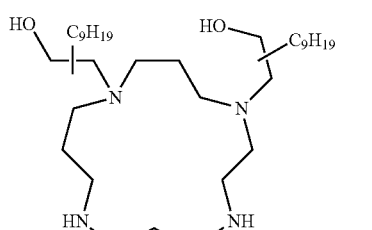
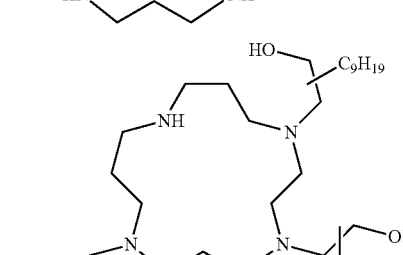
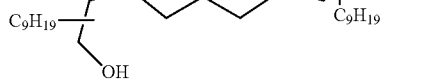

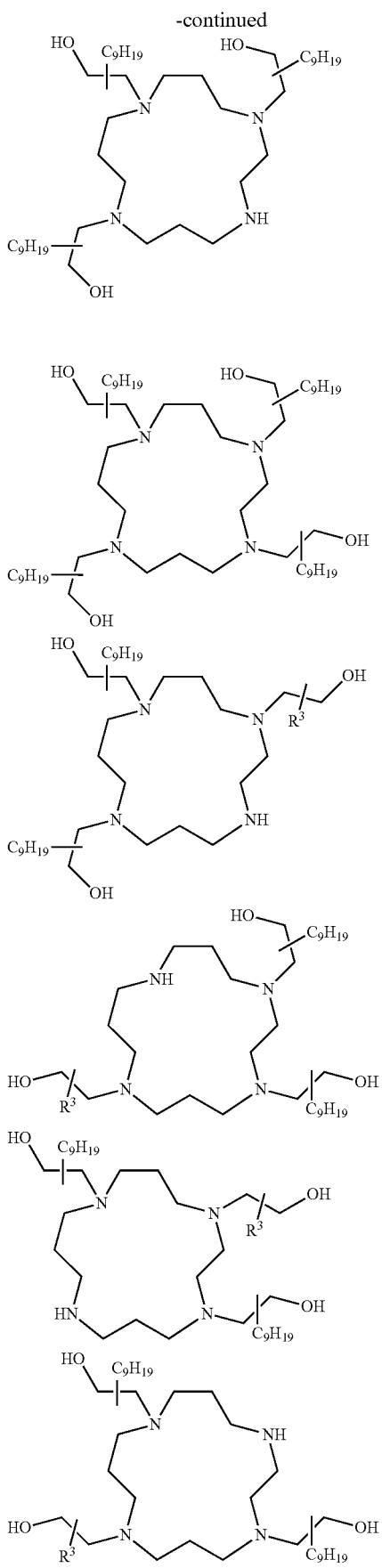
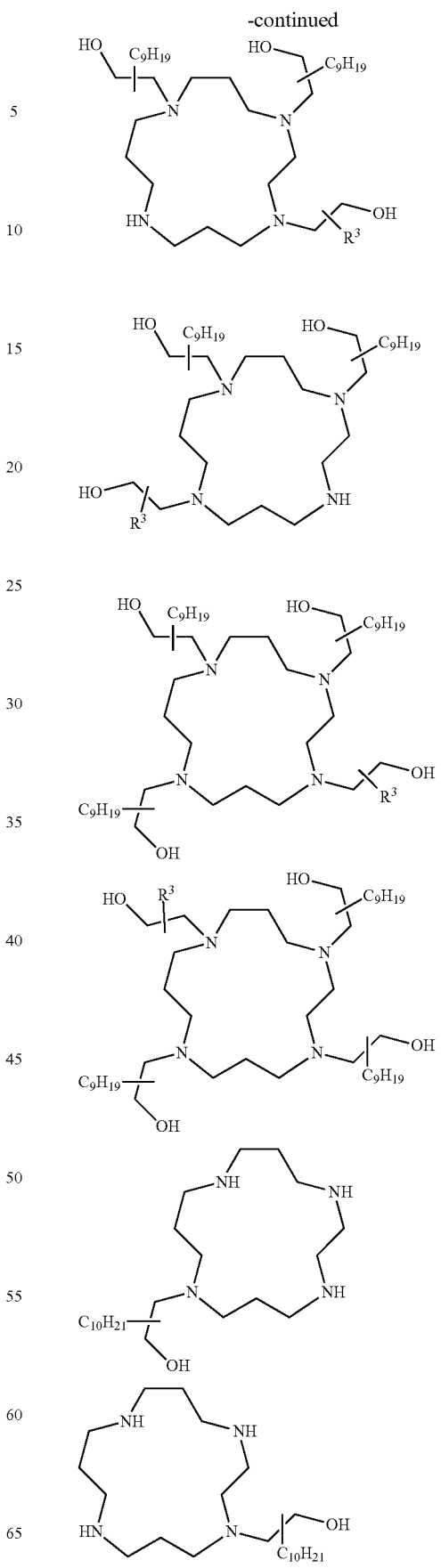

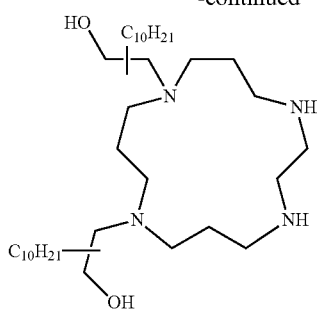
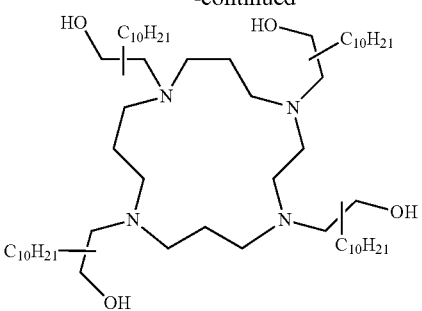
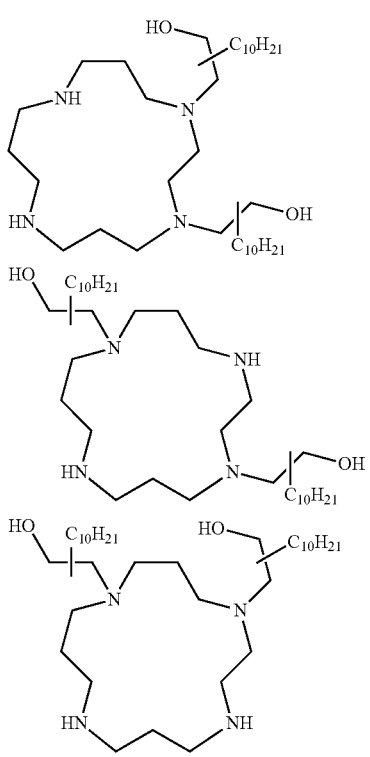
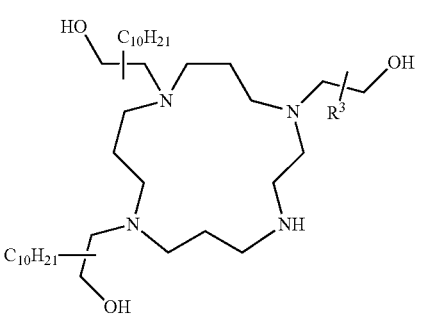
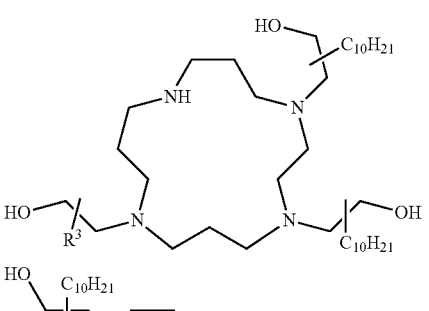
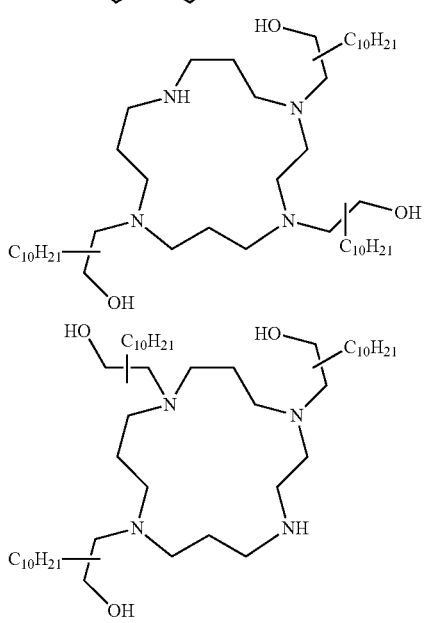
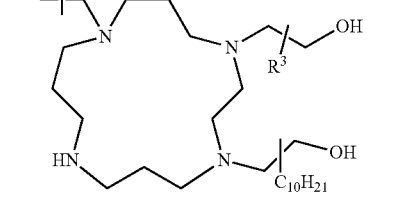
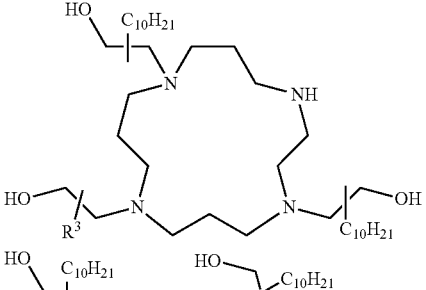
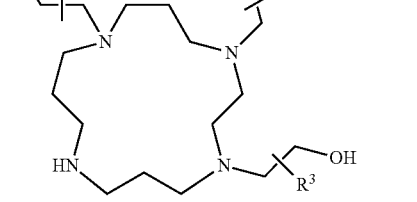

113
-continued
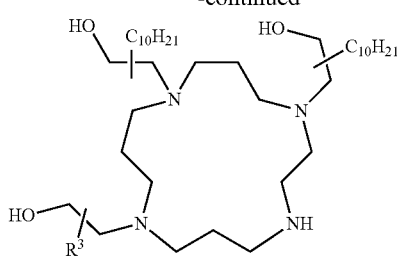
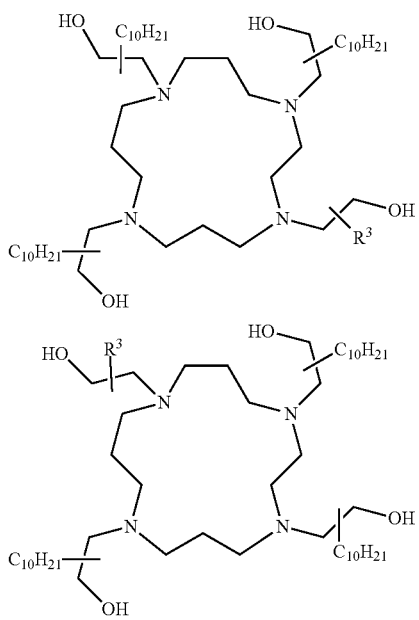
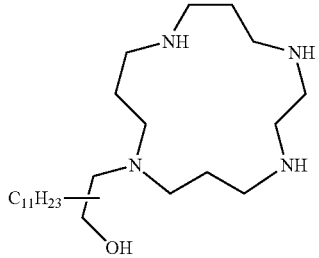
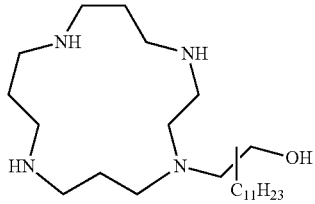
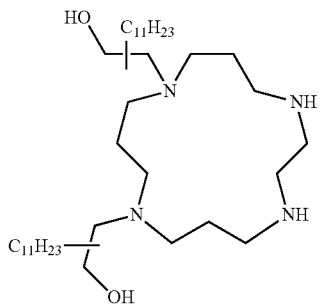
114
-continued
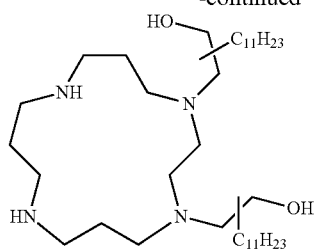
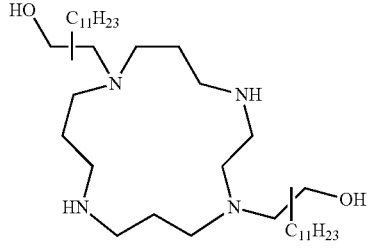
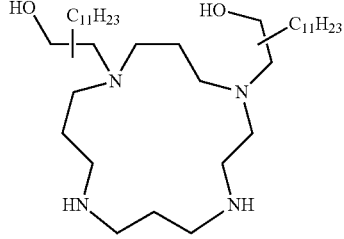
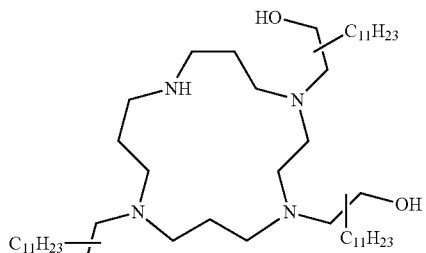
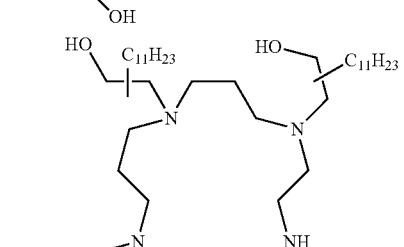
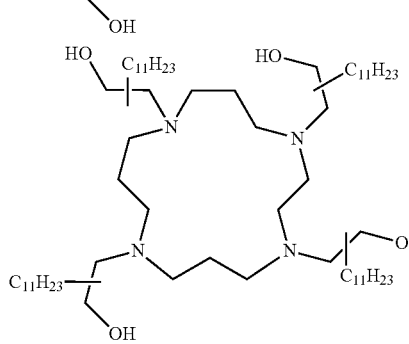

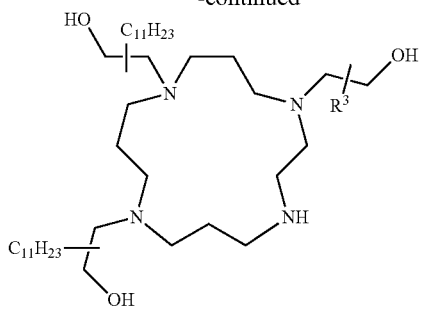
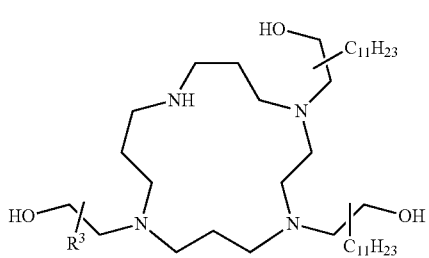
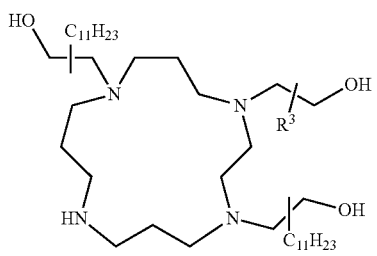
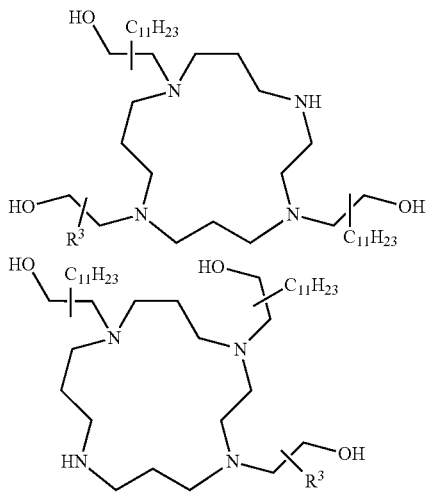
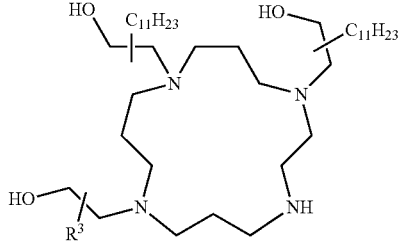
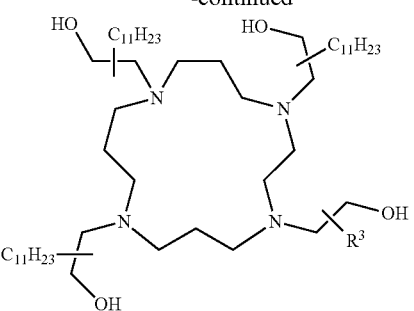
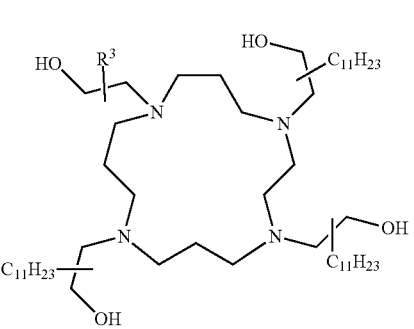
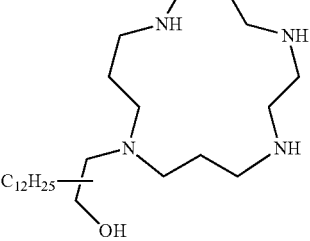
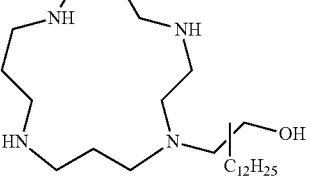
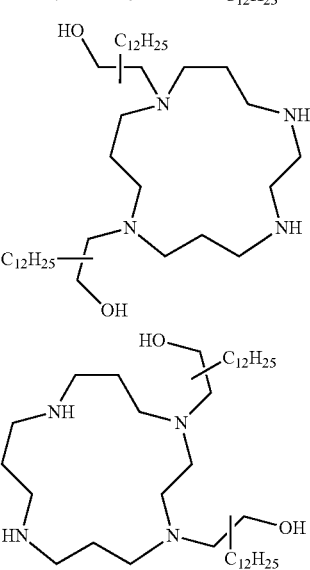

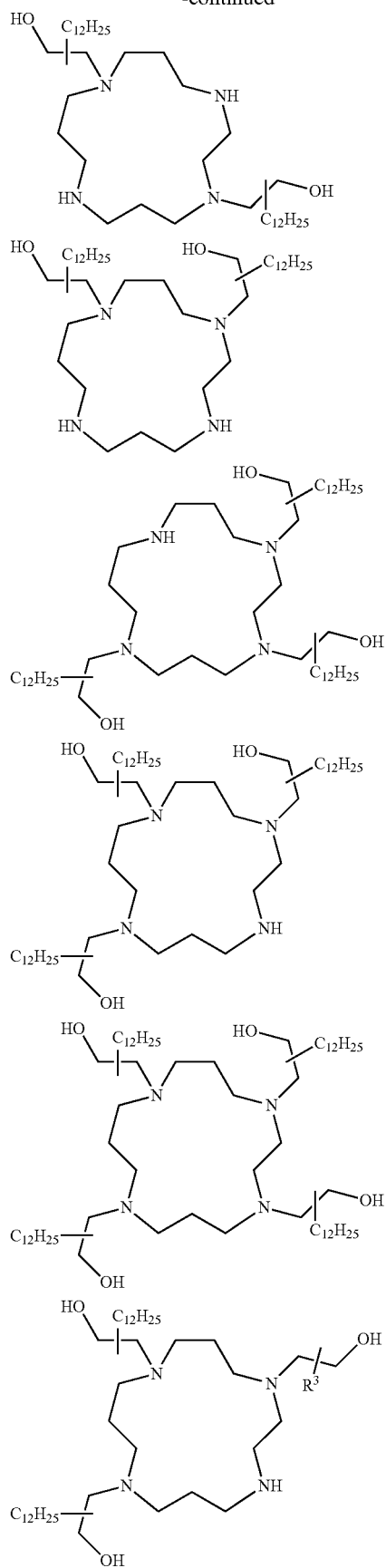
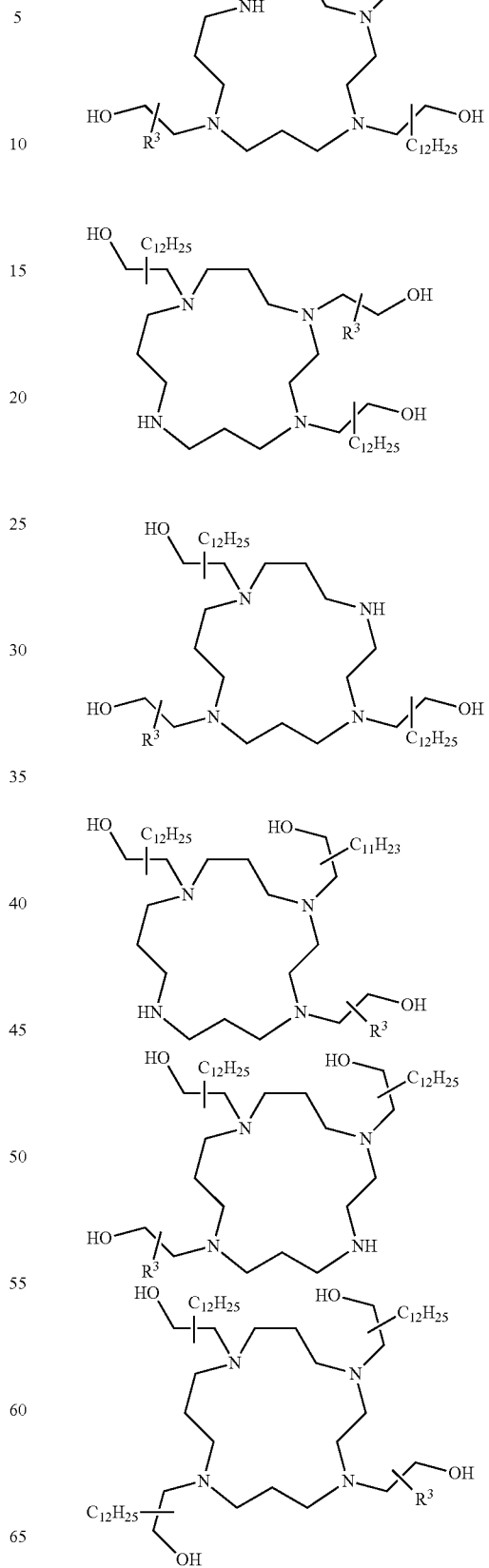

-continued
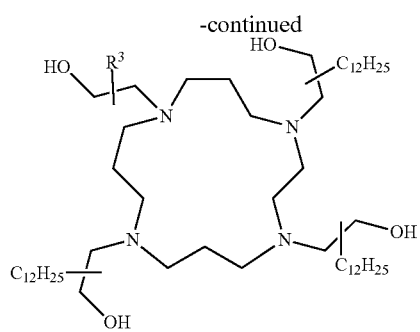
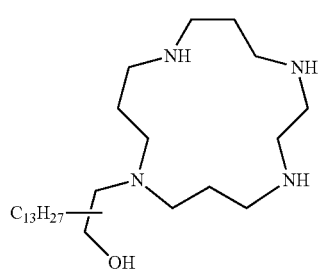
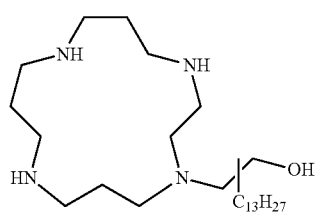
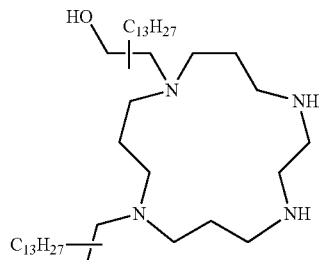
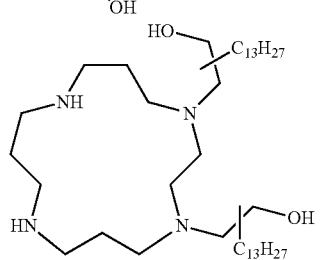
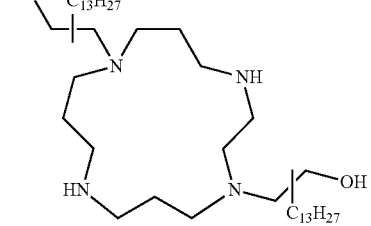
-continued
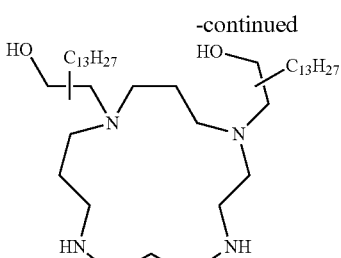
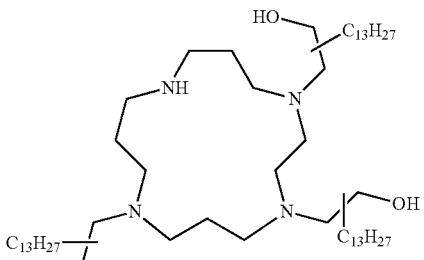
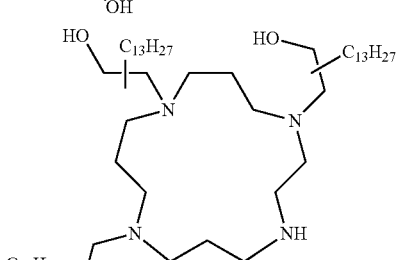
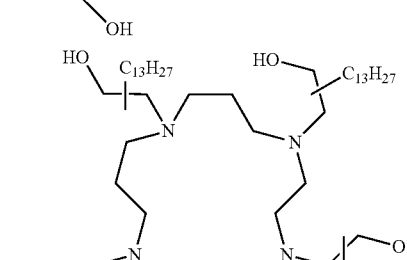
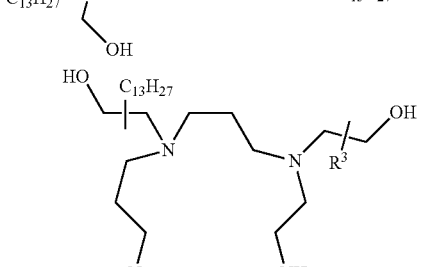
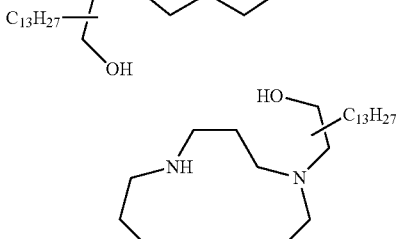
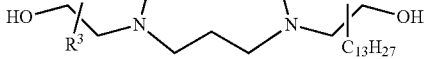

121
-continued
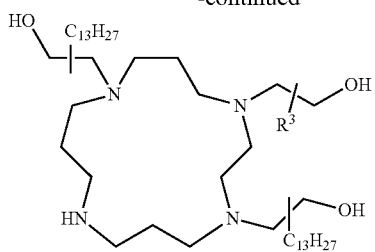
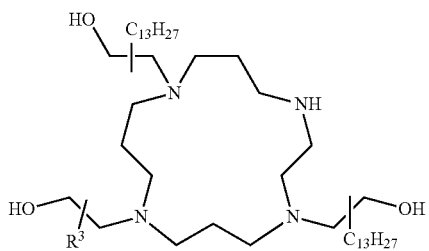
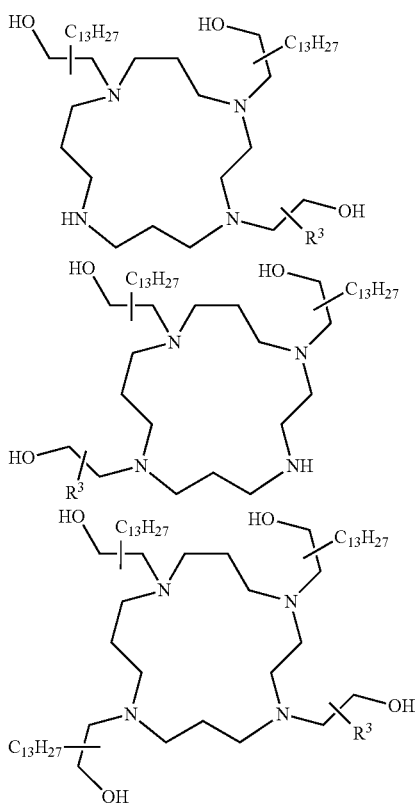
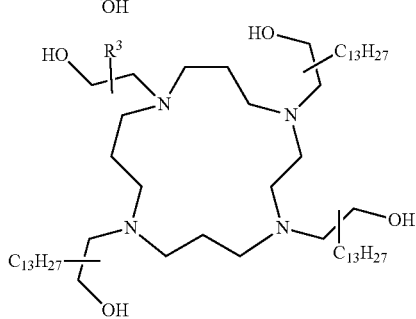
122
-continued
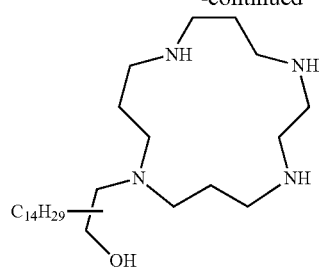
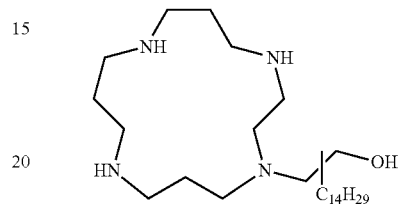
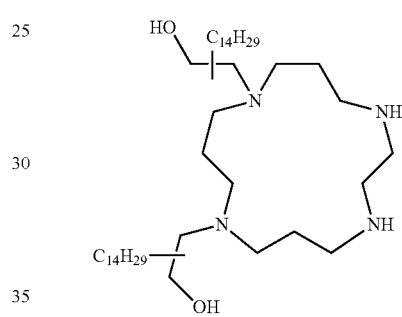
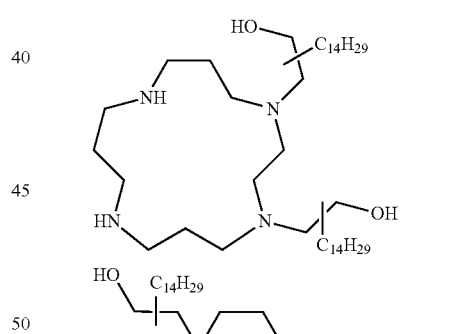
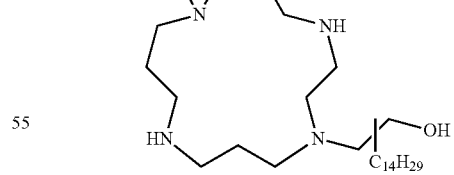
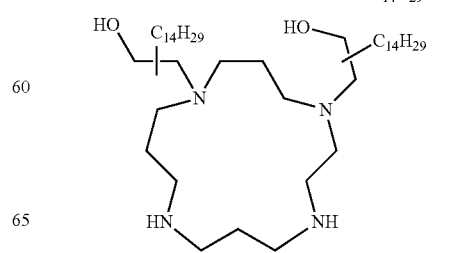

123
-continued
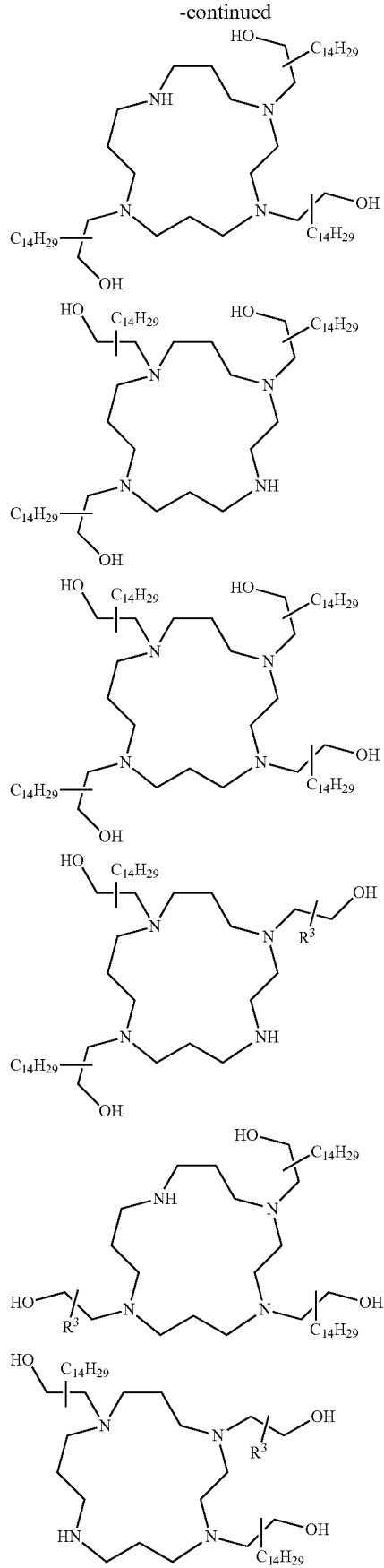
124
-continued
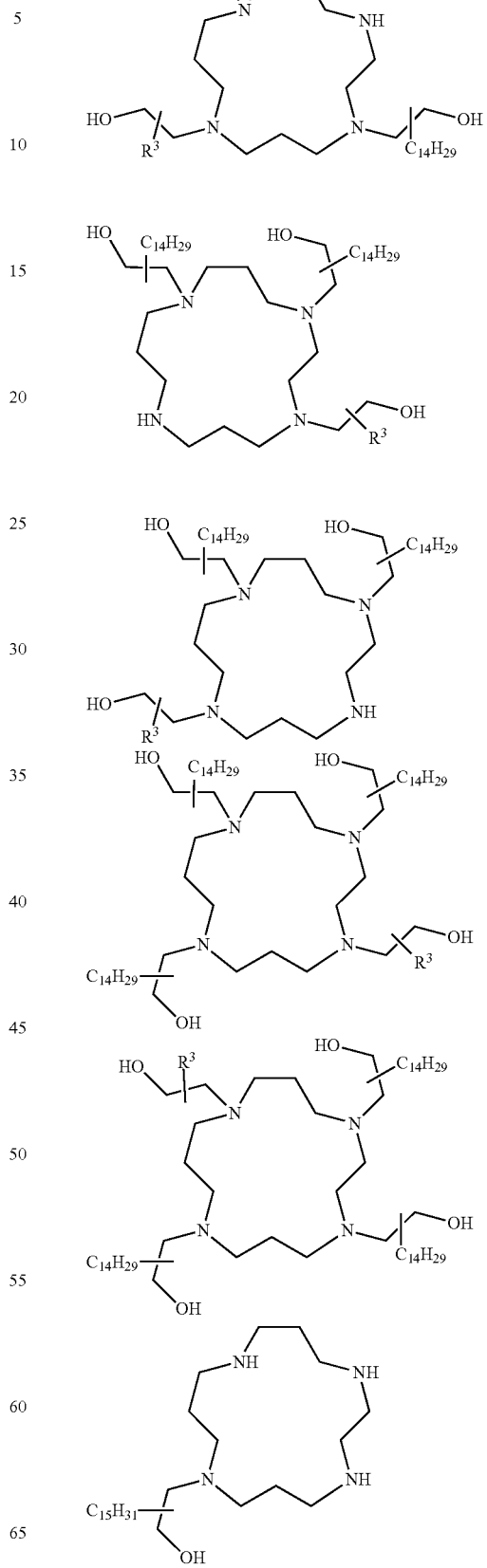

125
-continued
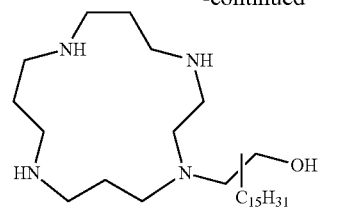
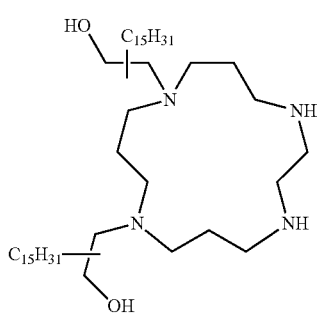
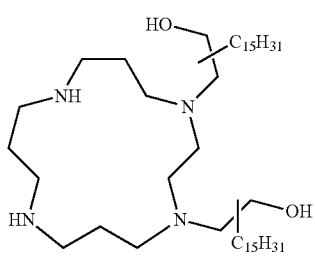
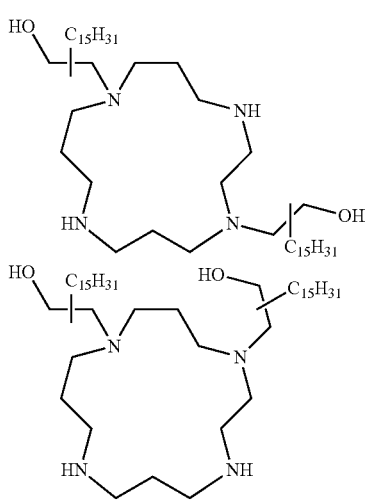
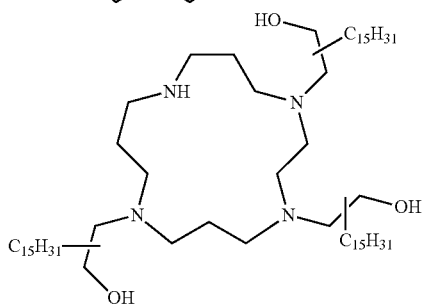
126
-continued
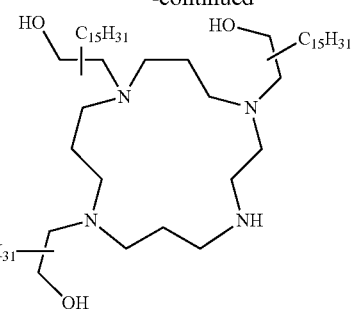
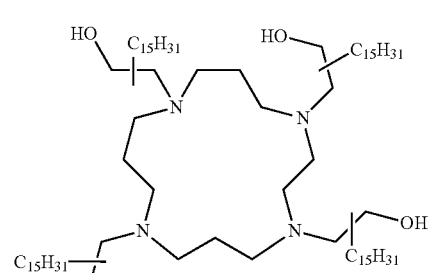
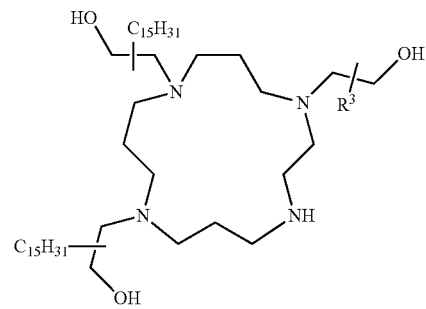
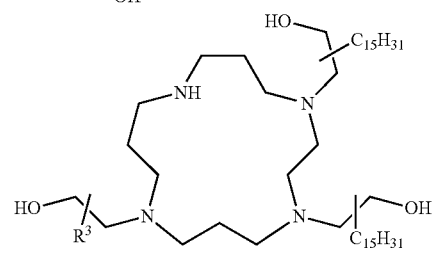
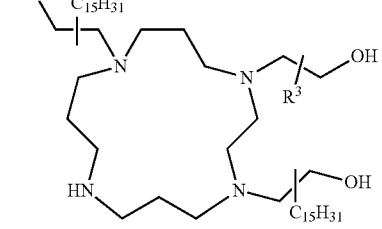
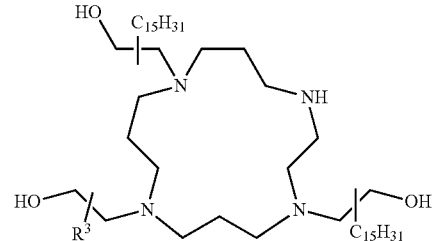

127
-continued
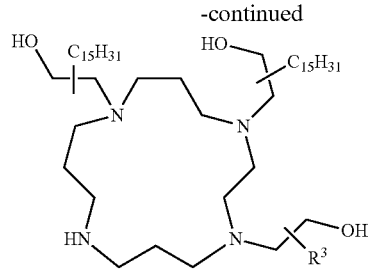
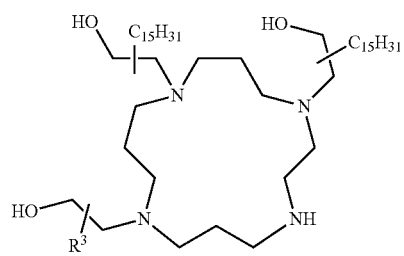
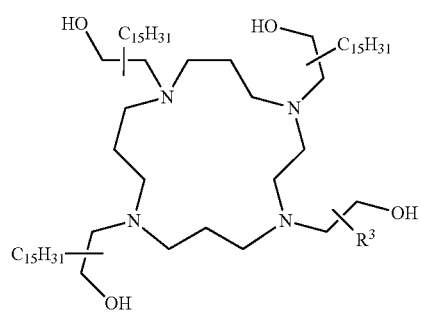
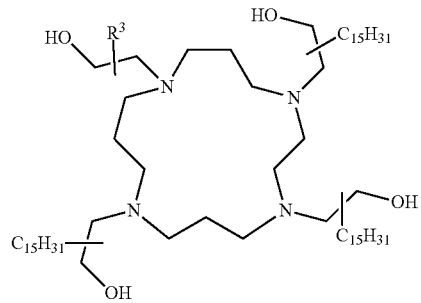
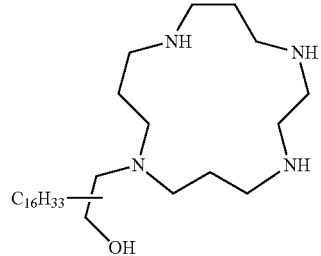
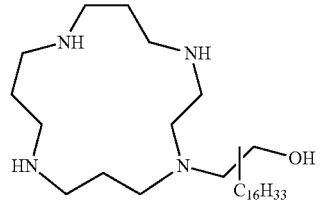
128
-continued
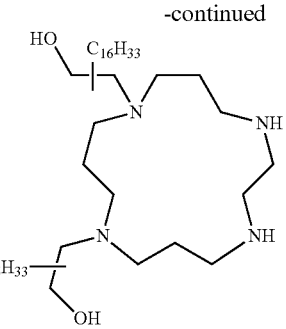
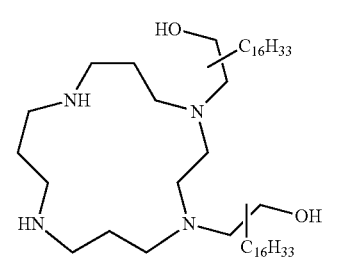
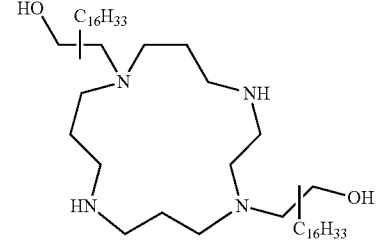
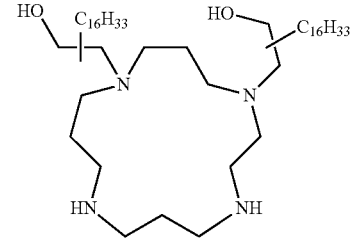
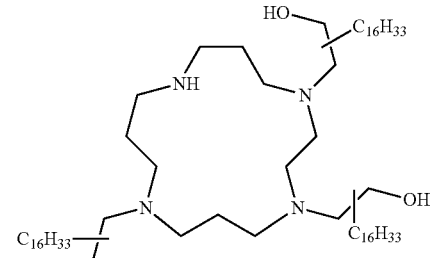
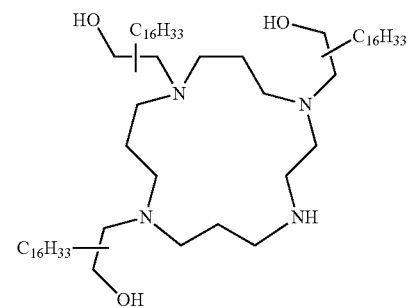

-continued
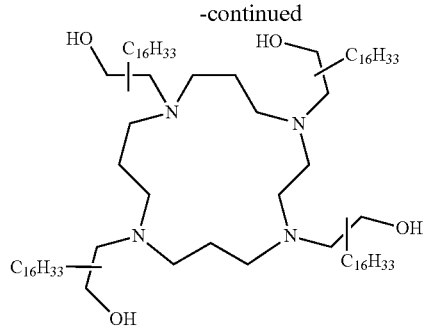
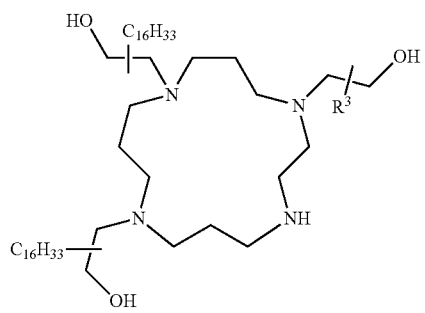
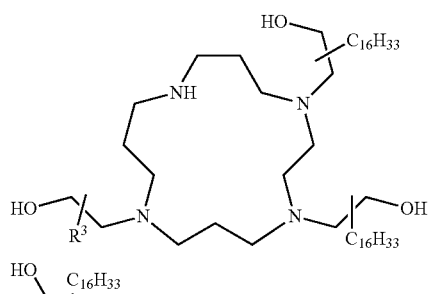
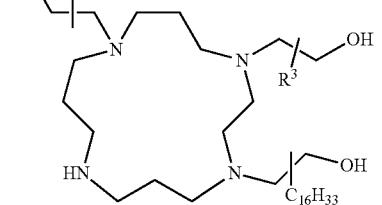
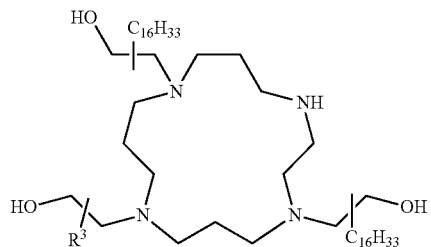
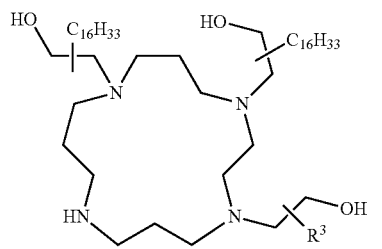
-continued
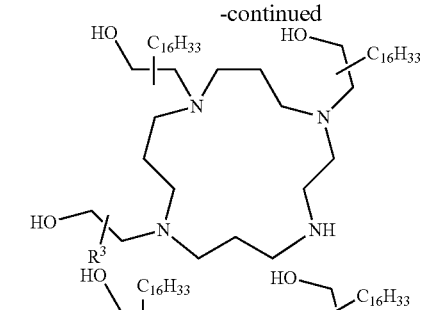
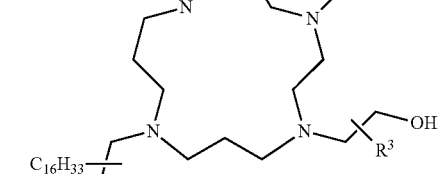
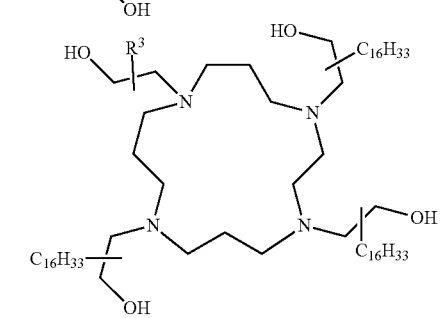
and salts thereof, wherein $R^3$ is defined herein. In certain embodiments, $R^3$ is a polyethyleglycol polymer. In certain embodiments, $R^3$ is $PEG_{1000}$. In certain embodiments, $R^3$ is $PEG_{2000}$. In certain embodiments, $R^3$ is $PEG_{1.5K}$.
Exemplary conjugated aza-macrocycles of the Formula (VII) include, but are not limited to:
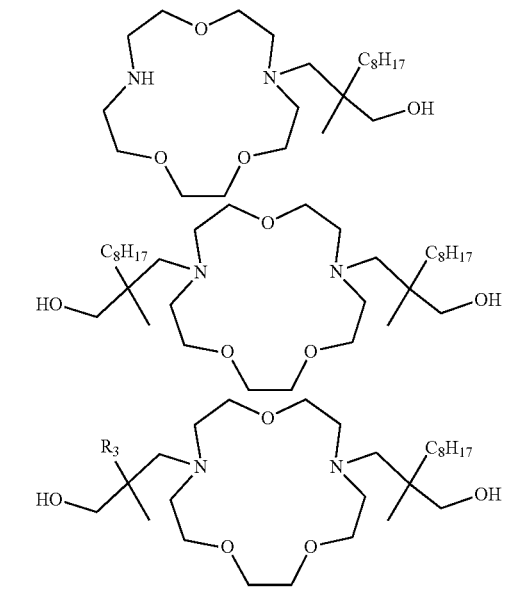

131
-continued
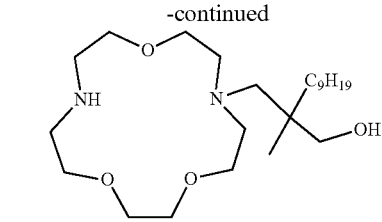
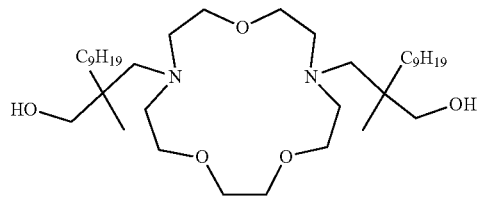
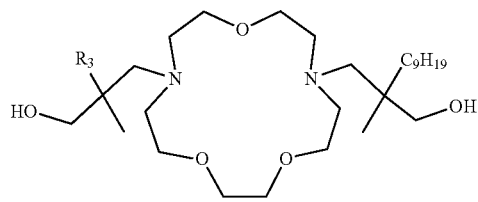
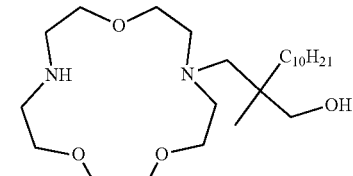
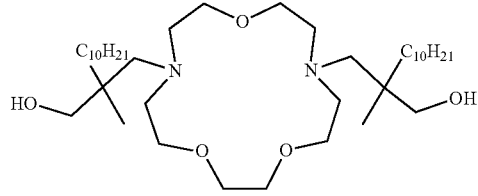
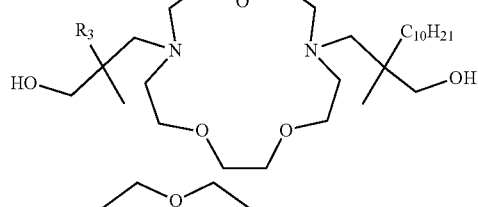
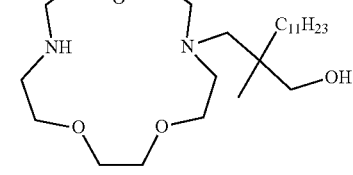
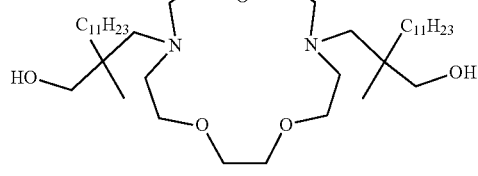
132
-continued
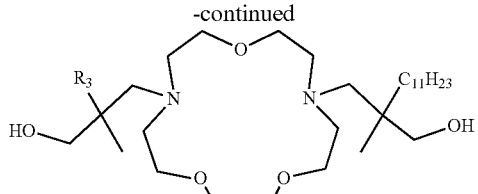
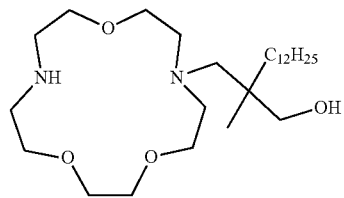
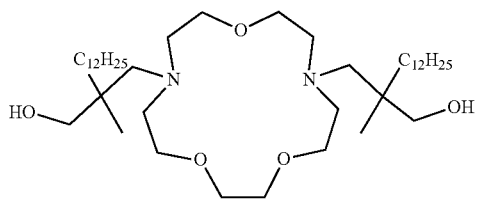
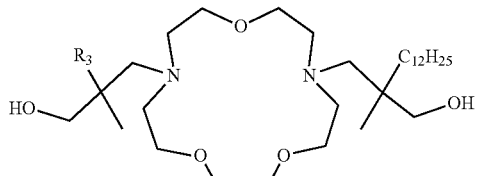
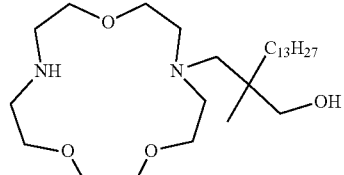
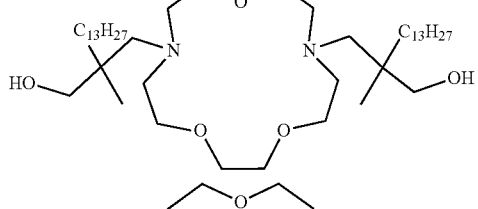
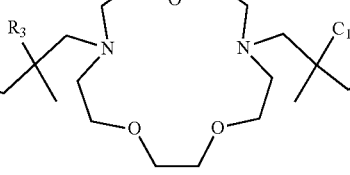
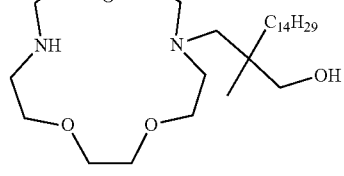

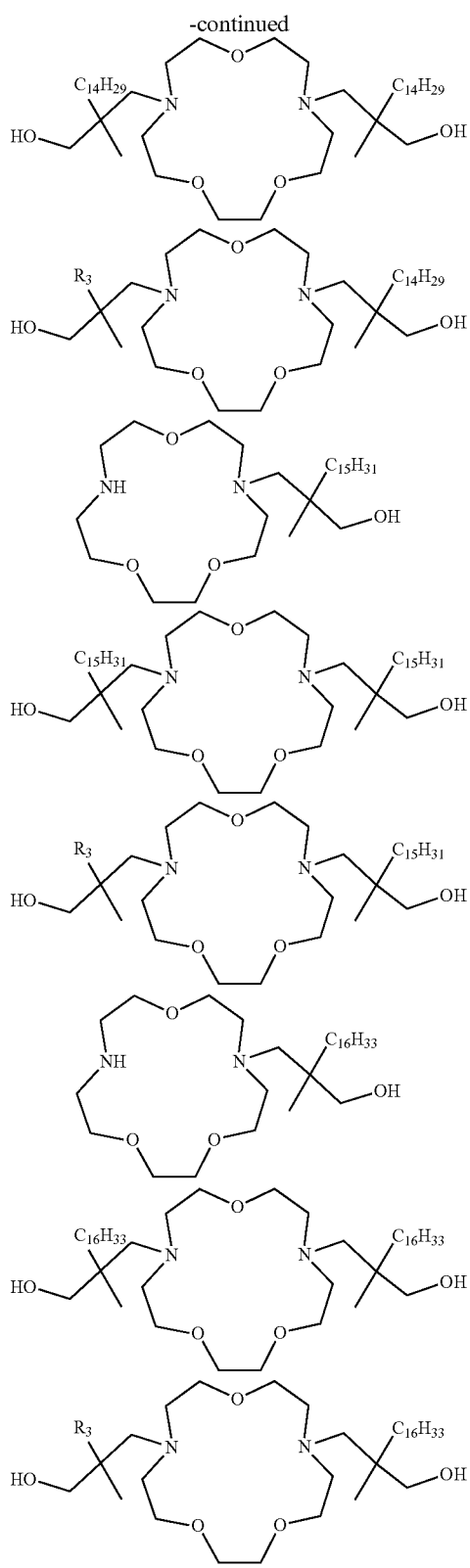
and salts thereof, wherein R³ is defined herein. In certain embodiments, R³ is a polyethyleglycol polymer. In certain embodiments, R³ is PEG$_{1000}$. In certain embodiments, R³ is PEG$_{2000}$. In certain embodiments, R³ is PEG$_{1.5K}$.
Exemplary conjugated aza-macrocycles of the Formula (VIII) include, but are not limited to:
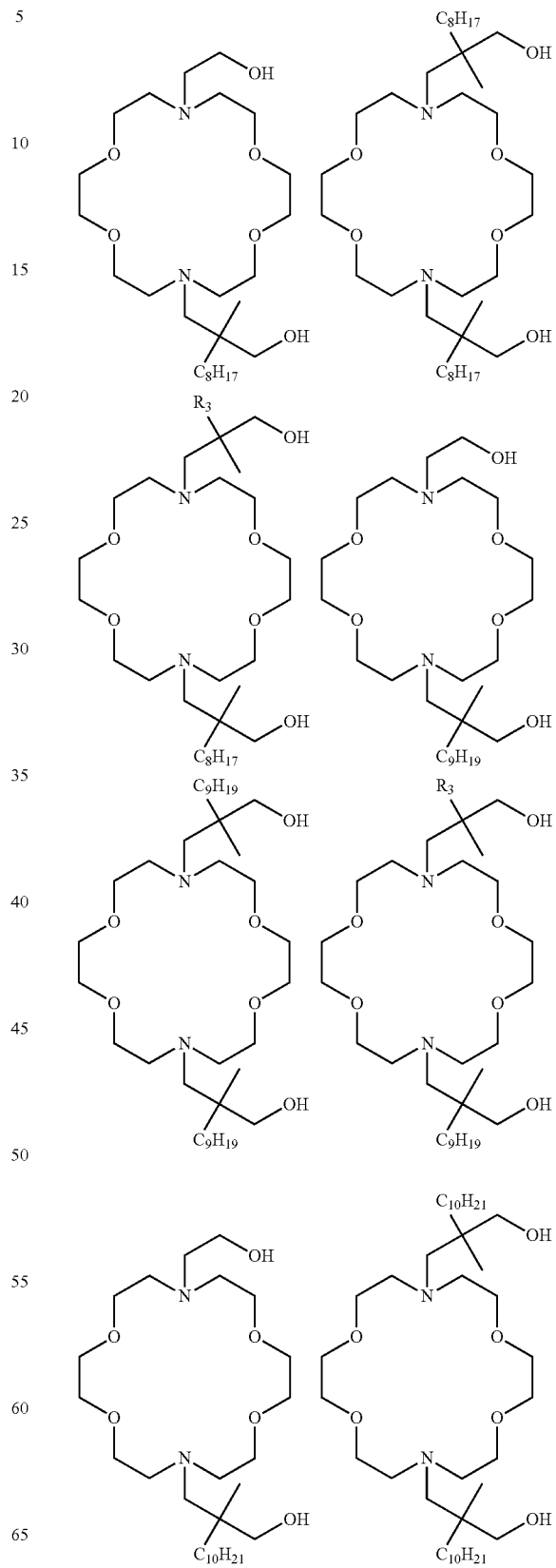

-continued
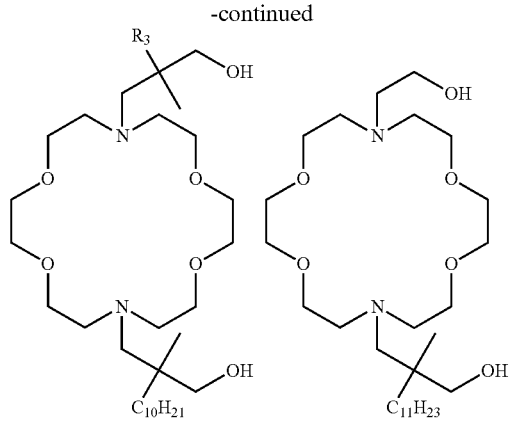
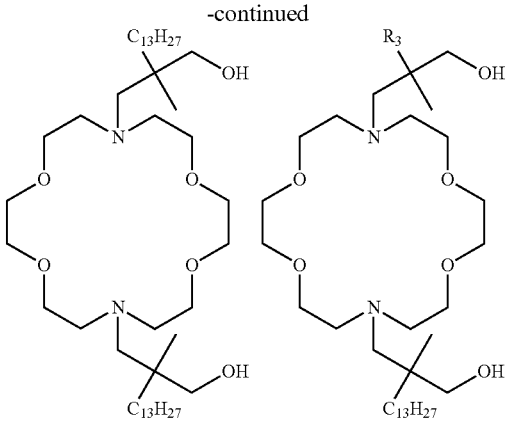
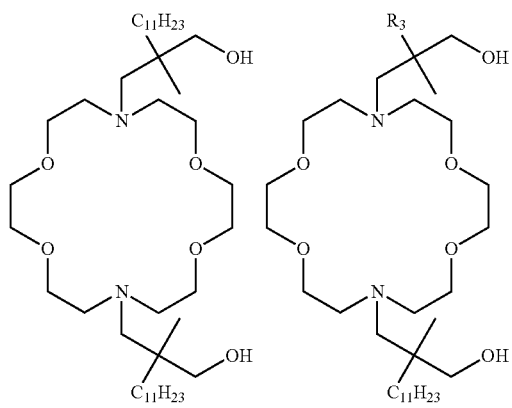
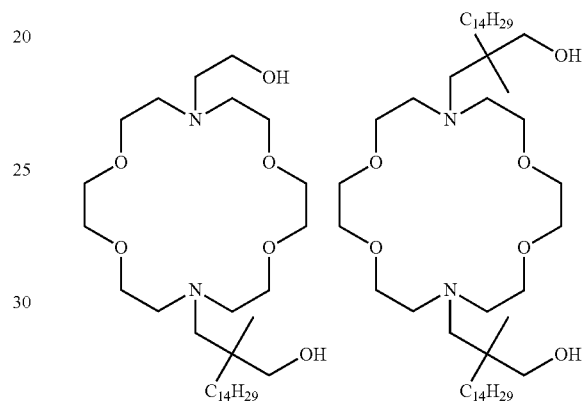
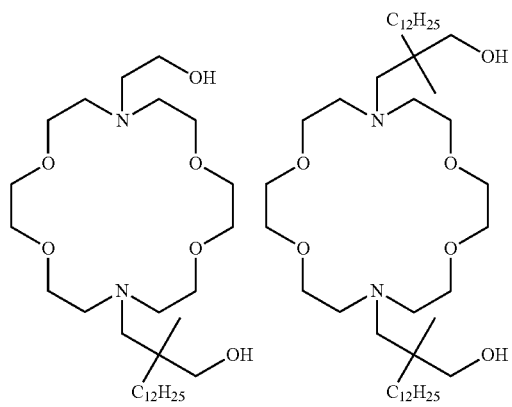
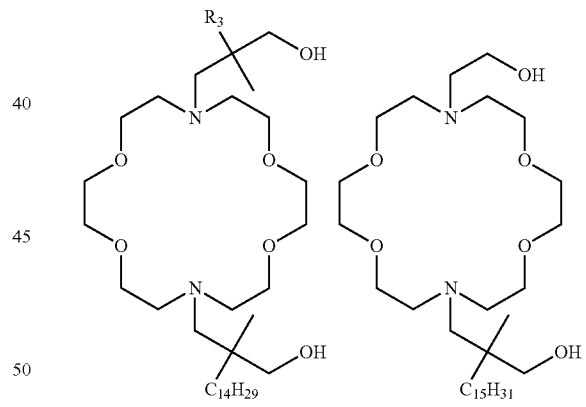
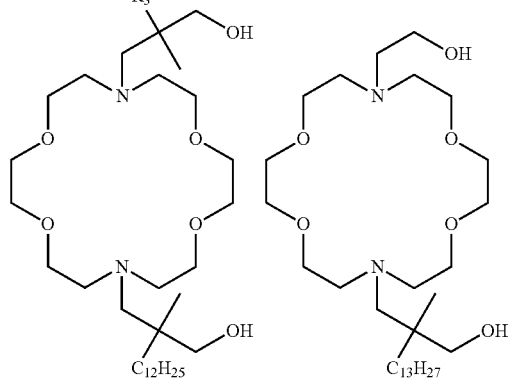
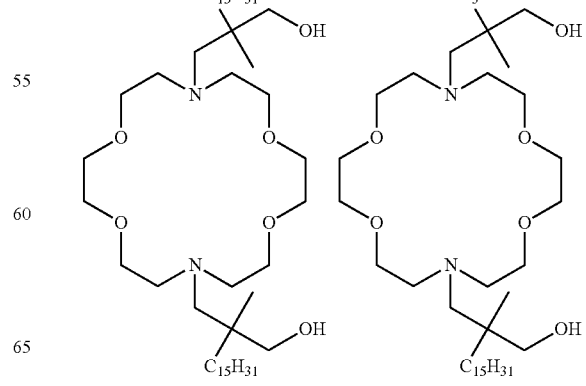

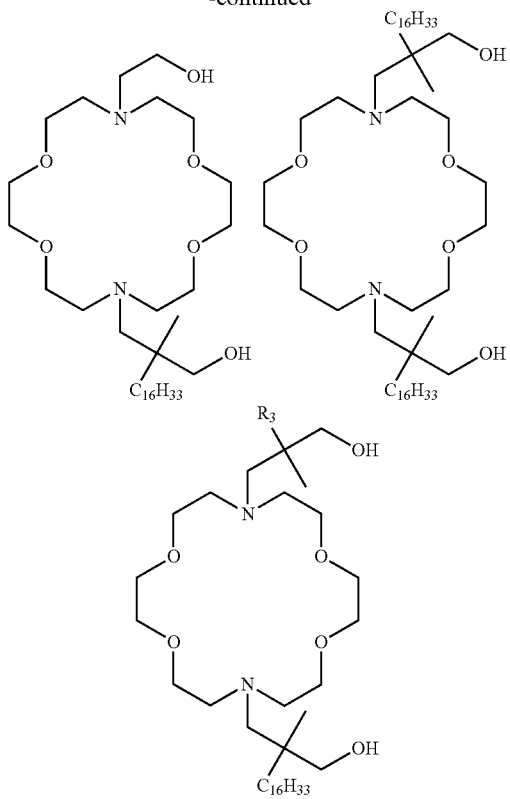

and salts thereof, wherein $R^3$ is defined herein. In certain embodiments, $R^3$ is a polyethyleglycol polymer. In certain embodiments, $R^3$ is $PEG_{1000}$. In certain embodiments, $R^3$ is $PEG_{2000}$. In certain embodiments, $R^3$ is $PEG_{1.5K}$.

Additional Methods of Preparation

As described herein, preparation of both conjugated polyethyleneimine complexes and conjugated macrocycles (also referred to herein as "conjugated lipomers" or "lipomers") is achieved using similar reaction conditions and reagents. In particular, the precursors are treated with one or more epoxide agents to provide the inventive conjugated lipomer. Each of the precursors is dissolved in an organic solvent (e.g., THF, $CH_2Cl_2$, MeOH, EtOH, $CHCl_3$, hexanes, toluene, benzene, $CCl_4$, glyme, diethyl ether, etc.), the one or more epoxides are added, and the reaction mixture is heated to yield the desired conjugated lipomer.

In certain embodiments, the reaction mixture is heated to between about 50° C. to about 150° C. In certain embodiments, the reaction mixture is heated to about 90° C.

In certain embodiments, the epoxide is chiral. The chiral epoxides useful in the invention can be obtained from a variety of sources which are familiar to those skilled in the art of organic synthesis. In some embodiments, the chiral epoxides useful in the invention can be obtained commercially. In some embodiments, the chiral epoxides useful in the invention can be synthesized according to methods known to those of skill in the art, such as, but not limited to the Sharpless epoxidation of primary and secondary allylic alcohols into 2,3-epoxyalcohols (Katsuki et al., *J. Am. Chem. Soc.* 1980, 102, 5974; Hill et al., *Org. Syn.*, Coll. Vol. 7, p. 461 (1990); Vol. 63, p. 66 (1985); Katsuki et al., *Org. React.* 1996, 48, 1-300; incorporated herein by reference.) In some embodiments, the chiral epoxides useful in the invention are obtained from the resolution of racemic epoxides. In some embodiments, the chiral epoxides useful in the invention are obtained by the separation of enantiomers or diastereoisomers using chiral chromatography.

As would be appreciated by one of skill in this art, the degree of conjugation may be controlled by the reaction conditions (e.g., temperature, starting materials, concentration, solvent, etc.) used in the synthesis.

The synthesized conjugated lipomer may be purified by any technique known in the art including, but not limited to, precipitation, crystallization, chromatography, distillation, etc. In certain embodiments, the conjugated lipomer is purified through repeated precipitations in organic solvent (e.g., diethyl ether, hexane, etc.).

In certain embodiments, the conjugated lipomer is isolated as a salt. For example, in certain embodiments, the conjugated lipomer is reacted with an acid (e.g., an organic acid or inorganic acid) to form the corresponding salt. In other embodiments, the tertiary amine is alkylated to form a quaternary ammonium salt of the conjugated lipomer. The tertiary amines may be alkylated with any alkylating agent, for example, alkyl halides such as methyl iodide may be used to from the quaternary amino groups. The anion associated with the quaternary amine may be any organic or inorganic anion. Preferably, the anion is a pharmaceutically acceptable anion.

The invention also provides libraries of the inventive conjugated lipomers prepared by the inventive methods. These conjugated lipomers may be prepared and/or screened using high-throughput techniques involving liquid handlers, robots, microtiter plates, computers, etc. In certain embodiments, the conjugated lipomers are screened for their ability to transfect polynucleotides or other agents (e.g., proteins, peptides, small molecules) into the cell.

In one embodiment, a library of different conjugated lipomers is prepared in parallel. A different precursor and/or epoxide is added to each vial in a set of vials or to each well of a multi-well plate used to prepare the library. The array of reaction mixtures is incubated at a temperature and length of time sufficient to allow formation of the conjugated lipomer. In one embodiment, the vials are incubated at approximately 90° C. overnight. In certain embodiments, the vials are incubated from 1 to 7 days at approximately 90° C. In certain embodiments, the vials are incubated from 3 to 4 days at approximately 90° C. In certain embodiments, the vials are incubated from 1 to 2 days at approximately 90° C. The conjugated lipomer may then be isolated and purified using techniques known in the art. The conjugated lipomer may then be screened using high-throughput techniques to identify conjugated lipomers with a desired characteristic (e.g., solubility in water, solubility at different pH, ability to bind polynucleotides, ability to bind heparin, ability to bind small molecules, ability to bind protein, ability to form microparticles, ability to increase transfection efficiency, etc.). In certain embodiments the conjugated lipomers may be screened for properties or characteristics useful as coatings, additives, materials, and excipients in biotechnology and biomedical applications such as the coating of medical devices or implants with films or multilayer films, as non-biofouling agents, micropatterning agents, and cellular encapsulation agents. In certain embodiments the conjugated lipomer may be screened for properties or characteristics useful in gene therapy (e.g., ability to bind polynucleotides, increase in transfection efficiency) or the administration and/or delivery of therapeutic agents (e.g., polynucleotide, small molecule, antigen, drug, protein, peptide, etc.) to a subject, patient, tissue, organ, or cell, etc.

Polynucleotide Complexes

The inventive conjugated lipomers are particularly useful in the administration of polynucleotides. For example, the inventive conjugated lipomers possess tertiary amines, and although these amines are hindered, they are available to interact with a polynucleotide (e.g., DNA, RNA, synthetic analogs of DNA and/or RNA, DNA/RNA hydrids, etc.). Polynucleotides or derivatives thereof are contacted with the inventive conjugated lipomers under conditions suitable to form polynucleotide/lipomer complexes. The interaction of the lipomer with the polynucleotide is thought to at least partially prevent the degradation of the polynucleotide. By neutralizing the charge on the backbone of the polynucleotide, the neutral or slightly-positively-charged complex is also able to more easily pass through the hydrophobic membranes (e.g., cytoplasmic, lysosomal, endosomal, nuclear) of the cell. In certain embodiments, the complex is slightly positively charged. In certain embodiments, the complex has a positive $\zeta$-potential, more preferably the $\zeta$-potential is between 0 and +30.

The conjugated lipomer is preferably at least partially provided as a salt (i.e., is protonated) so as to form a complex with the negatively charged polynucleotide. In certain embodiments, the polynucleotide/lipomer complexes form particles that are useful in the delivery of polynucleotides to cells. In certain embodiments, more than one conjugated lipomer may be associated with a polynucleotide molecule. For example, the complex may include 1-100 conjugated lipomers, 1-1000 conjugated lipomers, 10-1000 conjugated lipomers, or 100-10,000 conjugated lipomers.

In certain embodiments, the complex may form a particle. In certain embodiments, the diameter of the particles ranges from 10-500 micrometers. In certain embodiments, the diameter of the particles ranges from 10-1200 micrometers. In certain embodiments, the diameter of the particles ranges from 50-150 micrometers. In certain embodiments, the diameter of the particles ranges from 10-500 nm, more preferably the diameter of the particles ranges from 10-1200 nm, and most preferably from 50-150 nm. The particles may be associated with a targeting agent as described below. In certain embodiments, the diameter of the particles ranges from 10-500 pm, more preferably the diameter of the particles ranges from 10-1200 pm, and most preferably from 50-150 pm. The particles may be associated with a targeting agent as described below. The film architecture is precisely designed and can be controlled to 1 nm precision with a range from 1 to 150000 nm and with a definite knowledge of its molecular composition.

The polynucleotide may be complexed, encapsulated by the inventive conjugated lipomers, or included in a composition comprising the inventive conjugated lipomers. The polynucleotide may be any nucleic acid including, but not limited to, RNA and DNA. In certain embodiments, the polynucleotide is DNA. In certain embodiments, the polynucleotide is RNA.

In certain embodiments, the polynucleotide is an RNA that carries out RNA interference (RNAi). The phenomenon of RNAi is discussed in greater detail, for example, in the following references, each of which is incorporated herein by reference: Elbashir et al., 2001, *Genes Dev.*, 15:188; Fire et al., 1998, *Nature*, 391:806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553. In certain embodiments, the polynucleotide is a dsRNA (double-stranded RNA). In certain embodiments, the polynucleotide is an siRNA (short interfering RNA). In certain embodiments, the polynucleotide is an shRNA (short hairpin RNA).

In certain embodiments, the polynucleotide is an miRNA (micro RNA). micro RNAs (miRNAs) are genomically encoded non-coding RNAs of about 21-23 nucleotides in length that help regulate gene expression, particularly during development (see, e.g., Bartel, 2004, *Cell*, 116:281; Novina and Sharp, 2004, *Nature*, 430:161; and U.S. Patent Publication 2005/0059005; also reviewed in Wang and Li, 2007, *Front. Biosci.*, 12:3975; and Zhao, 2007, *Trends Biochem. Sci.*, 32:189; each of which are incorporated herein by reference).

In certain embodiments, the polynucleotide is an antisense RNA.

In some embodiments, dsRNA, siRNA, shRNA, miRNA and/or antisense RNA can be designed and/or predicted using one or more of a large number of available algorithms. To give but a few examples, the following resources can be utilized to design and/or predict dsRNA, siRNA, shRNA, and/or miRNA: algorithms found at Alnylum Online, Dharmacon Online, OligoEngine Online, Molecula Online, Ambion Online, BioPredsi Online, RNAi Web Online, Chang Bioscience Online, Invitrogen Online, LentiWeb Online GenScript Online, Protocol Online; Reynolds et al., 2004, *Nat. Biotechnol.*, 22:326; Naito et al., 2006, *Nucleic Acids Res.*, 34:W448; Li et al., 2007, *RNA*, 13:1765; Yiu et al., 2005, *Bioinformatics*, 21:144; and Jia et al., 2006, *BMC Bioinformatics*, 7:271; each of which is incorporated herein by reference).

The polynucleotides may be of any size or sequence, and they may be single- or double-stranded. In certain embodiments, the polynucleotide is greater than 100 base pairs long. In certain embodiments, the polynucleotide is greater than 1000 base pairs long and may be greater than 10,000 base pairs long. The polynucleotide is optionally purified and substantially pure. Preferably, the polynucleotide is greater than 50% pure, more preferably greater than 75% pure, and most preferably greater than 95% pure. The polynucleotide may be provided by any means known in the art. In certain embodiments, the polynucleotide has been engineered using recombinant techniques (for a more detailed description of these techniques, please see Ausubel et al., *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989); each of which is incorporated herein by reference). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry.

The polynucleotide may be modified by chemical or biological means. In certain embodiments, these modifications lead to increased stability of the polynucleotide. Modifications include methylation, phosphorylation, end-capping, etc.

Derivatives of polynucleotides may also be used in the present invention. These derivatives include modifications in the bases, sugars, and/or phosphate linkages of the polynucleotide. Modified bases include, but are not limited to, those found in the following nucleoside analogs: 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugars include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in this art, the modified polynucleotides are preferably prepared using synthetic chemistry in vitro.

The polynucleotides to be delivered may be in any form. For example, the polynucleotide may be a circular plasmid, a linearized plasmid, a cosmid, a viral genome, a modified viral genome, an artificial chromosome, etc.

The polynucleotide may be of any sequence. In certain embodiments, the polynucleotide encodes a protein or peptide. The encoded proteins may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc. The polynucleotide may also comprise regulatory regions to control the expression of a gene. These regulatory regions may include, but are not limited to, promoters, enhancer elements, repressor elements, TATA box, ribosomal binding sites, stop site for transcription, etc. In certain embodiments, the polynucleotide is not intended to encode a protein. For example, the polynucleotide may be used to fix an error in the genome of the cell being transfected.

The polynucleotide may also be provided as an antisense agent or RNA interference (RNAi) (Fire et al., Nature 391: 806-811, 1998; incorporated herein by reference). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular mechanisms of action of antisense drugs" Biochim. Biophys. Acta 1489 (1): 31-44, 1999; Crooke "Evaluating the mechanism of action of antiproliferative antisense drugs" Antisense Nucleic Acid Drug Dev. 10 (2): 123-126, discussion 127, 2000; Methods in Enzymology volumes 313-314, 1999; each of which is incorporated herein by reference). The binding may be by conventional base pair complementarity, or, for example, in the case of binding to DNA duplexes, through specific interactions in the major groove of the double helix (i.e., triple helix formation) (Chan et al., J. Mol. Med. 75 (4): 267-282, 1997; incorporated herein by reference).

In certain embodiments, the polynucleotide to be delivered comprises a sequence encoding an antigenic peptide or protein. Nanoparticles containing these polynucleotides can be delivered to an individual to induce an immunologic response sufficient to decrease the chance of a subsequent infection and/or lessen the symptoms associated with such an infection. The polynucleotide of these vaccines may be combined with interleukins, interferon, cytokines, and adjuvants such as cholera toxin, alum, Freund's adjuvant, etc. A large number of adjuvant compounds are known; a useful compendium of many such compounds is prepared by the National Institutes of Health (see Allison Dev. Biol. Stand. 92:3-11, 1998; Unkeless et al., Annu. Rev. Immunol. 6:251-281, 1998; and Phillips et al., Vaccine 10:151-158, 1992; each of which is incorporated herein by reference).

The antigenic protein or peptides encoded by the polynucleotide may be derived from such bacterial organisms as Streptococcus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni, and the like; from such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; and from such fungal, protozoan, and parasitic organisms such as Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni, and the like.

Table 3 of the Examples provides the nitrogen:phosphate ratio of conjugated lipomers of the present invention. The nitrogen:phosphate ratio (i.e., the ratio between the amino groups present in the lipomer, and the phosphate groups present in the polynucleotide) is between about 10:1 to about 50:1, inclusive. In certain embodiments, the nitrogen phosphate ratio is between about 10:1 to about 45:1, between about 15:1 to about 45:1, or between about 20:1 to about 40:1, inclusive. Increasing nitrogen:phosphate ratios have been shown to positively influence delivery of genetic material by increasing nucleic acid binding and negatively influence delivery by increasing toxicity (see, e.g., Incani et al., Soft Matter (2010) 6:2124-2138).

Table 3 of the Examples also provides the lipomer: polynucleotide mass ratio and molar ratios measured from complexes of polynucleotide and conjugated lipomers of the present invention. The conjugated lipomer:polynucleotide mass ratio is between about 10:1 to about 20:1, inclusive. In certain embodiments, the conjugated lipomer:polynucleotide mass ratio is about 15:1. The conjugated lipomer: polynucleotide molar ratio is between about 10:1 to about 400:1, inclusive. In certain embodiments, the conjugated lipomer:polynucleotide molar ratio is between about 10:1 to about 350:1, between about 15:1 to about 300:1, or between about 20:1 to about 250:1, inclusive.

Particles

The conjugated lipomers of the present invention may also be used to form drug delivery devices. The inventive conjugated lipomers have several properties that make them particularly suitable in the preparation of drug delivery devices. These include: 1) the ability of the lipomer to complex and "protect" labile agents; 2) the ability to buffer the pH in the endosome; 3) the ability to act as a "proton sponge" and cause endosomolysis; and 4) the ability to neutralize the charge on negatively charged agents.

Figures 5A, 5B:
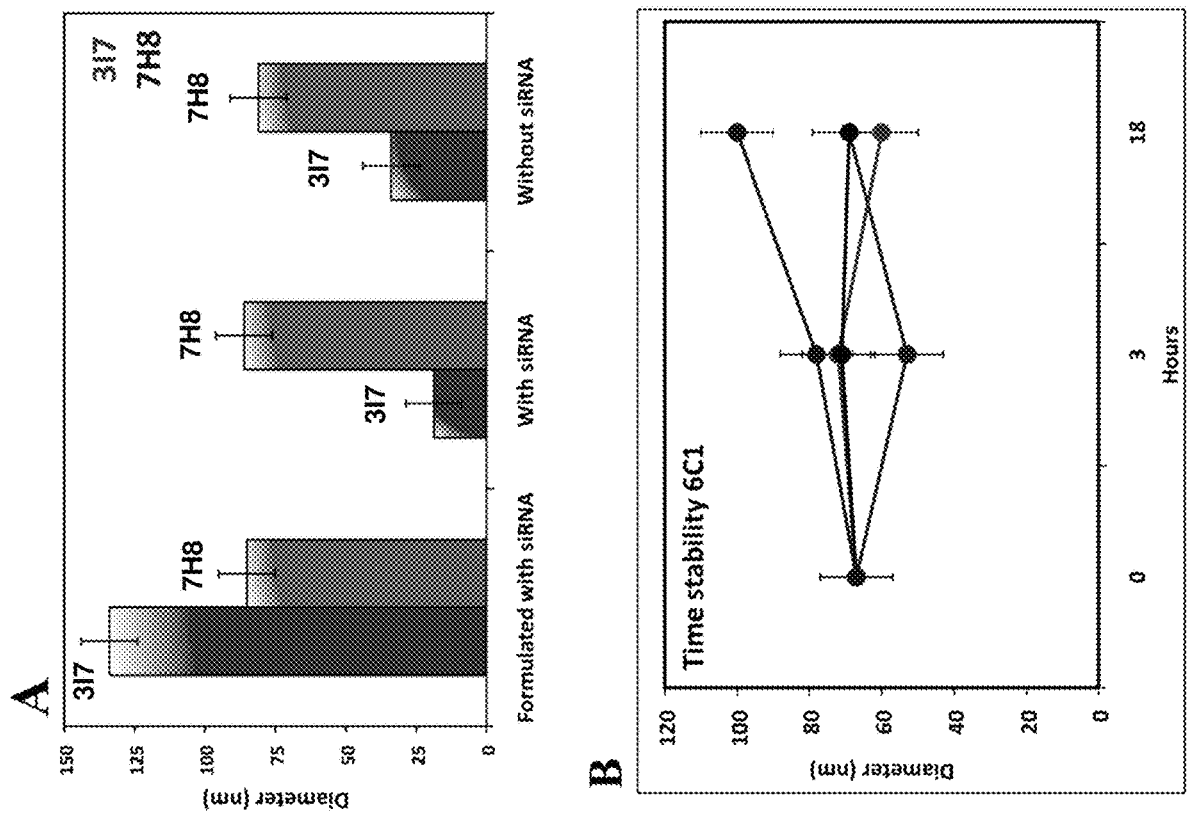
FIGS. 5A-5B.

In certain embodiments, the conjugated lipomers are used to form particles containing the agent to be delivered. The inventive conjugated lipomers may be used to encapsulate agents including, but not limited to, organic molecules (e.g., cholesterol), inorganic molecules, nucleic acids, proteins, peptides, polynucleotides, targeting agents, isotopically labeled organic or inorganic molecules, vaccines, immunological agents, etc. Other exemplary agents are described in greater detail herein. These particles may include other materials such as polymers (e.g., synthetic polymers (e.g., PEG, PLGA), natural polymers (e.g., phospholipids)). In certain embodiments, the conjugated lipomers are mixed with one or more agents (e.g., cholesterol) and/or one or more other materials (e.g., polymers). For example, as shown in FIGS. 5A-5B and described in the Examples, a conjugated lipomer was mixed with an agent and a polymer, or just mixed with an agent, to provide inventive particles.

In certain embodiments, the diameter of the particles range from between 1 micrometer to 1,000 micrometers. In certain embodiments, the diameter of the particles range from between from 1 micrometer to 100 micrometers. In certain embodiments, the diameter of the particles range from between from 1 micrometer to 10 micrometers. In certain embodiments, the diameter of the particles range from between from 10 micrometer to 100 micrometers. In certain embodiments, the diameter of the particles range from between from 100 micrometer to 1,000 micrometers. In certain embodiments, the particles range from 1-5 micrometers. In certain embodiments, the diameter of the particles range from between 1 nm to 1,000 nm. In certain embodiments, the diameter of the particles range from between from 1 nm to 100 nm. In certain embodiments, the diameter of the particles range from between from 1 nm to 10 nm. In certain embodiments, the diameter of the particles range from between from 10 nm to 100 nm. In certain embodiments, the diameter of the particles range from between from 100 nm to 1,000 nm. In certain embodiments, the particles range from 1-5 nm. In certain embodiments, the diameter of the particles range from between 1 pm to 1,000 pm. In certain embodiments, the diameter of the particles range from between from 1 pm to 100 pm. In certain embodiments, the diameter of the particles range from between from 1 pm to 10 pm. In certain embodiments, the diameter of the particles range from between from 10 pm to 100 pm. In certain embodiments, the diameter of the particles range from between from 100 pm to 1,000 pm. In certain embodiments, the particles range from 1-5 pm.

The inventive particles may be prepared using any method known in this art. These include, but are not limited to, spray drying, single and double emulsion solvent evaporation, solvent extraction, phase separation, simple and complex coacervation, and other methods well known to those of ordinary skill in the art. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, etc.). The method of preparing the particle and the conditions (e.g., solvent, temperature, concentration, air flow rate, etc.) used may also depend on the agent being encapsulated and/or the composition of the matrix.

Methods developed for making particles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al., *Reactive Polymers* 6:275-283, 1987; Mathiowitz et al., *J. Appl. Polymer Sci.* 35:755-774, 1988; each of which is incorporated herein by reference).

If the particles prepared by any of the above methods have a size range outside of the desired range, the particles can be sized, for example, using a sieve. The particle may also be coated. In certain embodiments, the particles are coated with a targeting agent. In other embodiments, the particles are coated to achieve desirable surface properties (e.g., a particular charge).

Micelles and Liposomes and Lipoplexes

The conjugated lipomers of the invention may also be used to prepare micelles liposomes. In addition, any agent may be included in a micelle or liposome. Micelles and liposomes are particularly useful in delivering hydrophobic agents such as hydrophobic small molecules. When the micelle or liposome is complexed with (e.g., encapsulates or covers) a polynucleotide it is referred to as a "lipoplex." Many techniques for preparing micelles, liposomes, and lipoplexes are known in the art, and any method may be used with the inventive conjugated lipomers to make micelles and liposomes.

In certain embodiments, liposomes are formed through spontaneous assembly. In other embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these particles have formed, reducing the size of the particle can be modified through input of sonic energy (sonication) or mechanical energy (extrusion). See Walde, P. "Preparation of Vesicles (Liposomes)" In *Encyclopedia of Nanoscience and Nanotechnology*; Nalwa, H. S. Ed. American Scientific Publishers: Los Angeles, 2004; Vol. 9, pp. 43-79; Szoka et al., "Comparative Properties and Methods of Preparation of Lipid Vesicles (Liposomes)" *Ann. Rev. Biophys. Bioeng.* 9:467-508, 1980; each of which is incorporated herein. The preparation of liposomes involves preparing the conjugated lipomers for hydration, hydrating the conjugated lipomers with agitation, and sizing the vesicles to achieve a homogenous distribution of liposomes. Conjugated lipomers are first dissolved in an organic solvent to assure a homogeneous mixture of conjugated lipomers. The solvent is then removed to form a polymer-derived film. This polymer-derived film is thoroughly dried to remove residual organic solvent by placing the vial or flask on a vacuum pump overnight. Hydration of the polymer-derived film is accomplished by adding an aqueous medium and agitating the mixture. Disruption of LMV suspensions using sonic energy typically produces small unilamellar vesicles (SUV) with diameters in the range of 15-50 nm. Lipid extrusion is a technique in which a lipid/polymer suspension is forced through a polycarbonate filter with a defined pore size to yield particles having a diameter near the pore size of the filter used. Extrusion through filters with 100 nm pores typically yields large, unilamellar polymer-derived vesicles (LUV) with a mean diameter of 120-140 nm.

In certain embodiments, the polynucleotide is an RNA molecule (e.g., an RNAi molecule). In other embodiments, the polynucleotide is a DNA molecule. In certain embodiments, the amount of poly(beta-amino alcohol) in the liposome ranges from 30-80 mol %, preferably 40-70 mol %, more preferably 60-70 mol %. These liposomes may be prepared using any method known in the art. In certain embodiments (e.g., liposomes containing RNAi molecules), the liposomes are prepared by lipid extrusion.

Certain conjugated lipomers can spontaneously self assemble around certain molecules, such as DNA and RNA, to form liposomes. In some embodiments, the application is the delivery of polynucleotides. Use of these conjugated lipomers allows for simple assembly of liposomes without the need for additional steps or devices such as an extruder.

The following scientific papers described other methods for preparing liposomes and micelles: Narang et al., "Cationic Lipids with Increased DNA Binding Affinity for Non-viral Gene Transfer in Dividing and Nondividing Cells" *Bioconjugate Chem.* 16:156-68, 2005; Hofland et al., "Formation of stable cationic lipid/DNA complexes for gene transfer" *Proc. Natl. Acad. Sci. USA* 93:7305-739 July 1996; Byk et al., "Synthesis, Activity, and Structure—Activity Relationship Studies of Novel Cationic Lipids for DNA Transfer" *J. Med. Chem.* 41 (2): 224-235, 1998; Wu et al., "Cationic Lipid Polymerization as a Novel Approach for Constructing New DNA Delivery Agents" *Bioconjugate Chem.* 12:251-57, 2001; Lukyanov et al., "Micelles from lipid derivatives of water-soluble polymers as delivery systems for poorly soluble drugs" *Advanced Drug Delivery Reviews* 56:1273-1289, 2004; Tranchant et al., "Physicochemical optimisation of plasmid delivery by cationic lipids" *J. Gene Med.* 6: S24-S35, 2004; van Balen et al., "Liposome/Water Lipophilicity: Methods, Information Content, and Pharmaceutical Applications" *Medicinal Research Rev.* 24 (3): 299-324, 2004; each of which is incorporated herein by reference.

Agents

The agents to be delivered by the systems of the present invention may be therapeutic, diagnostic, or prophylactic agents. Any chemical compound to be administered to an individual may be delivered using the inventive complexes, picoparticles, nanoparticles, microparticles, micelles, or liposomes. The agent may be an organic molecule (e.g., cholesterol, a drug), inorganic molecule, nucleic acid, protein, peptide, polynucleotide, targeting agent, isotopically labeled organic or inorganic molecule, vaccine, immunological agent, etc.

In certain embodiments, the agents are organic molecules with pharmaceutical activity, e.g., a drug. In certain embodiments, the drug is an antibiotic, anti-viral agent, anesthetic, steroidal agent, anti-inflammatory agent, anti-neoplastic agent, anti-cancer agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, etc.

In certain embodiments of the present invention, the agent to be delivered may be a mixture of agents.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents include antigens of such bacterial organisms as *Streptococcus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Targeting Agents

The inventive conjugated lipomers, and the complexes, liposomes, micelles, microparticles, picoparticles and nanoparticles, prepared therefrom, may be modified to include targeting agents since it is often desirable to target a particular cell, collection of cells, or tissue. A variety of targeting agents that direct pharmaceutical compositions to particular cells are known in the art (see, for example, Cotten et al., *Methods Enzym.* 217:618, 1993; incorporated herein by reference). The targeting agents may be included throughout the particle or may be only on the surface. The targeting agent may be a protein, peptide, carbohydrate, glycoprotein, lipid, small molecule, nucleic acids, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialycoproteins, gp120 envelope protein of the human immunodeficiency virus (HIV), carbohydrates, receptor ligands, sialic acid, aptamers, etc. If the targeting agent is included throughout the particle, the targeting agent may be included in the mixture that is used to form the particles. If the targeting agent is only on the surface, the targeting agent may be associated with (i.e., by covalent, hydrophobic, hydrogen bonding, van der Waals, or other interactions) the formed particles using standard chemical techniques.

Compositions

The present invention contemplates an inventive conjugated lipomer as a component of a composition which may be useful in a variety of medical and non-medical applications. For example, pharmaceutical compositions comprising an inventive conjugated lipomer may be useful in the delivery of an effective amount of an agent to a subject in need thereof. Nutraceutical compositions comprising an inventive conjugated lipomer may be useful in the delivery of an effective amount of a nutraceutical, e.g., a dietary supplement, to a subject in need thereof. Cosmetic compositions comprising an inventive conjugated lipomer may be formulated as a cream, ointment, balm, paste, film, or liquid, etc., and may be useful in the application of make-up, hair products, and materials useful for personal hygiene, etc. Compositions comprising an inventive conjugated lipomer may be useful for non-medical applications, e.g., such as an emulsion or emulsifier, useful, for example, as a food component, for extinguishing fires, for disinfecting surfaces, for oil cleanup, etc.

In certain embodiments, the composition comprises one or more conjugated lipomers of the present invention. "One or more conjugated lipomers" refers to one or more different types of conjugated lipomers included in the composition, and encompasses 1, 2, 3, 4, 5, 6, 7, 8, 9, 10 or more different types of conjugated lipomers.

In certain embodiments, the inventive conjugated lipomers are useful as compositions, either for delivery of an effective amount of an agent to a subject in need thereof (e.g., a pharmaceutical composition, a cosmetic composition) or for use as an excipient. For example, cosmetic compositions may further use the inventive lipomers as excipients rather than as a delivery system encapsulating an agent to be delivered. In certain embodiments, the composition is a pharmaceutical composition. In certain embodiments, the composition is a cosmetic composition.

In certain embodiments, the composition further comprises an agent, as described herein. For example, in certain embodiments, the agent is a small molecule, organometallic compound, nucleic acid, protein, peptide, polynucleotide, metal, targeting agent, an isotopically labeled chemical compound, drug, vaccine, or immunological agent. In certain embodiments, the agent is a polynucleotide. In certain embodiments, the polynucleotide is DNA or RNA. In certain embodiments, the RNA is RNAi, dsRNA, siRNA, shRNA, miRNA, or antisense RNA.

In certain embodiments, the polynucleotide and the one or more conjugated lipomers are not covalently attached.

In certain embodiments, the one or more conjugated lipomers are in the form of a particle. In certain embodiments, the particle is a nanoparticle or microparticle. In certain embodiments, the one or more conjugated lipomers are in the form of liposomes or micelles. It is understood that, in certain embodiments, these conjugated lipomers self-assemble to provide a particle, micelle or liposome. In certain embodiments, the particle, liposome, or micelle encapsulates an agent. The agent to be delivered by the particles, liposomes, or micelles may be in the form of a gas, liquid, or solid. The inventive conjugated lipomers may be combined with polymers (synthetic or natural), surfactants, cholesterol, carbohydrates, proteins, lipids etc. to form the particles. These particles may be combined with an excipient to form pharmaceutical and cosmetic compositions.

Once the complexes, micelles, liposomes, or particles have been prepared, they may be combined with one or more excipients to form a composition that is suitable to administer to animals including humans.

As would be appreciated by one of skill in this art, the excipients may be chosen based on the route of administration as described below, the agent being delivered, time course of delivery of the agent, etc.

In certain embodiments, provided is a composition comprising an inventive conjugated lipomer and, optionally, an excipient. As used herein, the term "excipient" means a non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

Methods of Use

In another aspect, provided are methods of using the inventive conjugated lipomers, e.g., for the treatment of a disease, disorder or condition from which a subject suffers. It is contemplated that the inventive conjugated lipomers will be useful in the treatment of a variety of diseases, disorders or conditions, especially as a system for delivering agents useful in the treatment of that particular disease, disorder or condition.

For example, in one aspect, provided is a method of treating cancer comprising administering to a subject in need thereof an effective amount of a conjugated lipomer of the present invention, e.g., a conjugated lipomer of the Formula (II) or (IV), or salt thereof, or a composition thereof. In certain embodiments, the method further comprises administering an anti-cancer agent. In certain embodiments, the conjugated lipomer encapsulates the anti-cancer agent. In certain embodiments, the conjugated lipomer and the anti-cancer agent form a particle (e.g., a nanoparticle, a microparticle, a micelle, a liposome, a lipoplex).

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), antimetabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

Examples

In order that the invention described herein may be more fully understood, the following examples are set forth. It should be understood that these examples are for illustrative purposes only and are not to be construed as limiting this invention in any manner.

Library Synthesis

The inventive lipomers were synthesized using (i) a polymer PEI backbone a linear PEI with a molecular weight of 600 ($LPEI_{600}$); a branched PEI with a molecular weight of 600 ($BPEI_{600}$); a branched PEI with a molecular weight of 1800 ($BPEI_{1800}$); or (ii) macrocyles comprising amino groups (e.g., aza-crown macrocycles). In each instance, the backbone was chemically modified with alkyl tails and/or PEG polymers by direct alkylation of one or more amino groups. Four structural parameters were varied in the screen: the number of alkyl tails and/or PEG polymers per backbone, and the length of the alkyl groups and/or PEG polymer per backbone. More specifically, the number of alkyl tails per backbone were varied from 0 to 43 alkyl groups per backbone or from 0 to 4 alkyl groups per macrocycle, while the number of PEG polymer per molecule ranged from 0.1 to 0.3 per backbone or macrocycle. The resulting lipomer library was screened for in vitro efficacy against one murine cancer cell line (qBEND.3), two human cancer cell lines (HeLa or HCT-116), and one primary human cell line (HMVEC). Seventeen lipomers were found to reduce gene expression in vitro by more than 80% at doses of 30 nM with negligible toxicity. These lipomers were then tested for systemic in vivo delivery in two animal models: a Factor 7 liver delivery model and a hepatocellular carcinoma tumor model. The in vivo data demonstrated that these new lipomers can deliver siRNA effectively in animals.

Figure 1B:
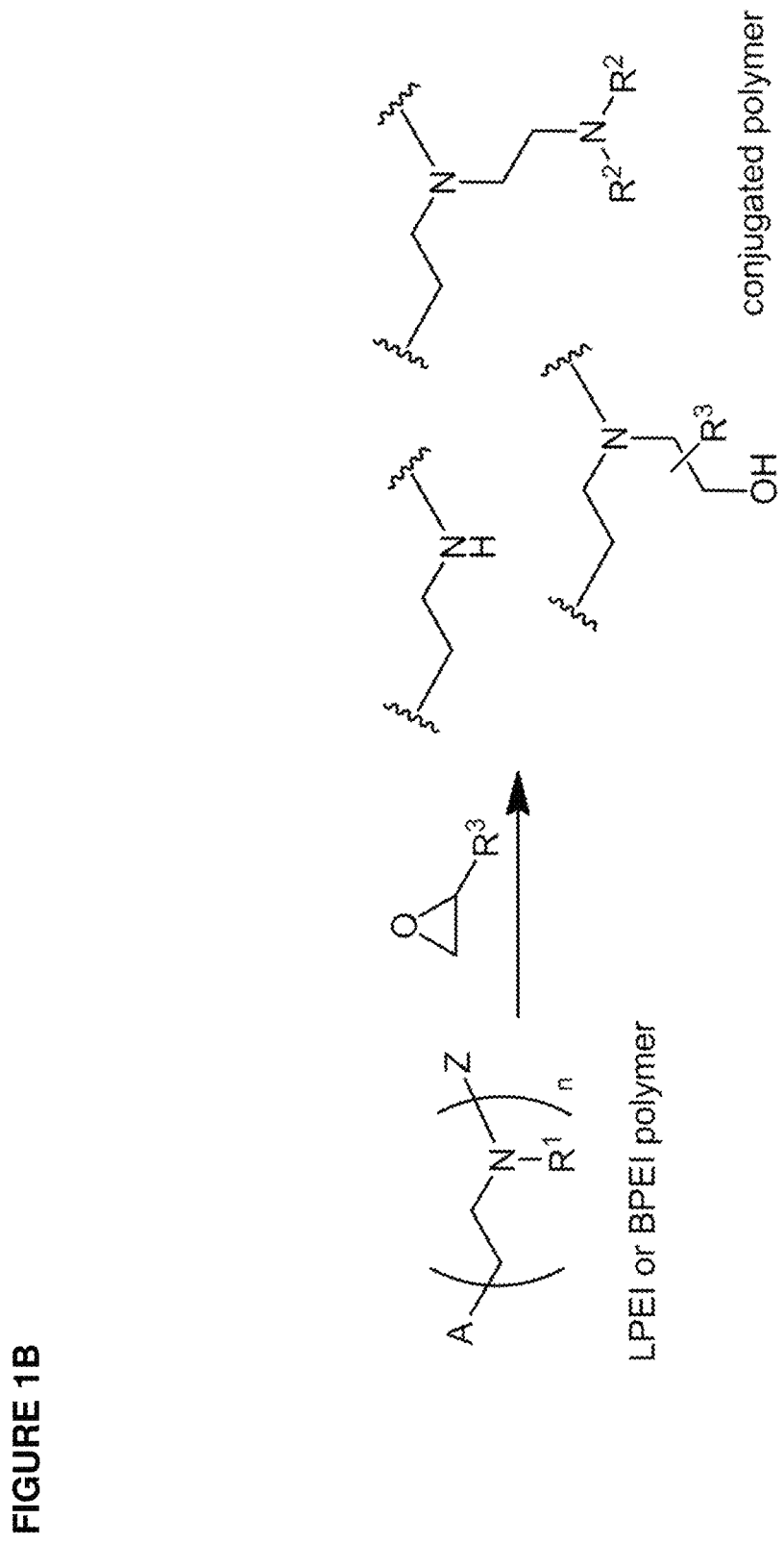
Figure 1C:
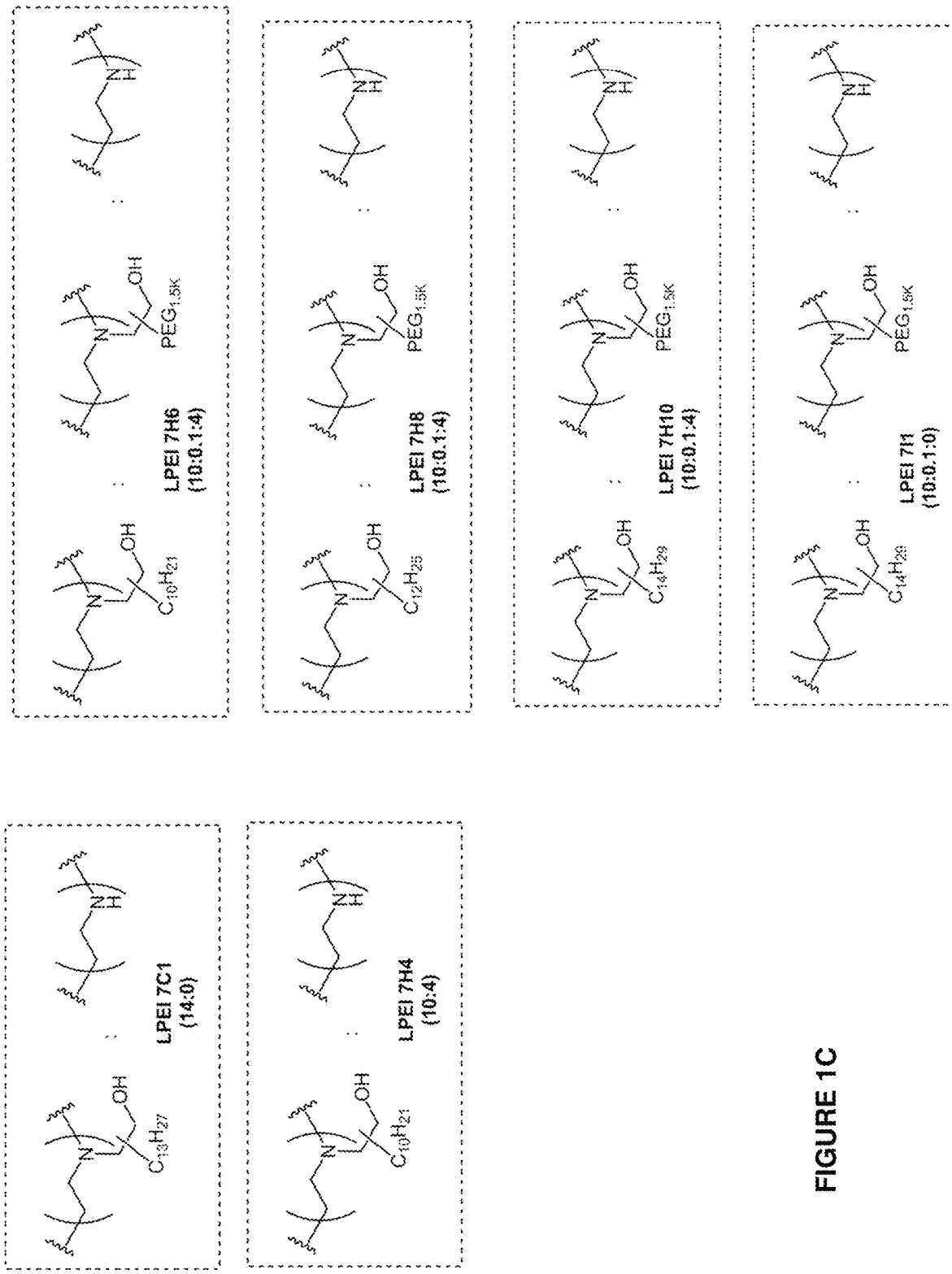
Figure 1D:
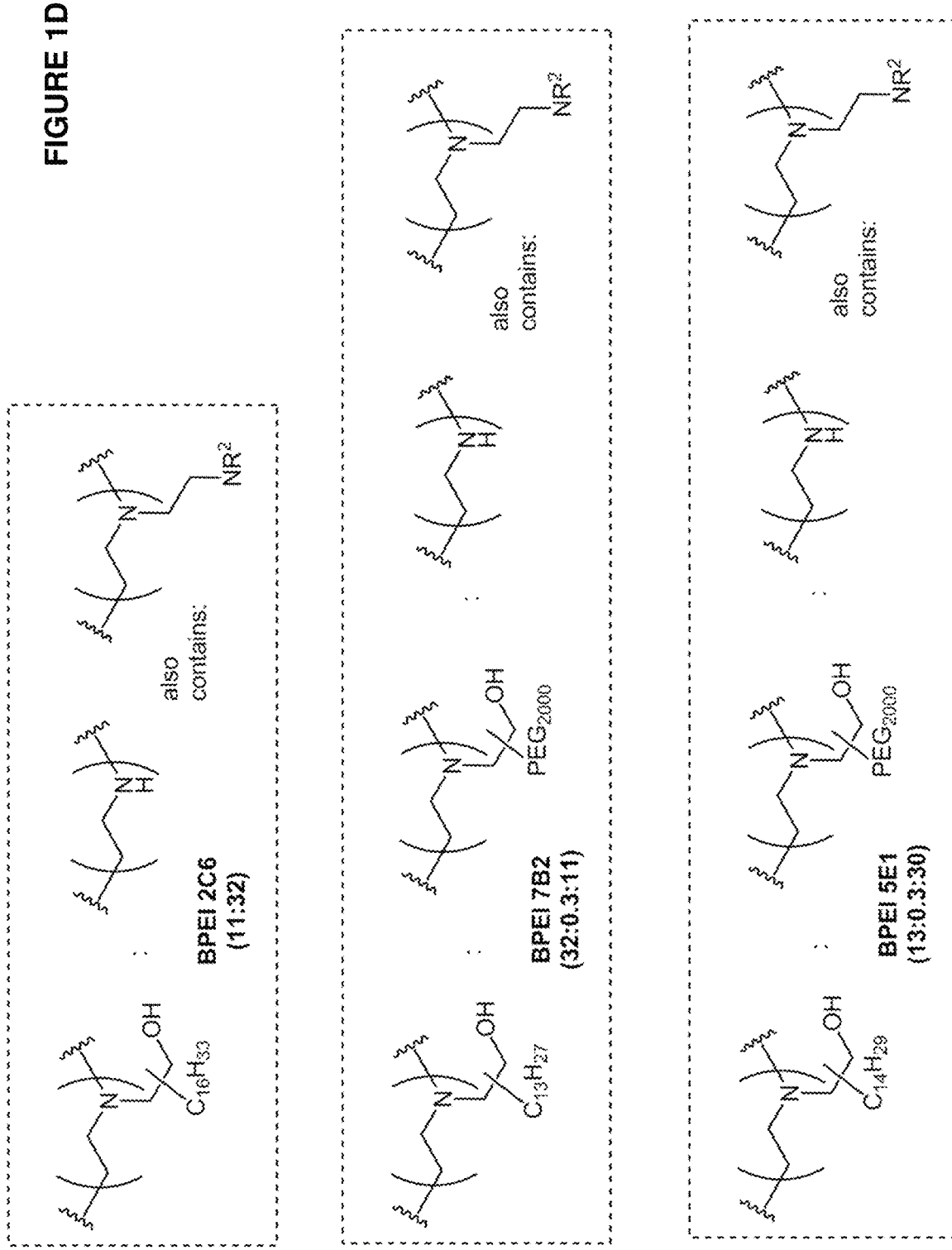
Figure 1E:
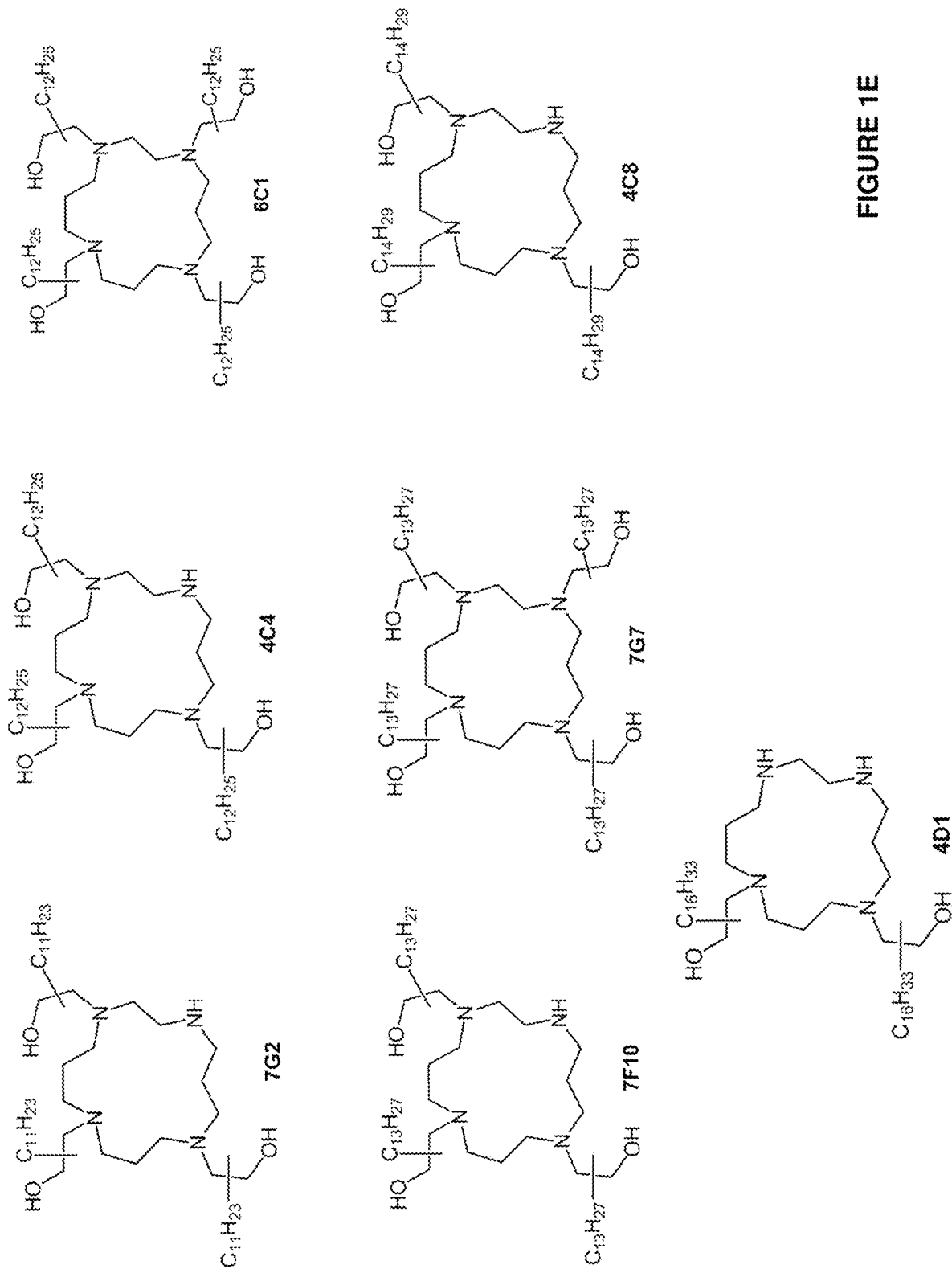
Figure 1F:
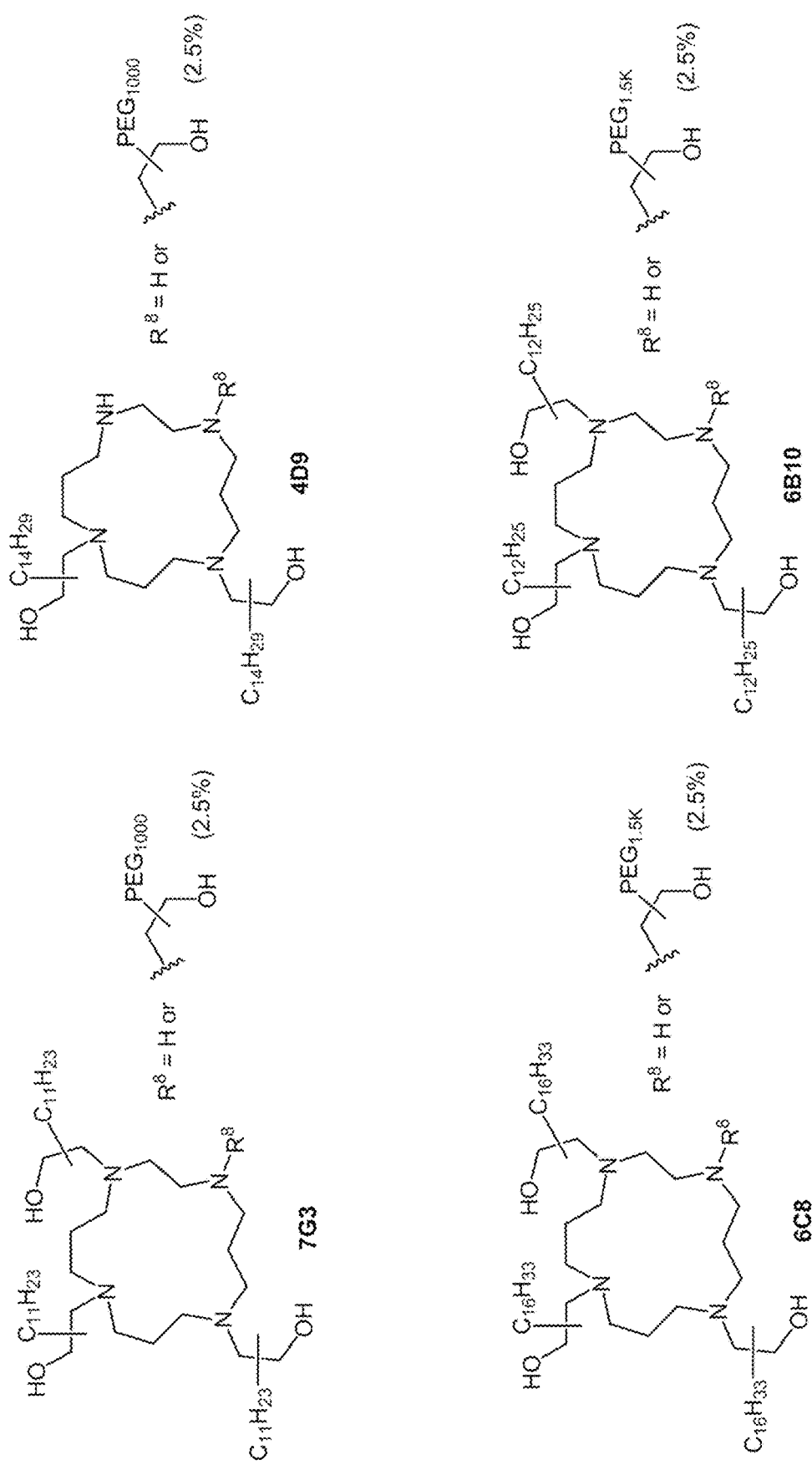

PEI polymers and aza-macrocycles (FIG. 1A) were conjugated to alkyl and PEG polymers via an epoxide ring-opening reaction shown in FIG. 1B. $LPEI_{600}$, $BPEI_{600}$, $BPEI_{1800}$ or aza-macrocycles were reacted with epoxides with alkyl chains having lengths between 10 and 18 carbons, inclusive. The reaction took place in 100% EtOH for 48-72 hours in capped glass vials at a temperature of about 90° C. After 48-72 hours, the solution was removed from the hotplate and the ethanol was removed via vacuum evaporation. In some of the reactions, $LPEI_{600}$, $BPEI_{600}$, $BPEI_{1800}$ or the aza-macrocycles were also simultaneously alkylated with $PEG_{1000}$ ($PEG_{1K}$), $PEG_{2000}$ ($PEG_{2K}$) or a 1:1 mixture of $PEG_{1K}$ and $PEG_{2K}$ ($PEG_{1.5K}$). This synthesis is ideal for high-throughput screening since it does not require protection/deprotection steps, organic solvents or complex environmental conditions (Love et al. *Proc Natl Acad Sci USA* (2010) 107: 1864-1869).

Table 3 lists the theoretical molecular weight, molar ratios, number of backbone nitrogens and nitrogen:phosphate ratios of compounds.

TABLE 3

|  | Molar Mass | Lipomer:siRNA Mass Ratio | Lipomer:siRNA Mole Ratio | Backbone Nitrogens | N:P Ratio |
|---|---|---|---|---|---|
| 7C1 | 3764.00 | 15.00 | 53.00 | 14.00 | 17.67 |
| 7H6 | 2667.00 | 15.00 | 74.80 | 14.00 | 24.93 |
| 7H4 | 2524.00 | 15.00 | 79.04 | 14.00 | 26.35 |
| 2C6 | 4603.28 | 15.00 | 43.34 | 43.00 | 44.37 |
| 7h8 | 2960.00 | 15.00 | 67.40 | 14.00 | 22.47 |
| 7G2 | 808.00 | 15.00 | 246.91 | 4.00 | 23.51 |

TABLE 3-continued

| | Molar Mass | Lipomer: siRNA Mass Ratio | Lipomer: siRNA Mole Ratio | Backbone Nitrogens | N:P Ratio |
|---|---|---|---|---|---|
| 7B2 | 9620.00 | 15.00 | 20.74 | 43.00 | 21.23 |
| 4D1 | 750.00 | 15.00 | 266.00 | 4.00 | 25.33 |
| 4C8 | 934.00 | 15.00 | 213.60 | 4.00 | 20.34 |
| 711 | 4102.00 | 15.00 | 48.63 | 14.00 | 16.21 |
| 6c8 | 1056.00 | 15.00 | 188.92 | 4.00 | 17.99 |
| 7F10 | 890.00 | 15.00 | 224.16 | 4.00 | 21.35 |
| 6810 | 888.00 | 15.00 | 224.66 | 4.00 | 21.40 |
| 4c4 | 850.00 | 15.00 | 234.71 | 4.00 | 22.35 |
| 4C5 | 1062.00 | 15.00 | 187.85 | 4.00 | 17.89 |
| 4C3 | 638.00 | 15.00 | 312.70 | 4.00 | 29.78 |

Reagents

BPEI with a number molecular weight ($M_n$) of 600 and a weight molecular weight ($M_w$) of 800 of ($BPEI_{600}$) was purchased from Sigma Aldrich (catalog number 408719). BPEI with a $M_n$ of 1800 and $M_w$ of 2000 ($BPEI_{1800}$) was purchased from Alfa Aesar (catalog number 40528).

Aza-macrocycles were purchased from Sigma Aldrich and Alfa Aesar (1,4,8,12 Tetraazacyclopentadecane TCI Catalog number 1691 or Sigma Aldrich Catalog Number 259512, 1,4,10,13-Tetraoxa-7,16-Diaazacyclooctade Sigma Aldrich Catalog Number 295809, 1,4,8,11 Tetraazacyclotetradecane TCI Catalog Number T1597, 1,4,7,10-tetraazacyclododecane TCI Catalog Number T1874.

The following epoxides were purchased from Sigma Aldrich or TCI America: 1,2-epoxydecane TCI Catolog number E0315 or Sigma Aldrich Catalog Number 260339, 1,2-epoxydodecane TCI Catalog number D1984 or Sigma Aldrich Catalog Number 260207, 1,2-epoxytetradecane TCI Catalog number E0314 or Sigma Aldrich Catalog Number 260266, 1,2-epoxyhexadecane TCI Catalog number E0316 or Sigma Aldrich Catalog Number 260215, 1,2-epoxyoctadecane TCI Catalog number E0313 or Sigma Aldrich Catalog Number 260231.

$PEG_{1000}$ and $PEG_{2000}$ were purchased from Creative Pegworks.

In Vitro Screening

Following synthesis, the ability to specifically reduce gene expression in vitro was tested against four cell lines; HeLa cells (ATCC, Manassas, VA) transfected by Alnylam Pharmaceuticals to express both Renilla and Firefly luciferase, HCT-116 human colorectal cells (Caliper Life Sciences) transfected to express Firefly luciferase, and qBEND.3 murine endothelial cells and HMVEC primary human endothelial cells, both expressing the endothelial marker Tie2 (Akinc et al. Nat Biotechnol (2008) 26: 561-569). Lipomers were complexed with anti-Firefly luciferase siRNA (siLuc) (Dharmacon, Boulder, Colorado) or anti-Tie2 siRNA (siTie2) (Alnylam, Cambridge, MA) by incubating the lipomer with siRNA in 25 mMol NaAc with a pH of 5.2. The siRNA and lipomers were bound via electrostatic interactions between the negative phosphate backbone of the siRNA and the protonated amine backbone. GapDH siRNA (siGap) (Alnylam, Cambridge, MA) was used as a control for Tie2 expression. More specifically, lipomers were conjugated with siTie2 or siGap. Tie2 expression was measured using both complexes and successful compounds were those that reduced Tie2 expression Both Tie2 and GapDH More specifically, and compounds that reduced Tie2 expression even when conjugated to GapDH were considered toxic. Similarly, HeLa cell toxicity was tested by measuring both (targeted) Firefly luciferase and (control) Renilla Luciferase. Successful compounds reduced target gene expression and did not influence control gene expression.

The in vitro screen was initiated by seeding cells onto a 96 well plate at a density of 15,000 cells/well. Twenty-four hours later, 30 nM lipomer-siRNA solution was placed in each well. The mixture was incubated overnight at 37° C. and 5% $CO_2$. Luciferase and Renilla gene expression was then tested using luminescence (Dual Glow Assay, Promega, Madison, WI) while Tie2 expression was measured using a Quantigene 2.0 BDNA assay (Panomics, Santa Clara, CA). Compounds were considered successful if they reduced target gene expression by more than 80% while off-target gene knockdown was less than 20%. In most cases, successful candidates reduced off-target gene expression by less than 10%.

Figure 2A:
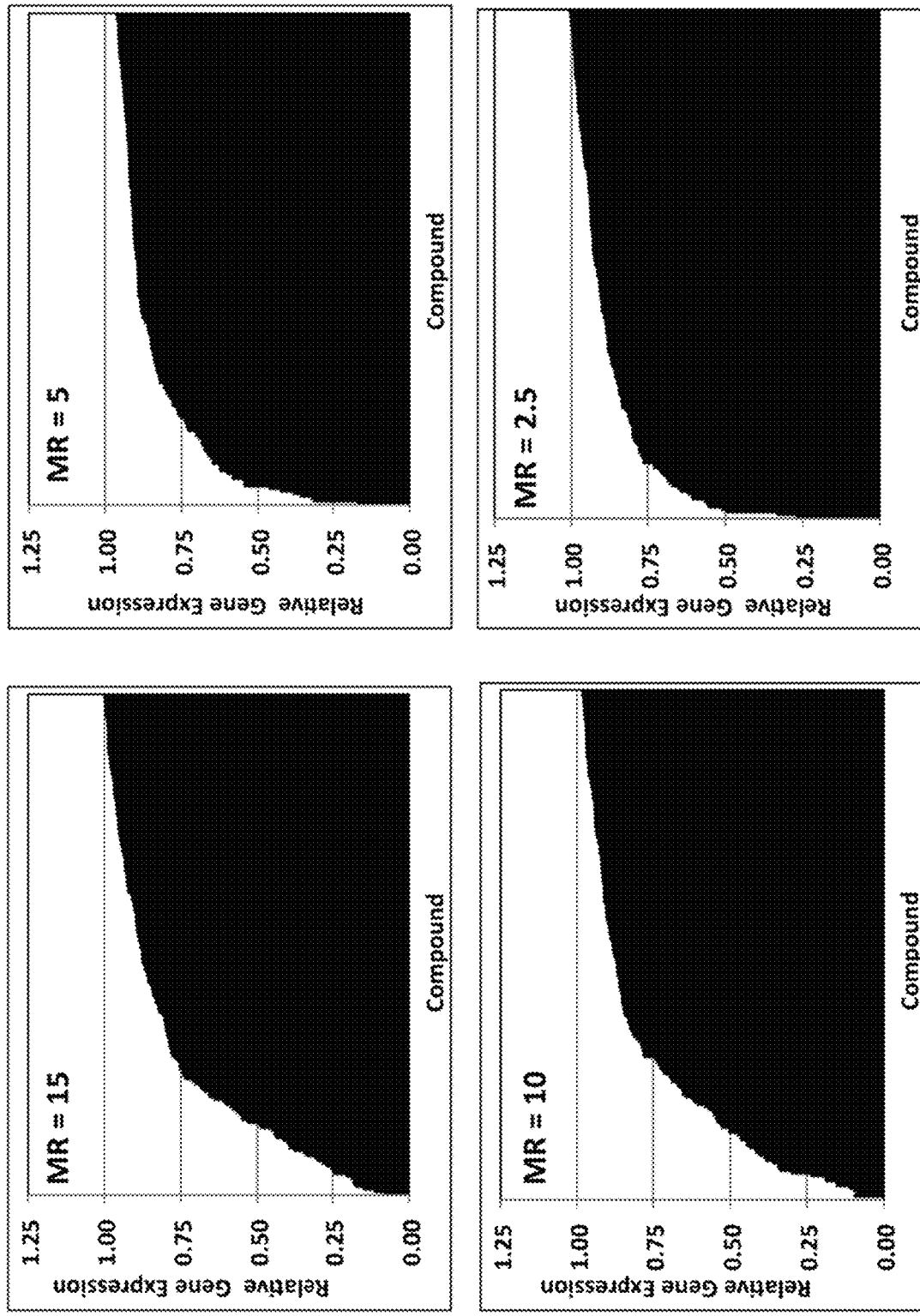
FIGS. 2A-2B demonstrate that non-toxic efficacy increases with lipomer:siRNA mass ratios (MR) up to 15 in HeLa cells. A library of 750 compounds was tested, of which a select subset reduced gene expression.
Figure 2B:
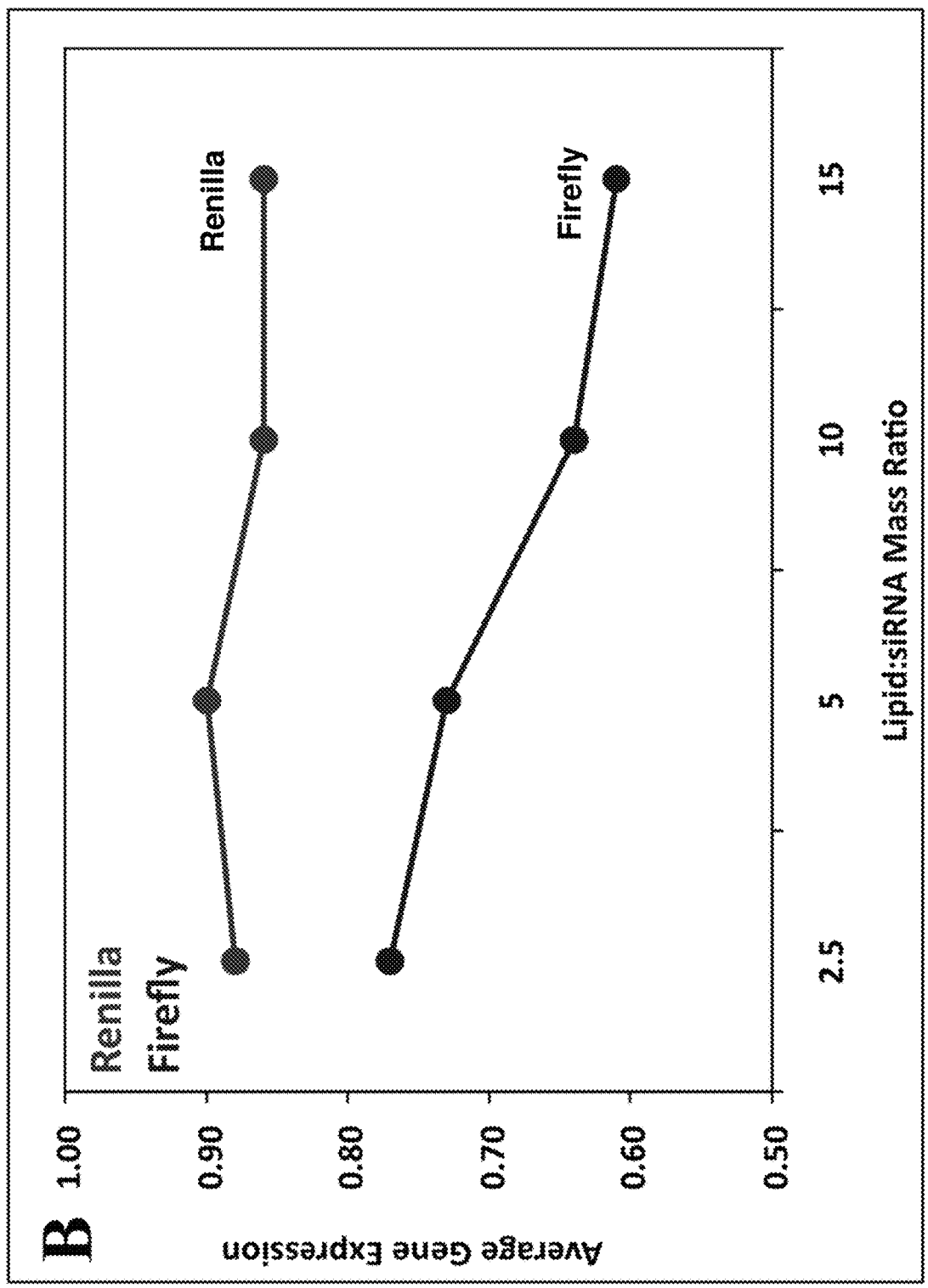
Figure 3:
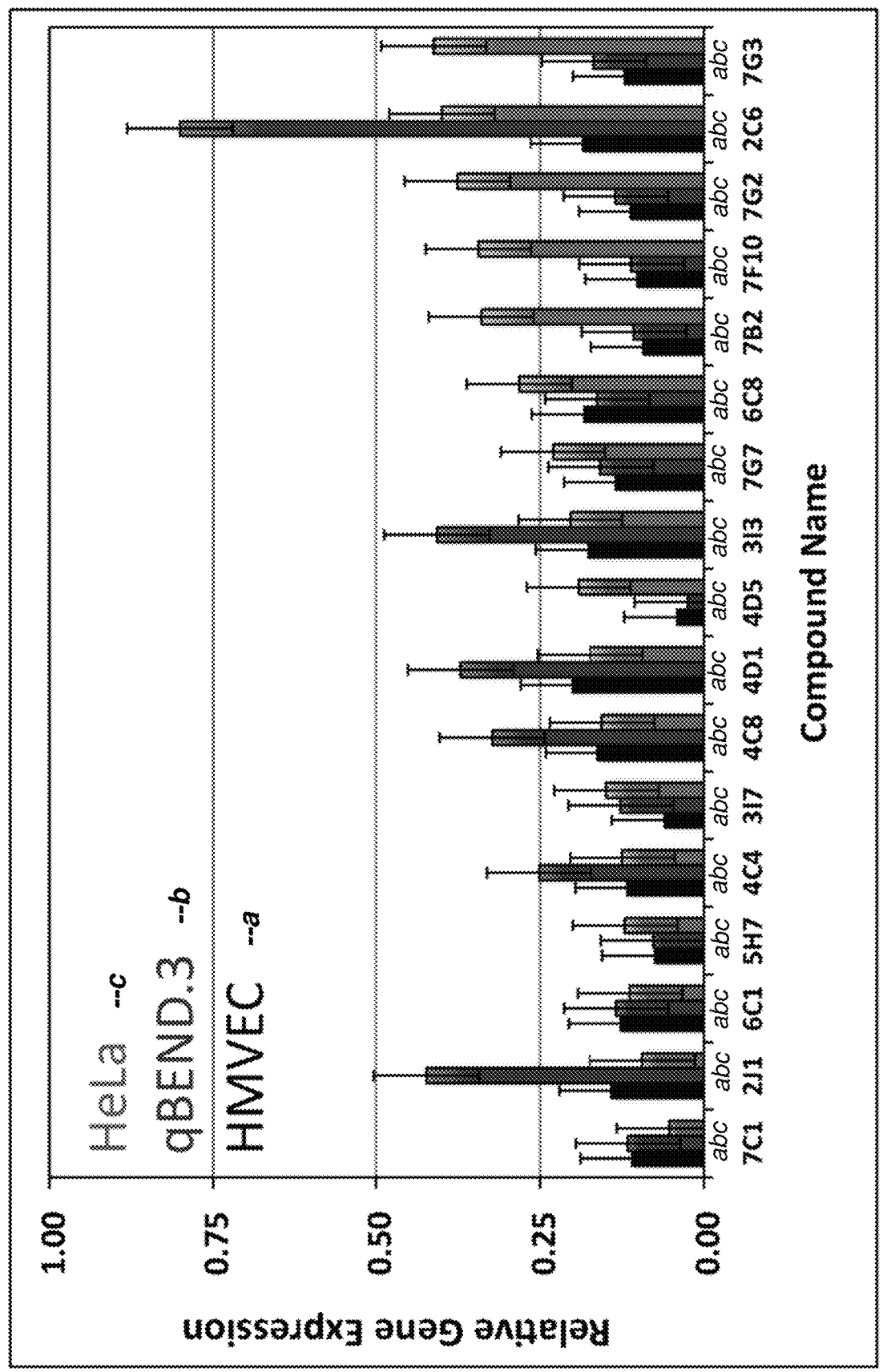
FIG. 3 depicts the gene expression data for seventeen lipomers screened against HeLa, qBEND.3 and HMVEC cells in vitro. The lipomer:siRNA mass ratio was 15 and siRNA dosing was 30 nM. All lipomers studied reduced gene expression in at least one cell line by 80% at this dose, indicating a high degree of in vitro potency, and driving subsequent interest for in vivo testing.

Since polymer:siRNA mass ratio has been shown to influence the delivery of genetic material, the library was screened at lipomer:siRNA mass ratios of 2.5, 5, 10 and 15 (FIG. 2). During mass ratio studies, the amount of lipomer changed while the amount of siRNA remained constant such that the siRNA molarity was 30 nM. Compounds effective against HeLa cells were tested for efficacy against endothelial cells at a dose of 30 nM, as shown in FIG. 3. Following the initial screening of the library, a subset of effective compounds was tested for dose response. The lipomer: siRNA mass ratio was maintained at 15:1 while the amount of molarity of the solution decreased from 30 nM to 0.4 nM. These results are shown in FIG. 4.

The mechanism of cellular uptake was then studied using fluorescently labeled siRNA. Briefly, cells can envelop external particles via a variety of different mechanisms. Each uptake mechanism results in different physiological processes. For this reason, identifying the specific uptake mechanism is important for nanoparticle delivery (Sahay et al., J. Controlled Release (2010) 145: 182-195). Fortunately, most pathways are identifiable via canonical molecules present during their activation. In this case, the caveolae-mediated pathway was identified by the presence of a molecule termed cholera toxin B. Specifically, HeLa nuclei (blue), cholera toxin B (green) and Cysteine-5 tagged siRNA (siCy5) (red) were stained concurrently after Cy5 tagged siRNA was conjugated to compound 6B10. It was confirmed by the overlap between the red Cy5 siRNA and cholera toxin B that some molecules were taken up via caveolae-mediated endocytosis.

In Vivo Formulation and Physical Characterization

All in vivo experiments were reviewed and approved by the MIT Institutional Animal Care and Welfare Committee and were conducted in the MIT division of comparative medicine. Using in vitro screening described above, approximately 20 compounds were identified as leading candidates for in vivo analysis. To test the compounds in vivo, lipomers were diluted in 100% EtOH and mixed with $C_{16}$-PEG (Aniara, Wilmington, OH) and cholesterol (Sigma Aldrich, St. Louis, MO) such that Lipomer:PEG:cholesterol molar ratios were 100:25:35. In another study, lipomers were diluted in 100% EtOH and combined with cholesterol, but not $C_{16}$-PEG. Particles, in 25 mMol buffered sodium acetate (pH 5.3), were extruded using a 10 mL Lipex extruder (Northern Lipids, Canada) at 40° C. through 50 nm pore-size polycarbonate membranes until size distribution was uniform. siRNA was then added to the lipomer dispersion for 30 minutes, facilitating electrostatic interactions that led to siRNA complexation. Then, lipomers were dialyzed against 1×PBS (pH 7.4) for 75 minutes to remove unbound siRNA and excess acetate. Particle size and charge were measured immediately after mixing with PEG and cholesterol, after conjugation to siRNA, and after dialysis. Particle size was measured with dynamic light scattering (DLS) and surface charge was estimated using zeta potential analysis (Zetapals, Brookhaven Instruments, Holtsville, NY). Finally, to measure the stability of particles after conjugation of siRNA, compound size was measured 1 hour, 3 hours, 6 hours and 18 hours after formulation at 37° C., 25° C., 4° C. and −20° C. Both size and stability are shown in FIG. 5A-5B.

After dialysis, samples were injected into one of two animal models. In the first model, lipomers with anti-Factor 7 siRNA were injected to 8-wk-old Fox Chase female mice (Charles River, Boston, MA). 48 hours after injection, blood serum was collected and analyzed for Factor 7 expression (Biophen, Aniara, Mason, OH). Serum Factor 7 levels were compared to mice injected with PBS (see FIGS. 6, 7, and 8).

In a second study, 8 to 12-week-old Fox Chase female mice, bearing a ~1 cm luciferase-expressing HEPg2 tumor in the flank, were injected with anti-LUC siRNA. Before, and 72 hr after intravenous siRNA administration (dosed at 2.0 mg/kg). Luciferase expression was measured by injecting 150 mg/kg D-luciferin ip (XenoLight Redijéct D-Luciferin Ultra, Caliper Life Sciences, Hopkinton, MA) and recording luminescence with an IVIS Spectrum (Xenogen-Calipers Life Science). Reduction in luciferase expression was determined by comparing luciferase expression pre- and post-siRNA treatment (see FIGS. 9A-9B).

Figure 10A:
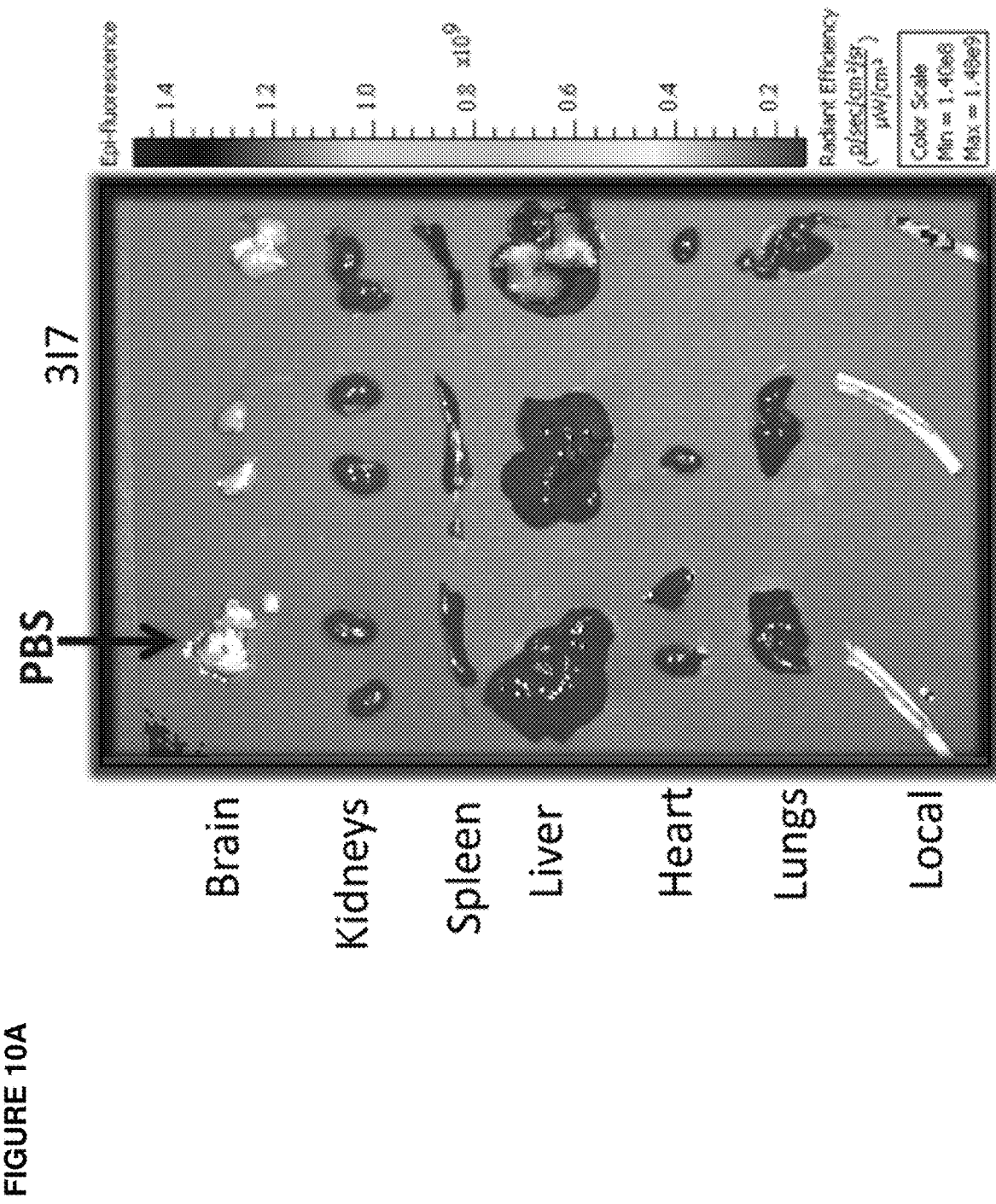
FIGS. 10A-10B depict the biodistribution of three different successful lipomers (7H6, 7I1 and 3I7) evaluated using Cy5.5 labeled siRNA (AllStars Control siRNA, Qiagen, Valencia, CA). Mice were injected with Cy5.5 siRNA (2.5 mg/kg) via the tail vein and sacrificed 1 or 14 hours later. Major organs were harvested and fluorescently imaged to evaluate distribution of Cy5.5 siRNA nanoparticles at 670 (ex. 670 nm, em. 710 nm) using an IVIS imaging system. Lipomers were found in the liver, spleen, kidney lungs and near the injection point. This indicates that they may be used for a variety of ailments, both systemic and within different organs. Since many siRNA delivery vehicles hone primarily to the liver, the delivery to lungs and kidneys may present new clinical targets.
Figure 10B:
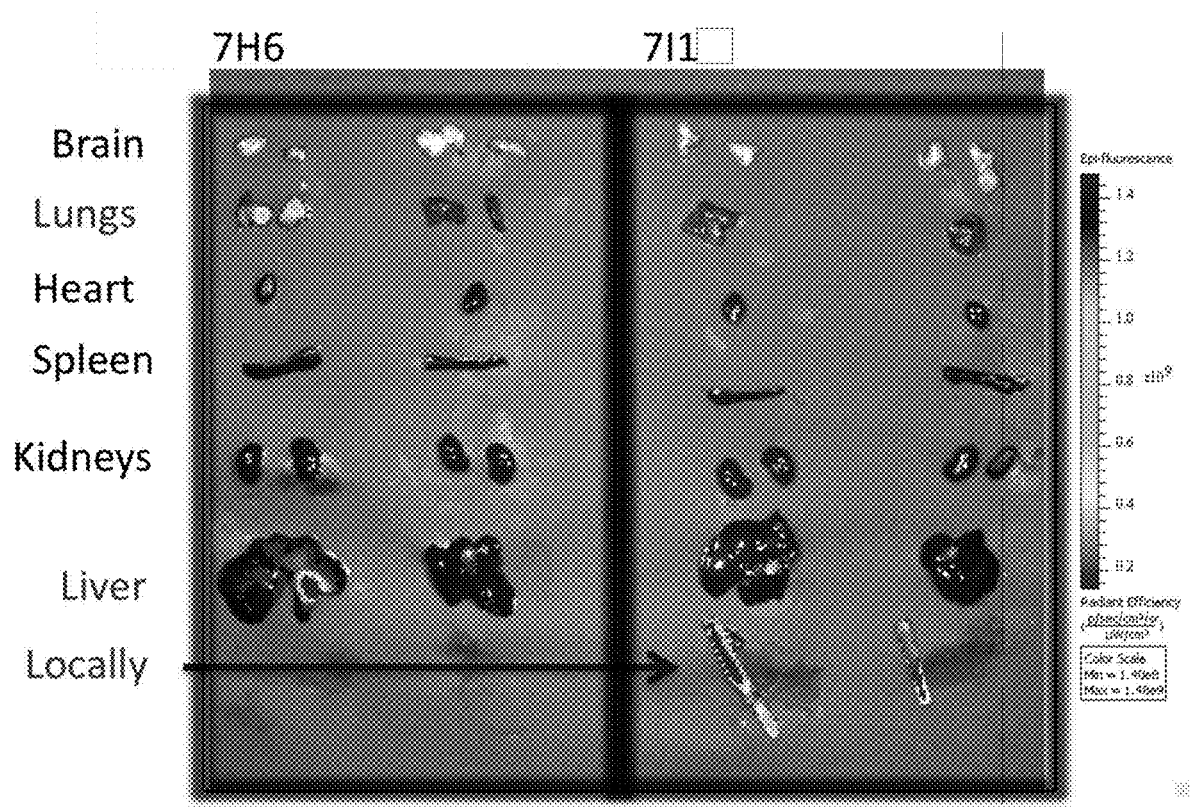
Figure 11:
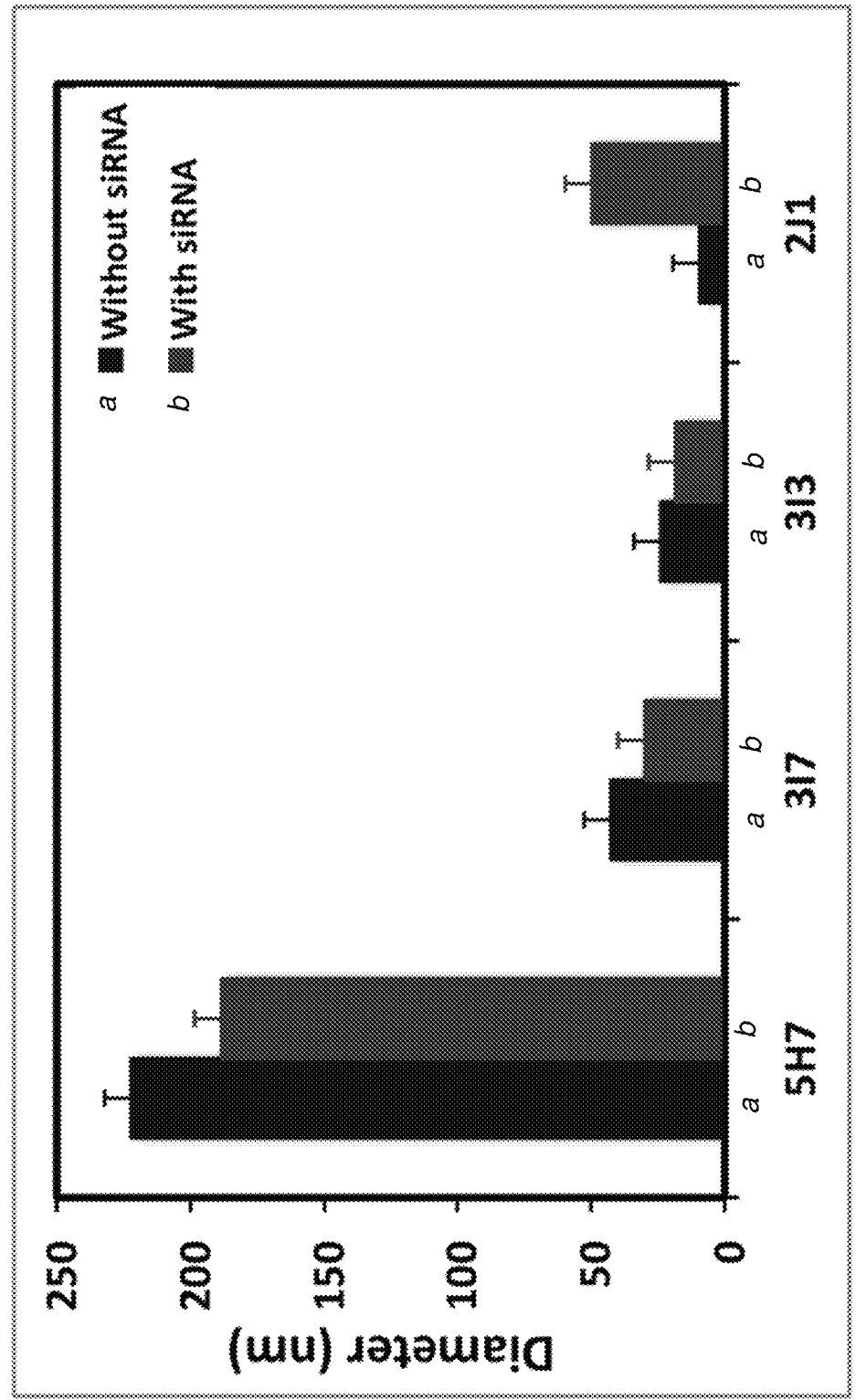
FIG. 11 depicts particle size before and after conjugation of siRNA at a pH of 5.3 (before dialysis). Nanoparticles are kept from aggregating by repulsive factors including steric and electrostatic forces. Upon conjugation of siRNA, electrostatic forces may be reduced, which can lead to aggregation. However, many particles showed stability even after conjugation of siRNA. Note that together, FIGS. 11-15 demonstrate that the lipomer size, surface charge and chemical composition have been characterized. Importantly, different lipomers have different physical properties, making them ideal for different types of applications. As an example, small particles with diameters below 50 nm may be well suited for kidney delivery while larger particles may be better for delivery of genetic material to the lung.
Figures 12A, 12B:
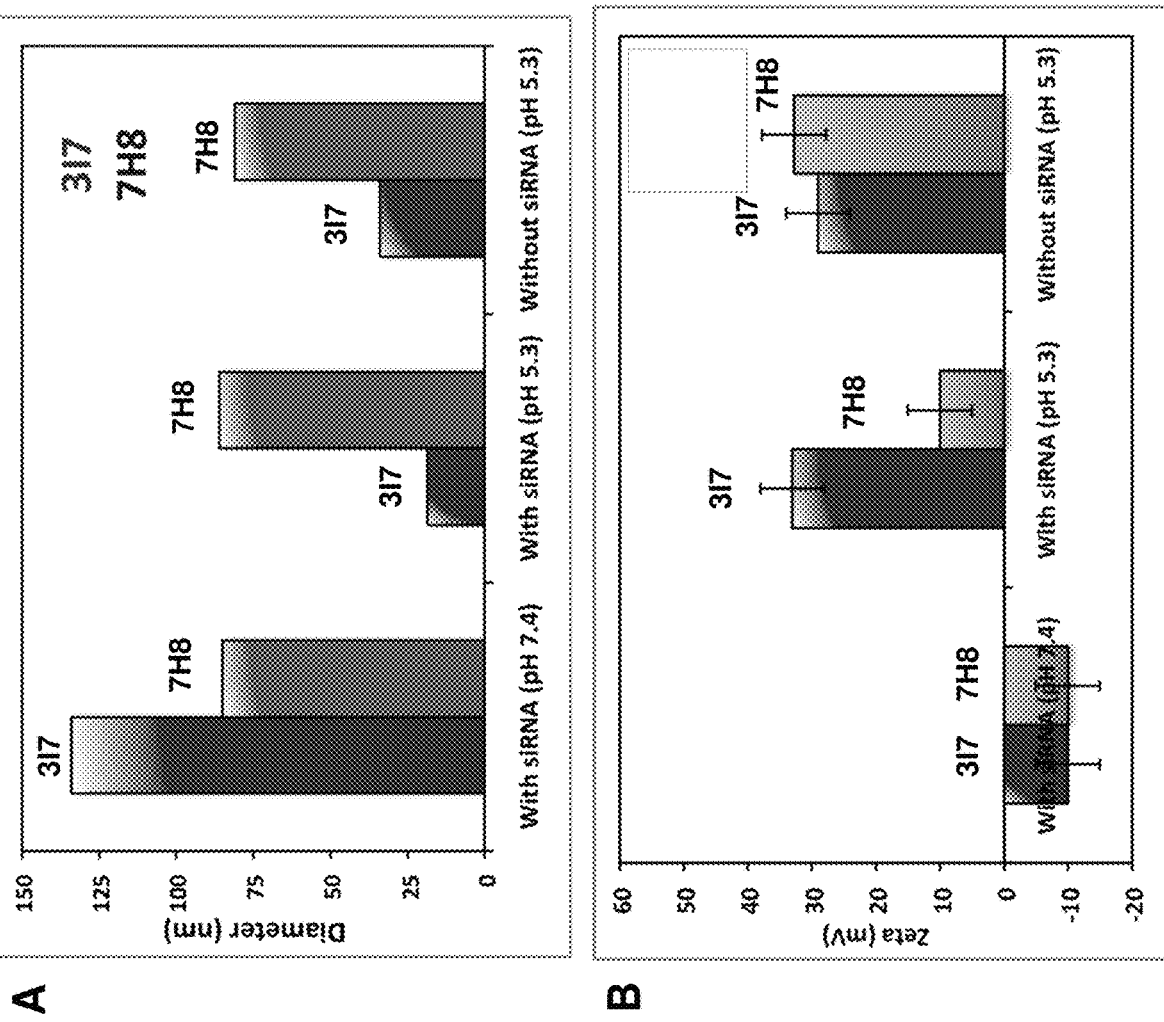
FIGS. 12A-12B depict particle size (FIG. 12A) and surface charge (FIG. 12B) (zeta potential) before and after conjugation of siRNA at pH of 5.3, and after dialysis to a pH of 7.4.
Figures 13A, 13B:
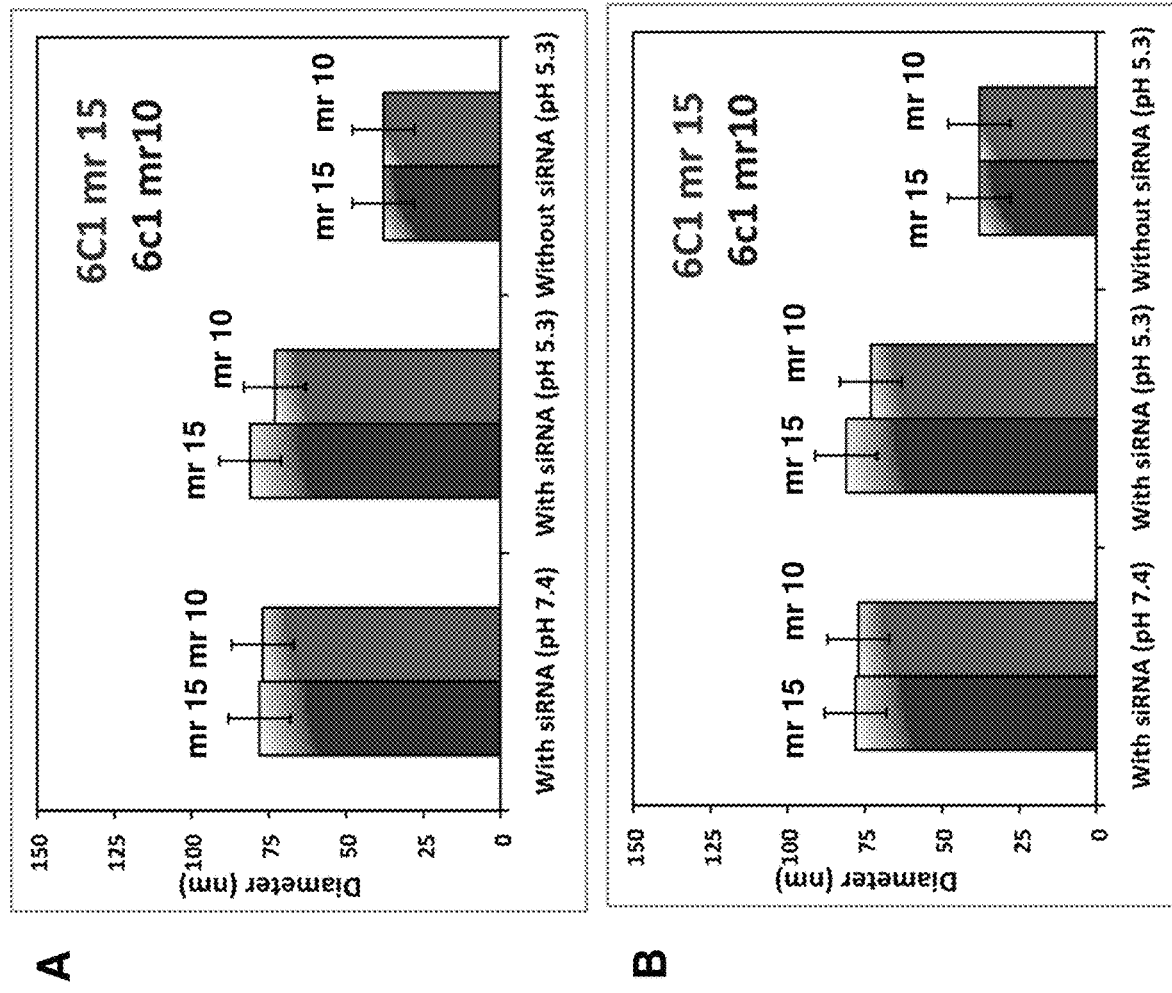
FIGS. 13A-13B demonstrate the effect of lipomer:siRNA mass ratio (mr) on the size (FIG. 13A) and zeta potential (FIG. 13B) of particles before and after dialysis. The diameter of 6C1 was found to be constant at mr=10 and 15. The lipomer:siRNA did not greatly influence size and zeta potential, indicating a high degree of physical stability.

Finally, the biodistribution of three different successful compounds (7H6, 7I1 and 3I7) was evaluated using Cy5.5 labeled siRNA (AllStars Control siRNA, Qiagen, Valencia, CA). Mice were injected with Cy5.5 siRNA (2.5 mg/kg) via the tail vein and sacrificed 1 or 14 hours later. Major organs were harvested and fluorescently imaged at 670 (ex. 670 nm, em. 710 nm) using an IVIS imaging system (see FIGS. 10A-10B).

The Factor 7 siRNA was provided by Alnylam Pharmaceuticals and had a sense sequence of 5'-GGAucAucucAAGucuuAcT*T-3' (SEQ ID NO 1) as previously reported (Akinc, A. et al. *Nature Biotechnology* 26, 561-569). The Cy5-tagged siRNA was purchased from Qiagen and had a proprietary sequence (Product Number 1027297). The Luciferase targeting siRNA was purchased from Dharmacon and had a proprietary sequence (Product Number D-002050-0120).

Results

To identify compounds that effectively transfect multiple cell lines in vitro, 750 lipomers were screened against HeLa and HCT-116 cells. Since lipomer:siRNA mass ratios have been related in other studies to both efficacy and toxicity, the library was screened at lipomer:siRNA mass ratios of 2.5, 5, 10 and 15. Slightly less than 5% of the compounds transfected HeLa cells effectively, as shown qualitatively in FIG. 2A and quantitatively in FIG. 2B. Furthermore, lipomer:siRNA mass ratios of 10 and 15 were found to be most efficacious (FIG. 2A), while FIG. 2B indicates that at these ratios off-target effects (i.e., any decrease in Renilla luciferase expression) are negligible.

Compounds found to be efficacious (>80% knockdown and <20% toxicity) against HeLa cells were then screened for knockdown against primary human endothelial cells and murine endothelial cells. FIG. 3 presents compounds that were found to be highly efficacious in multiple cell lines. Interestingly, the reduction in gene expression varied from one cell line to another, where, in general, primary endothelial cells were easier to transfect.

Figures 4A, 4B:
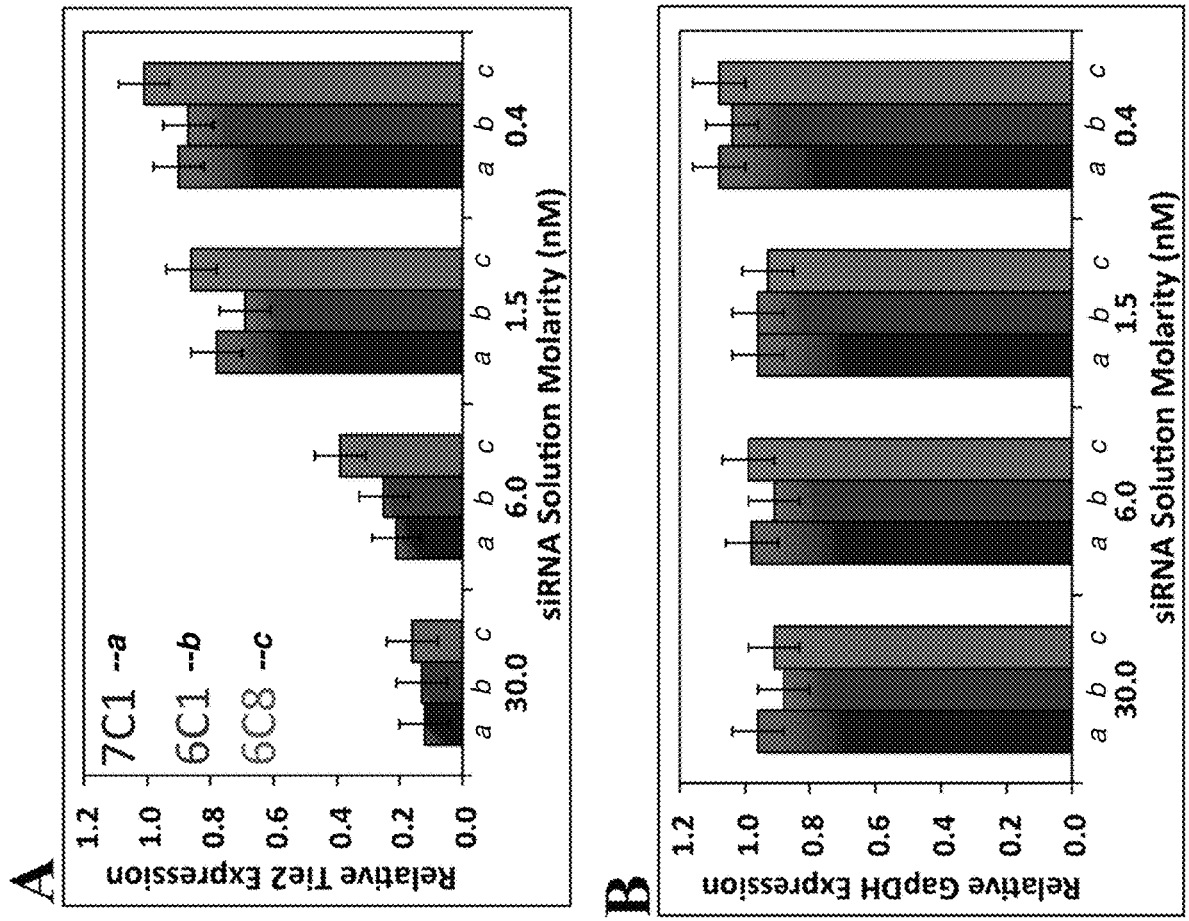
FIGS. 4A-4B depict the dose response of lipomers 7C1, 6C1 and 6C8 in qBEND.3 murine endothelial cells.

Compounds were then tested for in vitro siRNA dose response against qBEND.3 cells. Increasing siRNA dosing led to decreased gene expression in vitro (FIG. 4A). At a dose of 30 nM, gene expression was reduced by up to 95% while GapDH (i.e., control gene) expression remained constant. Compounds reduced expression by nearly 80% at a dose of 6 nM, and by 25% at 1.2 nM, suggesting a 3.4 nM siRNA (~400 nM lipomer) dose would reduce gene expression by 50%. Furthermore, off-target effects were abrogated, as shown by the constant gene expression of the GapDH control (FIG. 4B).

Figure 6:
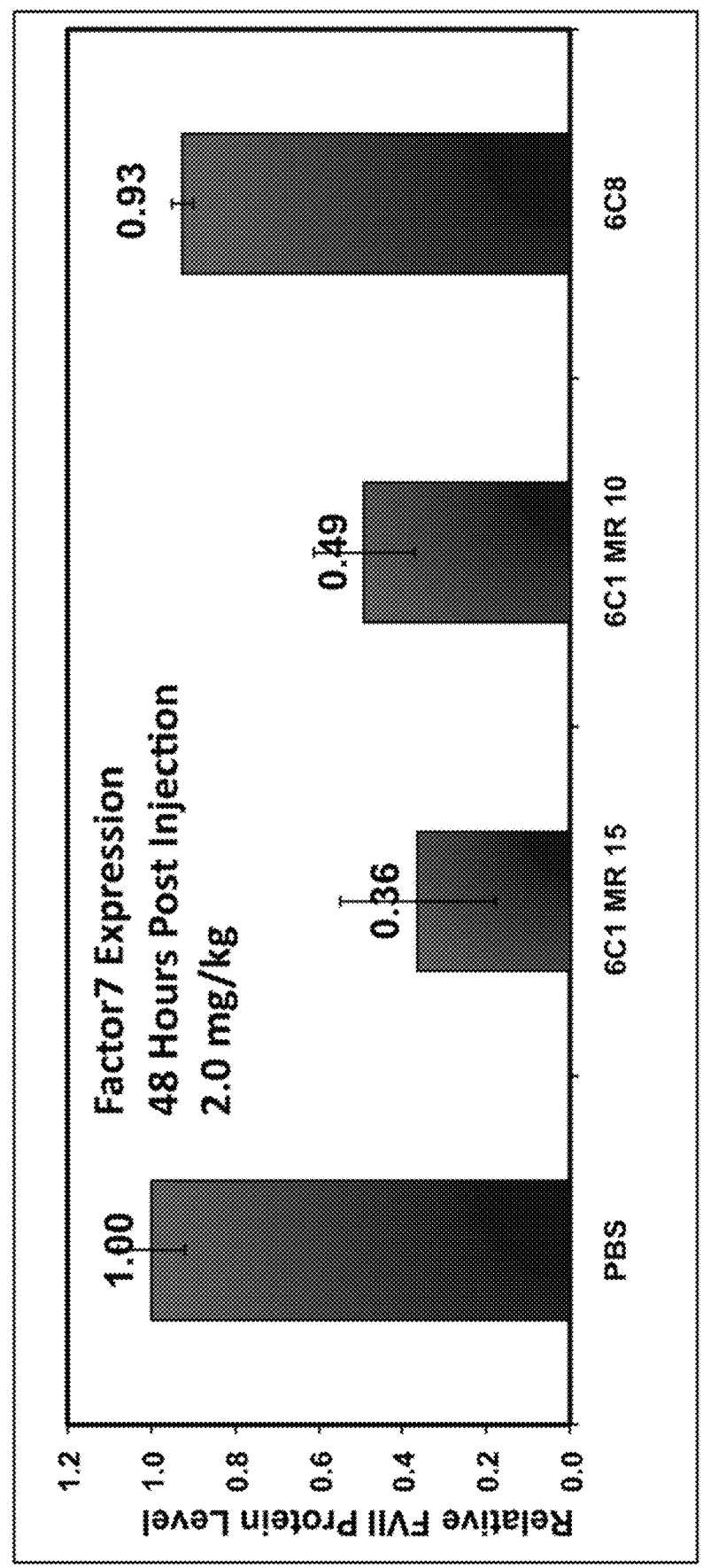
FIG. 6 depicts Factor 7 in vivo expression after tail-vein injection of lipomers 6C1 and 6C8. Lipomers were formulated with cholesterol at a lipomer:cholesterol mole ratio of 100:35, but without $C_{16}$-PEG. 6C1 was tested at two lipomer:siRNA mass ratios, 15:1 and 10:1. As seen during the in vitro assays, 15:1 mass ratios resulted in higher knockdown. 6C1 reduced gene expression by 64% while 6C8 did not reduced gene expression in vivo. Importantly, these results indicate that lipomers can deliver siRNA effectively in vivo when delivered systemically.
Figure 7:
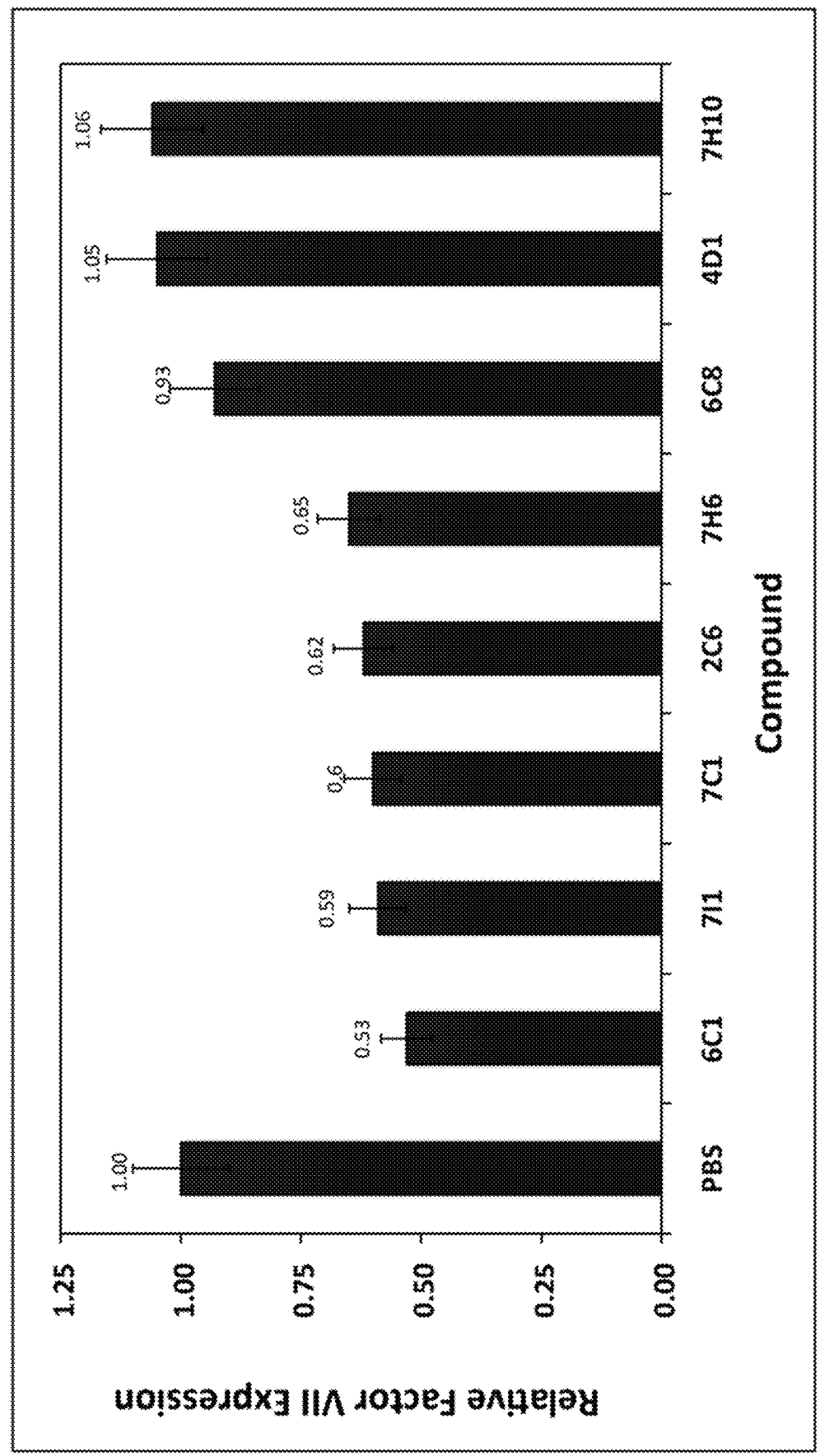
FIG. 7 depicts the relative expression of Factor 7 after systemic dosing with 2 mg/kg siRNA. In this study, lipomers were formulated with cholesterol and $C_{16}$-PEG such that the Lipomer:Cholesterol:PEG molar ratio was 100:35:25. The lipomer:siRNA mass ratio was held constant at 15:1. Lipomers were then injected via the tail vein, and Factor 7 expression was measured 48 hours later. Several lipomers were shown to decrease in vivo Factor 7 expression, suggesting that in vivo success was not limited to 6C1 and that other lipomer compounds could reduce gene expression in vivo.
Figure 8:
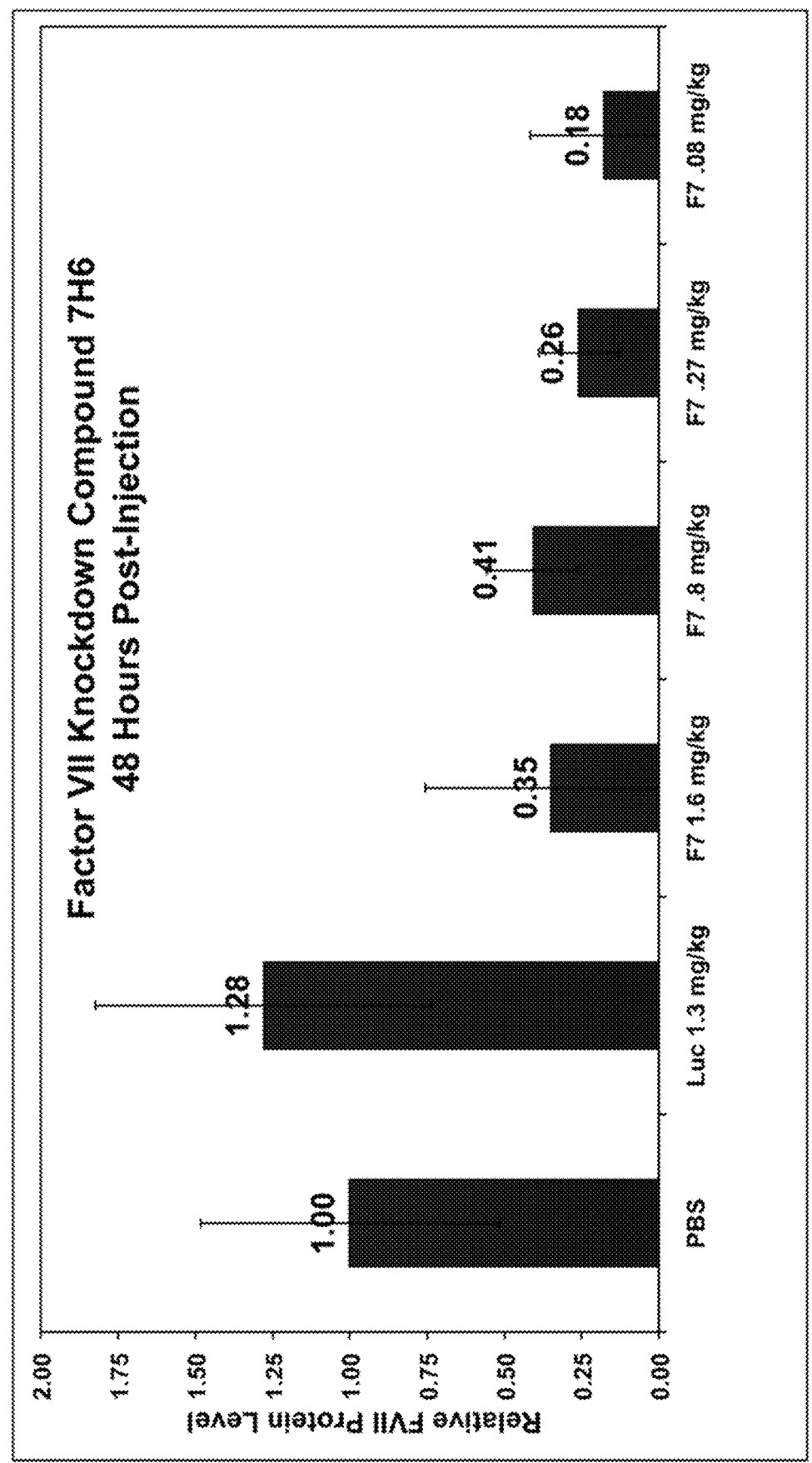
FIG. 8 depicts in vivo gene expression of Factor 7. Lipomer 7H6 reduced gene expression by 66% systemic injection into mice at a dose of 1.5 mg/kg. When 7H6 was combined with a luciferase targeting siRNA, it did not reduce F7 expression, that the gene expression is reduced by siRNA action and not toxicity. This lipomer reduced gene expression by 35% in the study described in FIG. 7.

Compounds were then tested for in vivo efficacy against the expression of Factor 7, a serum protein produced by the liver. In an initial study, lipomers formulated with cholesterol (but without $C_{16}$-PEG) were complexed with anti-Factor 7 siRNA (siF7, Alnylam Pharmaceuticals) and injected to the tail vein, at an siRNA dose of 2 mg/kg and a lipomer:siRNA mass ratio of 15:1 or 10:1 (FIG. 6). Analyzing Factor 7 in the blood demonstrated more than 64% knockdown and that a 15:1 mass ratio resulted in higher knockdown. Adding $C_{16}$-PEG to the formulation (lipomer:cholesterol:$C_{16}$-PEG mole ratio 100:35:25) reduced knockdown slightly (FIGS. 7 and 8). No change in animal weight was measured in the several days post administration, pointing to the good in vivo tolerability of the compounds.

Figure 9A:
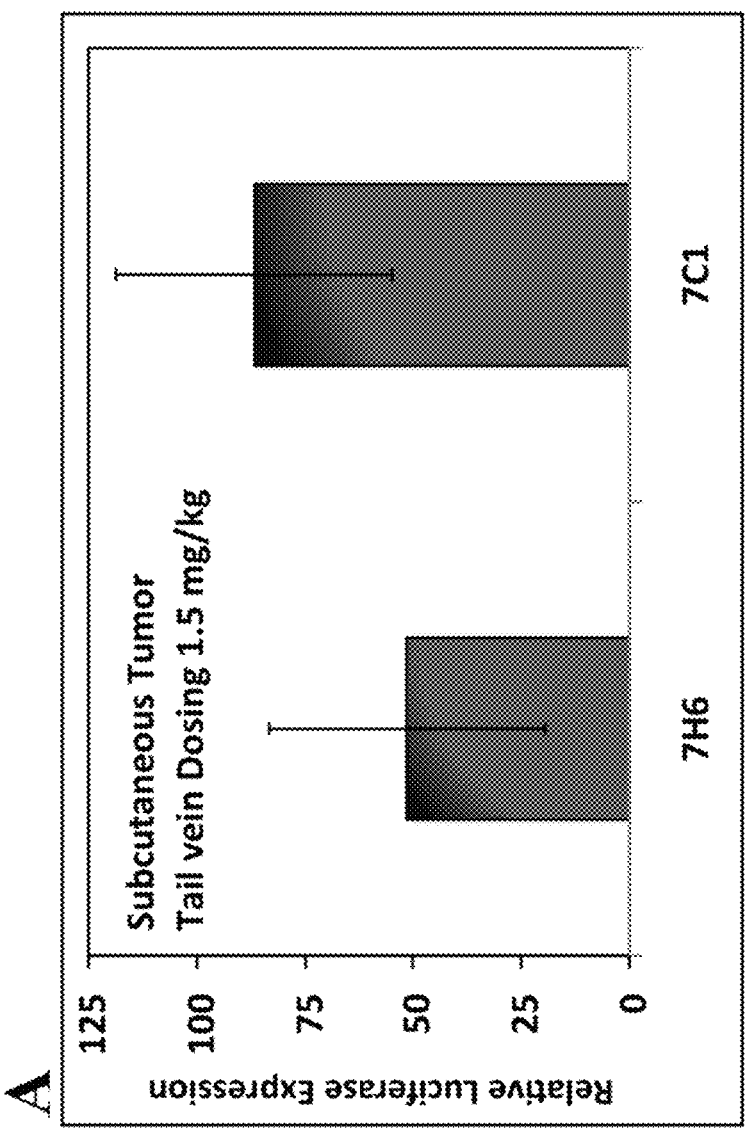
FIGS. 9A-9B depict thein vivo reduction of tumor gene expression in a subcutaneous tumor model. Mice were injected with luciferase expressing tumor cells subcutaneously and tumors were allowed to grow for two weeks. Before injection of siRNA, luciferase expression was measured, and used as baseline.
Figure 9B:
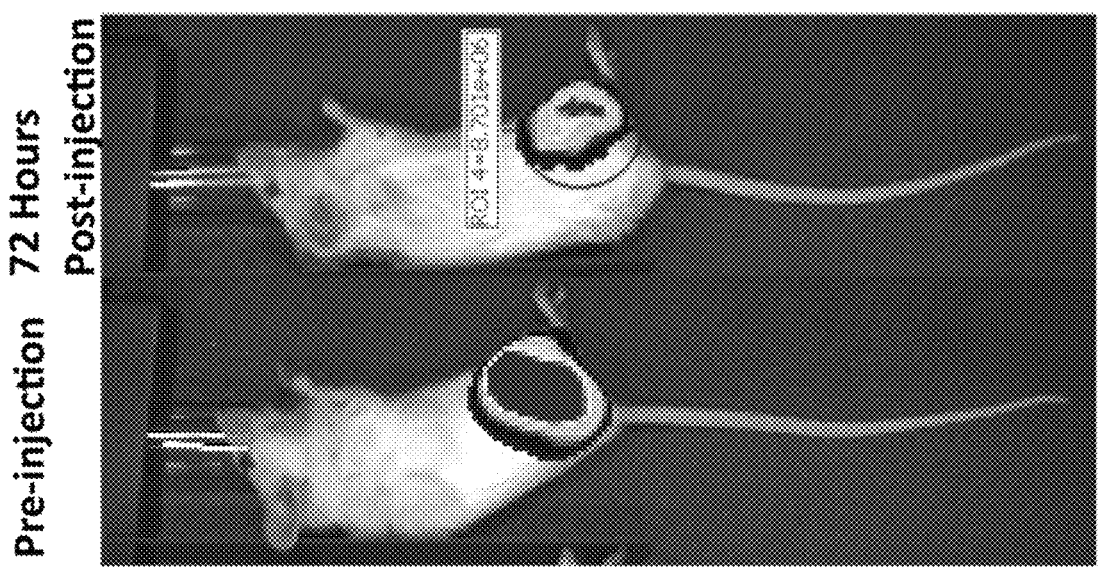

In vivo efficacy was further evaluated in a tumor model. Fox Chase mice bearing subcutaneous HepG2 tumors (~1 cm diameter) that express Firefly-luciferase were injected with anti-Luc siRNA (1.5 mg/kg). Tumor luminescence was measured before, and 72 hr after, siRNA administration. A 51% decrease in tumor luminescence, was measured when using a representative efficacious compound—7H6 (FIG. 9A).

Finally, siRNA delivery systems 3I7, 7H6, and 7I1B complexing fluorescently labeled siRNA were injected to the tail vein. The resulting biodistribution showed that siRNA accumulates in the liver, spleen, kidney and lungs and the tail of mice (FIG. 10). All compounds had high selectivity to the liver. A significant amount of 7H6 accumulated in the lungs while 7I1B also tended to accumulate in the kidneys. This suggests that different compounds can be optimized for delivery in different organs.

Other Embodiments

All patents, patent applications, and literature references cited herein are incorporated herein by reference.

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function. Use of terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

-continued

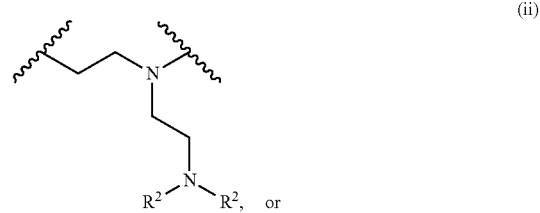
(ii)

What is claimed is:

1. A conjugated lipomer of the Formula (II):

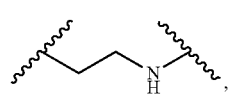

(II)

or salt thereof; wherein:
each instance of $L^1$ is independently formula:

(i)

-continued

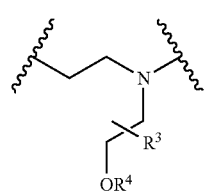
(iii)

provided that at least one $L^1$ is formula (ii) and at least one $L^1$ is formula (iii);

n is an integer between 3 and 45, inclusive;

each instance of $R^2$ is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; a substituted or unsubstituted polyethyleneimine; or a group of the formula (iii'):

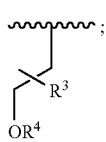

or the two $R^2$ groups are joined to form a substituted or unsubstituted heterocyclyl;

each instance of $R^3$ is —$C_{13}H_{27}$;

each instance of $R^4$ is independently hydrogen, acyl; silyl; a hydroxyl protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl;

A is —$N(R^5)_2$, wherein each instance of $R^5$ is hydrogen; and

Z is hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl, or a group of the formula (iii'):

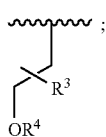

or Z and the nitrogen atom to which it is attached form a substituted or unsubstituted heterocyclyl group.

2. The conjugated lipomer of claim 1, or salt thereof, wherein the conjugated lipomer is prepared from a polyethyleneimine polymer having a number average molecule weight (Mn) of less than 800 g/mol.

3. The conjugated lipomer of claim 1, or salt thereof, wherein n is an integer between 3 and 5, inclusive.

4. The conjugated lipomer of claim 1, or salt thereof, wherein each instance of $R^2$ is independently hydrogen; a substituted or unsubstituted polyethyleneimine; or a group of the formula (iii').

5. A composition comprising one or more conjugated lipomers of claim 1, or salt thereof, and, optionally, an excipient.

6. The composition of claim 5, wherein the composition is a pharmaceutical composition or a cosmetic composition.

7. The composition of claim 5, wherein the composition further comprises an agent.

8. The composition of claim 7, wherein the agent is an organic molecule, inorganic molecule, nucleic acid, protein, peptide, polynucleotide, targeting agent, an isotopically labeled chemical compound, vaccine, or an immunological agent.

9. The composition of claim 8, wherein the agent is a polynucleotide, and the polynucleotide is DNA or RNA.

10. The composition of claim 9, wherein the RNA is RNAi, dsRNA, siRNA, shRNA, miRNA, or antisense RNA.

11. A method of preparing a conjugated lipomer of claim 1, or salt thereof, the method comprising contacting a compound of the Formula (I), or salt thereof, with an epoxide of the formula (xii):

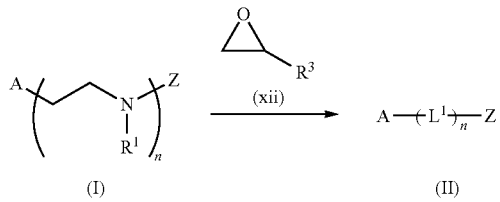

wherein each instance of $R^1$ is independently hydrogen or a group of the formula (ii'):

to provide the conjugated lipomer of the Formula (II), or salt thereof.

12. A conjugated lipomer, or salt thereof, prepared by contacting a compound of Formula (I):

or salt thereof, with one or more different epoxides of the formula (xii):

wherein:
n is an integer between 3 and 45, inclusive;
each instance of $R^1$ is independently selected from hydrogen or a group of the formula (ii'):

A is —N(R⁵)₂, wherein each instance of R⁵ is hydrogen;

Z is hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl; or Z and the nitrogen atom to which it is attached form a substituted or unsubstituted heterocyclyl group;

each instance of R² is independently hydrogen; acyl; silyl; sulfonyl; an amino protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; a substituted or unsubstituted polyethyleneimine; or a group of the formula (iii'):

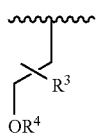

(iii')

or the two R² groups are joined to form a substituted or unsubstituted heterocyclyl;

each instance of R³ is —C₁₃H₂₇;

each instance of R⁴ is independently hydrogen, acyl; silyl; a hydroxyl protecting group; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; or substituted or unsubstituted heteroaryl;

provided that the number average molar mass (Mn) of the compound of Formula (I) does not exceed 2000 g/mol (about 2 kDa).

13. The conjugated lipomer of claim 1, or salt thereof, wherein each instance of R⁴ is hydrogen.

14. The conjugated lipomer of claim 4, or salt thereof, wherein the polyethyleneimine is of formula (iv):

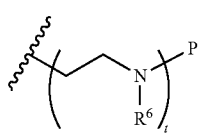

(iv)

wherein:
t is 1;
P is hydrogen or a group of the formula (iii'):

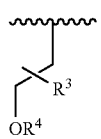

(iii')

R⁶ is hydrogen or a group of formula (iii'), wherein:
each instance of R³ is —C₁₃H₂₇; and
each instance of R⁴ is hydrogen.

15. The conjugated lipomer of claim 1, or salt thereof, wherein each instance of formula (iii) is

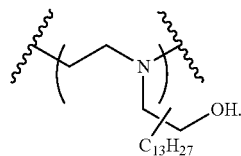

16. The conjugated lipomer of claim 1, or salt thereof, wherein each instance of L¹ is independently of formula (ii) or (iii), wherein each instance of formula (ii) is

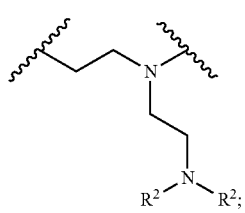

and each instance of formula (iii) is

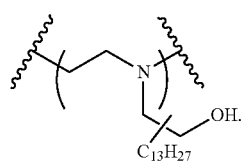

17. The conjugated lipomer of claim 1, or salt thereof, wherein:
each instance of L¹ is independently formula (ii) or (iii);
n is an integer between 10 and 15, inclusive;
each instance of R² is independently a substituted polyethyleneimine, or a group of formula (iii');
each instance of R⁴ is hydrogen; and
Z is a group of formula (iii').

18. The conjugated lipomer of claim 12, or salt thereof, wherein each instance of R² is independently hydrogen; a substituted or unsubstituted polyethyleneimine; or a group of the formula (iii').

19. The conjugated lipomer of claim 12, or salt thereof, wherein Z is hydrogen.

20. The conjugated lipomer of claim 1, or salt thereof, wherein Z is hydrogen or a group of the formula (iii').

* * * * *

SEQUENCE LISTING

```
<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: Factor VII siRNA sense sequence
<220> FEATURE:
<221> NAME/KEY: misc_feature
<222> LOCATION: (4)..(5)
<223> OTHER INFORMATION: 2-fluoro modified nucleotides
<220> FEATURE:
<221> NAME/KEY: misc_feature
<222> LOCATION: (7)..(10)
<223> OTHER INFORMATION: 2-fluoro modified nucleotides
<220> FEATURE:
<221> NAME/KEY: misc_feature
<222> LOCATION: (14)..(17)
<223> OTHER INFORMATION: 2-fluoro modified nucleotides
<220> FEATURE:
<221> NAME/KEY: misc_feature
<222> LOCATION: (19)..(19)
<223> OTHER INFORMATION: 2-fluoro modified nucleotide
<220> FEATURE:
<221> NAME/KEY: misc_feature
<222> LOCATION: (20)..(21)
<223> OTHER INFORMATION: phosphorothioate linkage

<400> SEQUENCE: 1
ggaucaucuc aagucuuact t                                              21
```